US012441725B2

(12) United States Patent
Yang et al.

(10) Patent No.: US 12,441,725 B2
(45) Date of Patent: Oct. 14, 2025

(54) ISO-CITRATE DEHYDROGENASE (IDH) INHIBITOR

(71) Applicant: ZHEJIANG METON PHARMACEUTICAL CO., LTD, Zhejiang (CN)

(72) Inventors: Jibin Yang, Shanghai (CN); Feng Yan, Shanghai (CN); Jinlong Zhu, Shanghai (CN); Jianxin Yang, Princeton, NJ (US)

(73) Assignee: ZHEJIANG METON PHARMACEUTICAL CO., LTD, Zhejiang (CN)

( * ) Notice: Subject to any disclaimer, the term of this patent is extended or adjusted under 35 U.S.C. 154(b) by 796 days.

(21) Appl. No.: 17/767,480

(22) PCT Filed: Sep. 8, 2020

(86) PCT No.: PCT/CN2020/113945

§ 371 (c)(1),
(2) Date: Apr. 8, 2022

(87) PCT Pub. No.: WO2021/068698

PCT Pub. Date: Apr. 15, 2021

(65) Prior Publication Data

US 2024/0116917 A1 Apr. 11, 2024

(30) Foreign Application Priority Data

Oct. 12, 2019 (WO) ................ PCT/CN2019/110793

(51) Int. Cl.
*C07D 471/04* (2006.01)
*A61P 35/00* (2006.01)
*C07D 519/00* (2006.01)

(52) U.S. Cl.
CPC ............ *C07D 471/04* (2013.01); *A61P 35/00* (2018.01); *C07D 519/00* (2013.01)

(58) Field of Classification Search
CPC ...... C07D 471/04; C07D 519/00; A61P 35/00
See application file for complete search history.

(56) References Cited

FOREIGN PATENT DOCUMENTS

| | | | | |
|---|---|---|---|---|
| WO | 2008136756 A1 | | 11/2008 | |
| WO | 2010139953 A1 | | 12/2010 | |
| WO | 2016171755 A1 | | 10/2016 | |
| WO | WO-2018010637 A1 | * | 1/2018 | ........... C07D 471/04 |

OTHER PUBLICATIONS

The International Search Report of PCT/CN2020/113945, mailed on Dec. 3, 2020.

STN. "2470419-22-6, 2467859-28-3, 2467645-59-4, 2467447-17-0 et al." Registry, Sep. 2, 2020 (Feb. 9, 2020), cited in the ISR of corresponding PCT/CN2020/113945.

* cited by examiner

*Primary Examiner* — Adam C Milligan
*Assistant Examiner* — Ernesto Valle, Jr.
(74) *Attorney, Agent, or Firm* — Junhe Law Office P.C.; James J. Zhu

(57) ABSTRACT

Disclosed are compounds inhibiting the conversion of α-KG to D-2-HG, pharmaceutically acceptable salts, hydrates, solvates or stereoisomers thereof and pharmaceutical compositions comprising the compounds. The compound and the pharmaceutical composition can effectively treat IDH associated diseases, including cancer.

14 Claims, 1 Drawing Sheet

Specification includes a Sequence Listing.

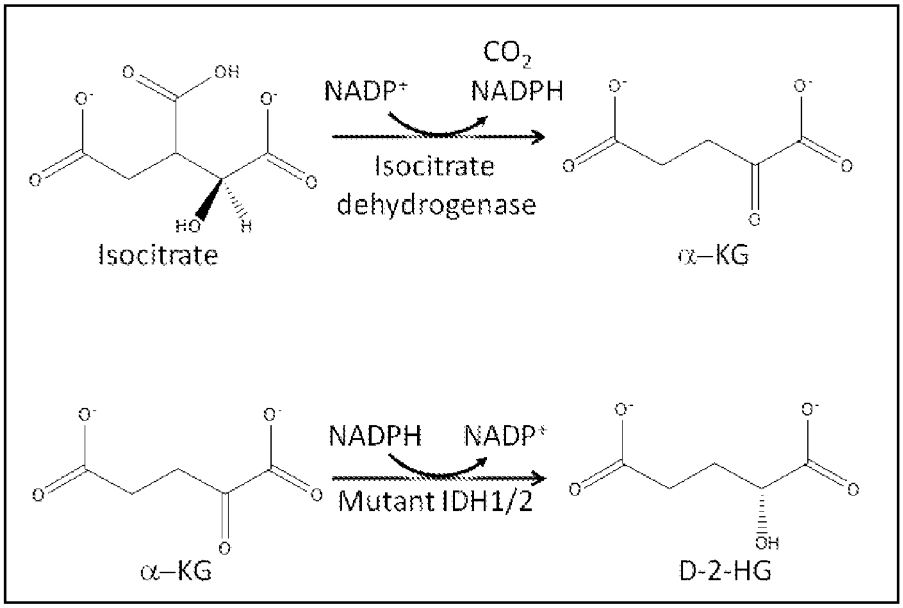
NADP+
$CO_2$
NADPH
Isocitrate
dehydrogenase
Isocitrate
α–KG
NADPH
NADP+
Mutant IDH1/2
α–KG
D-2-HG

SEQUENCE LISTING

```
<160> NUMBER OF SEQ ID NOS: 2

<210> SEQ ID NO 1
<211> LENGTH: 414
<212> TYPE: PRT
<213> ORGANISM: Homo sapiens

<400> SEQUENCE: 1

Met Ser Lys Lys Ile Ser Gly Gly Ser Val Val Glu Met Gln Gly Asp
1               5                   10                  15

Glu Met Thr Arg Ile Ile Trp Glu Leu Ile Lys Glu Lys Leu Ile Phe
            20                  25                  30

Pro Tyr Val Glu Leu Asp Leu His Ser Tyr Asp Leu Gly Ile Glu Asn
        35                  40                  45

Arg Asp Ala Thr Asn Asp Gln Val Thr Lys Asp Ala Ala Glu Ala Ile
    50                  55                  60

Lys Lys His Asn Val Gly Val Lys Cys Ala Thr Ile Thr Pro Asp Glu
65                  70                  75                  80

Lys Arg Val Glu Glu Phe Lys Leu Lys Gln Met Trp Lys Ser Pro Asn
                85                  90                  95

Gly Thr Ile Arg Asn Ile Leu Gly Gly Thr Val Phe Arg Glu Ala Ile
            100                 105                 110

Ile Cys Lys Asn Ile Pro Arg Leu Val Ser Gly Trp Val Lys Pro Ile
        115                 120                 125

Ile Ile Gly Arg His Ala Tyr Gly Asp Gln Tyr Arg Ala Thr Asp Phe
    130                 135                 140

Val Val Pro Gly Pro Gly Lys Val Glu Ile Thr Tyr Thr Pro Ser Asp
145                 150                 155                 160

Gly Thr Gln Lys Val Thr Tyr Leu Val His Asn Phe Glu Glu Gly Gly
                165                 170                 175

Gly Val Ala Met Gly Met Tyr Asn Gln Asp Lys Ser Ile Glu Asp Phe
            180                 185                 190

Ala His Ser Ser Phe Gln Met Ala Leu Ser Lys Gly Trp Pro Leu Tyr
        195                 200                 205

Leu Ser Thr Lys Asn Thr Ile Leu Lys Lys Tyr Asp Gly Arg Phe Lys
    210                 215                 220

Asp Ile Phe Gln Glu Ile Tyr Asp Lys Gln Tyr Lys Ser Gln Phe Glu
```

-continued

```
225                 230                 235                 240

Ala Gln Lys Ile Trp Tyr Glu His Arg Leu Ile Asp Asp Met Val Ala
                245                 250                 255

Gln Ala Met Lys Ser Glu Gly Gly Phe Ile Trp Ala Cys Lys Asn Tyr
            260                 265                 270

Asp Gly Asp Val Gln Ser Asp Ser Val Ala Gln Gly Tyr Gly Ser Leu
        275                 280                 285

Gly Met Met Thr Ser Val Leu Val Cys Pro Asp Gly Lys Thr Val Glu
    290                 295                 300

Ala Glu Ala Ala His Gly Thr Val Thr Arg His Tyr Arg Met Tyr Gln
305                 310                 315                 320

Lys Gly Gln Glu Thr Ser Thr Asn Pro Ile Ala Ser Ile Phe Ala Trp
                325                 330                 335

Thr Arg Gly Leu Ala His Arg Ala Lys Leu Asp Asn Asn Lys Glu Leu
            340                 345                 350

Ala Phe Phe Ala Asn Ala Leu Glu Glu Val Ser Ile Glu Thr Ile Glu
        355                 360                 365

Ala Gly Phe Met Thr Lys Asp Leu Ala Ala Cys Ile Lys Gly Leu Pro
    370                 375                 380

Asn Val Gln Arg Ser Asp Tyr Leu Asn Thr Phe Glu Phe Met Asp Lys
385                 390                 395                 400

Leu Gly Glu Asn Leu Lys Ile Lys Leu Ala Gln Ala Lys Leu
                405                 410


<210> SEQ ID NO 2
<211> LENGTH: 452
<212> TYPE: PRT
<213> ORGANISM: Homo sapiens

<400> SEQUENCE: 2

Met Ala Gly Tyr Leu Arg Val Val Arg Ser Leu Cys Arg Ala Ser Gly
1               5                   10                  15

Ser Arg Pro Ala Trp Ala Pro Ala Ala Leu Thr Ala Pro Thr Ser Gln
            20                  25                  30

Glu Gln Pro Arg Arg His Tyr Ala Asp Lys Arg Ile Lys Val Ala Lys
        35                  40                  45

Pro Val Val Glu Met Asp Gly Asp Glu Met Thr Arg Ile Ile Trp Gln
    50                  55                  60

Phe Ile Lys Glu Lys Leu Ile Leu Pro His Val Asp Ile Gln Leu Lys
65                  70                  75                  80

Tyr Phe Asp Leu Gly Leu Pro Asn Arg Asp Gln Thr Asp Asp Gln Val
                85                  90                  95

Thr Ile Asp Ser Ala Leu Ala Thr Gln Lys Tyr Ser Val Ala Val Lys
            100                 105                 110

Cys Ala Thr Ile Thr Pro Asp Glu Ala Arg Val Glu Glu Phe Lys Leu
        115                 120                 125

Lys Lys Met Trp Lys Ser Pro Asn Gly Thr Ile Arg Asn Ile Leu Gly
    130                 135                 140

Gly Thr Val Phe Arg Glu Pro Ile Ile Cys Lys Asn Ile Pro Arg Leu
145                 150                 155                 160

Val Pro Gly Trp Thr Lys Pro Ile Thr Ile Gly Arg His Ala His Gly
                165                 170                 175

Asp Gln Tyr Lys Ala Thr Asp Phe Val Ala Asp Arg Ala Gly Thr Phe
            180                 185                 190
```

-continued

```
Lys Met Val Phe Thr Pro Lys Asp Gly Ser Gly Val Lys Glu Trp Glu
        195                 200                 205

Val Tyr Asn Phe Pro Ala Gly Gly Val Gly Met Gly Met Tyr Asn Thr
    210                 215                 220

Asp Glu Ser Ile Ser Gly Phe Ala His Ser Cys Phe Gln Tyr Ala Ile
225                 230                 235                 240

Gln Lys Lys Trp Pro Leu Tyr Met Ser Thr Lys Asn Thr Ile Leu Lys
                245                 250                 255

Ala Tyr Asp Gly Arg Phe Lys Asp Ile Phe Gln Glu Ile Phe Asp Lys
            260                 265                 270

His Tyr Lys Thr Asp Phe Asp Lys Asn Lys Ile Trp Tyr Glu His Arg
        275                 280                 285

Leu Ile Asp Asp Met Val Ala Gln Val Leu Lys Ser Ser Gly Gly Phe
    290                 295                 300

Val Trp Ala Cys Lys Asn Tyr Asp Gly Asp Val Gln Ser Asp Ile Leu
305                 310                 315                 320

Ala Gln Gly Phe Gly Ser Leu Gly Leu Met Thr Ser Val Leu Val Cys
                325                 330                 335

Pro Asp Gly Lys Thr Ile Glu Ala Glu Ala Ala His Gly Thr Val Thr
            340                 345                 350

Arg His Tyr Arg Glu His Gln Lys Gly Arg Pro Thr Ser Thr Asn Pro
        355                 360                 365

Ile Ala Ser Ile Phe Ala Trp Thr Arg Gly Leu Glu His Arg Gly Lys
    370                 375                 380

Leu Asp Gly Asn Gln Asp Leu Ile Arg Phe Ala Gln Met Leu Glu Lys
385                 390                 395                 400

Val Cys Val Glu Thr Val Glu Ser Gly Ala Met Thr Lys Asp Leu Ala
                405                 410                 415

Gly Cys Ile His Gly Leu Ser Asn Val Lys Leu Asn Glu His Phe Leu
            420                 425                 430

Asn Thr Thr Asp Phe Leu Asp Thr Ile Lys Ser Asn Leu Asp Arg Ala
        435                 440                 445

Leu Gly Arg Gln
    450
```

ISO-CITRATE DEHYDROGENASE (IDH) INHIBITOR

CROSS-REFERENCE TO RELATED APPLICATIONS

This application is a national phase application, filed pursuant to 35 U.S.C § 371 of PCT Application No. PCT/CN2020/113945 filed on Sep. 8, 2020, which claims foreign priority of PCT Application No. PCT/CN2019/110793 filed on Oct. 12, 2019, now abandoned. Each of these applications is hereby incorporated by reference herein in its entirety.

FIELD OF THE DISCLOSURE

The present disclosure relates to compounds that inhibiting the conversion of α-ketoglutarate (α-KG) to 2-hydroxyglutarate (2-HG) such as D-2-HG, a pharmaceutical composition comprising the compound(s) as an active ingredient, and use of the compounds in the manufacture of medicaments for treating diseases associated with the conversion of α-KG to D-2-HG.

BACKGROUND

Isocitrate dehydrogenase (IDH) is an essential enzyme for cellular respiration in the tricarboxylic acid (TCA) cycle which catalyzes the oxidative decarboxylation of isocitrate, producing alpha-ketoglutarate (α-ketoglutarate, α-KG) and $CO_2$. In humans, IDH exists in three isoforms: IDH3 catalyzes the third step of the citric acid cycle while converting $NAD^+$ to NADH in the mitochondria. The isoforms IDH1 and IDH2 catalyze the same reaction outside the context of the citric acid cycle and use NADP+ as a cofactor instead of NAD+. They localize to the cytosol and peroxisome or the mitochondrion respectively.

Specific mutations in the IDH1 have been found in several brain tumors including astrocytoma, oligodendroglioma and glioblastoma multiforme, with mutations found in nearly all cases of secondary glioblastomas, which develop from lower-grade gliomas, but rarely in primary glioblastoma multiforme. Glioma patients whose tumor had an IDH1-R132X mutation had longer survival ["An integrated genomic analysis of human glioblastoma multiforme", Parsons, D. W., et al., Science, (2008); "Analysis of the IDH1 codon 132 mutation in brain tumors", Balss, J., et al., Acta Neuropathol, (2008); Bleeker, F. E., et al., "IDH1 mutations at residue p.R132 (IDH1(R132)) occur frequently in high-grade gliomas but not in other solid tumors", Hum Mutat, (2009)]. IDH1 and IDH2 mutations occur before p53 mutation and the loss of 1p/19q chromosomes and are believed to be the first event of gliomagenesis ["IDH1 mutations are early events in the development of astrocytomas and oligodendrogliomas", Watanabe, T., et al., Am J Pathol, (2009); "Mutational landscape and clonal architecture in grade II and III gliomas", Suzuki, H., et al., Nat Genet, (2015); "Comprehensive, Integrative Genomic Analysis of Diffuse Lower-Grade Gliomas", Brat, D. J., et al., N Engl J Med, (2015)]. Furthermore, mutations of IDH2 and IDH1 were found in up to 20% of cytogenetically normal acute myeloid leukemia (AML) ["Recurring mutations found by sequencing an acute myeloid leukemia genome", Mardis, E. R., et al., N Engl J Med, (2009); "Prognostic impact of IDH2 mutations in cytogenetically normal acute myeloid leukemia", Thol, F., et al., Blood, (2010); "Acquired mutations in the genes encoding IDH1 and IDH2 both are recurrent aberrations in acute myeloid leukemia: prevalence and prognostic value", Abbas, S., et al., Blood, (2010); "The prognostic significance of IDH1 mutations in younger adult patients with acute myeloid leukemia is dependent on FLT3/ITD status", Green, C. L., et al., Blood, (2010); "IDH1 mutations are detected in 6.6% of 1414 AML patients and are associated with intermediate risk karyotype and unfavorable prognosis in adults younger than 60 years and unmutated NPM1 status", Schnittger, S., et al., Blood, (2010); "Genomic and epigenomic landscapes of adult de novo acute myeloid leukemia", N Engl J Med, (2013)]. IDH mutation was also reported in other type of cancer, including 75% chondrosarcoma ["IDH1 and IDH2 mutations are frequent events in central chondrosarcoma and central and periosteal chondromas but not in other mesenchymal tumours", Amary, M. F., et al., J Pathol, (2011); "Ollier disease and Maffucci syndrome are caused by somatic mosaic mutations of IDH1 and IDH2", Amary, M. F., et al., Nat Genet, (2011)], 10-23% intrahepatic cholangiocarcinoma ["Frequent mutation of isocitrate dehydrogenase IDH1 and IDH2 in cholangiocarcinoma identified through broad-based tumor genotyping", Borger, D. R., et al., Oncologist, (2012); "Mutations in isocitrate dehydrogenase 1 and 2 occur frequently in intrahepatic cholangiocarcinomas and share hypermethylation targets with glioblastomas", Wang, P., et al., Oncogene, (2012)], and some patients of angioimmunoblastic T-Cell Lymphoma and melanoma ["The consensus coding sequences of human breast and colorectal cancers", Sjoblom, T., et al., Science, (2006)]. So far, IDH1 and IDH2 are the most frequently mutated metabolic enzyme genes in human cancer.

These above-mentioned mutations lead to the change of amino acid residues (R132 on IDH1, R140 or R172 on IDH2) critical for enzymatic activity and thus impair the isocitrate to α-KG catalyzation by IDH enzymes. In the meantime, these IDH mutants acquire neomorphic catalytic activity that converts α-KG to D-2-HG. In tumor cells harboring above-mentioned IDH mutations, D-2-HG accumulates to a very high level and inhibits the function of enzymes that are dependent on α-KG. This leads to a hypermethylated state of DNA and histones, which results in different gene expression that can activate oncogenes and inactivate tumor -suppressor genes. Ultimately, this may lead to the types of cancer disclosed above ["The consensus coding sequences of human breast and colorectal cancers", Sjoblom, T., et al., Science, (2006)].

It is therefore desired to develop an inhibitor which inhibiting the process of converting α-KG to D-2-HG.

SUMMARY

In one aspect, the present disclosure provides a compound of Formula (I):

Formula (I)

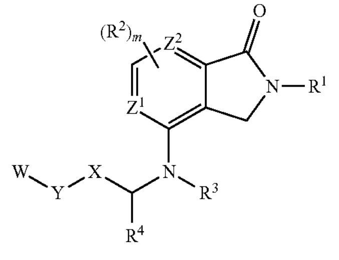

or a pharmaceutically acceptable salt thereof, wherein, $Z^1$ and $Z^2$ are independently selected from C and N;

X is selected from the group consisting of aryl, heteroaryl, or saturated or partially unsaturated heterocyclyl, said aryl, heteroaryl, or saturated or partially unsaturated heterocyclyl are optionally substituted by one or more groups independently selected from the group consisting of halogen, hydroxyl, cyano, nitro, alkoxy, alkyl, alkenyl, alkynyl, heteroalkyl, heteroalkenyl, and heteroalkynyl;

Y is selected from a group consisting of null, a bond, $—CR^5R^6—$, $—O(CH_2)_n—$, $—N(R^a)—$, —S—, —S(═O)—, $—S(═O)_2—$, —C(O)—, and $—C(O)N(R^b)—$;

W is selected from a group consisting of null, saturated or partially unsaturated cycloalkyl, saturated or partially unsaturated heterocyclyl, aryl, and heteroaryl, wherein said saturated or partially unsaturated cycloalkyl, saturated or partially unsaturated heterocyclyl, aryl, and heteroaryl are optionally substituted by one or more $R^7$;

$R^1$ is selected from the group consisting of alkyl, alkenyl, alkynyl, heteroalkyl, heteroalkenyl, and heteroalkynyl, wherein said alkyl, alkenyl, alkynyl, heteroalkyl, heteroalkenyl, and heteroalkynyl are optionally substituted by one or more groups independently selected from the group consisting of halogen, hydroxyl, cyano, nitro, and alkoxy;

$R^2$ is selected from the group consisting of halogen, hydroxyl, cyano, and nitro;

$R^3$ is selected from the group consisting of hydrogen, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein said alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl are optionally substituted with one or more groups independently selected from the group consisting of halogen, hydroxyl, cyano, nitro, carboxy, carbamoyl, alkyl, alkenyl, alkynyl, and alkoxyl;

$R^4$ is selected from the group consisting of hydrogen, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein said alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl are optionally substituted with one or more groups independently selected from the group consisting of halogen, hydroxyl, cyano, nitro, carboxy, carbamoyl, alkyl, alkenyl, alkynyl, and alkoxyl;

$R^5$ and $R^6$ are each independently selected from the group consisting of hydrogen, halogen, hydroxyl, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein said alkyl, alkenyl, alkynyl, heteroalkyl, heteroalkenyl, heteroalkynyl, alkoxy, saturated and partially unsaturated cycloalkyl, saturated and partially unsaturated heterocyclyl, aryl, and heteroaryl are optionally substituted with one or more groups independently selected from the group consisting of halogen, cyano, alkyl, alkenyl, alkynyl, heteroalkyl, heteroalkenyl, heteroalkynyl, saturated and partially unsaturated cycloalkyl, saturated and partially unsaturated heterocyclyl, aryl, and heteroaryl;

$R^7$ is independently selected from the group consisting of halogen, hydroxyl, cyano, nitro, alkoxyl, alkyl, alkenyl, alkynyl, heteroalkyl, heteroalkenyl, heteroalkynyl, haloalkyl, saturated or partially unsaturated cycloalkyl, saturated or partially unsaturated heterocyclyl, aryl, heteroaryl, $—NR^cR^d$, and $—C(O)R^e$, wherein said alkoxyl, alkyl, alkenyl, alkynyl, heteroalkyl, heteroalkenyl, heteroalkynyl, haloalkyl, saturated or partially unsaturated cycloalkyl, saturated or partially unsaturated heterocyclyl, aryl, heteroaryl are optionally substituted with one or more groups independently selected from the group consisting of halogen, hydroxyl, cyano, alkyl, haloalkyl, alkoxyl, saturated or partially unsaturated cycloalkyl, $—C(O)N(R^c)(R^d)$;

$R^a$, $R^b$, $R^c$, and $R^d$ are each independently selected from the group consisting of hydrogen, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein said alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl are optionally substituted with one or more groups independently selected from the group consisting of halogen, hydroxyl, cyano, nitro, carboxy, carbamoyl, alkyl, alkenyl, alkynyl, and alkoxyl;

$R^e$ is selected from the group consisting of alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein said alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl are optionally substituted with one or more groups independently selected from the group consisting of halogen, hydroxyl, cyano, nitro, carboxy, carbamoyl, alkyl, alkenyl, alkynyl, and alkoxyl;

m is 0, 1 or 2; and n is 0, 1 or 2.

In another aspect, the present disclosure provides a compound of Formula (Ia):

Formula (Ia)

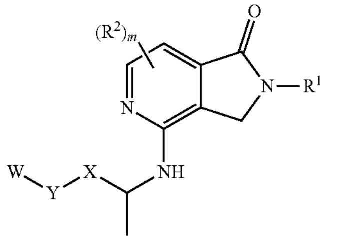

or a pharmaceutically acceptable salt thereof, wherein $R^1$ is alkyl optionally substituted by one or more groups independently selected from the group consisting of halogen, hydroxyl, cyano, nitro, and alkoxy, $R^2$, X, Y, W and m are defined as supra.

In a further aspect, the present disclosure provides a compound of Formula (Ib):

Formula (Ib)

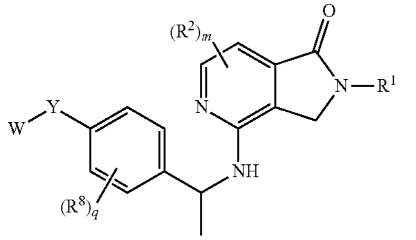

or a pharmaceutically acceptable salt thereof, wherein $R^1$ is alkyl optionally substituted by one or more groups independently selected from the group consisting of halogen, hydroxyl, cyano, nitro, and alkoxy, $R^1$ is halogen, q is 1 or 2, $R^2$, X, Y, W and m are defined as supra.

In another aspect, the present disclosure provides a compound of Formula (Ic):

Formula (Ic)

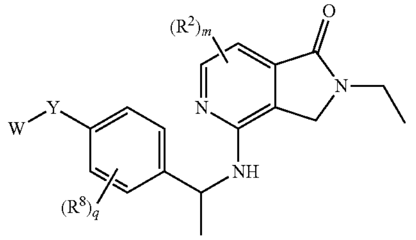

or a pharmaceutically acceptable salt thereof, wherein $R^2$, $R^8$, Y, W, m and q are defined as supra.

In a further aspect, the present disclosure provides a compound of Formula (Id):

Formula (Id)

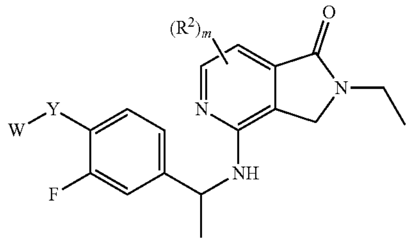

or a pharmaceutically acceptable salt thereof, wherein $R^2$, Y, W, and m are defined as supra.

In still a further aspect, the present disclosure provides a compound of Formula (Ie):

Formula (Ie)

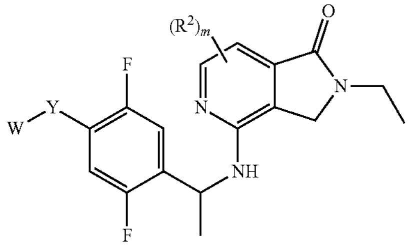

or a pharmaceutically acceptable salt thereof, wherein $R^2$, Y, W, and m are defined as supra.

In another aspect, the present disclosure provides a pharmaceutical composition comprising a compound of Formula (I), (Ia), (Ib), (Ic), (Id) or (Ie) or a pharmaceutically acceptable salt thereof, and at least one pharmaceutically acceptable excipient.

In a further aspect, the present disclosure provides a method of treating a disease associated with conversion of α-KG to D-2-HG, comprising administering to a subject a therapeutically effective amount of a compound of Formula (I), (Ia), (Ib), (Ic), (Id) or (Ie) or a pharmaceutically acceptable salt thereof, or a pharmaceutical composition of the present disclosure.

In another aspect, the present disclosure provides a method of inhibiting conversion of α-KG to D-2-HG by using a compound of Formula (I), (Ia), (Ib), (Ic), (Id) or (Ie) or a pharmaceutically acceptable salt thereof, or a pharmaceutical composition of the present disclosure.

In a further aspect, the present disclosure provides a method of inhibiting mutant IDH, wild-type IDH or both by using a compound of Formula (I), (Ia), (Ib), (Ic), (Id) or (Ie) or a pharmaceutically acceptable salt thereof, or a pharmaceutical composition of the present disclosure.

DESCRIPTION OF THE DRAWINGS

FIG. 1 shows representative reactions catalyzed by wild-type and mutant IDH1/2.

DETAILED DESCRIPTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, tern usage, described techniques, or the like, this application controls.

It is appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable sub-combination.

Definitions

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, $5^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, $3^{rd}$ Edition, Cambridge University Press, Cambridge, 1987; the entire contents of each of which are incorporated herein by reference.

At various places in the present disclosure, linking substituents are described. Where the structure clearly requires a linking group, the Markush variables listed for that group are understood to be linking groups. For example, if the structure requires a linking group and the Markush group definition for that variable lists "alkyl", then it is understood that the "alkyl" represents a linking alkylene group.

As used herein, the term "substituted", whether preceded by the term "optionally" or not, means that one or more hydrogens of the designated moiety are replaced with a suitable substituent. It will be understood that "substitution" or "substituted with" includes the implicit proviso that such substitution is in accordance with permitted valence of the substituted atom and that the substitution results in a stable or chemically feasible compound, e.g., which does not spontaneously undergo transformation such as by rearrangement, cyclization, elimination, etc. Unless otherwise indicated, an "optionally substituted" group may have a suitable substituent at each substitutable position of the group, and when more than one position in any given structure may be substituted with more than one substituent selected from a specified group, the substituent may be either the same or different at every position. It will be understood by those skilled in the art that substituents can themselves be substituted, if appropriate. Unless specifically stated as "unsubstituted", references to chemical moieties herein are understood to include substituted variants. For example, reference to an "aryl" group or moiety implicitly includes both substituted and unsubstituted variants.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R^i$) occurs more than one time in any constituent or formula for a compound, its definition at each occurrence is independent of its definition at every other occurrence. Thus, for example, if a group is shown to be substituted with 0-2 $R^i$ moieties, then the group may optionally be substituted with up to two $R^i$ moieties and $R^i$ at each occurrence is selected independently from the definition of $R^i$. Also, combinations of substituents and/or variables are permissible, but only if such combinations result in stable compounds.

As used herein, the term "$C_{i-j}$" indicates a range of the carbon atoms numbers, wherein i and j are integers and the range of the carbon atoms numbers includes the endpoints (i.e. i and j) and each integer point in between, and wherein j is greater than i. For examples, $C_{1-6}$ indicates a range of one to six carbon atoms, including one carbon atom, two carbon atoms, three carbon atoms, four carbon atoms, five carbon atoms and six carbon atoms. In some embodiments, the term "$C_{1-12}$" indicates 1 to 12, particularly 1 to 10, particularly 1 to 8, particularly 1 to 6, particularly 1 to 5, particularly 1 to 4, particularly 1 to 3 or particularly 1 to 2 carbon atoms.

As used herein, the term "alkyl", whether as part of another term or used independently, refers to a saturated linear or branched-chain hydrocarbon radical. The term "$C_{i-j}$ alkyl" refers to an alkyl having i to j carbon atoms. In some embodiments, alkyl groups contain 1 to 12 carbon atoms. In some embodiments, alkyl groups contain 1 to 11 carbon atoms. In some embodiments, alkyl groups contain 1 to 11 carbon atoms, 1 to 10 carbon atoms, 1 to 9 carbon atoms, 1 to 8 carbon atoms, 1 to 7 carbon atoms, 1 to 6 carbon atoms, 1 to 5 carbon atoms, 1 to 4 carbon atoms, 1 to 3 carbon atoms, or 1 to 2 carbon atoms. Examples of alkyl group include, but are not limited to, methyl, ethyl, 1-propyl (n-propyl), 2-propyl (isopropyl), 1-butyl (n-butyl), 2-methyl-1-propyl (i-butyl), 2-butyl (s-butyl), 2-methyl-2-propyl (t-butyl), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Examples of "$C_{1-2}$ alkyl" include, but are not limited to, methyl, ethyl, propyl, butyl, pentyl, hexyl, heptyl, octyl, nonyl, decyl, undecyl, dodecyl. Examples of "$C_{1-6}$ alkyl" are methyl, ethyl, propyl, isopropyl, n-butyl, i-butyl, s-butyl, t-butyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, and the like.

The alkyl groups can be optionally substituted by substituents which independently replace one or more hydrogen atoms on one or more carbons of the alkyl groups. Examples of such substituents can include, but are not limited to, halogen, hydroxyl, cyano, nitro, azido, acyl, alkyl, alkenyl, alkynyl, heteroalkyl, heteroalkenyl, heteroalkynyl, alkoxyl, haloalkyl, haloalkoxyl, alkylcarbonyloxy, arylcarbonyloxy, alkoxycarbonyloxy, aryloxycarbonyloxy, carboxylate, alkylaryl, alkylcarbonyl, arylcarbonyl, alkoxycarbonyl, aminocarbonyl, alkylaminocarbonyl, dialkylaminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfmyl, sulfonate, sulfamoyl, sulfonamido, aryl, heteroaryl, saturated or partially unsaturated cycloalkyl, or saturated or partially unsaturated heterocyclyl. Alkenyl, alkynyl, aryl, heteroaryl, saturated or partially unsaturated cycloalkyl, and saturated or partially unsaturated heterocyclyl groups as described below may also be similarly substituted.

As used herein, the term "alkenyl", whether as part of another term or used independently, refers to linear or branched-chain hydrocarbon radical having at least one carbon-carbon double bond, which may be optionally substituted independently with one or more substituents described herein, and includes radicals having "cis" and "trans" orientations, or alternatively, "E" and "Z" orientations. In some embodiments, alkenyl groups contain 2 to 12 carbon atoms.

In some embodiments, alkenyl groups contain 2 to 11 carbon atoms. In some embodiments, alkenyl groups contain 2 to 11 carbon atoms, 2 to 10 carbon atoms, 2 to 9 carbon atoms, 2 to 8 carbon atoms, 2 to 7 carbon atoms, 2 to 6 carbon atoms, 2 to 5 carbon atoms, 2 to 4 carbon atoms, 2 to 3 carbon atoms, and in some embodiments, alkenyl groups contain 2 carbon atoms.

Examples of alkenyl group include, but are not limited to, ethylenyl (or vinyl), propenyl, butenyl, pentenyl, 1-methyl-2 buten-1-yl, 5-hexenyl, and the like.

As used herein, the term "alkynyl", whether as part of another term or used independently, refers to a linear or branched hydrocarbon radical having at least one carbon-carbon triple bond, which may be optionally substituted independently with one or more substituents described herein. In some embodiments, alkenyl groups contain 2 to 12 carbon atoms. In some embodiments, alkynyl groups contain 2 to 11 carbon atoms. In some embodiments, alkynyl groups contain 2 to 11 carbon atoms, 2 to 10 carbon atoms, 2 to 9 carbon atoms, 2 to 8 carbon atoms, 2 to 7 carbon atoms, 2 to 6 carbon atoms, 2 to 5 carbon atoms, 2 to 4 carbon atoms, 2 to 3 carbon atoms, and in some embodiments, alkynyl groups contain 2 carbon atoms.

Examples of alkynyl group include, but are not limited to, ethynyl, 1-propynyl, 2-propynyl, and the like.

As used herein, the term "alkoxy" or "alkoxyl", whether as part of another term or used independently, refers to an alkyl group, as previously defined, attached to the parent molecule through an oxygen atom. The term "$C_{i-j}$ alkoxy" means that the alkyl moiety of the alkoxy group has i to j carbon atoms. In some embodiments, alkoxy groups contain 1 to 12 carbon atoms. In some embodiments, alkoxy groups contain 1 to 11 carbon atoms. In some embodiments, alkoxy groups contain 1 to 11 carbon atoms, 1 to 10 carbon atoms, 1 to 9 carbon atoms, 1 to 8 carbon atoms, 1 to 7 carbon atoms, 1 to 6 carbon atoms, 1 to 5 carbon atoms, 1 to 4 carbon atoms, 1 to 3 carbon atoms, or 1 to 2 carbon atoms. Examples of "$C_{1-12}$ alkoxyl" include, but are not limited to, methoxy, ethoxy, propoxy (e.g. n-propoxy and isopropoxy), t-butoxy, neopentoxy, n-hexoxy, and the like.

As used herein, the term "aryl" or "aromatic", whether as part of another term or used independently, refers to monocyclic and polycyclic ring systems having a total of 5 to 20 ring members, which may be optionally substituted independently with one or more substituents described herein, wherein at least one ring in the system is aromatic and wherein each ring in the system contains 3 to 12 ring members. Examples of "aryl" include, but are not limited to, phenyl, biphenyl, naphthyl, anthracyl and the like, which may bear one or more substituents. Also included within the scope of the term "aryl", as it is used herein, is a group in which an aromatic ring is fused to one or more additional rings. In the case of polycyclic ring system, only one of the rings needs to be aromatic (e.g., 2,3-dihydroindole), although all of the rings may be aromatic (e.g., quinoline). The second ring can also be fused or bridged. Examples of polycyclic aryl include, but are not limited to, benzofuranyl, indanyl, phthalimidyl, naphthimidyl, phenanthridinyl, or tetrahydronaphthyl, and the like. Aryl groups may be optionally substituted at one or more ring positions with one or more substituents as described herein.

As used herein, the terms "cycloalkyl", "carbocyclyl" and "carbocycle" are interchangeable and whether as part of another term or used independently, refer to a monovalent, saturated or partially unsaturated or fully unsaturated monocyclic and polycyclic ring system which may be optionally substituted independently with one or more substituents described herein, in which all the ring atoms are carbon and which contains at least three ring forming carbon atoms. In some embodiments, the cycloalkyl may contain 3 to 12 ring forming carbon atoms, 3 to 10 ring forming carbon atoms, 3 to 9 ring forming carbon atoms, 3 to 8 ring forming carbon atoms, 3 to 7 ring forming carbon atoms, 3 to 6 ring forming carbon atoms, 3 to 5 ring forming carbon atoms, 4 to 12 ring forming carbon atoms, 4 to 10 ring forming carbon atoms, 4 to 9 ring forming carbon atoms, 4 to 8 ring forming carbon atoms, 4 to 7 ring forming carbon atoms, 4 to 6 ring forming carbon atoms, 4 to 5 ring forming carbon atoms. Cycloalkyl groups may be saturated or partially unsaturated. Cycloalkyl groups may be optionally substituted independently with one or more substituents described herein.

In some embodiments, the cycloalkyl group may be a saturated cyclic alkyl group. In some embodiments, the cycloalkyl group may be an unsaturated cyclic alkyl group that contains at least one double bond or triple bond in its ring system.

In some embodiments, the cycloalkyl group may be saturated or unsaturated monocyclic carbocyclic ring system, examples of which include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl.

In some embodiments, the cycloalkyl group may be saturated or unsaturated polycyclic (e.g., bicyclic and tricyclic) carbocyclic ring system, which can be arranged as a fused, spiro or bridged ring system. As used herein, the term "fused ring" refers to a ring system having two rings sharing two adjacent atoms, the term "spiro ring" refers to a ring systems having two rings connected through one single common atom, and the term "bridged ring" refers to a ring system with two rings sharing three or more atoms. Examples of fused carbocyclyl include, but are not limited to, naphthyl, benzopyrenyl, anthracenyl, acenaphthenyl, fluorenyl and the like. Examples of spiro carbocyclyl include, but are not limited to, spiro[5.5]undecanyl, spiro-pentadienyl, spiro[3.6]-decanyl, and the like. Examples of bridged carbocyclyl include, but are not limited to bicyclo [1,1,1]pentenyl, bicyclo[2,2,1]heptenyl, bicyclo[2.2.1]heptanyl, bicyclo[2.2.2]octanyl, bicyclo[3.3.1]nonanyl, bicyclo [3.3.3]undecanyl, and the like.

As used herein, the term "cyano" refers to —CN.

As used herein, the term "halo" or "halogen" refers to an atom selected from fluorine (or fluoro), chlorine (or chloro), bromine (or bromo) and iodine (or iodo).

As used herein, the term "haloalkyl" refers to alkyl groups substituted by one or more halogen atoms which independently replace one or more hydrogen atoms on one or more carbons of the alkyl groups.

As used herein, the term "heteroalkyl" refers to an alkyl, at least one of the carbon atoms of which is replaced with a heteroatom selected from N, O, S or P. The heteroalkyl may be a carbon radical or heteroatom radical (i.e., the heteroatom may appear in the middle or at the end of the radical), and may be optionally substituted independently with one or more substituents described herein. The term "heteroalkyl" encompasses alkoxy and heteroalkoxy radicals.

As used herein, the term "heteroalkenyl" refers to an alkenyl, at least one of the carbon atoms of which is replaced with a heteroatom selected from N, O, S or P. The heteroalkenyl may be a carbon radical or heteroatom radical (i.e., the heteroatom may appear in the middle or at the end of the radical), and may be optionally substituted independently with one or more substituents described herein.

As used herein, the term "heteroalkynyl" refers to an alkynyl, at least one of the carbon atoms of which is replaced with a heteroatom selected from N, O, S or P. The heteroalkynyl may be a carbon radical or heteroatom radical (i.e., the heteroatom may appear in the middle or at the end of the radical), and may be optionally substituted independently with one or more substituents described herein.

As used herein, the term "heteroatom" refers to nitrogen, oxygen, sulfur or phosphor, and includes any oxidized form of nitrogen or sulfur, and any quaternized form of a basic nitrogen.

As used herein, the term "heteroaryl", whether as part of another term or used independently, refers to an aryl group having, in addition to carbon atoms, one or more heteroatoms, and may be optionally substituted independently with one or more substituents described herein. Examples of heteroaryl include, but are not limited to, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The heteroaryl also includes groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. In some embodiments, the term "5- to 10-membered heteroaryl" refers to a 5- to 6-membered heteroaryl ring having 1 to 3 heteroatoms independently selected from nitrogen, oxygen, sulfur or phosphor, or an 8- to 10-membered bicyclic heteroaryl ring having 1 to 4 heteroatoms independently selected from nitrogen, oxygen, sulfur or phosphor. In certain embodiments, the term "5- to 12-membered heteroaryl" refers to a 5- to 6-membered heteroaryl ring having 1 to 3 heteroatoms independently selected from nitrogen, oxygen, sulfur or phosphor, or an 8- to 12-membered bicyclic heteroaryl ring having 1 to 4 heteroatoms independently selected from nitrogen, oxygen, sulfur or phosphor.

As used herein, the term "heterocycle" or "heterocyclyl" refers to a saturated, partially unsaturated or fully unsaturated carbocyclyl group in which one or more ring atoms are heteroatoms independently selected from oxygen, sulfur, nitrogen, phosphorus, and the like, the remaining ring atoms being carbon, wherein one or more ring atoms may be optionally substituted independently with one or more substitutents. In some embodiments, the heterocyclyl is a saturated heterocyclyl. In some embodiments, the heterocyclyl is an unsaturated heterocyclyl having one or more double bonds in its ring system. In some embodiments, the heterocyclyl may contains any oxidized form of carbon, nitrogen, sulfur or phosphor, and any quaternized form of a basic nitrogen. "Heterocyclyl" also includes radicals wherein the heterocyclyl radicals are fused with a saturated, partially unsaturated, or fully unsaturated (i.e., aromatic) carbocyclic or heterocyclic ring. The heterocyclyl radical may be carbon linked or nitrogen linked where such is possible. In some embodiments, the heterocycle is carbon linked. In some embodiments, the heterocycle is nitrogen linked. For example, a group derived from pyrrole may be pyrrol-1-yl (nitrogen linked) or pyrrol-3-yl (carbon linked). Further, a group derived from imidazole may be imidazol-1-yl (nitrogen linked) or imidazol-3-yl (carbon linked).

In some embodiments, the term "3- to 12-membered heterocyclyl" refers to a 3- to 12-membered saturated or partially unsaturated monocyclic or polycyclic heterocyclic ring system having 1 to 3 heteroatoms independently selected from nitrogen, oxygen, or sulfur. The fused, spiro and bridged ring systems are also included within the scope of this definition. Examples of monocyclic heterocyclyl include, but are not limited to oxetanyl, 1,1-dioxothietanylpyrrolidyl, tetrahydrofuryl, tetrahydrothienyl, pyrrolyl, furanyl, thienyl, pyrazolyl, imidazolyl, triazolyl, oxazolyl, thiazolyl, piperidyl, piperazinyl, morpholinyl, pyridinyl, pyrazinyl, pyrimidinyl, pyridazinyl, triazinyl, pyridonyl, pyrimidonyl, pyrazinonyl, pyrimidonyl, pyridazonyl, pyrrolidinyl, triazinonyl, and the like. Examples of fused heterocyclyl include, but are not limited to, phenyl fused ring or pyridinyl fused ring, such as quinolinyl, isoquinolinyl, quinoxalinyl, quinolizinyl, quinazolinyl, azaindolizinyl, pteridinyl, chromenyl, isochromenyl, indolyl, isoindolyl, indolizinyl, indazolyl, purinyl, benzofuranyl, isobenzofuranyl, benzimidazolyl, benzothienyl, benzothiazolyl, carbazolyl, phenazinyl, phenothiazinyl, phenanthridinyl, imidazo[1,2-a]pyridinyl, [1,2,4]triazolo[4,3-a]pyridinyl, [1,2,3]triazolo[4,3-a]pyridinyl groups, and the like. Examples of spiro heterocyclyl include, but are not limited to, spiropyranyl, spirooxazinyl, and the like. Examples of bridged heterocyclyl include, but are not limited to, morphanyl, hexamethylenetetraminyl, 3-aza-bicyclo[3.1.0]hexane, 8-aza-bicyclo[3.2.1]octane, 1-aza-bicyclo[2.2.2]octane, 1,4-diazabicyclo[2.2.2]octane (DABCO), and the like.

As used herein, the term "hydroxyl" or "hydroxy" refers to —OH group.

As used herein, the term "nitro" refers to —$NO_2$ group.

As used herein, the term "partially unsaturated" refers to a radical that includes at least one double or triple bond. The term "partially unsaturated" is intended to encompass rings having multiple sites of unsaturation, but is not intended to include aromatic (i.e., fully unsaturated) moieties.

Unless otherwise specified, "IDH" or "wild-type IDH" refers to normal IDH enzymes which catalyze the conversion of isocitrate to α-KG. Exemplary normal IDH enzymes include:

Human IDH1 protein (NCBI accession number: 075874.2, SEQ ID NO: 1)

1 mskkisggsv vemqgdemtr iiwelikekl ifpyveldlh sydlgienrd atndqvtkda
61 aeaikkhnvg vkcatitpde krveefklkq mwkspngtir nilggtvfre aiicknipri
121 vsgwvkpiii grhaygdqyr atdfvvpgpg kveitytpsd gtqkvtylvh nfeegggvam
181 gmyngdksie dfahssfqma lskgwplyls tkntilkkyd grfkdifqei ydkqyksqfe
241 aqkiwyehrl iddmvaqamk seggfiwack nydgdvqsds vaqgygslgm mtsvlvcpdg
301 ktveaeaahg tvtrhyrmyq kgqetstnpi asifawtrgl ahrakldnnk elaffanale
361 evsietieag fmtkdlaaci kglpnvqrsd ylntfefmdk lgenlkikla qakl Human IDH2 protein (NCBI accession number: P48735.2, SEQ ID NO: 2)

1 magylrvvrs lcrasgsrpa wapaaltapt sqeqprrhya dkrikvakpv vemdgdemtr 61 iiwqfikekl ilphvdiqlk yfdlglpnrd qtddqvtids alatqkysva vkcatitpde 121 arveefklkk mwkspngtir nilggtvfre piicknipri vpgwtkpiti grhahgdqyk 181 atdfvadrag tfkmvftpkd gsgvkewevy nfpaggvgmg myntdesisg fahscfqyai 241 qkkwplymst kntilkaydg rfkdifqeif dkhyktdfdk nkiwyehrli ddmvaqvlks 301 sggfvwackn ydgdvqsdil aggfgslglm tsvlvcpdgk tieaeaahgt vtrhyrehqk 361 grptstnpia sifawtrgle hrgkldgnqd lirfaqmlek vcvetvesga mtkdlagcih 421 glsnvklneh flnttdfldt iksnldralg rq As used herein, the term "IDH mutations" refers to the any mutations to the IDH enzymes which enable the "IDH mutants", "mutant IDH" or "mutated IDH" to catalyze the conversion of α-KG to D-2-HG. In some embodiments, "mutant IDH" catalyses both the conversion of α-KG to D-2-HG and the conversion of isocitrate to α-KG. Such mutations include but are not limited to, R132H, R132C, R132G, R132L, R132S in IDH1; or R172K, R172M, R172W in IDH2.

Compound

In one aspect, the present disclosure provides a compound of Formula (I):

Formula (I)

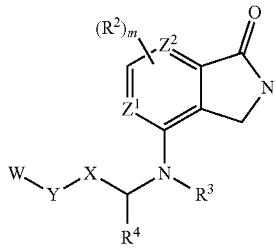

or a pharmaceutically acceptable salt thereof, wherein, $Z^1$ and $Z^2$ are independently selected from C and N;

X is selected from the group consisting of aryl, heteroaryl, or saturated or partially unsaturated heterocyclyl, said aryl, heteroaryl, or saturated or partially unsaturated heterocyclyl are optionally substituted by one or more groups independently selected from the group consisting of halogen, hydroxyl, cyano, nitro, alkoxy, alkyl, alkenyl, alkynyl, heteroalkyl, heteroalkenyl, and heteroalkynyl;

Y is selected from a group consisting of null, a bond, $—CR^5R^6—$, $—O(CH_2)_n—$, $—N(R^a)—$, —S—, —S(═O)—, $—S(═O)_2—$, —C(O)—, and $—C(O)N(R^b)—$;

W is selected from a group consisting of null, saturated or partially unsaturated cycloalkyl, saturated or partially unsaturated heterocyclyl, aryl, and heteroaryl, wherein said saturated or partially unsaturated cycloalkyl, saturated or partially unsaturated heterocyclyl, aryl, and heteroaryl are optionally substituted by one or more $R^7$;

$R^1$ is selected from the group consisting of alkyl, alkenyl, alkynyl, heteroalkyl, heteroalkenyl, and heteroalkynyl, wherein said alkyl, alkenyl, alkynyl, heteroalkyl, heteroalkenyl, and heteroalkynyl are optionally substituted by one or more groups independently selected from the group consisting of halogen, hydroxyl, cyano, nitro, and alkoxy;

$R^2$ is selected from the group consisting of halogen, hydroxyl, cyano, and nitro;

$R^3$ is selected from the group consisting of hydrogen, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein said alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl are optionally substituted with one or more groups independently selected from the group consisting of halogen, hydroxyl, cyano, nitro, carboxy, carbamoyl, alkyl, alkenyl, alkynyl, and alkoxyl;

$R^4$ is selected from the group consisting of hydrogen, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein said alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl are optionally substituted with one or more groups independently selected from the group consisting of halogen, hydroxyl, cyano, nitro, carboxy, carbamoyl, alkyl, alkenyl, alkynyl, and alkoxyl;

$R^5$ and $R^6$ are each independently selected from the group consisting of hydrogen, halogen, hydroxyl, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein said alkyl, alkenyl, alkynyl, heteroalkyl, heteroalkenyl, heteroalkynyl, alkoxy, saturated and partially unsaturated cycloalkyl, saturated and partially unsaturated heterocyclyl, aryl, and heteroaryl are optionally substituted with one or more groups independently selected from the group consisting of halogen, cyano, alkyl, alkenyl, alkynyl, heteroalkyl, heteroalkenyl, heteroalkynyl, saturated and partially unsaturated cycloalkyl, saturated and partially unsaturated heterocyclyl, aryl, and heteroaryl;

$R^7$ is independently selected from the group consisting of halogen, hydroxyl, cyano, nitro, alkoxyl, alkyl, alkenyl, alkynyl, heteroalkyl, heteroalkenyl, heteroalkynyl, haloalkyl, saturated or partially unsaturated cycloalkyl, saturated or partially unsaturated heterocyclyl, aryl, heteroaryl, $—NR^cR^d$, and $—C(O)R^e$, wherein said alkoxyl, alkyl, alkenyl, alkynyl, heteroalkyl, heteroalkenyl, heteroalkynyl, haloalkyl, saturated or partially unsaturated cycloalkyl, saturated or partially unsaturated heterocyclyl, aryl, heteroaryl are optionally substituted with one or more groups independently selected from the group consisting of halogen, hydroxyl, cyano, alkyl, haloalkyl, alkoxyl, saturated or partially unsaturated cycloalkyl, $—C(O)N(R^c)(R^d)$;

$R^a$, $R^b$, $R^c$, and $R^d$ are each independently selected from the group consisting of hydrogen, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein said alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl are optionally substituted with one or more groups independently selected from the group consisting of halogen, hydroxyl, cyano, nitro, carboxy, carbamoyl, alkyl, alkenyl, alkynyl, and alkoxyl;

$R^e$ is selected from the group consisting of alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein said alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl are optionally substituted with one or more groups independently selected from the group consisting of halogen, hydroxyl, cyano, nitro, carboxy, carbamoyl, alkyl, alkenyl, alkynyl, and alkoxyl;

m is 0, 1 or 2; and n is 0, 1 or 2.

In some embodiments, $Z^1$ is N.

In some embodiments, $Z^1$ is C.

In some embodiments, $Z^2$ is N.

In some embodiments, $Z^2$ is C.

In some embodiments, $Z^1$ is N and $Z^2$ is N.

In some embodiments, $Z^1$ is N and $Z^2$ is C.

In some embodiments, X is aryl, heteroaryl, or saturated or partially unsaturated heterocyclyl, each of which is optionally by one or more groups independently selected from the group consisting of halogen, hydroxyl, cyano, nitro, and alkyl.

In some embodiments, X is selected from the group consisting of halogen substituted aryl, unsubstituted heteroaryl, halogen substituted heteroaryl, alkyl substituted heteroaryl, or halogen substituted saturated or partially unsaturated heterocyclyl.

In some embodiments, Y is selected from the group consisting of a bond, $—CR^5R_6—$, $—O(CH_2)_n—$, $—N(R^a)—$, $—C(O)—$, and $—C(O)N(R^b)—$.

In some embodiments, n is 0 or 1. In some embodiments, n is 0. In some embodiments, n is 1.

In some embodiments, W is null, 3 to 10 membered saturated or partially unsaturated cycloalkyl, 3 to 10 membered saturated or partially unsaturated heterocyclyl, 3 to 10 membered aryl, and 3 to 10 membered heteroaryl, wherein said saturated or partially unsaturated cycloalkyl, saturated or partially unsaturated heterocyclyl, aryl, and heteroaryl are optionally substituted by one or more $R^7$.

In some embodiments, W is null.

In some embodiments, W is selected from the group consisting of:

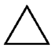, 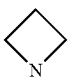, 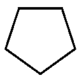, 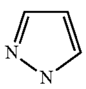, 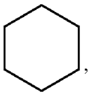,

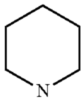, 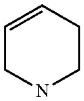, 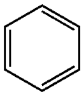, 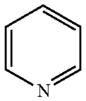,

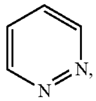, 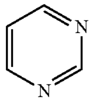, 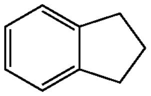,

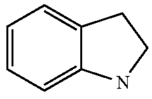, 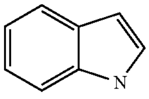, 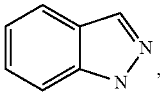,

-continued

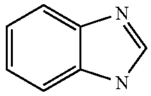, 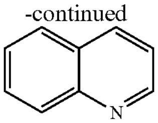, 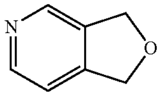, each of which is optionally substituted by one or more $R^7$.

In some embodiments, $R^1$ is selected from the group consisting of alkyl, alkenyl, and alkynyl, wherein said alkyl, alkenyl, and alkynyl are optionally substituted by one or more groups independently selected from the group consisting of halogen, hydroxyl, and alkoxy.

In some embodiments, $R^1$ is alkyl optionally substituted by one or more groups independently selected from the group consisting of halogen, hydroxyl, cyano, nitro, and alkoxy.

In some embodiments, $R^1$ is alkyl optionally substituted by one or more groups independently selected from the group consisting of halogen, hydroxyl, and alkoxy.

In some embodiments, $R^1$ is ethyl optionally substituted by one or more groups independently selected from the group consisting of fluoro, hydroxyl, and methoxyl.

In some embodiments, $R^2$ is halogen. In some embodiments, $R^2$ is fluoro, chloro or bromo. In some embodiments, $R^2$ is fluoro or chloro. In some embodiments, $R^2$ is fluoro.

In some embodiments, m is 0, 1 or 2. In some embodiments, m is 0 or 1. In some embodiments, m is 0. In some embodiments, m is 1.

In some embodiments, $R^2$ is halogen and m is 0, 1 or 2. In some embodiments, $R^2$ is fluoro or chloro and m is 0, 1 or 2. In some embodiments, $R^2$ is fluoro or chloro and m is 0 or 1. In some embodiments, $R^2$ is fluoro and m is 0 or 1.

In some embodiments, $R^3$ is selected from the group consisting of hydrogen, alkyl, alkenyl, alkynyl, heteroalkyl, heteroalkenyl, and heteroalkynyl, wherein said alkyl, alkenyl, alkynyl, heteroalkyl, heteroalkenyl, and heteroalkynyl are optionally substituted with one or more groups independently selected from the group consisting of halogen, hydroxyl, cyano, nitro, carboxy, carbamoyl, alkyl, alkenyl, alkynyl, and alkoxyl.

In some embodiments, $R^3$ is hydrogen or alkyl. In some embodiments, $R^3$ is hydrogen.

In some embodiments, $R^4$ is selected from the group consisting of hydrogen, alkyl, alkenyl, alkynyl, heteroalkyl, heteroalkenyl, and heteroalkynyl, wherein said alkyl, alkenyl, alkynyl, heteroalkyl, heteroalkenyl, and heteroalkynyl are optionally substituted with one or more groups independently selected from the group consisting of halogen, hydroxyl, cyano, nitro, carboxy, carbamoyl, alkyl, alkenyl, alkynyl, and alkoxyl.

In some embodiments, $R^4$ is alkyl. In some embodiments, $R^4$ is methyl, ethyl, propyl or butyl.

In some embodiments, $R^5$ and $R^6$ are each independently selected from the group consisting of hydrogen, halogen, hydroxyl, alkyl, alkenyl, alkynyl, heteroalkyl, heteroalkenyl, and heteroalkynyl, wherein said alkyl, alkenyl, alkynyl, heteroalkyl, heteroalkenyl, and heteroalkynyl are optionally substituted with one or more groups independently selected from the group consisting of halogen, cyano, alkyl, alkenyl, alkynyl, heteroalkyl, heteroalkenyl, heteroalkynyl, saturated and partially unsaturated cycloalkyl, saturated and partially unsaturated heterocyclyl, aryl, and heteroaryl.

In some embodiments, $R^5$ and $R^6$ are each independently selected from hydrogen, halogen, hydroxyl and alkyl. In some embodiments, $R^5$ and $R^6$ are hydrogen.

In some embodiments, $R^7$ is selected from the group consisting of halogen, hydroxyl, cyano, alkoxyl, alkyl, alkenyl, haloalkyl, saturated or partially unsaturated cycloalkyl, saturated or partially unsaturated heterocyclyl, aryl, heteroaryl, —$NR^cR^d$, and —$C(O)R^e$, wherein said alkoxyl, alkyl, alkenyl, haloalkyl, saturated or partially unsaturated cycloalkyl, saturated or partially unsaturated heterocyclyl, aryl, heteroaryl are optionally substituted with one or more groups independently selected from the group consisting of halogen, hydroxyl, cyano, alkyl, haloalkyl, alkoxyl, saturated or partially unsaturated cycloalkyl, —$C(O)N(R^c)(R^d)$.

In some embodiments, $R^7$ is selected from the group consisting of halogen, hydroxyl, cyano, alkoxyl, alkyl, alkenyl, haloalkyl, and saturated or partially unsaturated cycloalkyl, wherein said alkoxyl, alkyl, alkenyl, haloalkyl, and saturated or partially unsaturated cycloalkyl are optionally substituted with one or more groups independently selected from the group consisting of halogen, haloalkyl, and alkoxyl.

In some embodiments, $R^a$, $R^b$, $R^c$, and $R^d$ are each independently selected from the group consisting of hydrogen, alkyl, alkenyl, alkynyl, heteroalkyl, heteroalkenyl, and heteroalkynyl, wherein said alkyl, alkenyl, alkynyl, heteroalkyl, heteroalkenyl, and heteroalkynyl, are optionally substituted with one or more groups independently selected from the group consisting of halogen, hydroxyl, cyano, nitro, carboxy, carbamoyl, alkyl, alkenyl, alkynyl, and alkoxyl.

In some embodiments, $R^a$, $R^b$, $R^c$, and $R^d$ are each independently selected from the group consisting of hydrogen, and alkyl.

In some embodiments, $R^e$ is selected from the group consisting of saturated or partially unsaturated cycloalkyl, saturated or partially unsaturated heterocyclyl, aryl, and heteroaryl, wherein said saturated or partially unsaturated cycloalkyl, saturated or partially unsaturated heterocyclyl, aryl, and heteroaryl are optionally substituted with one or more groups independently selected from the group consisting of halogen, hydroxyl, cyano, nitro, carboxy, carbamoyl, alkyl, alkenyl, alkynyl, and alkoxyl. In some embodiments, $R^e$ is saturated or partially unsaturated cycloalkyl.

In another aspect, the present disclosure provides a compound of Formula (Ia):

Formula (Ia)

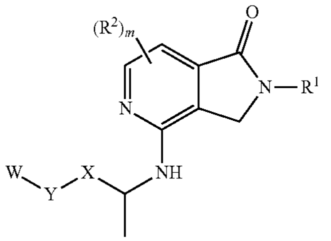

wherein $R^1$ is alkyl optionally substituted by one or more groups independently selected from the group consisting of halogen, hydroxyl, cyano, nitro, and alkoxy, $R^2$, X, Y, W and m are defined as supra.

In another aspect, the present disclosure provides a compound of Formula (Ic):

Formula (Ic)

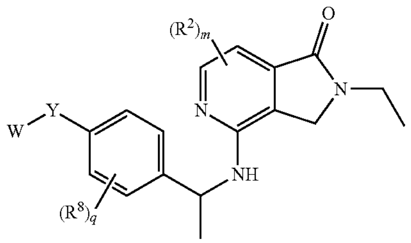

or a pharmaceutically acceptable salt thereof, wherein $R^2$, $R^8$, Y, W, m and q are defined as supra.

In a further aspect, the present disclosure provides a compound of Formula (Id):

Formula (Id)

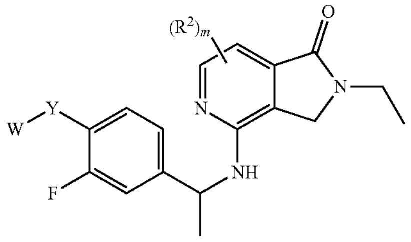

or a pharmaceutically acceptable salt thereof, wherein $R^2$, Y, W, and m are defined as supra.

In still a further aspect, the present disclosure provides a compound of Formula (Ie):

Formula (Ie)

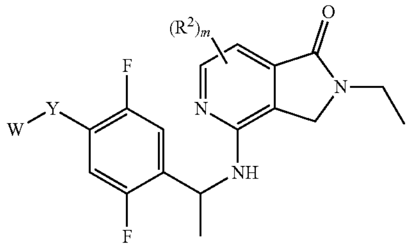

or a pharmaceutically acceptable salt thereof, wherein $R^2$, Y, W, and m are defined as supra.

In a further aspect, the present disclosure provides a compound of Formula (I) or a pharmaceutically acceptable salt thereof selected from the group consisting of:

| Compound No. | Structure and Nomenclature |
|---|---|
| 1 | 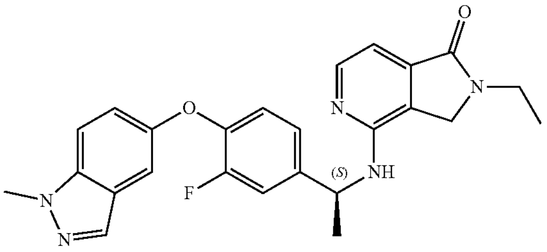 (S)-2-ethyl-4-((1-(3-fluoro-4-((1-methyl-1H-indazol-5-yl)oxy)phenyl)ethyl)amino)-2,3-dihydro-1H-pyrrolo[3,4-c]pyridin-1-one |
| 2 | 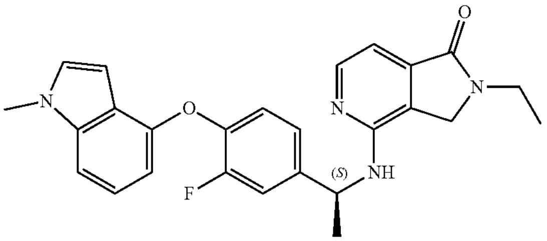 (S)-2-ethyl-4-((1-(3-fluoro-4-((1-methyl-1H-indol-4-yl)oxy)phenyl)ethyl)amino)-2,3-dihydro-1H-pyrrolo[3,4-c]pyridin-1-one |
| 3 | 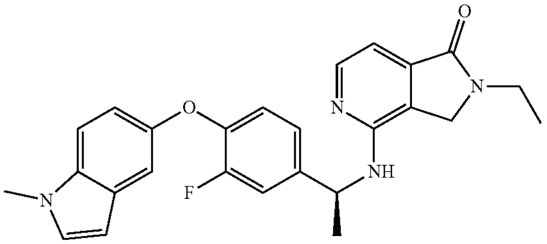 [SMILES: CCN1Cc2c(ccnc2N[C@@H](C)c2ccc(Oc3ccc4c(ccn4C)c3)c(F)c2)C1=O] (S)-2-ethyl-4-((1-(3-fluoro-4-((1-methyl-1H-indol-5-yl)oxy)phenyl)ethyl)amino)-2,3-dihydro-1H-pyrrolo[3,4-c]pyridin-1-one |
| 4 | 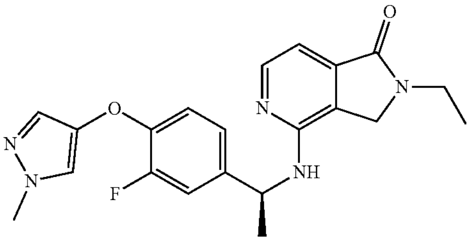 [SMILES: CCN1Cc2c(ccnc2N[C@@H](C)c2ccc(Oc3cnn(C)c3)c(F)c2)C1=O] (S)-2-ethyl-4-((1-(3-fluoro-4-((1-methyl-1H-pyrazol-4-yl)oxy)phenyl)ethyl)amino)-2,3-dihydro-1H-pyrrolo[3,4-c]pyridin-1-one |
| 5 | 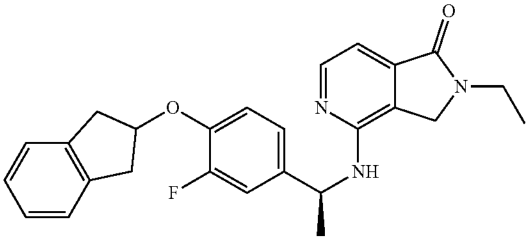 [SMILES: CCN1Cc2c(ccnc2N[C@@H](C)c2ccc(OC3Cc4ccccc4C3)c(F)c2)C1=O] (S)-4-((1-(4-((2,3-dihydro-1H-inden-2-yl)oxy)-3-fluorophenyl)ethyl)amino)-2-ethyl-2,3-dihydro-1H-pyrrolo[3,4-c]pyridin-1-one |

-continued

| Compound No. | Structure and Nomenclature |
|---|---|
| 6 | 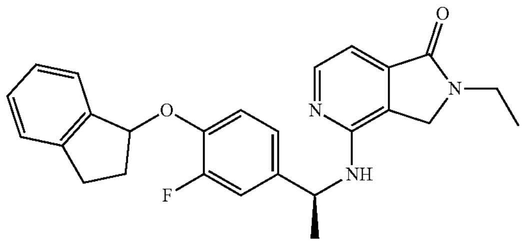 [SMILES: CCN1Cc2c(ccnc2N[C@@H](C)c2ccc(OC3CCc4ccccc43)c(F)c2)C1=O] 4-(((1S)-1-(4-((2,3-dihydro-1H-inden-1-yl)oxy)-3-fluorophenyl)ethyl)amino)-2-ethyl-2,3-dihydro-1H-pyrrolo[3,4-c]pyridin-1-one |
| 7 | 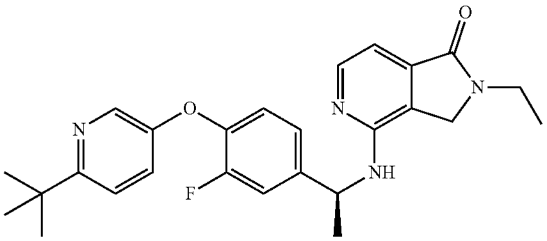 [SMILES: CCN1Cc2c(ccnc2N[C@@H](C)c2ccc(Oc3ccc(C(C)(C)C)nc3)c(F)c2)C1=O] (S)-4-((1-(4-((6-(tert-butyl)pyridin-3-yl)oxy)-3-fluorophenyl)ethyl)amino)-2-ethyl-2,3-dihydro-1H-pyrrolo[3,4-c]pyridin-1-one |
| 8 | 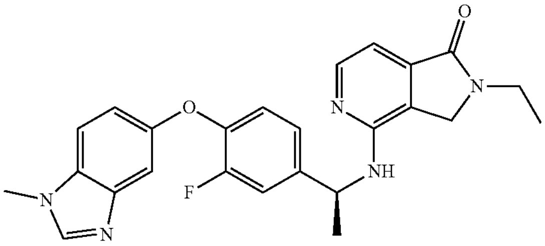 [SMILES: CCN1Cc2c(ccnc2N[C@@H](C)c2ccc(Oc3ccc4c(c3)ncn4C)c(F)c2)C1=O] (S)-2-ethyl-4-((1-(3-fluoro-4-((1-methyl-1H-benzo[d]imidazol-5-yl)oxy)phenyl)ethyl)amino)-2,3-dihydro-1H-pyrrolo[3,4-c]pyridin-1-one |
| 9 | 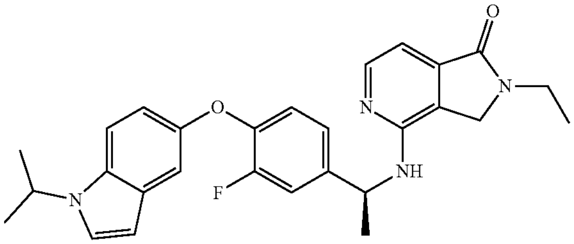 [SMILES: CCN1Cc2c(ccnc2N[C@@H](C)c2ccc(Oc3ccc4c(ccn4C(C)C)c3)c(F)c2)C1=O] (S)-2-ethyl-4-((1-(3-fluoro-4-((1-isopropyl-1H-indol-5-yl)oxy)phenyl)ethyl)amino)-2,3-dihydro-1H-pyrrolo[3,4-c]pyridin-1-one |
| 10 | 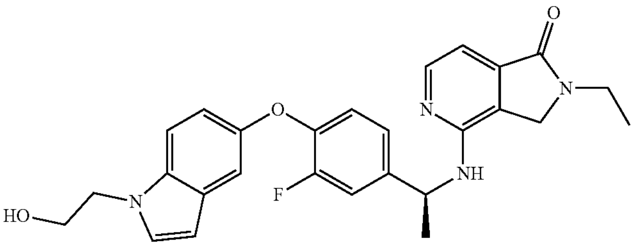 [SMILES: CCN1Cc2c(ccnc2N[C@@H](C)c2ccc(Oc3ccc4c(ccn4CCO)c3)c(F)c2)C1=O] (S)-2-ethyl-4-((1-(3-fluoro-4-((1-(2-hydroxyethyl)-1H-indol-5-yl)oxy)phenyl)ethyl)amino)-2,3-dihydro-1H-pyrrolo[3,4-c]pyridin-1-one |

-continued

| Compound No. | Structure and Nomenclature |
|---|---|
| 11 | 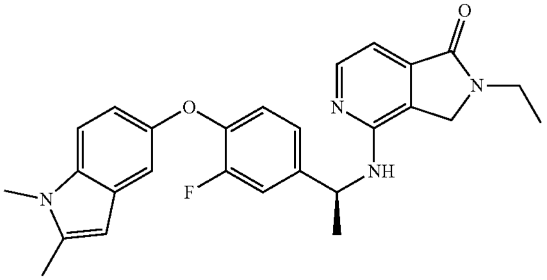 [SMILES: CCN1Cc2c(ccnc2N[C@@H](C)c2ccc(Oc3ccc4c(c3)cc(C)n4C)c(F)c2)C1=O] (S)-4-((1-(4-((1,2-dimethyl-1H-indol-5-yl)oxy)-3-fluorophenyl)ethyl)amino)-2-ethyl-2,3-dihydro-1H-pyrrolo[3,4-c]pyridin-1-one |
| 12 | 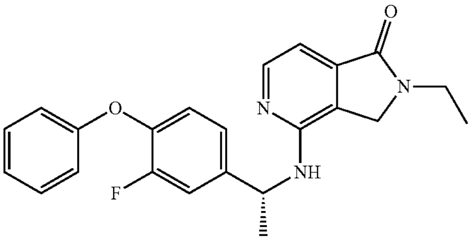 [SMILES: CCN1Cc2c(ccnc2N[C@H](C)c2ccc(Oc3ccccc3)c(F)c2)C1=O] (R)-2-ethyl-4-((1-(3-fluoro-4-phenoxyphenyl)ethyl)amino)-2,3-dihydro-1H-pyrrolo[3,4-c]pyridin-1-one |
| 13 | 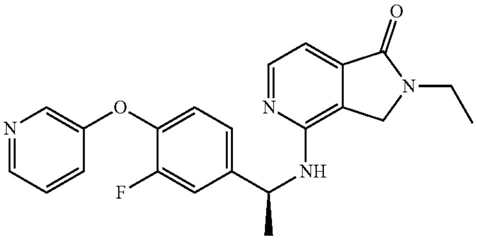 [SMILES: CCN1Cc2c(ccnc2N[C@@H](C)c2ccc(Oc3cccnc3)c(F)c2)C1=O] (S)-2-ethyl-4-((1-(3-fluoro-4-(pyridin-3-yloxy)phenyl)ethyl)amino)-2,3-dihydro-1H-pyrrolo[3,4-c]pyridin-1-one |
| 14 | 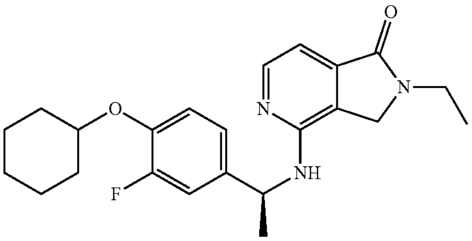 [SMILES: CCN1Cc2c(ccnc2N[C@@H](C)c2ccc(OC3CCCCC3)c(F)c2)C1=O] (S)-4-((1-(4-(cyclohexyloxy)-3-fluorophenyl)ethyl)amino)-2-ethyl-2,3-dihydro-1H-pyrrolo[3,4-c]pyridin-1-one |
| 15 | 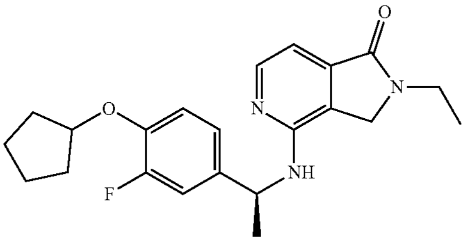 [SMILES: CCN1Cc2c(ccnc2N[C@@H](C)c2ccc(OC3CCCC3)c(F)c2)C1=O] |

-continued

| Compound No. | Structure and Nomenclature |
|---|---|
| | (S)-4-((1-(4-(cyclopentyloxy)-3-fluorophenyl)ethyl)amino)-2-ethyl-2,3-dihydro-1H-pyrrolo[3,4-c]pyridin-1-one |
| 16 | 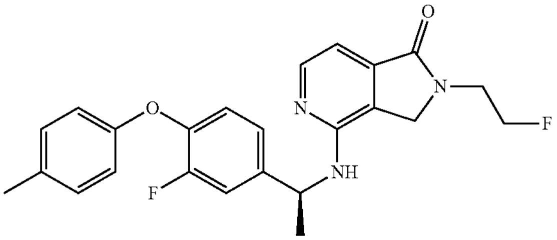 [SMILES: Cc1ccc(Oc2ccc([C@H](C)Nc3nccc4c3CN(CCF)C4=O)cc2F)cc1] (S)-4-((1-(3-fluoro-4-(p-tolyloxy)phenyl)ethyl)amino)-2-(2-fluoroethyl)-2,3-dihydro-1H-pyrrolo[3,4-c]pyridin-1-one |
| 17 | 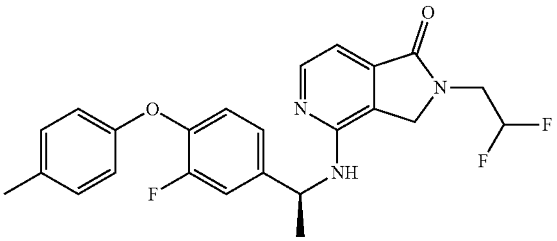 [SMILES: Cc1ccc(Oc2ccc([C@H](C)Nc3nccc4c3CN(CC(F)F)C4=O)cc2F)cc1] (S)-2-(2,2-difluoroethyl)-4-((1-(3-fluoro-4-(p-tolyloxy)phenyl)ethyl)amino)-2,3-dihydro-1H-pyrrolo[3,4-c]pyridin-1-one |
| 18 | 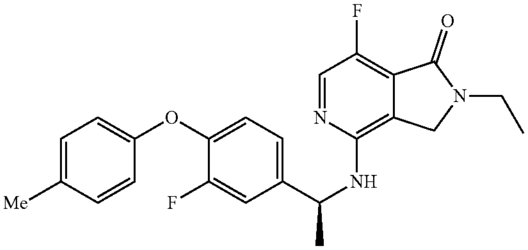 [SMILES: CCN1Cc2c(N[C@@H](C)c3ccc(Oc4ccc(C)cc4)c(F)c3)ncc(F)c2C1=O] (S)-2-ethyl-7-fluoro-4-((1-(3-fluoro-4-(p-tolyloxy)phenyl)ethyl)amino)-2,3-dihydro-1H-pyrrolo[3,4-c]pyridin-1-one |
| 19 | 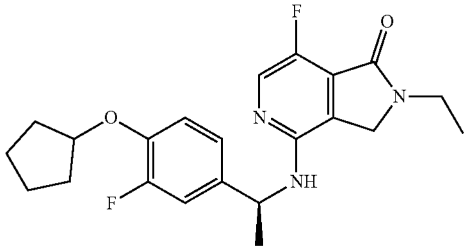 [SMILES: CCN1Cc2c(N[C@@H](C)c3ccc(OC4CCCC4)c(F)c3)ncc(F)c2C1=O] (S)-4-((1-(4-(cyclopentyloxy)-3-fluorophenyl)ethyl)amino)-2-ethyl-7-fluoro-2,3-dihydro-1H-pyrrolo[3,4-c]pyridin-1-one |

-continued

| Compound No. | Structure and Nomenclature |
|---|---|
| 20 | 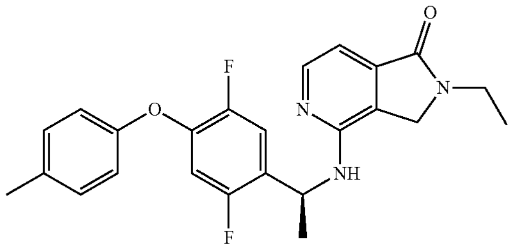 [SMILES: CCN1Cc2c(ccnc2N[C@@H](C)c2cc(F)c(Oc3ccc(C)cc3)cc2F)C1=O]<br>(S)-4-((1-(2,5-difluoro-4-(p-tolyloxy)phenyl)ethyl)amino)-2-ethyl-2,3-dihydro-1H-pyrrolo[3,4-c]pyridin-1-one |
| 21 | 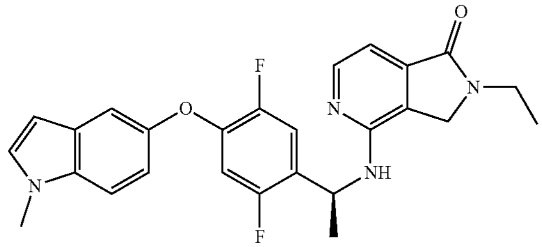 [SMILES: CCN1Cc2c(ccnc2N[C@@H](C)c2cc(F)c(Oc3ccc4c(ccn4C)c3)cc2F)C1=O]<br>(S)-4-((1-(2,5-difluoro-4-((1-methyl-1H-indol-5-yl)oxy)phenyl)ethyl)amino)-2-ethyl-2,3-dihydro-1H-pyrrolo[3,4-c]pyridin-1-one |
| 22 | 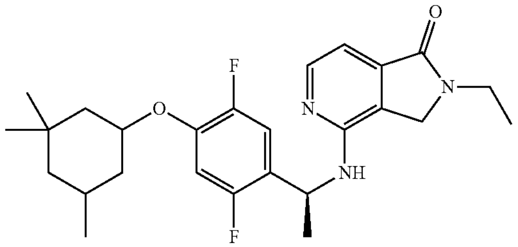 [SMILES: CCN1Cc2c(ccnc2N[C@@H](C)c2cc(F)c(OC3CC(C)CC(C)(C)C3)cc2F)C1=O]<br>4-(((1S)-1-(2,5-difluoro-4-((3,3,5-trimethylcyclohexyl)oxy)phenyl)ethyl)amino)-2-ethyl-2,3-dihydro-1H-pyrrolo[3,4-c]pyridin-1-one |
| 23 | 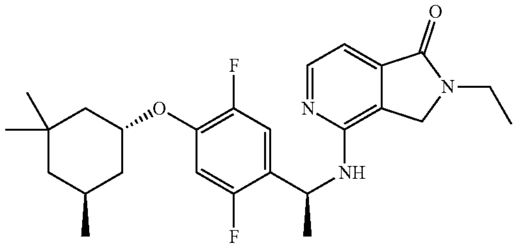 [SMILES: CCN1Cc2c(ccnc2N[C@@H](C)c2cc(F)c(O[C@@H]3C[C@@H](C)CC(C)(C)C3)cc2F)C1=O]<br>4-(((S)-1-(2,5-difluoro-4-(((1R,5S)-3,3,5-trimethylcyclohexyl)oxy)phenyl)ethyl)amino)-2-ethyl-2,3-dihydro-1H-pyrrolo[3,4-c]pyridin-1-one |
| 24 | 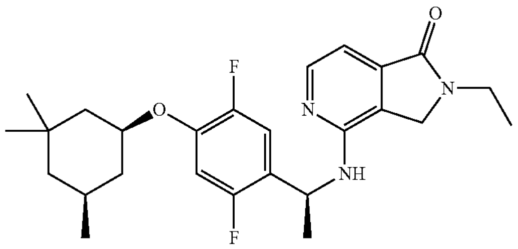 [SMILES: CCN1Cc2c(ccnc2N[C@@H](C)c2cc(F)c(O[C@H]3C[C@@H](C)CC(C)(C)C3)cc2F)C1=O] |

-continued

| Compound No. | Structure and Nomenclature |
| --- | --- |
| | 4-(((S)-1-(2,5-difluoro-4-(((1S,5S)-3,3,5-trimethylcyclohexyl)oxy)phenyl)ethyl)amino)-2-ethyl-2,3-dihydro-1H-pyrrolo[3,4-c]pyridin-1-one |
| 25 | 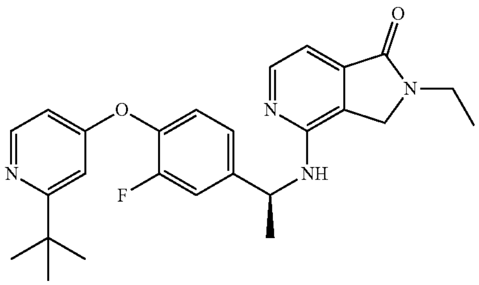 [SMILES: CCN1Cc2c(ccnc2N[C@@H](C)c2ccc(Oc3ccnc(C(C)(C)C)c3)c(F)c2)C1=O] (S)-4-((1-(4-((2-(tert-butyl)pyridin-4-yl)oxy)-3-fluorophenyl)ethyl)amino)-2-ethyl-2,3-dihydro-1H-pyrrolo[3,4-c]pyridin-1-one |
| 26 | 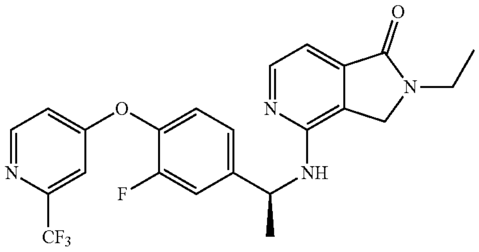 [SMILES: CCN1Cc2c(ccnc2N[C@@H](C)c2ccc(Oc3ccnc(C(F)(F)F)c3)c(F)c2)C1=O] (S)-2-ethyl-4-((1-(3-fluoro-4-((2-(trifluoromethyl)pyridin-4-yl)oxy)phenyl)ethyl)amino)-2,3-dihydro-1H-pyrrolo[3,4-c]pyridin-1-one |
| 27 | 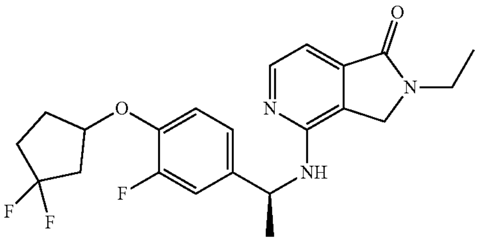 [SMILES: CCN1Cc2c(ccnc2N[C@@H](C)c2ccc(OC3CCC(F)(F)C3)c(F)c2)C1=O] 4-(((1S)-1-(4-((3,3-difluorocyclopentyl)oxy)-3-fluorophenyl)ethyl)amino)-2-ethyl-2,3-dihydro-1H-pyrrolo[3,4-c]pyridin-1-one |
| 28 | 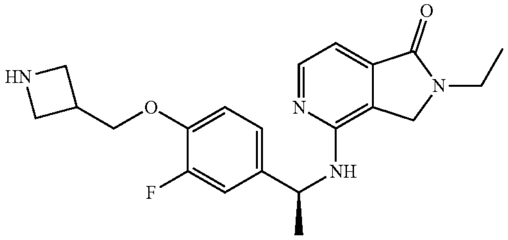 [SMILES: CCN1Cc2c(ccnc2N[C@@H](C)c2ccc(OCC3CNC3)c(F)c2)C1=O] (S)-4-((1-(4-(azetidin-3-ylmethoxy)-3-fluorophenyl)ethyl)amino)-2-ethyl-2,3-dihydro-1H-pyrrolo[3,4-c]pyridin-1-one |

-continued

| Compound No. | Structure and Nomenclature |
|---|---|
| 29 | 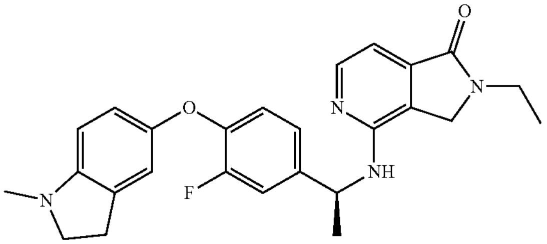 [SMILES: CCN1Cc2c(ccnc2N[C@@H](C)c2ccc(Oc3ccc4c(c3)CCN4C)c(F)c2)C1=O] (S)-2-ethyl-4-((1-(3-fluoro-4-((1-methylindolin-5-yl)oxy)phenyl)ethyl)amino)-2,3-dihydro-1H-pyrrolo[3,4-c]pyridin-1-one |
| 30 | 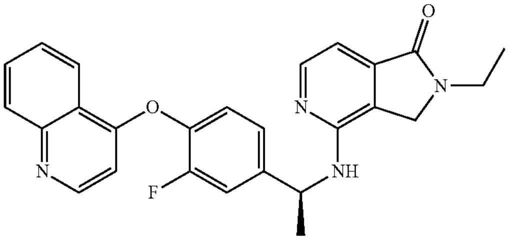 [SMILES: CCN1Cc2c(ccnc2N[C@@H](C)c2ccc(Oc3ccnc4ccccc34)c(F)c2)C1=O] (S)-2-ethyl-4-((1-(3-fluoro-4-(quinolin-4-yloxy)phenyl)ethyl)amino)-2,3-dihydro-1H-pyrrolo[3,4-c]pyridin-1-one |
| 31 | 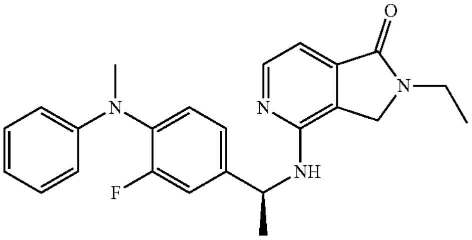 [SMILES: CCN1Cc2c(ccnc2N[C@@H](C)c2ccc(N(C)c3ccccc3)c(F)c2)C1=O] (S)-2-ethyl-4-((1-(3-fluoro-4-(methyl(phenyl)amino)phenyl)ethyl)amino)-2,3-dihydro-1H-pyrrolo[3,4-c]pyridin-1-one |
| 32 | 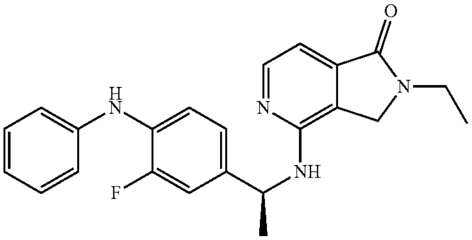 [SMILES: CCN1Cc2c(ccnc2N[C@@H](C)c2ccc(Nc3ccccc3)c(F)c2)C1=O] (S)-2-ethyl-4-((1-(3-fluoro-4-(phenylamino)phenyl)ethyl)amino)-2,3-dihydro-1H-pyrrolo[3,4-c]pyridin-1-one |
| 33 | 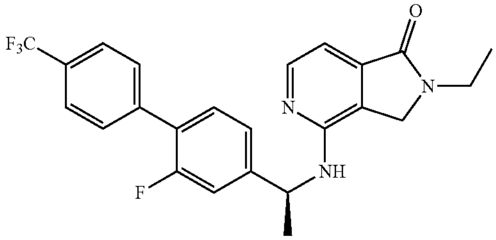 [SMILES: CCN1Cc2c(ccnc2N[C@@H](C)c2ccc(-c3ccc(C(F)(F)F)cc3)c(F)c2)C1=O] (S)-2-ethyl-4-((1-(2-fluoro-4'-(trifluoromethyl)-[1,1'-biphenyl]-4-yl)ethyl)amino)-2,3-dihydro-1H-pyrrolo[3,4-c]pyridin-1-one |

-continued

| Compound No. | Structure and Nomenclature |
|---|---|
| 34 | 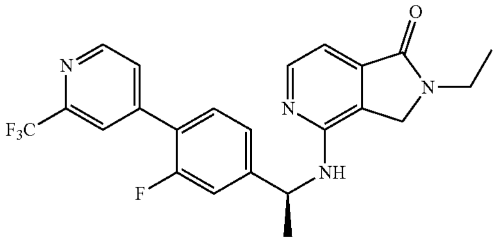 [SMILES: CCN1Cc2c(ccnc2N[C@@H](C)c2ccc(-c3ccnc(C(F)(F)F)c3)c(F)c2)C1=O] (S)-2-ethyl-4-((1-(3-fluoro-4-(2-(trifluoromethyl)pyridin-4-yl)phenyl)ethyl)amino)-2,3-dihydro-1H-pyrrolo[3,4-c]pyridin-1-one |
| 35 | 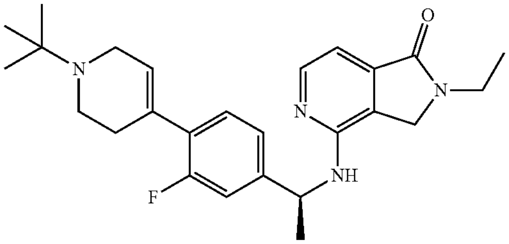 [SMILES: CCN1Cc2c(ccnc2N[C@@H](C)c2ccc(C3=CCN(C(C)(C)C)CC3)c(F)c2)C1=O] (S)-4-((1-(4-(1-(tert-butyl)-1,2,3,6-tetrahydropyridin-4-yl)-3-fluorophenyl)ethyl)amino)-2-ethyl-2,3-dihydro-1H-pyrrolo[3,4-c]pyridin-1-one |
| 36 | 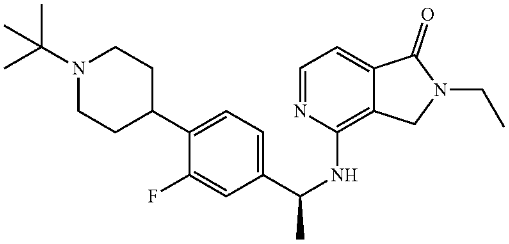 [SMILES: CCN1Cc2c(ccnc2N[C@@H](C)c2ccc(C3CCN(C(C)(C)C)CC3)c(F)c2)C1=O] (S)-4-((1-(4-(1-(tert-butyl)piperidin-4-yl)-3-fluorophenyl)ethyl)amino)-2-ethyl-2,3-dihydro-1H-pyrrolo[3,4-c]pyridin-1-one |
| 37 | 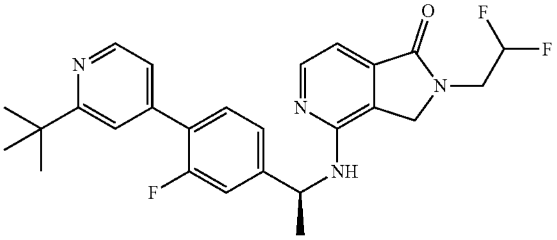 [SMILES: C[C@H](Nc1nccc2c1CN(CC(F)F)C2=O)c1ccc(-c2ccnc(C(C)(C)C)c2)c(F)c1] (S)-4-((1-(4-(2-(tert-butyl)pyridin-4-yl)-3-fluorophenyl)ethyl)amino)-2-(2,2-difluoroethyl)-2,3-dihydro-1H-pyrrolo[3,4-c]pyridin-1-one |
| 38 | 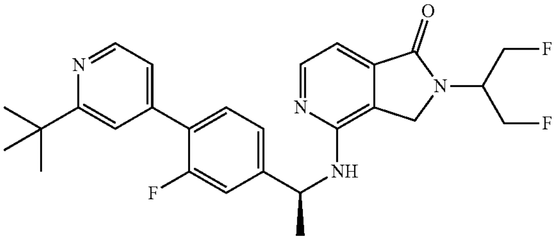 [SMILES: C[C@H](Nc1nccc2c1CN(C(CF)CF)C2=O)c1ccc(-c2ccnc(C(C)(C)C)c2)c(F)c1] (S)-4-((1-(4-(2-(tert-butyl)pyridin-4-yl)-3-fluorophenyl)ethyl)amino)-2-(1,3-difluoropropan-2-yl)-2,3-dihydro-1H-pyrrolo[3,4-c]pyridin-1-one |

-continued

| Compound No. | Structure and Nomenclature |
| --- | --- |
| 39 | 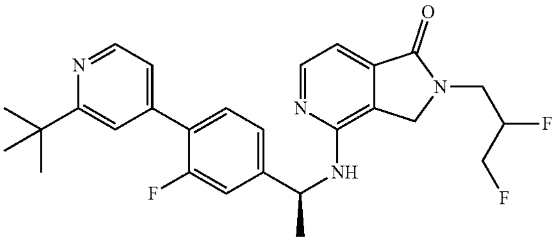 [SMILES: C[C@H](Nc1nccc2c1CN(CC(F)CF)C2=O)c1ccc(-c2ccnc(C(C)(C)C)c2)c(F)c1]<br>4-(((S)-1-(4-(2-(tert-butyl)pyridin-4-yl)-3-fluorophenyl)ethyl)amino)-2-(2,3-difluoropropyl)-2,3-dihydro-1H-pyrrolo[3,4-c]pyridin-1-one |
| 40 | 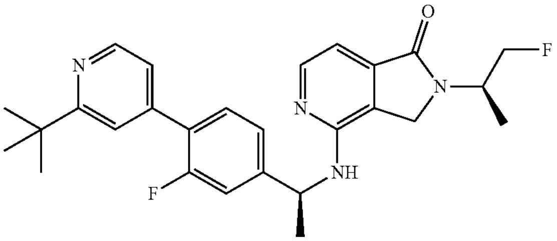 [SMILES: C[C@H](Nc1nccc2c1CN([C@H](C)CF)C2=O)c1ccc(-c2ccnc(C(C)(C)C)c2)c(F)c1]<br>4-(((S)-1-(4-(2-(tert-butyl)pyridin-4-yl)-3-fluorophenyl)ethyl)amino)-2-((R)-1-fluoropropan-2-yl)-2,3-dihydro-1H-pyrrolo[3,4-c]pyridin-1-one |
| 41 | 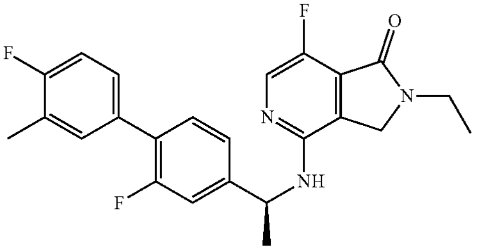 [SMILES: CCN1Cc2c(N[C@@H](C)c3ccc(-c4ccc(F)c(C)c4)c(F)c3)ncc(F)c2C1=O]<br>(S)-4-((1-(2,4'-difluoro-3'-methyl-[1,1'-biphenyl]-4-yl)ethyl)amino)-2-ethyl-7-fluoro-2,3-dihydro-1H-pyrrolo[3,4-c]pyridin-1-one |
| 42 | 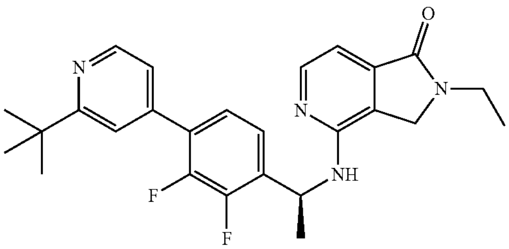 [SMILES: CCN1Cc2c(ccnc2N[C@@H](C)c2ccc(-c3ccnc(C(C)(C)C)c3)c(F)c2F)C1=O]<br>(S)-4-((1-(4-(2-(tert-butyl)pyridin-4-yl)-2,3-difluorophenyl)ethyl)amino)-2-ethyl-2,3-dihydro-1H-pyrrolo[3,4-c]pyridin-1-one |
| 43 | 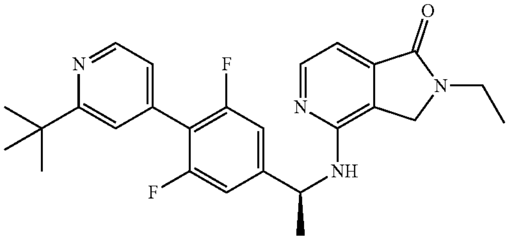 [SMILES: CCN1Cc2c(ccnc2N[C@@H](C)c2cc(F)c(-c3ccnc(C(C)(C)C)c3)c(F)c2)C1=O]<br>(S)-4-((1-(4-(2-(tert-butyl)pyridin-4-yl)-3,5-difluorophenyl)ethyl)amino)-2-ethyl-2,3-dihydro-1H-pyrrolo[3,4-c]pyridin-1-one |

-continued

| Compound No. | Structure and Nomenclature |
|---|---|
| 44 | 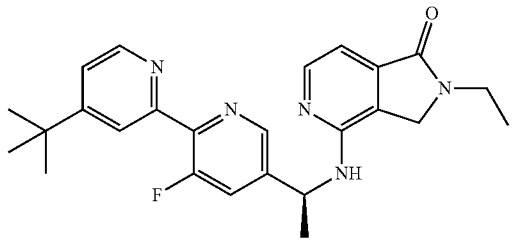 [SMILES: CCN1Cc2c(ccnc2N[C@@H](C)c2cnc(-c3cc(C(C)(C)C)ccn3)c(F)c2)C1=O]<br>(S)-4-((1-(4'-(tert-butyl)-3-fluoro-[2,2'-bipyridin]-5-yl)ethyl)amino)-2-ethyl-2,3-dihydro-1H-pyrrolo[3,4-c]pyridin-1-one |
| 45 | 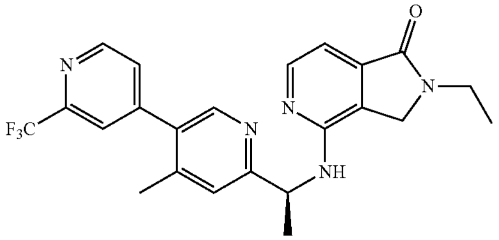 [SMILES: CCN1Cc2c(ccnc2N[C@@H](C)c2cc(C)c(-c3ccnc(C(F)(F)F)c3)cn2)C1=O]<br>(S)-2-ethyl-4-((1-(4-methyl-2'-(trifluoromethyl)-[3,4'-bipyridin]-6-yl)ethyl)amino)-2,3-dihydro-1H-pyrrolo[3,4-c]pyridin-1-one |
| 46 | 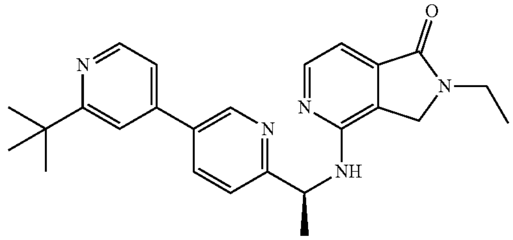 [SMILES: CCN1Cc2c(ccnc2N[C@@H](C)c2ccc(-c3ccnc(C(C)(C)C)c3)cn2)C1=O]<br>(S)-4-((1-(2'-(tert-butyl)-[3,4'-bipyridin]-6-yl)ethyl)amino)-2-ethyl-2,3-dihydro-1H-pyrrolo[3,4-c]pyridin-1-one |
| 47 | 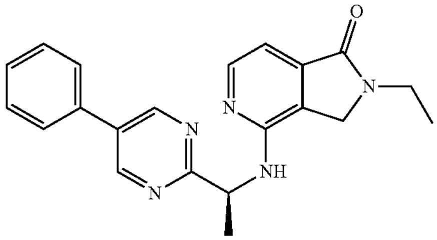 [SMILES: CCN1Cc2c(ccnc2N[C@@H](C)c2ncc(-c3ccccc3)cn2)C1=O]<br>(S)-2-ethyl-4-((1-(5-phenylpyrimidin-2-yl)ethyl)amino)-2,3-dihydro-1H-pyrrolo[3,4-c]pyridin-1-one |
| 48 | 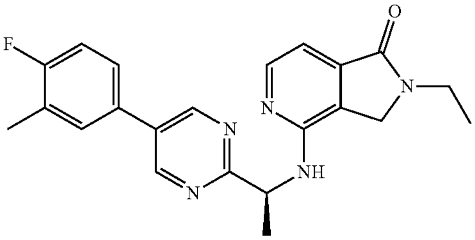 [SMILES: CCN1Cc2c(ccnc2N[C@@H](C)c2ncc(-c3ccc(F)c(C)c3)cn2)C1=O]<br>(S)-2-ethyl-4-((1-(5-(4-fluoro-3-methylphenyl)pyrimidin-2-yl)ethyl)amino)-2,3-dihydro-1H-pyrrolo[3,4-c]pyridin-1-one |

-continued

| Compound No. | Structure and Nomenclature |
|---|---|
| 49 | 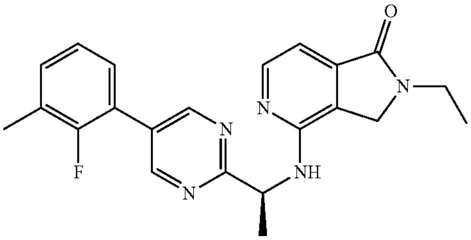 [SMILES: CCN1Cc2c(ccnc2N[C@@H](C)c2ncc(-c3cccc(C)c3F)cn2)C1=O]<br>(S)-2-ethyl-4-((1-(5-(2-fluoro-3-methylphenyl)pyrimidin-2-yl)ethyl)amino)-2,3-dihydro-1H-pyrrolo[3,4-c]pyridin-1-one |
| 50 | 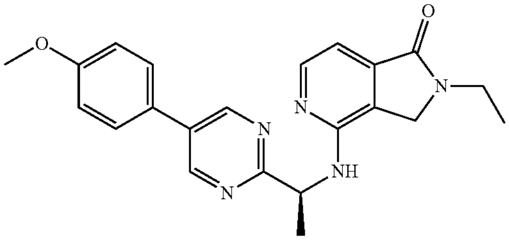 [SMILES: CCN1Cc2c(ccnc2N[C@@H](C)c2ncc(-c3ccc(OC)cc3)cn2)C1=O]<br>(S)-2-ethyl-4-((1-(5-(4-methoxyphenyl)pyrimidin-2-yl)ethyl)amino)-2,3-dihydro-1H-pyrrolo[3,4-c]pyridin-1-one |
| 51 | 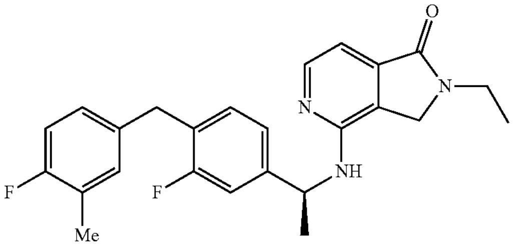 [SMILES: CCN1Cc2c(ccnc2N[C@@H](C)c2ccc(Cc3ccc(F)c(C)c3)c(F)c2)C1=O]<br>(S)-2-ethyl-4-((1-(3-fluoro-4-(4-fluoro-3-methylbenzyl)phenyl)ethyl)amino)-2,3-dihydro-1H-pyrrolo[3,4-c]pyridin-1-one |
| 52 | 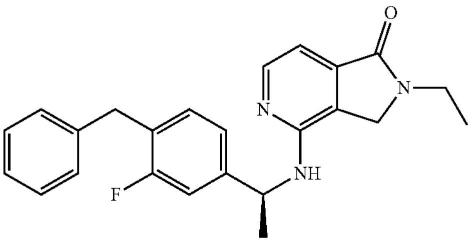 [SMILES: CCN1Cc2c(ccnc2N[C@@H](C)c2ccc(Cc3ccccc3)c(F)c2)C1=O]<br>(S)-4-((1-(4-benzyl-3-fluorophenyl)ethyl)amino)-2-ethyl-2,3-dihydro-1H-pyrrolo[3,4-c]pyridin-1-one |
| 53 | 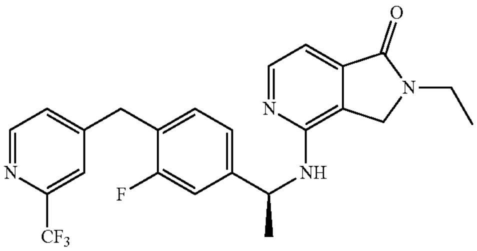 [SMILES: CCN1Cc2c(ccnc2N[C@@H](C)c2ccc(Cc3ccnc(C(F)(F)F)c3)c(F)c2)C1=O] |

-continued

| Compound No. | Structure and Nomenclature |
|---|---|
| | (S)-2-ethyl-4-((1-(3-fluoro-4-((2-(trifluoromethyl)pyridin-4-yl)methyl)phenyl)ethyl)amino)-2,3-dihydro-1H-pyrrolo[3,4-c]pyridin-1-one |
| 54 | 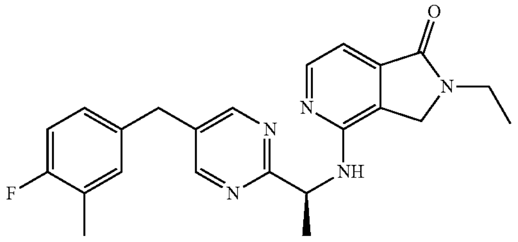 [SMILES: CCN1Cc2c(ccnc2N[C@@H](C)c2ncc(Cc3ccc(F)c(C)c3)cn2)C1=O] (S)-2-ethyl-4-((1-(5-(4-fluoro-3-methylbenzyl)pyrimidin-2-yl)ethyl)amino)-2,3-dihydro-1H-pyrrolo[3,4-c]pyridin-1-one |
| 55 | 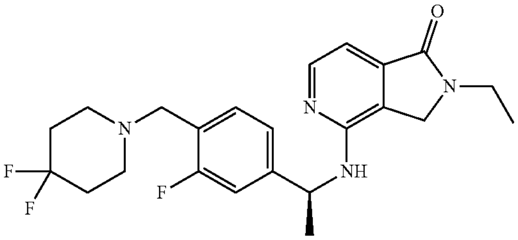 [SMILES: CCN1Cc2c(ccnc2N[C@@H](C)c2ccc(CN3CCC(F)(F)CC3)c(F)c2)C1=O] (S)-4-((1-(4-((4,4-difluoropiperidin-1-yl)methyl)-3-fluorophenyl)ethyl)amino)-2-ethyl-2,3-dihydro-1H-pyrrolo[3,4-c]pyridin-1-one |
| 56 | 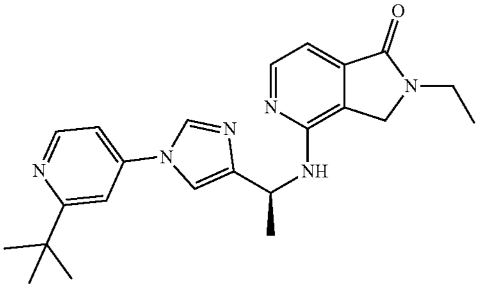 [SMILES: CCN1Cc2c(ccnc2N[C@@H](C)c2cn(-c3ccnc(C(C)(C)C)c3)cn2)C1=O] (S)-4-((1-(1-(2-(tert-butyl)pyridin-4-yl)-1H-imidazol-4-yl)ethyl)amino)-2-ethyl-2,3-dihydro-1H-pyrrolo[3,4-c]pyridin-1-one |
| 57 | 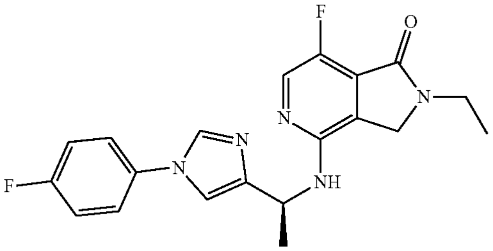 [SMILES: CCN1Cc2c(N[C@@H](C)c3cn(-c4ccc(F)cc4)cn3)ncc(F)c2C1=O] (S)-2-ethyl-7-fluoro-4-((1-(1-(4-fluorophenyl)-1H-imidazol-4-yl)ethyl)amino)-2,3-dihydro-1H-pyrrolo[3,4-c]pyridin-1-one |

-continued

| Compound No. | Structure and Nomenclature |
|---|---|
| 58 | 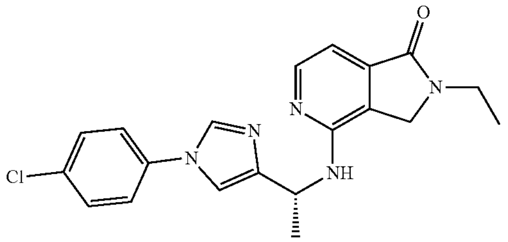 [SMILES: CCN1Cc2c(ccnc2N[C@H](C)c2cn(-c3ccc(Cl)cc3)cn2)C1=O] (R)-4-((1-(1-(4-chlorophenyl)-1H-imidazol-4-yl)ethyl)amino)-2-ethyl-2,3-dihydro-1H-pyrrolo[3,4-c]pyridin-1-one |
| 59 | 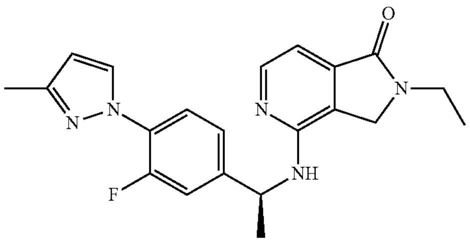 [SMILES: CCN1Cc2c(ccnc2N[C@@H](C)c2ccc(-n3ccc(C)n3)c(F)c2)C1=O] (S)-2-ethyl-4-((1-(3-fluoro-4-(3-methyl-1H-pyrazol-1-yl)phenyl)ethyl)amino)-2,3-dihydro-1H-pyrrolo[3,4-c]pyridin-1-one |
| 60 | 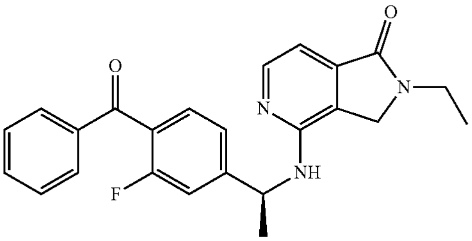 [SMILES: CCN1Cc2c(ccnc2N[C@@H](C)c2ccc(C(=O)c3ccccc3)c(F)c2)C1=O] (S)-4-((1-(4-benzoyl-3-fluorophenyl)ethyl)amino)-2-ethyl-2,3-dihydro-1H-pyrrolo[3,4-c]pyridin-1-one |
| 61 | 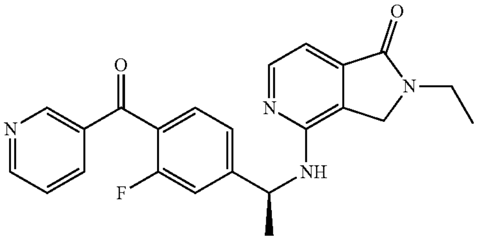 [SMILES: CCN1Cc2c(ccnc2N[C@@H](C)c2ccc(C(=O)c3cccnc3)c(F)c2)C1=O] (S)-2-ethyl-4-((1-(3-fluoro-4-nicotinoylphenyl)ethyl)amino)-2,3-dihydro-1H-pyrrolo[3,4-c]pyridin-1-one |
| 62 | 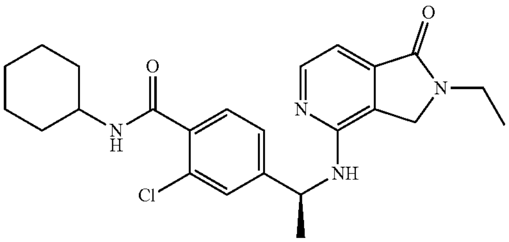 [SMILES: CCN1Cc2c(ccnc2N[C@@H](C)c2ccc(C(=O)NC3CCCCC3)c(Cl)c2)C1=O] (S)-2-chloro-N-cyclohexyl-4-(1-((2-ethyl-1-oxo-2,3-dihydro-1H-pyrrolo[3,4-c]pyridin-4-yl)amino)ethyl)benzamide |

-continued

| Compound No. | Structure and Nomenclature |
|---|---|
| 63 | 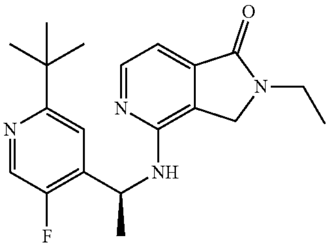 [SMILES: CCN1Cc2c(ccnc2N[C@@H](C)c2cc(C(C)(C)C)ncc2F)C1=O] (S)-4-((1-(2-(tert-butyl)-5-fluoropyridin-4-yl)ethyl)amino)-2-ethyl-2,3-dihydro-1H-pyrrolo[3,4-c]pyridin-1-one |
| 64 | 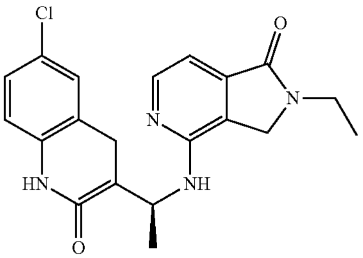 (S)-6-chloro-3-(1-((2-ethyl-1-oxo-2,3-dihydro-1H-pyrrolo[3,4-c]pyridin-4-yl)amino)ethyl)quinolin-2(1H)-one |
| 65 | 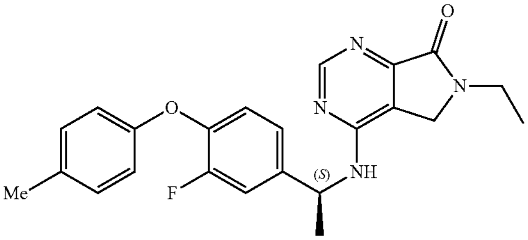 (S)-6-ethyl-4-((1-(3-fluoro-4-(p-tolyloxy)phenyl)ethyl)amino)-5H-pyrrolo[3,4-d]pyrimidin-7(6H)-one |
| 66 | 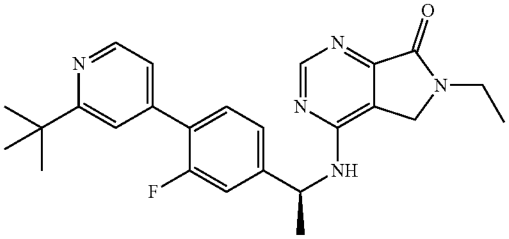 [SMILES: CCN1Cc2c(N[C@@H](C)c3ccc(-c4ccnc(C(C)(C)C)c4)c(F)c3)ncnc2C1=O] (S)-4-((1-(4-(2-(tert-butyl)pyridin-4-yl)-3-fluorophenyl)ethyl)amino)-6-ethyl-5H-pyrrolo[3,4-d]pyrimidin-7(6H)-one |
| 67 | 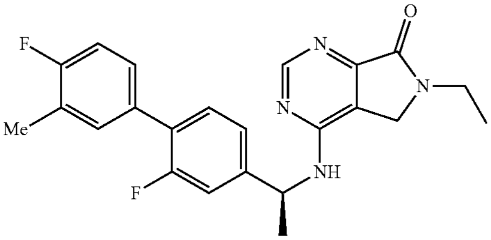 [SMILES: CCN1Cc2c(N[C@@H](C)c3ccc(-c4ccc(F)c(C)c4)c(F)c3)ncnc2C1=O] (S)-4-((1-(2,4'-difluoro-3'-methyl-[1,1'-biphenyl]-4-yl)ethyl)amino)-6-ethyl-5H-pyrrolo[3,4-d]pyrimidin-7(6H)-one |

-continued

| Compound No. | Structure and Nomenclature |
|---|---|
| 68 | 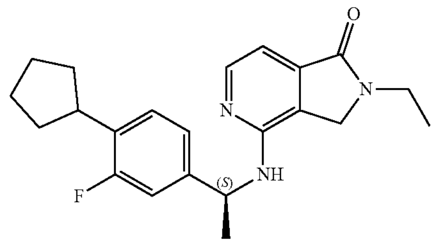<br>(S)-4-((1-(4-cyclopentyl-3-fluorophenyl)ethyl)amino)-2-ethyl-2,3-dihydro-1H-pyrrolo[3,4-c]pyridin-1-one |
| 69 | 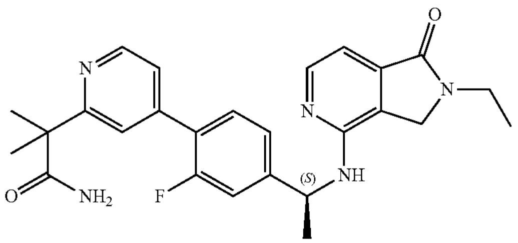<br>(S)-2-(4-(4-(1-((2-ethyl-1-oxo-2,3-dihydro-1H-pyrrolo[3,4-c]pyridin-4-yl)amino)ethyl)-2-fluorophenyl)pyridin-2-yl)-2-methylpropanamide |
| 70 | 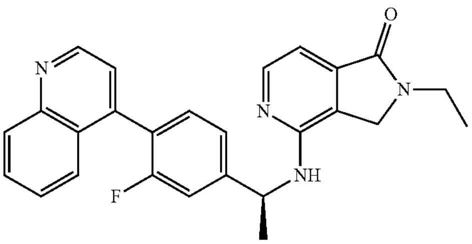 [SMILES: CCN1Cc2c(ccnc2N[C@@H](C)c2ccc(-c3ccnc4ccccc34)c(F)c2)C1=O]<br>(S)-2-ethyl-4-((1-(3-fluoro-4-(quinolin-4-yl)phenyl)ethyl)amino)-2,3-dihydro-1H-pyrrolo[3,4-c]pyridin-1-one |
| 71 | 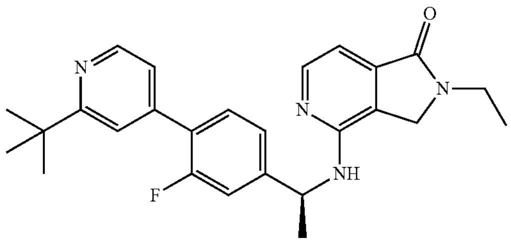 [SMILES: CCN1Cc2c(ccnc2N[C@@H](C)c2ccc(-c3ccnc(C(C)(C)C)c3)c(F)c2)C1=O]<br>(S)-4-((1-(4-(2-(tert-butyl)pyridin-4-yl)-3-fluorophenyl)ethyl)amino)-2-ethyl-2,3-dihydro-1H-pyrrolo[3,4-c]pyridin-1-one |
| 72 | 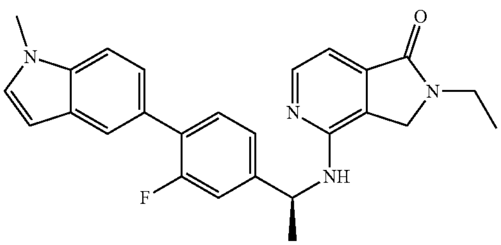 [SMILES: CCN1Cc2c(ccnc2N[C@@H](C)c2ccc(-c3ccc4c(ccn4C)c3)c(F)c2)C1=O]<br>(S)-2-ethyl-4-((1-(3-fluoro-4-(1-methyl-1H-indol-5-yl)phenyl)ethyl)amino)-2,3-dihydro-1H-pyrrolo[3,4-c]pyridin-1-one |

-continued

| Compound No. | Structure and Nomenclature |
|---|---|
| 73 | 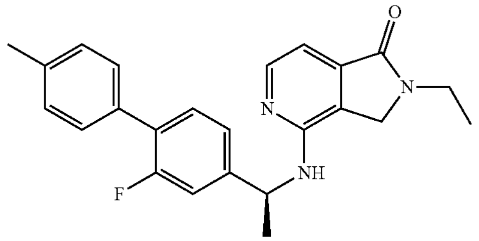 [SMILES: CCN1Cc2c(ccnc2N[C@@H](C)c2ccc(-c3ccc(C)cc3)c(F)c2)C1=O] (S)-2-ethyl-4-((1-(2-fluoro-4'-methyl-[1,1'-biphenyl]-4-yl)ethyl)amino)-2,3-dihydro-1H-pyrrolo[3,4-c]pyridin-1-one |
| 74 | 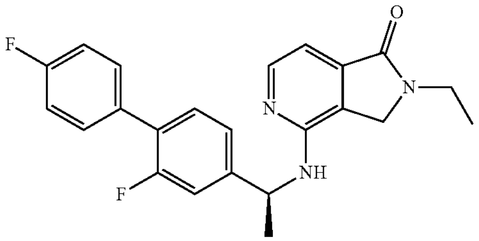 [SMILES: CCN1Cc2c(ccnc2N[C@@H](C)c2ccc(-c3ccc(F)cc3)c(F)c2)C1=O] (S)-4-((1-(2,4'-difluoro-[1,1'-biphenyl]-4-yl)ethyl)amino)-2-ethyl-2,3-dihydro-1H-pyrrolo[3,4-c]pyridin-1-one |
| 75 | 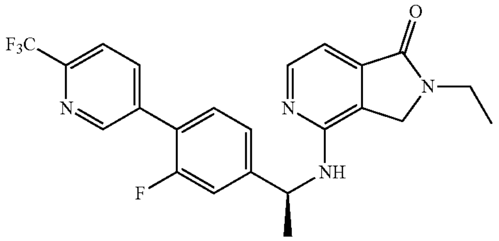 [SMILES: CCN1Cc2c(ccnc2N[C@@H](C)c2ccc(-c3ccc(C(F)(F)F)nc3)c(F)c2)C1=O] (S)-2-ethyl-4-((1-(3-fluoro-4-(6-(trifluoromethyl)pyridin-3-yl)phenyl)ethyl)amino)-2,3-dihydro-1H-pyrrolo[3,4-c]pyridin-1-one |
| 76 | 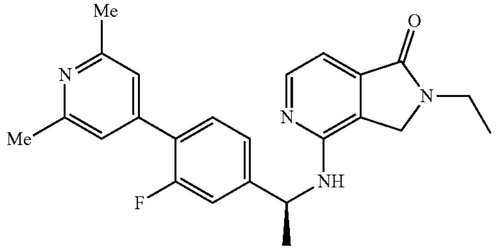 [SMILES: CCN1Cc2c(ccnc2N[C@@H](C)c2ccc(-c3cc(C)nc(C)c3)c(F)c2)C1=O] (S)-4-((1-(4-(2,6-dimethylpyridin-4-yl)-3-fluorophenyl)ethyl)amino)-2-ethyl-2,3-dihydro-1H-pyrrolo[3,4-c]pyridin-1-one |
| 77 | 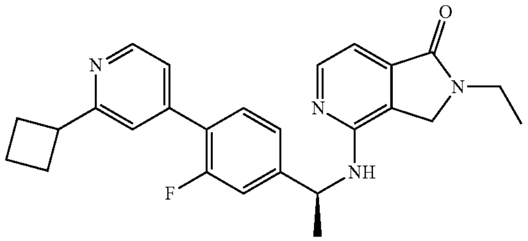 [SMILES: CCN1Cc2c(ccnc2N[C@@H](C)c2ccc(-c3ccnc(C4CCC4)c3)c(F)c2)C1=O] (S)-4-((1-(4-(2-cyclobutylpyridin-4-yl)-3-fluorophenyl)ethyl)amino)-2-ethyl-2,3-dihydro-1H-pyrrolo[3,4-c]pyridin-1-one |

-continued

| Compound No. | Structure and Nomenclature |
|---|---|
| 78 | 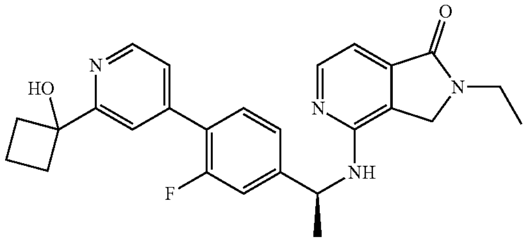 [SMILES: CCN1Cc2c(ccnc2N[C@@H](C)c2ccc(-c3ccnc(C4(O)CCC4)c3)c(F)c2)C1=O] (S)-2-ethyl-4-((1-(3-fluoro-4-(2-(1-hydroxycyclobutyl)pyridin-4-yl)phenyl)ethyl)amino)-2,3-dihydro-1H-pyrrolo[3,4-c]pyridin-1-one |
| 79 | 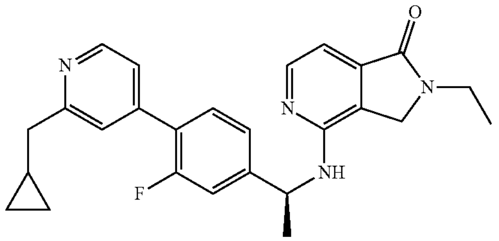 [SMILES: CCN1Cc2c(ccnc2N[C@@H](C)c2ccc(-c3ccnc(CC4CC4)c3)c(F)c2)C1=O] (S)-4-((1-(4-(2-(cyclopropylmethyl)pyridin-4-yl)-3-fluorophenyl)ethyl)amino)-2-ethyl-2,3-dihydro-1H-pyrrolo[3,4-c]pyridin-1-one |
| 80 | 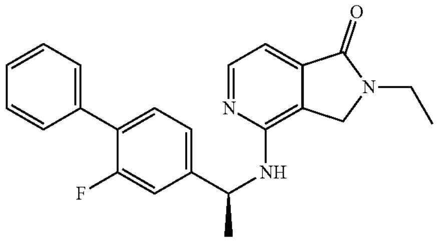 [SMILES: CCN1Cc2c(ccnc2N[C@@H](C)c2ccc(-c3ccccc3)c(F)c2)C1=O] (S)-2-ethyl-4-((1-(2-fluoro-[1,1'-biphenyl]-4-yl)ethyl)amino)-2,3-dihydro-1H-pyrrolo[3,4-c]pyridin-1-one |
| 81 | 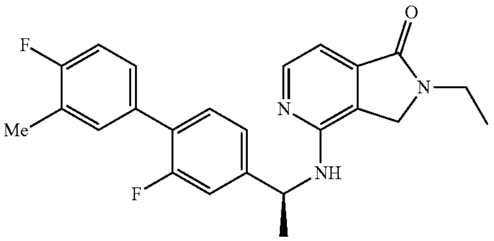 [SMILES: CCN1Cc2c(ccnc2N[C@@H](C)c2ccc(-c3ccc(F)c(C)c3)c(F)c2)C1=O] (S)-4-((1-(2,4'-difluoro-3'-methyl-[1,1'-biphenyl]-4-yl)ethyl)amino)-2-ethyl-2,3-dihydro-1H-pyrrolo[3,4-c]pyridin-1-one |
| 82 | 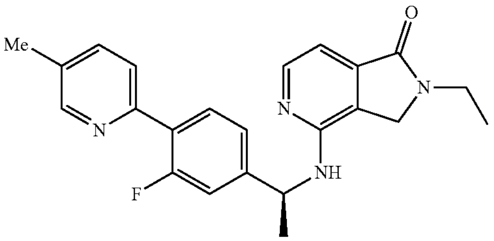 [SMILES: CCN1Cc2c(ccnc2N[C@@H](C)c2ccc(-c3ccc(C)cn3)c(F)c2)C1=O] |

-continued

| Compound No. | Structure and Nomenclature |
|---|---|
| | (S)-2-ethyl-4-((1-(3-fluoro-4-(5-methylpyridin-2-yl)phenyl)ethyl)amino)-2,3-dihydro-1H-pyrrolo[3,4-c]pyridin-1-one |
| 83 | 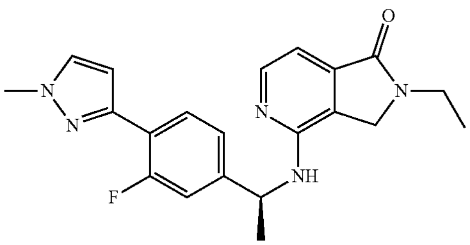 [SMILES: CCN1Cc2c(ccnc2N[C@@H](C)c2ccc(-c3ccn(C)n3)c(F)c2)C1=O] (S)-2-ethyl-4-((1-(3-fluoro-4-(1-methyl-1H-pyrazol-3-yl)phenyl)ethyl)amino)-2,3-dihydro-1H-pyrrolo[3,4-c]pyridin-1-one |
| 84 | 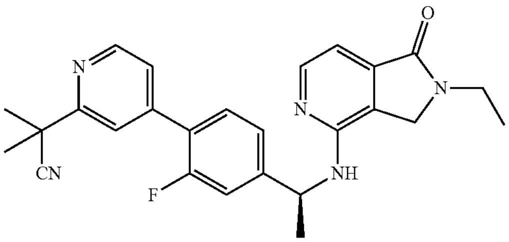 [SMILES: CCN1Cc2c(ccnc2N[C@@H](C)c2ccc(-c3ccnc(C(C)(C)C#N)c3)c(F)c2)C1=O] (S)-2-(4-(4-(1-((2-ethyl-1-oxo-2,3-dihydro-1H-pyrrolo[3,4-c]pyridin-4-yl)amino)ethyl)-2-fluorophenyl)pyridin-2-yl)-2-methylpropanenitrile |
| 85 | 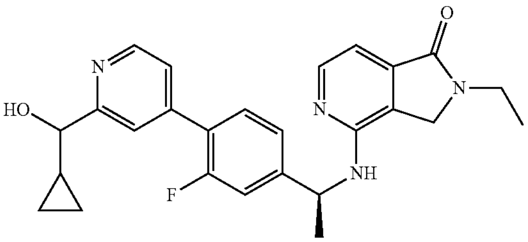 [SMILES: CCN1Cc2c(ccnc2N[C@@H](C)c2ccc(-c3ccnc(C(O)C4CC4)c3)c(F)c2)C1=O] 4-(((1S)-1-(4-(2-(cyclopropyl(hydroxy)methyl)pyridin-4-yl)-3-fluorophenyl)ethyl)amino)-2-ethyl-2,3-dihydro-1H-pyrrolo[3,4-c]pyridin-1-one |
| 86 | 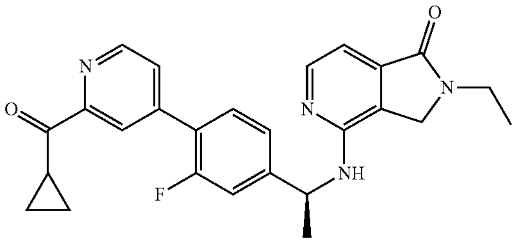 [SMILES: CCN1Cc2c(ccnc2N[C@@H](C)c2ccc(-c3ccnc(C(=O)C4CC4)c3)c(F)c2)C1=O] (S)-4-((1-(4-(2-(cyclopropanecarbonyl)pyridin-4-yl)-3-fluorophenyl)ethyl)amino)-2-ethyl-2,3-dihydro-1H-pyrrolo[3,4-c]pyridin-1-one |

-continued

| Compound No. | Structure and Nomenclature |
|---|---|
| 87 | 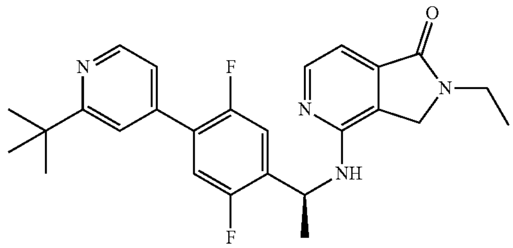 [SMILES: CCN1Cc2c(ccnc2N[C@@H](C)c2cc(F)c(-c3ccnc(C(C)(C)C)c3)cc2F)C1=O] (S)-4-((1-(4-(2-(tert-butyl)pyridin-4-yl)-2,5-difluorophenyl)ethyl)amino)-2-ethyl-2,3-dihydro-1H-pyrrolo[3,4-c]pyridin-1-one |
| 88 | 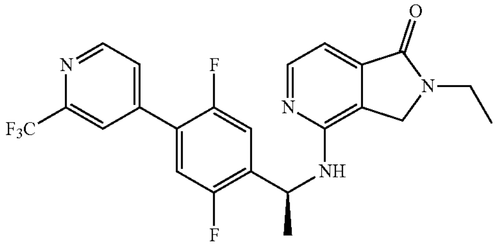 [SMILES: CCN1Cc2c(ccnc2N[C@@H](C)c2cc(F)c(-c3ccnc(C(F)(F)F)c3)cc2F)C1=O] (S)-4-((1-(2,5-difluoro-4-(2-(trifluoromethyl)pyridin-4-yl)phenyl)ethyl)amino)-2-ethyl-2,3-dihydro-1H-pyrrolo[3,4-c]pyridin-1-one |
| 89 | 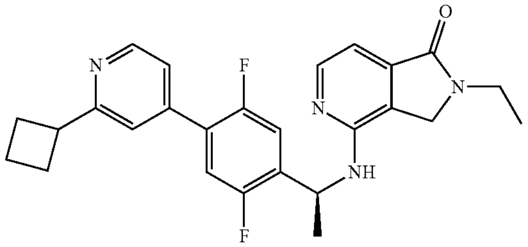 [SMILES: CCN1Cc2c(ccnc2N[C@@H](C)c2cc(F)c(-c3ccnc(C4CCC4)c3)cc2F)C1=O] (S)-4-((1-(4-(2-cyclobutylpyridin-4-yl)-2,5-difluorophenyl)ethyl)amino)-2-ethyl-2,3-dihydro-1H-pyrrolo[3,4-c]pyridin-1-one |
| 90 | 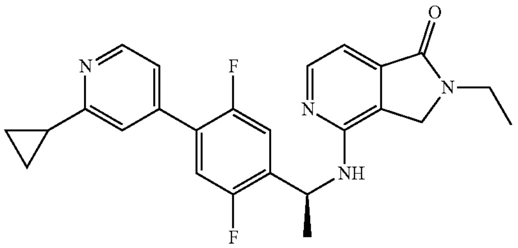 [SMILES: CCN1Cc2c(ccnc2N[C@@H](C)c2cc(F)c(-c3ccnc(C4CC4)c3)cc2F)C1=O] (S)-4-((1-(4-(2-cyclopropylpyridin-4-yl)-2,5-difluorophenyl)ethyl)amino)-2-ethyl-2,3-dihydro-1H-pyrrolo[3,4-c]pyridin-1-one |
| 91 | 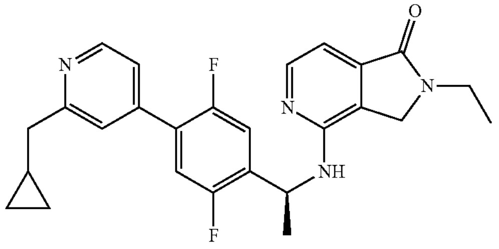 [SMILES: CCN1Cc2c(ccnc2N[C@@H](C)c2cc(F)c(-c3ccnc(CC4CC4)c3)cc2F)C1=O] |

-continued

| Compound No. | Structure and Nomenclature |
|---|---|
| | (S)-4-((1-(4-(2-(cyclopropylmethyl)pyridin-4-yl)-2,5-difluorophenyl)ethyl)amino)-2-ethyl-2,3-dihydro-1H-pyrrolo[3,4-c]pyridin-1-one |
| 92 | 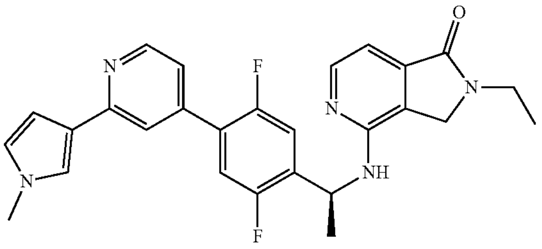 [SMILES: CCN1Cc2c(ccnc2N[C@@H](C)c2cc(F)c(-c3ccnc(-c4ccn(C)c4)c3)cc2F)C1=O] (S)-4-((1-(2,5-difluoro-4-(2-(1-methyl-1H-pyrrol-3-yl)pyridin-4-yl)phenyl)ethyl)amino)-2-ethyl-2,3-dihydro-1H-pyrrolo[3,4-c]pyridin-1-one |
| 93 | 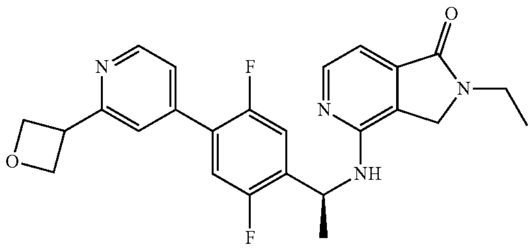 [SMILES: CCN1Cc2c(ccnc2N[C@@H](C)c2cc(F)c(-c3ccnc(C4COC4)c3)cc2F)C1=O] (S)-4-((1-(2,5-difluoro-4-(2-(oxetan-3-yl)pyridin-4-yl)phenyl)ethyl)amino)-2-ethyl-2,3-dihydro-1H-pyrrolo[3,4-c]pyridin-1-one |
| 94 | 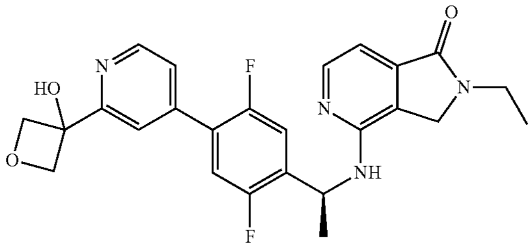 [SMILES: CCN1Cc2c(ccnc2N[C@@H](C)c2cc(F)c(-c3ccnc(C4(O)COC4)c3)cc2F)C1=O] (S)-4-((1-(2,5-difluoro-4-(2-(3-hydroxyoxetan-3-yl)pyridin-4-yl)phenyl)ethyl)amino)-2-ethyl-2,3-dihydro-1H-pyrrolo[3,4-c]pyridin-1-one |
| 95 | 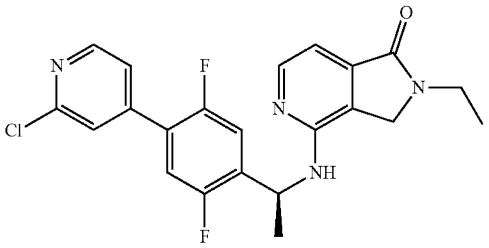 [SMILES: CCN1Cc2c(ccnc2N[C@@H](C)c2cc(F)c(-c3ccnc(Cl)c3)cc2F)C1=O] (S)-4-((1-(4-(2-chloropyridin-4-yl)-2,5-difluorophenyl)ethyl)amino)-2-ethyl-2,3-dihydro-1H-pyrrolo[3,4-c]pyridin-1-one |

-continued

| Compound No. | Structure and Nomenclature |
|---|---|
| 96 | 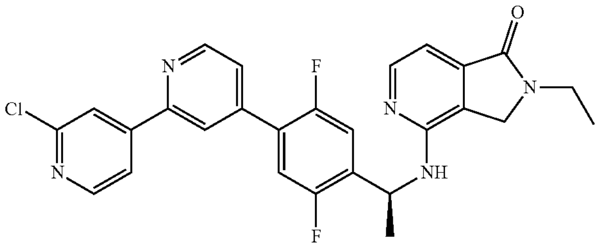 [SMILES: CCN1Cc2c(ccnc2N[C@@H](C)c2cc(F)c(-c3ccnc(-c4ccnc(Cl)c4)c3)cc2F)C1=O] (S)-4-((1-(4-(2'-chloro-[2,4'-bipyridin]-4-yl)-2,5-difluorophenyl)ethyl)amino)-2-ethyl-2,3-dihydro-1H-pyrrolo[3,4-c]pyridin-1-one |
| 97 | 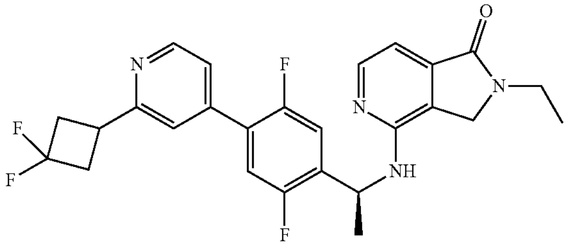 [SMILES: CCN1Cc2c(ccnc2N[C@@H](C)c2cc(F)c(-c3ccnc(C4CC(F)(F)C4)c3)cc2F)C1=O] (S)-4-((1-(4-(2-(3,3-difluorocyclobutyl)pyridin-4-yl)-2,5-difluorophenyl)ethyl)amino)-2-ethyl-2,3-dihydro-1H-pyrrolo[3,4-c]pyridin-1-one |
| 98 | 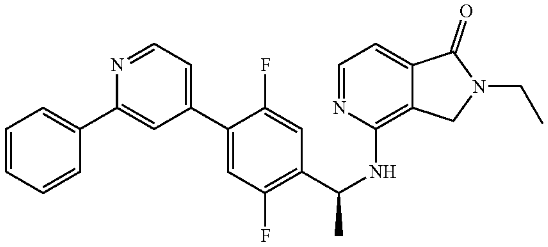 [SMILES: CCN1Cc2c(ccnc2N[C@@H](C)c2cc(F)c(-c3ccnc(-c4ccccc4)c3)cc2F)C1=O] (S)-4-((1-(2,5-difluoro-4-(2-phenylpyridin-4-yl)phenyl)ethyl)amino)-2-ethyl-2,3-dihydro-1H-pyrrolo[3,4-c]pyridin-1-one |
| 99 | 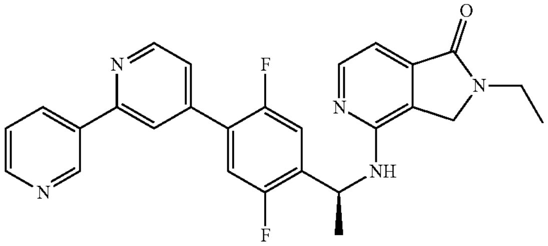 [SMILES: CCN1Cc2c(ccnc2N[C@@H](C)c2cc(F)c(-c3ccnc(-c4cccnc4)c3)cc2F)C1=O] (S)-4-((1-(4-([2,3'-bipyridin]-4-yl)-2,5-difluorophenyl)ethyl)amino)-2-ethyl-2,3-dihydro-1H-pyrrolo[3,4-c]pyridin-1-one |
| 100 | 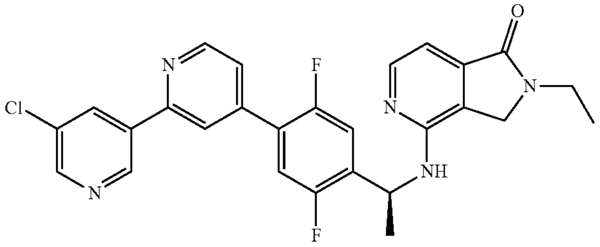 [SMILES: CCN1Cc2c(ccnc2N[C@@H](C)c2cc(F)c(-c3ccnc(-c4cncc(Cl)c4)c3)cc2F)C1=O] |

-continued

| Compound No. | Structure and Nomenclature |
|---|---|
| | (S)-4-((1-(4-(5'-chloro-[2,3'-bipyridin]-4-yl)-2,5-difluorophenyl)ethyl)amino)-2-ethyl-2,3-dihydro-1H-pyrrolo[3,4-c]pyridin-1-one |
| 101 | 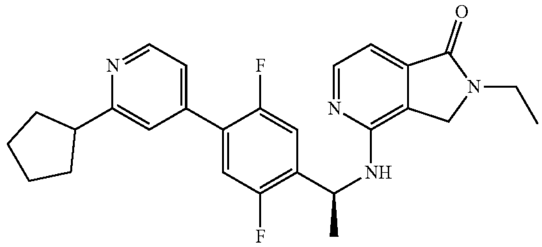 [SMILES: CCN1Cc2c(ccnc2N[C@@H](C)c2cc(F)c(-c3ccnc(C4CCCC4)c3)cc2F)C1=O] (S)-4-((1-(4-(2-cyclopentylpyridin-4-yl)-2,5-difluorophenyl)ethyl)amino)-2-ethyl-2,3-dihydro-1H-pyrrolo[3,4-c]pyridin-1-one |
| 102 | 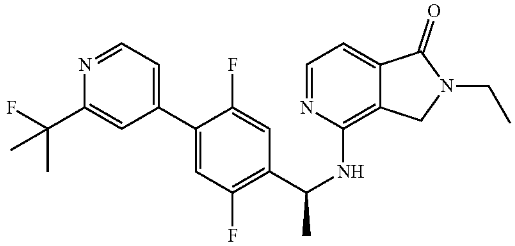 [SMILES: CCN1Cc2c(ccnc2N[C@@H](C)c2cc(F)c(-c3ccnc(C(C)(C)F)c3)cc2F)C1=O] (S)-4-((1-(2,5-difluoro-4-(2-(2-fluoropropan-2-yl)pyridin-4-yl)phenyl)ethyl)amino)-2-ethyl-2,3-dihydro-1H-pyrrolo[3,4-c]pyridin-1-one |
| 103 | 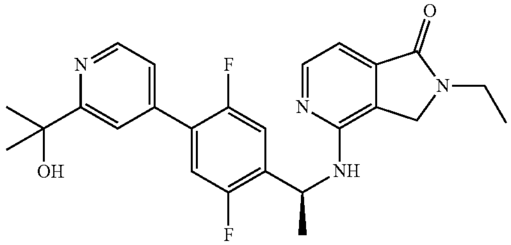 [SMILES: CCN1Cc2c(ccnc2N[C@@H](C)c2cc(F)c(-c3ccnc(C(C)(C)O)c3)cc2F)C1=O] (S)-4-((1-(2,5-difluoro-4-(2-(2-hydroxypropan-2-yl)pyridin-4-yl)phenyl)ethyl)amino)-2-ethyl-2,3-dihydro-1H-pyrrolo[3,4-c]pyridin-1-one |
| 104 | 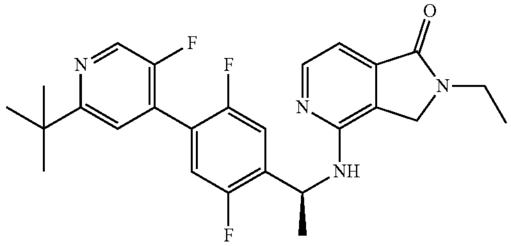 [SMILES: CCN1Cc2c(ccnc2N[C@@H](C)c2cc(F)c(-c3cc(C(C)(C)C)ncc3F)cc2F)C1=O] (S)-4-((1-(4-(2-(tert-butyl)-5-fluoropyridin-4-yl)-2,5-difluorophenyl)ethyl)amino)-2-ethyl-2,3-dihydro-1H-pyrrolo[3,4-c]pyridin-1-one |

-continued

| Compound No. | Structure and Nomenclature |
|---|---|
| 105 | 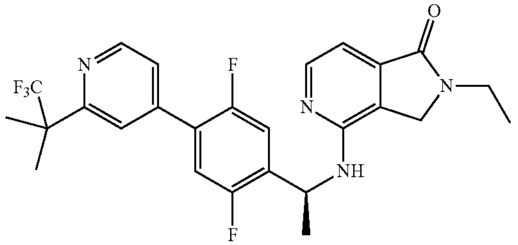 [SMILES: CCN1Cc2c(ccnc2N[C@@H](C)c2cc(F)c(-c3ccnc(C(C)(C)C(F)(F)F)c3)cc2F)C1=O] (S)-4-((1-(2,5-difluoro-4-(2-(1,1,1-trifluoro-2-methylpropan-2-yl)pyridin-4-yl)phenyl)ethyl)amino)-2-ethyl-2,3-dihydro-1H-pyrrolo[3,4-c]pyridin-1-one |
| 106 | 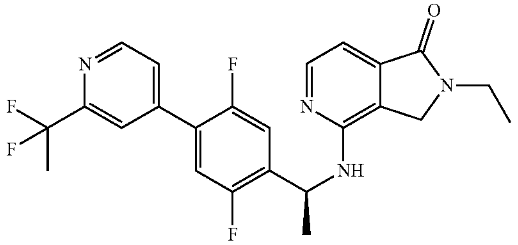 [SMILES: CCN1Cc2c(ccnc2N[C@@H](C)c2cc(F)c(-c3ccnc(C(C)(F)F)c3)cc2F)C1=O] (S)-4-((1-(4-(2-(1,1-difluoroethyl)pyridin-4-yl)-2,5-difluorophenyl)ethyl)amino)-2-ethyl-2,3-dihydro-1H-pyrrolo[3,4-c]pyridin-1-one |
| 107 | 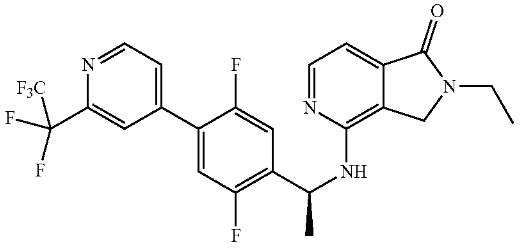 [SMILES: CCN1Cc2c(ccnc2N[C@@H](C)c2cc(F)c(-c3ccnc(C(F)(F)C(F)(F)F)c3)cc2F)C1=O] (S)-4-((1-(2,5-difluoro-4-(2-(perfluoroethyl)pyridin-4-yl)phenyl)ethyl)amino)-2-ethyl-2,3-dihydro-1H-pyrrolo[3,4-c]pyridin-1-one |
| 108 | 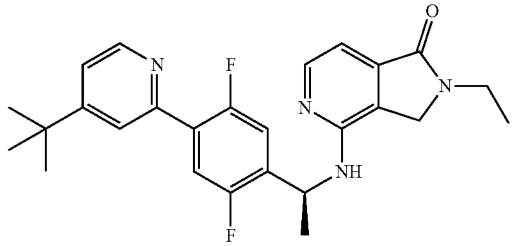 [SMILES: CCN1Cc2c(ccnc2N[C@@H](C)c2cc(F)c(-c3cc(C(C)(C)C)ccn3)cc2F)C1=O] (S)-4-((1-(4-(4-(tert-butyl)pyridin-2-yl)-2,5-difluorophenyl)ethyl)amino)-2-ethyl-2,3-dihydro-1H-pyrrolo[3,4-c]pyridin-1-one |
| 109 | 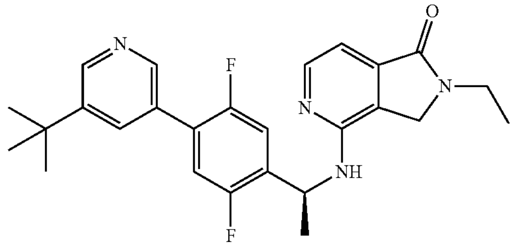 [SMILES: CCN1Cc2c(ccnc2N[C@@H](C)c2cc(F)c(-c3cncc(C(C)(C)C)c3)cc2F)C1=O] |

-continued

| Compound No. | Structure and Nomenclature |
|---|---|
| | (S)-4-((1-(4-(5-(tert-butyl)pyridin-3-yl)-2,5-difluorophenyl)ethyl)amino)-2-ethyl-2,3-dihydro-1H-pyrrolo[3,4-c]pyridin-1-one |
| 110 | 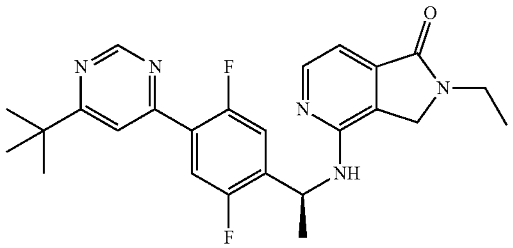 [SMILES: CCN1Cc2c(ccnc2N[C@@H](C)c2cc(F)c(-c3cc(C(C)(C)C)ncn3)cc2F)C1=O] (S)-4-((1-(4-(6-(tert-butyl)pyrimidin-4-yl)-2,5-difluorophenyl)ethyl)amino)-2-ethyl-2,3-dihydro-1H-pyrrolo[3,4-c]pyridin-1-one |
| 111 | 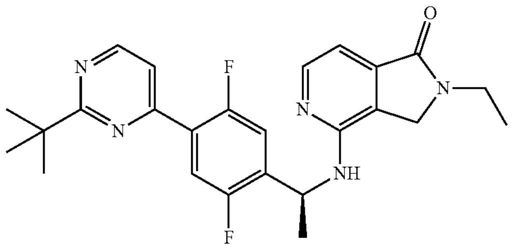 [SMILES: CCN1Cc2c(ccnc2N[C@@H](C)c2cc(F)c(-c3ccnc(C(C)(C)C)n3)cc2F)C1=O] (S)-4-((1-(4-(2-(tert-butyl)pyrimidin-4-yl)-2,5-difluorophenyl)ethyl)amino)-2-ethyl-2,3-dihydro-1H-pyrrolo[3,4-c]pyridin-1-one |
| 112 | 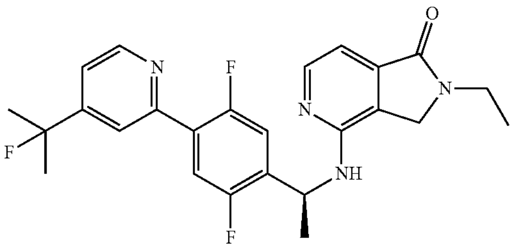 [SMILES: CCN1Cc2c(ccnc2N[C@@H](C)c2cc(F)c(-c3cc(C(C)(C)F)ccn3)cc2F)C1=O] (S)-4-((1-(2,5-difluoro-4-(4-(2-fluoropropan-2-yl)pyridin-2-yl)phenyl)ethyl)amino)-2-ethyl-2,3-dihydro-1H-pyrrolo[3,4-c]pyridin-1-one |
| 113 | 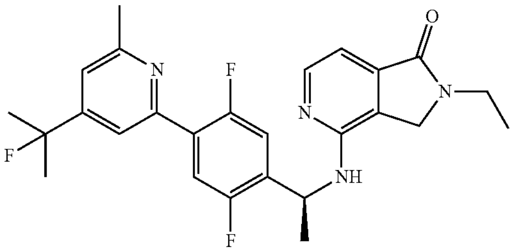 [SMILES: CCN1Cc2c(ccnc2N[C@@H](C)c2cc(F)c(-c3cc(C(C)(C)F)cc(C)n3)cc2F)C1=O] (S)-4-((1-(2,5-difluoro-4-(4-(2-fluoropropan-2-yl)-6-methylpyridin-2-yl)phenyl)ethyl)amino)-2-ethyl-2,3-dihydro-1H-pyrrolo[3,4-c]pyridin-1-one |

-continued

| Compound No. | Structure and Nomenclature |
|---|---|
| 114 | 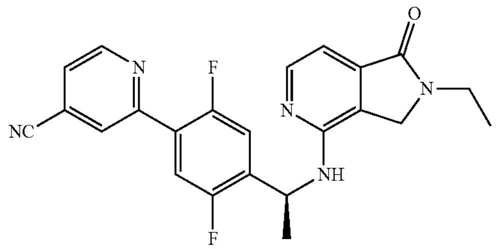 [SMILES: CCN1Cc2c(ccnc2N[C@@H](C)c2cc(F)c(-c3cc(C#N)ccn3)cc2F)C1=O] (S)-2-(4-(1-((2-ethyl-1-oxo-2,3-dihydro-1H-pyrrolo[3,4-c]pyridin-4-yl)amino)ethyl)-2,5-difluorophenyl)isonicotinonitrile |
| 115 | 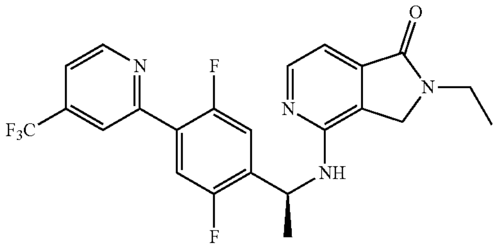 [SMILES: CCN1Cc2c(ccnc2N[C@@H](C)c2cc(F)c(-c3cc(C(F)(F)F)ccn3)cc2F)C1=O] (S)-4-((1-(2,5-difluoro-4-(4-(trifluoromethyl)pyridin-2-yl)phenyl)ethyl)amino)-2-ethyl-2,3-dihydro-1H-pyrrolo[3,4-c]pyridin-1-one |
| 116 | 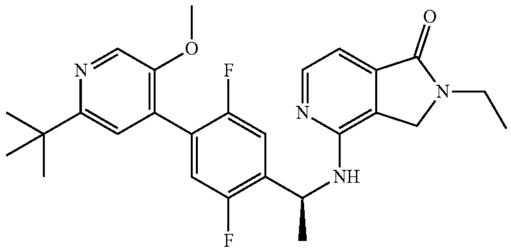 [SMILES: CCN1Cc2c(ccnc2N[C@@H](C)c2cc(F)c(-c3cc(C(C)(C)C)ncc3OC)cc2F)C1=O] (S)-4-((1-(4-(2-(tert-butyl)-5-methoxypyridin-4-yl)-2,5-difluorophenyl)ethyl)amino)-2-ethyl-2,3-dihydro-1H-pyrrolo[3,4-c]pyridin-1-one |
| 117 | 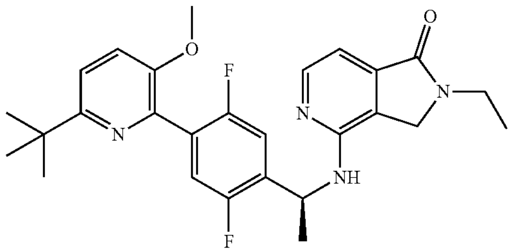 [SMILES: CCN1Cc2c(ccnc2N[C@@H](C)c2cc(F)c(-c3nc(C(C)(C)C)ccc3OC)cc2F)C1=O] (S)-4-((1-(4-(6-(tert-butyl)-3-methoxypyridin-2-yl)-2,5-difluorophenyl)ethyl)amino)-2-ethyl-2,3-dihydro-1H-pyrrolo[3,4-c]pyridin-1-one |

-continued

| Compound No. | Structure and Nomenclature |
| --- | --- |
| 118 | 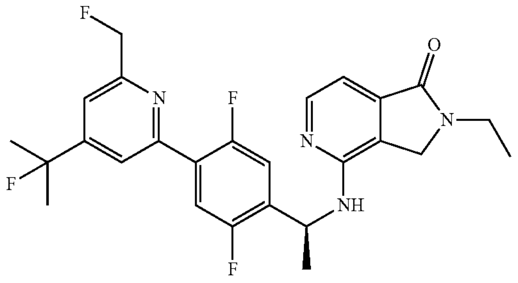 [SMILES: CCN1Cc2c(ccnc2N[C@@H](C)c2cc(F)c(-c3cc(C(C)(C)F)cc(CF)n3)cc2F)C1=O] (S)-4-((1-(2,5-difluoro-4-(6-(fluoromethyl)-4-(2-fluoropropan-2-yl)pyridin-2-yl)phenyl)ethyl)amino)-2-ethyl-2,3-dihydro-1H-pyrrolo[3,4-c]pyridin-1-one |
| 119 | 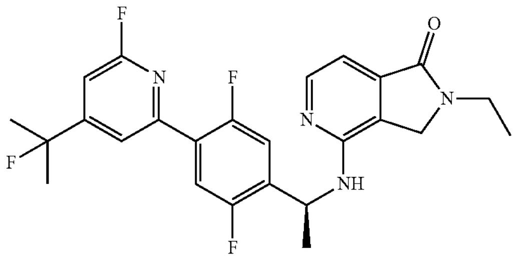 [SMILES: CCN1Cc2c(ccnc2N[C@@H](C)c2cc(F)c(-c3cc(C(C)(C)F)cc(F)n3)cc2F)C1=O] (S)-4-((1-(2,5-difluoro-4-(6-fluoro-4-(2-fluoropropan-2-yl)pyridin-2-yl)phenyl)ethyl)amino)-2-ethyl-2,3-dihydro-1H-pyrrolo[3,4-c]pyridin-1-one |
| 120 | 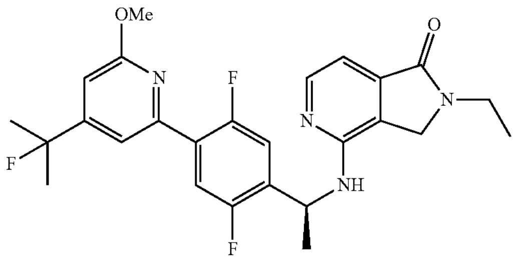 [SMILES: CCN1Cc2c(ccnc2N[C@@H](C)c2cc(F)c(-c3cc(C(C)(C)F)cc(OC)n3)cc2F)C1=O] (S)-4-((1-(2,5-difluoro-4-(4-(2-fluoropropan-2-yl)-6-methoxypyridin-2-yl)phenyl)ethyl)amino)-2-ethyl-2,3-dihydro-1H-pyrrolo[3,4-c]pyridin-1-one |
| 121 | 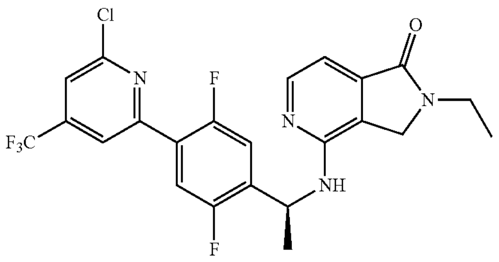 (S)-4-((1-(4-(6-chloro-4-(trifluoromethyl)pyridin-2-yl)-2,5-difluorophenyl)ethyl)amino)-2-ethyl-2,3-dihydro-1H-pyrrolo[3,4-c]pyridin-1-one |

-continued

| Compound No. | Structure and Nomenclature |
|---|---|
| 122 | 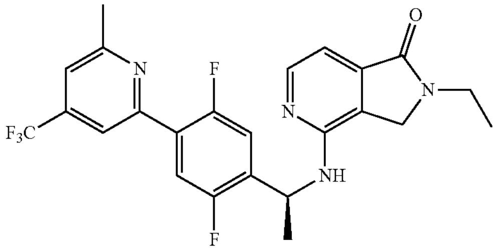 [SMILES: CCN1Cc2c(ccnc2N[C@@H](C)c2cc(F)c(-c3cc(C(F)(F)F)cc(C)n3)cc2F)C1=O] (S)-4-((1-(2,5-difluoro-4-(6-methyl-4-(trifluoromethyl)pyridin-2-yl)phenyl)ethyl)amino)-2-ethyl-2,3-dihydro-1H-pyrrolo[3,4-c]pyridin-1-one |
| 123 | 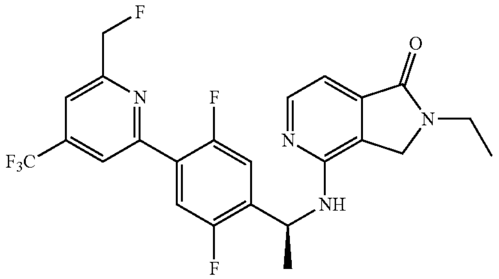 [SMILES: CCN1Cc2c(ccnc2N[C@@H](C)c2cc(F)c(-c3cc(C(F)(F)F)cc(CF)n3)cc2F)C1=O] (S)-4-((1-(2,5-difluoro-4-(6-(fluoromethyl)-4-(trifluoromethyl)pyridin-2-yl)phenyl)ethyl)amino)-2-ethyl-2,3-dihydro-1H-pyrrolo[3,4-c]pyridin-1-one |
| 124 | 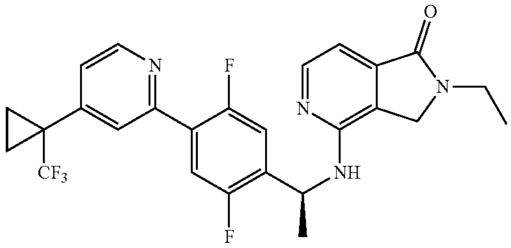 [SMILES: CCN1Cc2c(ccnc2N[C@@H](C)c2cc(F)c(-c3cc(C4(C(F)(F)F)CC4)ccn3)cc2F)C1=O] (S)-4-((1-(2,5-difluoro-4-(4-(1-(trifluoromethyl)cyclopropyl)pyridin-2-yl)phenyl)ethyl)amino)-2-ethyl-2,3-dihydro-1H-pyrrolo[3,4-c]pyridin-1-one |
| 125 | 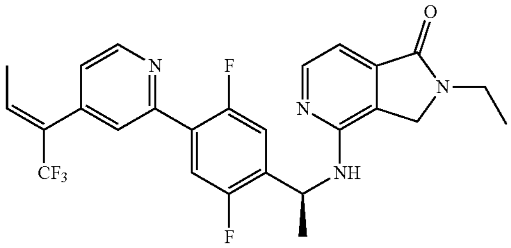 [SMILES: C/C=C(\c1ccnc(-c2cc(F)c([C@H](C)Nc3nccc4c3CN(CC)C4=O)cc2F)c1)C(F)(F)F] (S,E)-4-((1-(2,5-difluoro-4-(4-(1,1,1-trifluorobut-2-en-2-yl)pyridin-2-yl)phenyl)ethyl)amino)-2-ethyl-2,3-dihydro-1H-pyrrolo[3,4-c]pyridin-1-one |

-continued

| Compound No. | Structure and Nomenclature |
|---|---|
| 126 | 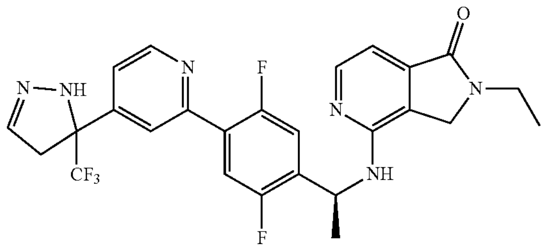 [SMILES: CCN1Cc2c(ccnc2N[C@@H](C)c2cc(F)c(-c3cc(C4(C(F)(F)F)CC=NN4)ccn3)cc2F)C1=O]<br>4-(((1S)-1-(2,5-difluoro-4-(4-(5-(trifluoromethyl)-4,5-dihydro-1H-pyrazol-5-yl)pyridin-2-yl)phenyl)ethyl)amino)-2-ethyl-2,3-dihydro-1H-pyrrolo[3,4-c]pyridin-1-one |
| 127 | 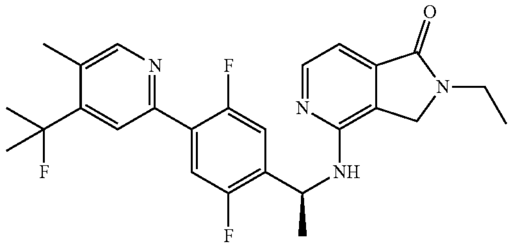 [SMILES: CCN1Cc2c(ccnc2N[C@@H](C)c2cc(F)c(-c3cc(C(C)(C)F)c(C)cn3)cc2F)C1=O]<br>(S)-4-((1-(2,5-difluoro-4-(4-(2-fluoropropan-2-yl)-5-methylpyridin-2-yl)phenyl)ethyl)amino)-2-ethyl-2,3-dihydro-1H-pyrrolo[3,4-c]pyridin-1-one |
| 128 | 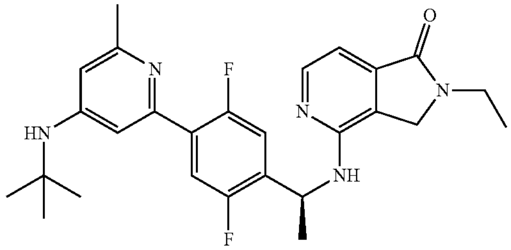<br>(S)-4-((1-(4-(4-(tert-butylamino)-6-methylpyridin-2-yl)-2,5-difluorophenyl)ethyl)amino)-2-ethyl-2,3-dihydro-1H-pyrrolo[3,4-c]pyridin-1-one |
| 129 | 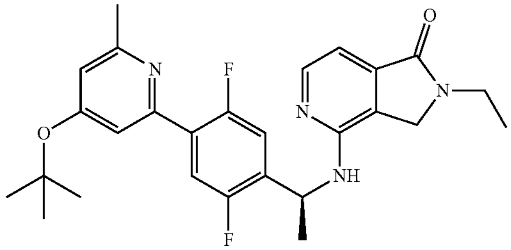 [SMILES: CCN1Cc2c(ccnc2N[C@@H](C)c2cc(F)c(-c3cc(OC(C)(C)C)cc(C)n3)cc2F)C1=O]<br>(S)-4-((1-(4-(4-(tert-butoxy)-6-methylpyridin-2-yl)-2,5-difluorophenyl)ethyl)amino)-2-ethyl-2,3-dihydro-1H-pyrrolo[3,4-c]pyridin-1-one |

-continued

| Compound No. | Structure and Nomenclature |
| --- | --- |
| 130 | 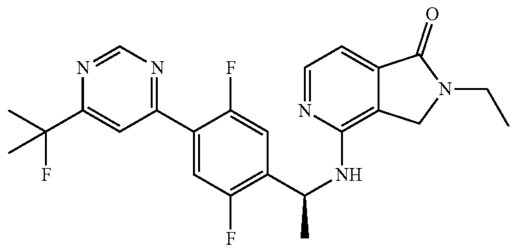 [SMILES: CCN1Cc2c(ccnc2N[C@@H](C)c2cc(F)c(-c3cc(C(C)(C)F)ncn3)cc2F)C1=O] (S)-4-((1-(2,5-difluoro-4-(6-(2-fluoropropan-2-yl)pyrimidin-4-yl)phenyl)ethyl)amino)-2-ethyl-2,3-dihydro-1H-pyrrolo[3,4-c]pyridin-1-one |
| 131 | 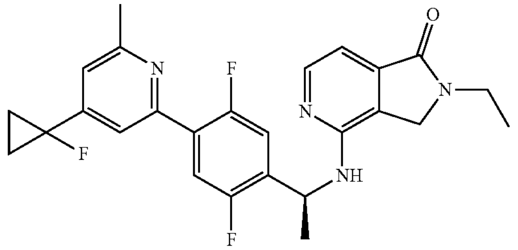 [SMILES: CCN1Cc2c(ccnc2N[C@@H](C)c2cc(F)c(-c3cc(C4(F)CC4)cc(C)n3)cc2F)C1=O] (S)-4-((1-(2,5-difluoro-4-(4-(1-fluorocyclopropyl)-6-methylpyridin-2-yl)phenyl)ethyl)amino)-2-ethyl-2,3-dihydro-1H-pyrrolo[3,4-c]pyridin-1-one |
| 132 | 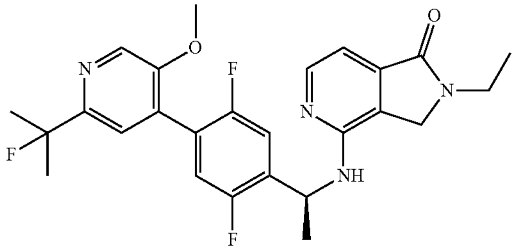 [SMILES: CCN1Cc2c(ccnc2N[C@@H](C)c2cc(F)c(-c3cc(C(C)(C)F)ncc3OC)cc2F)C1=O] (S)-4-((1-(2,5-difluoro-4-(2-(2-fluoropropan-2-yl)-5-methoxypyridin-4-yl)phenyl)ethyl)amino)-2-ethyl-2,3-dihydro-1H-pyrrolo[3,4-c]pyridin-1-one |
| 133 | 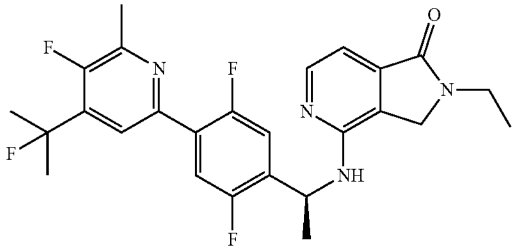 [SMILES: CCN1Cc2c(ccnc2N[C@@H](C)c2cc(F)c(-c3cc(C(C)(C)F)c(F)c(C)n3)cc2F)C1=O] (S)-4-((1-(2,5-difluoro-4-(5-fluoro-4-(2-fluoropropan-2-yl)-6-methylpyridin-2-yl)phenyl)ethyl)amino)-2-ethyl-2,3-dihydro-1H-pyrrolo[3,4-c]pyridin-1-one |

-continued

| Compound No. | Structure and Nomenclature |
|---|---|
| 134 | 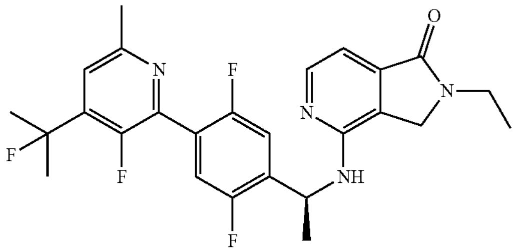 [SMILES: CCN1Cc2c(ccnc2N[C@@H](C)c2cc(F)c(-c3nc(C)cc(C(C)(C)F)c3F)cc2F)C1=O] (S)-4-((1-(2,5-difluoro-4-(3-fluoro-4-(2-fluoropropan-2-yl)-6-methylpyridin-2-yl)phenyl)ethyl)amino)-2-ethyl-2,3-dihydro-1H-pyrrolo[3,4-c]pyridin-1-one |
| 135 | 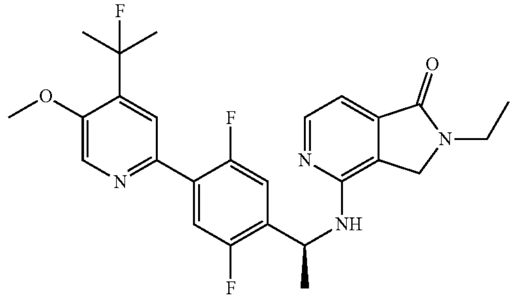 [SMILES: CCN1Cc2c(ccnc2N[C@@H](C)c2cc(F)c(-c3cc(C(C)(C)F)c(OC)cn3)cc2F)C1=O] (S)-4-((1-(2,5-difluoro-4-(4-(2-fluoropropan-2-yl)-5-methoxypyridin-2-yl)phenyl)ethyl)amino)-2-ethyl-2,3-dihydro-1H-pyrrolo[3,4-c]pyridin-1-one |
| 136 | 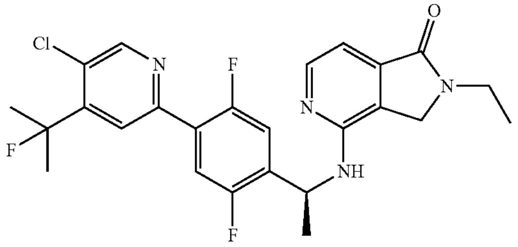 [SMILES: CCN1Cc2c(ccnc2N[C@@H](C)c2cc(F)c(-c3cc(C(C)(C)F)c(Cl)cn3)cc2F)C1=O] (S)-4-((1-(4-(5-chloro-4-(2-fluoropropan-2-yl)pyridin-2-yl)-2,5-difluorophenyl)ethyl)amino)-2-ethyl-2,3-dihydro-1H-pyrrolo[3,4-c]pyridin-1-one |
| 137 | 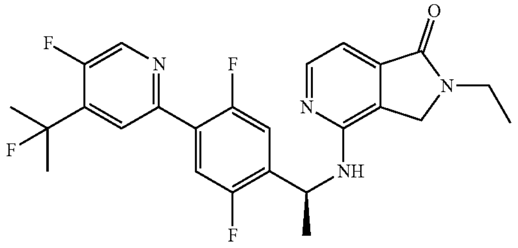 [SMILES: CCN1Cc2c(ccnc2N[C@@H](C)c2cc(F)c(-c3cc(C(C)(C)F)c(F)cn3)cc2F)C1=O] (S)-4-((1-(2,5-difluoro-4-(5-fluoro-4-(2-fluoropropan-2-yl)pyridin-2-yl)phenyl)ethyl)amino)-2-ethyl-2,3-dihydro-1H-pyrrolo[3,4-c]pyridin-1-one |

-continued

| Compound No. | Structure and Nomenclature |
|---|---|
| 138 | 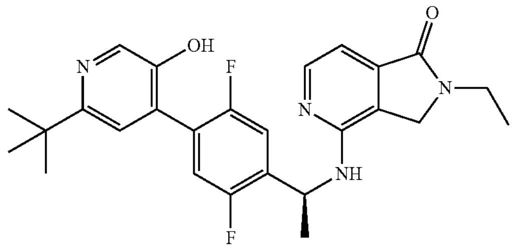 [SMILES: CCN1Cc2c(ccnc2N[C@@H](C)c2cc(F)c(-c3cc(C(C)(C)C)ncc3O)cc2F)C1=O] (S)-4-((1-(4-(2-(tert-butyl)-5-hydroxypyridin-4-yl)-2,5-difluorophenyl)ethyl)amino)-2-ethyl-2,3-dihydro-1H-pyrrolo[3,4-c]pyridin-1-one |
| 139 | 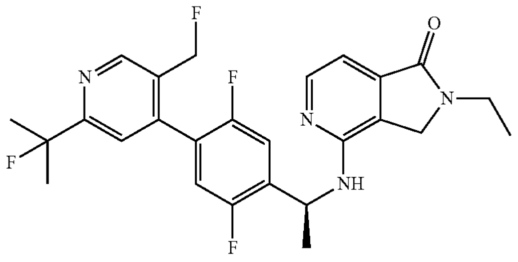 [SMILES: CCN1Cc2c(ccnc2N[C@@H](C)c2cc(F)c(-c3cc(C(C)(C)F)ncc3CF)cc2F)C1=O] (S)-4-((1-(2,5-difluoro-4-(5-(fluoromethyl)-2-(2-fluoropropan-2-yl)pyridin-4-yl)phenyl)ethyl)amino)-2-ethyl-2,3-dihydro-1H-pyrrolo[3,4-c]pyridin-1-one |
| 141 | 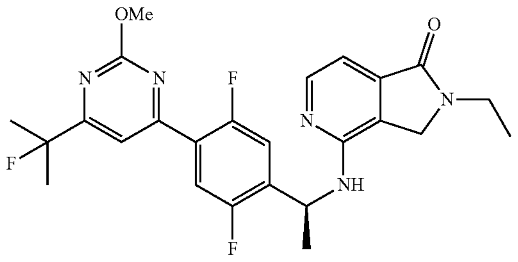 [SMILES: CCN1Cc2c(ccnc2N[C@@H](C)c2cc(F)c(-c3cc(C(C)(C)F)nc(OC)n3)cc2F)C1=O] (S)-4-((1-(2,5-difluoro-4-(6-(2-fluoropropan-2-yl)-2-methoxypyrimidin-4-yl)phenyl)ethyl)amino)-2-ethyl-2,3-dihydro-1H-pyrrolo[3,4-c]pyridin-1-one |
| 142 | 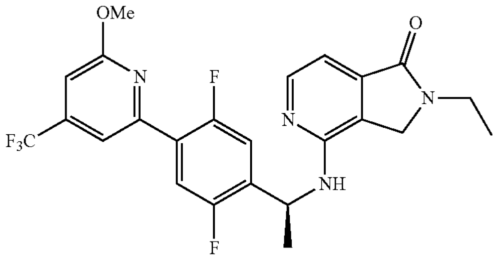 [SMILES: CCN1Cc2c(ccnc2N[C@@H](C)c2cc(F)c(-c3cc(C(F)(F)F)cc(OC)n3)cc2F)C1=O] (S)-4-((1-(2,5-difluoro-4-(6-methoxy-4-(trifluoromethyl)pyridin-2-yl)phenyl)ethyl)amino)-2-ethyl-2,3-dihydro-1H-pyrrolo[3,4-c]pyridin-1-one |

-continued

| Compound No. | Structure and Nomenclature |
|---|---|
| 143 | 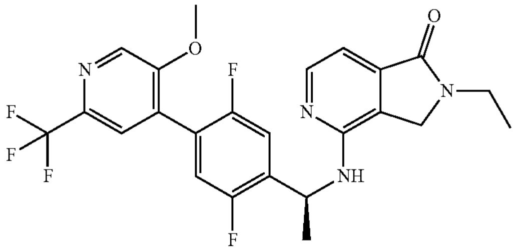 [SMILES: CCN1Cc2c(ccnc2N[C@@H](C)c2cc(F)c(-c3cc(C(F)(F)F)ncc3OC)cc2F)C1=O] (S)-4-((1-(2,5-difluoro-4-(5-methoxy-2-(trifluoromethyl)pyridin-4-yl)phenyl)ethyl)amino)-2-ethyl-2,3-dihydro-1H-pyrrolo[3,4-c]pyridin-1-one |
| 144 | 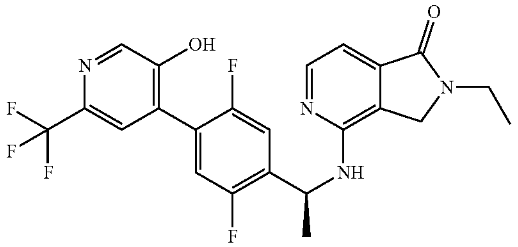 [SMILES: CCN1Cc2c(ccnc2N[C@@H](C)c2cc(F)c(-c3cc(C(F)(F)F)ncc3O)cc2F)C1=O] (S)-4-((1-(2,5-difluoro-4-(5-hydroxy-2-(trifluoromethyl)pyridin-4-yl)phenyl)ethyl)amino)-2-ethyl-2,3-dihydro-1H-pyrrolo[3,4-c]pyridin-1-one |
| 145 | 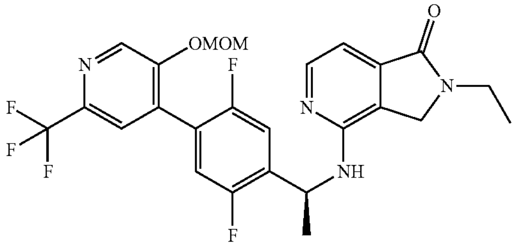 (S)-4-((1-(2,5-difluoro-4-(5-(methoxymethoxy)-2-(trifluoromethyl)pyridin-4-yl)phenyl)ethyl)amino)-2-ethyl-2,3-dihydro-1H-pyrrolo[3,4-c]pyridin-1-one |
| 146 | 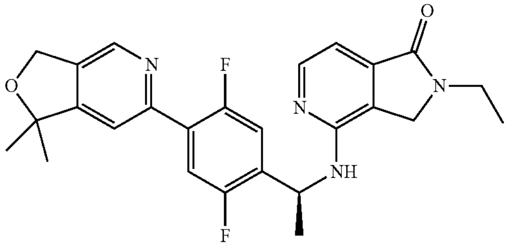 [SMILES: CCN1Cc2c(ccnc2N[C@@H](C)c2cc(F)c(-c3cc4c(cn3)COC4(C)C)cc2F)C1=O] (S)-4-((1-(4-(1,1-dimethyl-1,3-dihydrofuro[3,4-c]pyridin-6-yl)-2,5-difluorophenyl)ethyl)amino)-2-ethyl-2,3-dihydro-1H-pyrrolo[3,4-c]pyridin-1-one |

-continued

| Compound No. | Structure and Nomenclature |
|---|---|
| 147 | 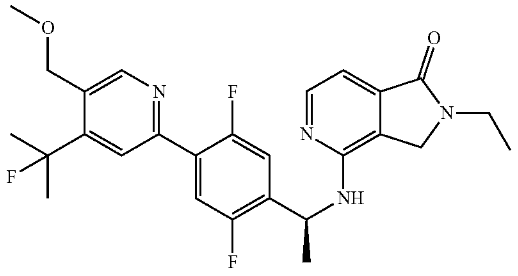 [SMILES: CCN1Cc2c(ccnc2N[C@@H](C)c2cc(F)c(-c3cc(C(C)(C)F)c(COC)cn3)cc2F)C1=O] (S)-4-((1-(2,5-difluoro-4-(4-(2-fluoropropan-2-yl)-5-(methoxymethyl)pyridin-2-yl)phenyl)ethyl)amino)-2-ethyl-2,3-dihydro-1H-pyrrolo[3,4-c]pyridin-1-one |
| 148 | 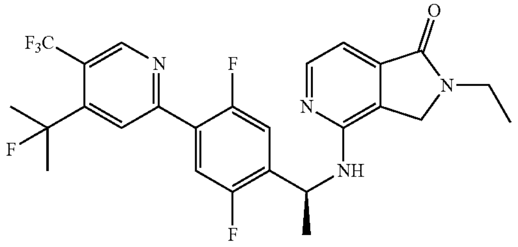 [SMILES: CCN1Cc2c(ccnc2N[C@@H](C)c2cc(F)c(-c3cc(C(C)(C)F)c(C(F)(F)F)cn3)cc2F)C1=O] (S)-4-((1-(2,5-difluoro-4-(4-(2-fluoropropan-2-yl)-5-(trifluoromethyl)pyridin-2-yl)phenyl)ethyl)amino)-2-ethyl-2,3-dihydro-1H-pyrrolo[3,4-c]pyridin-1-one |
| 149 | 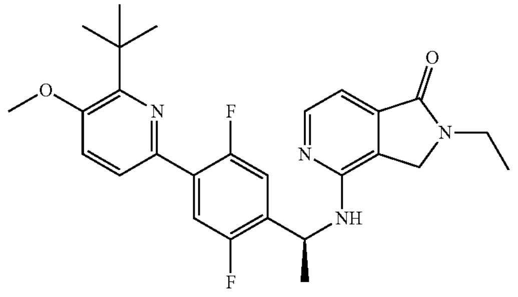 [SMILES: CCN1Cc2c(ccnc2N[C@@H](C)c2cc(F)c(-c3ccc(OC)c(C(C)(C)C)n3)cc2F)C1=O] (S)-4-((1-(4-(6-(tert-butyl)-5-methoxypyridin-2-yl)-2,5-difluorophenyl)ethyl)amino)-2-ethyl-2,3-dihydro-1H-pyrrolo[3,4-c]pyridin-1-one |
| 150 | 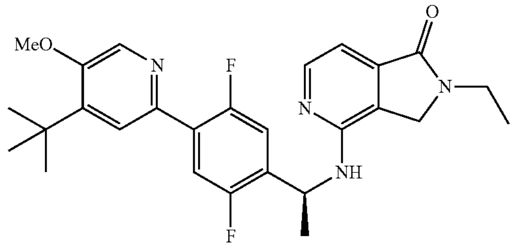 [SMILES: CCN1Cc2c(ccnc2N[C@@H](C)c2cc(F)c(-c3cc(C(C)(C)C)c(OC)cn3)cc2F)C1=O] (S)-4-((1-(4-(4-(tert-butyl)-5-methoxypyridin-2-yl)-2,5-difluorophenyl)ethyl)amino)-2-ethyl-2,3-dihydro-1H-pyrrolo[3,4-c]pyridin-1-one |

-continued

| Compound No. | Structure and Nomenclature |
| --- | --- |
| 151 | 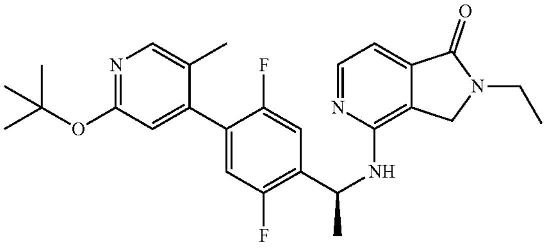 [SMILES: CCN1Cc2c(ccnc2N[C@@H](C)c2cc(F)c(-c3cc(OC(C)(C)C)ncc3C)cc2F)C1=O] (S)-4-((1-(4-(2-(tert-butoxy)-5-methylpyridin-4-yl)-2,5-difluorophenyl)ethyl)amino)-2-ethyl-2,3-dihydro-1H-pyrrolo[3,4-c]pyridin-1-one |
| 152 | 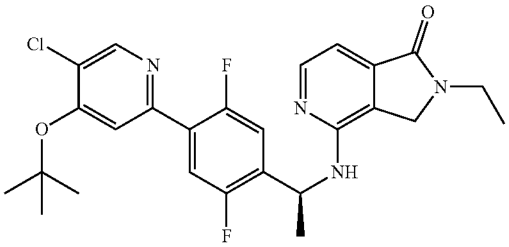 [SMILES: CCN1Cc2c(ccnc2N[C@@H](C)c2cc(F)c(-c3cc(OC(C)(C)C)c(Cl)cn3)cc2F)C1=O] (S)-4-((1-(4-(4-(tert-butoxy)-5-chloropyridin-2-yl)-2,5-difluorophenyl)ethyl)amino)-2-ethyl-2,3-dihydro-1H-pyrrolo[3,4-c]pyridin-1-one |
| 153 | 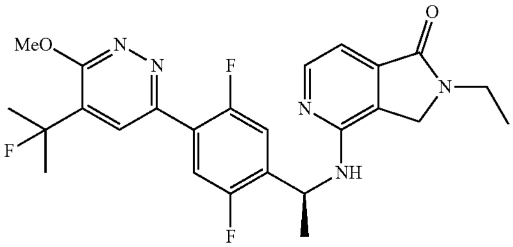 (S)-4-((1-(2,5-difluoro-4-(5-(2-fluoropropan-2-yl)-6-methoxypyridazin-3-yl)phenyl)ethyl)amino)-2-ethyl-2,3-dihydro-1H-pyrrolo[3,4-c]pyridin-1-one |
| 154 | 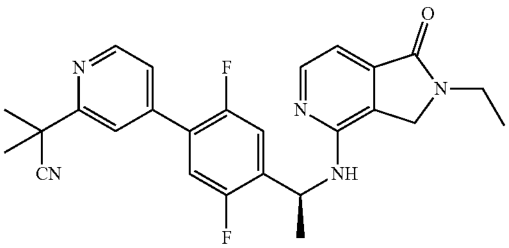 [SMILES: CCN1Cc2c(ccnc2N[C@@H](C)c2cc(F)c(-c3ccnc(C(C)(C)C#N)c3)cc2F)C1=O] (S)-2-(4-(4-(1-((2-ethyl-1-oxo-2,3-dihydro-1H-pyrrolo[3,4-c]pyridin-4-yl)amino)ethyl)-2,5-difluorophenyl)pyridin-2-yl)-2-methylpropanenitrile |

-continued

| Compound No. | Structure and Nomenclature |
|---|---|
| 155 | 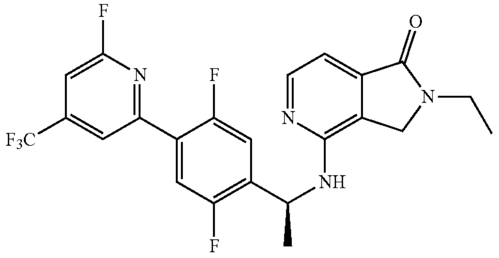 [SMILES: CCN1Cc2c(ccnc2N[C@@H](C)c2cc(F)c(-c3cc(C(F)(F)F)cc(F)n3)cc2F)C1=O] (S)-4-((1-(2,5-difluoro-4-(6-fluoro-4-(trifluoromethyl)pyridin-2-yl)phenyl)ethyl)amino)-2-ethyl-2,3-dihydro-1H-pyrrolo[3,4-c]pyridin-1-one |
| 156 | 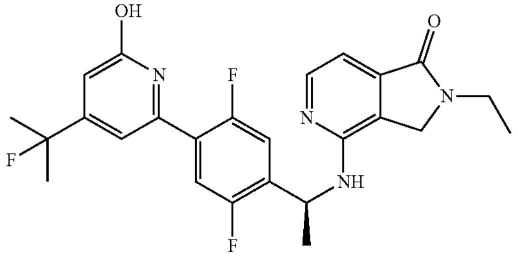 [SMILES: CCN1Cc2c(ccnc2N[C@@H](C)c2cc(F)c(-c3cc(C(C)(C)F)cc(O)n3)cc2F)C1=O] (S)-4-((1-(2,5-difluoro-4-(4-(2-fluoropropan-2-yl)-6-hydroxypyridin-2-yl)phenyl)ethyl)amino)-2-ethyl-2,3-dihydro-1H-pyrrolo[3,4-c]pyridin-1-one |
| 157 | 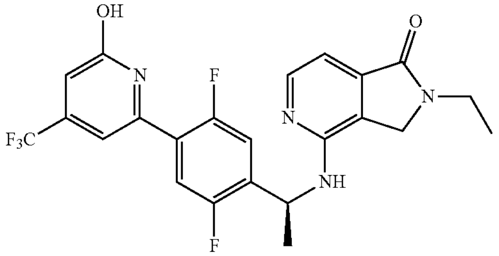 [SMILES: CCN1Cc2c(ccnc2N[C@@H](C)c2cc(F)c(-c3cc(C(F)(F)F)cc(O)n3)cc2F)C1=O] (S)-4-((1-(2,5-difluoro-4-(6-hydroxy-4-(trifluoromethyl)pyridin-2-yl)phenyl)ethyl)amino)-2-ethyl-2,3-dihydro-1H-pyrrolo[3,4-c]pyridin-1-one |
| 158 | 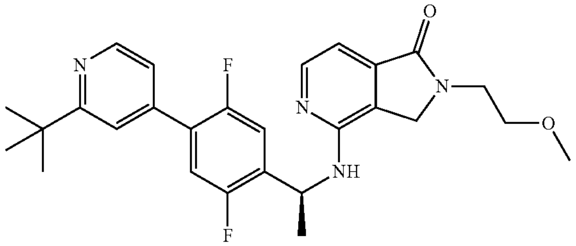 [SMILES: COCCN1Cc2c(ccnc2N[C@@H](C)c2cc(F)c(-c3ccnc(C(C)(C)C)c3)cc2F)C1=O] (S)-4-((1-(4-(2-(tert-butyl)pyridin-4-yl)-2,5-difluorophenyl)ethyl)amino)-2-(2-methoxyethyl)-2,3-dihydro-1H-pyrrolo[3,4-c]pyridin-1-one |

-continued

| Compound No. | Structure and Nomenclature |
|---|---|
| 159 | 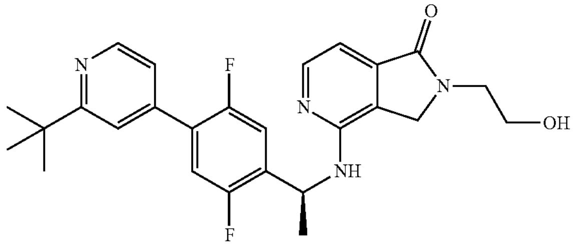 [SMILES: C[C@H](Nc1nccc2c1CN(CCO)C2=O)c1cc(F)c(-c2ccnc(C(C)(C)C)c2)cc1F] (S)-4-((1-(4-(2-(tert-butyl)pyridin-4-yl)-2,5-difluorophenyl)ethyl)amino)-2-(2-hydroxyethyl)-2,3-dihydro-1H-pyrrolo[3,4-c]pyridin-1-one |
| 160 | 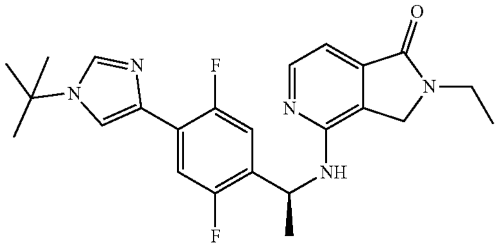 [SMILES: CCN1Cc2c(ccnc2N[C@@H](C)c2cc(F)c(-c3cn(C(C)(C)C)cn3)cc2F)C1=O] (S)-4-((1-(4-(1-(tert-butyl)-1H-imidazol-4-yl)-2,5-difluorophenyl)ethyl)amino)-2-ethyl-2,3-dihydro-1H-pyrrolo[3,4-c]pyridin-1-one |
| 161 | 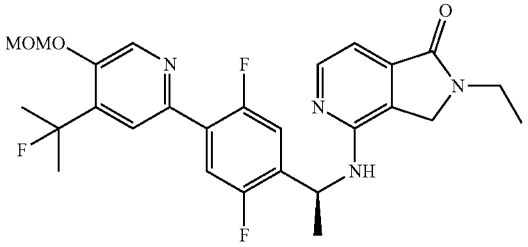 (S)-4-((1-(2,5-difluoro-4-(4-(2-fluoropropan-2-yl)-5-(methoxymethoxy)pyridin-2-yl)phenyl)ethyl)amino)-2-ethyl-2,3-dihydro-1H-pyrrolo[3,4-c]pyridin-1-one |
| 162 | 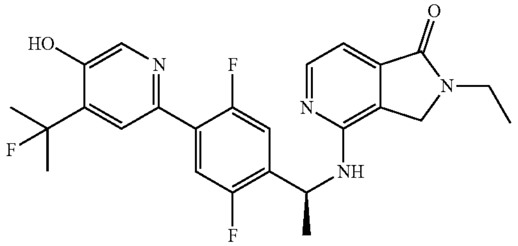 (S)-4-((1-(2,5-difluoro-4-(4-(2-fluoropropan-2-yl)-5-hydroxypyridin-2-yl)phenyl)ethyl)amino)-2-ethyl-2,3-dihydro-1H-pyrrolo[3,4-c]pyridin-1-one |
| 163 | 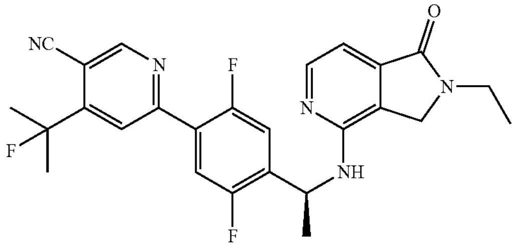 |

-continued

| Compound No. | Structure and Nomenclature |
|---|---|
| | (S)-6-(4-(1-((2-ethyl-1-oxo-2,3-dihydro-1H-pyrrolo[3,4-c]pyridin-4-yl)amino)ethyl)-2,5-difluorophenyl)-4-(2-fluoropropan-2-yl)nicotinonitrile |
| 164 | 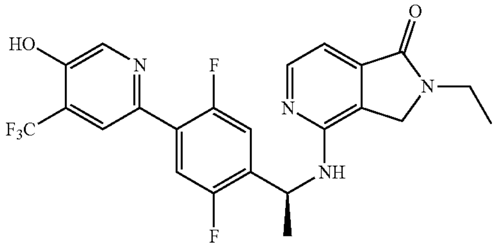 [SMILES: CCN1Cc2c(ccnc2N[C@@H](C)c2cc(F)c(-c3cc(C(F)(F)F)c(O)cn3)cc2F)C1=O] (S)-4-((1-(2,5-difluoro-4-(5-hydroxy-4-(trifluoromethyl)pyridin-2-yl)phenyl)ethyl)amino)-2-ethyl-2,3-dihydro-1H-pyrrolo[3,4-c]pyridin-1-one |
| 165 | 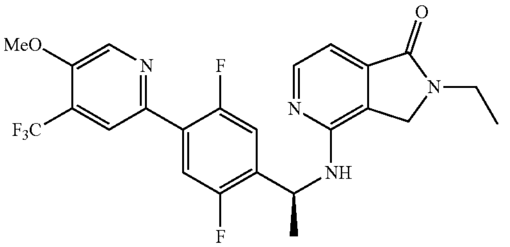 [SMILES: CCN1Cc2c(ccnc2N[C@@H](C)c2cc(F)c(-c3cc(C(F)(F)F)c(OC)cn3)cc2F)C1=O] (S)-4-((1-(2,5-difluoro-4-(5-methoxy-4-(trifluoromethyl)pyridin-2-yl)phenyl)ethyl)amino)-2-ethyl-2,3-dihydro-1H-pyrrolo[3,4-c]pyridin-1-one |

Compounds provided herein are described with reference to both generic formulae and specific compounds. In addition, compounds of the present disclosure may exist in a number of different forms or derivatives, all within the scope of the present disclosure. These include, for example, tautomers, stereoisomers, racemic mixtures, regioisomers, salts, prodrugs, solvated forms, different crystal forms or polymorphs, and active metabolites.

The compounds of present disclosure can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the present disclosure are enantiopure compounds. In certain embodiments, mixtures of enantiomers or diastereomers are provided.

The term "enantiomer" refers to two stereoisomers of a compound which are non-superimposable mirror images of one another. The term "diastereomer" refers to a pair of optical isomers which are not mirror images of one another. Diastereomers have different physical properties, e.g. melting points, boiling points, spectral properties, and reactivities.

Furthermore, certain compounds, as described herein may have one or more double bonds that can exist as either the Z or E isomer, unless otherwise indicated. The present disclosure additionally encompasses the compounds as individual isomers substantially free of other isomers and alternatively, as mixtures of various isomers, e.g., racemic mixtures of enantiomers. In addition to the above-mentioned compounds per se, this disclosure also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a stereoisomer may, in some embodiments, be provided substantially free of one or more corresponding stereoisomers, and may also be referred to as "stereochemically enriched".

Where a particular enantiomer is preferred, it may, in some embodiments be provided substantially free of the opposite enantiomer, and may also be referred to as "optically enriched". "Optically enriched", as used herein, means that the compound is made up of a significantly greater proportion of one enantiomer. In certain embodiments, the compound is made up of at least about 90% by weight of a preferred enantiomer. In other embodiments, the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, IN 1972).

The compounds of the present disclosure may also exist in different tautomeric forms, and all such forms are embraced within the scope of the present disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol, amide-imidic acid, lactam-lactim, imine-enamine isomerizations and annular forms where a proton can occupy two or more positions of a heterocyclic system (for example, 1H- and 3H-imidazole, 1H-, 2H- and 4H-1,2,4-triazole, 1H- and 2H-isoindole, and 1H- and 2H-pyrazole). Valence tautomers include interconversions by reorganization of some of the bonding electrons. Tautomers can be in equilibrium or sterically locked into one form by appropriate substitution. Compounds of the present disclosure identified by name or structure as one particular tautomeric form are intended to include other tautomeric forms unless otherwise specified.

The compounds of the present disclosure also include prodrugs, active metabolic derivatives (active metabolites), active intermediates, and their pharmaceutically acceptable salts.

As used herein, the term "prodrugs" refers to compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound. Prodrugs may proceed from prodrug form to active form in a single step or may have one or more intermediate forms which may themselves have activity or may be inactive. Preparation and use of prodrugs is discussed in T. Higuchi and V. Stella, "Pro-drugs as Novel Delivery Systems", Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

As used herein, the term "metabolite", e.g., active metabolite overlaps with prodrug as described above. Thus, such metabolites are pharmacologically active compounds or compounds that further metabolize to pharmacologically active compounds that are derivatives resulting from metabolic process in the body of a subject. For example, such metabolites may result from oxidation, reduction, hydrolysis, amidation, deamidation, esterification, deesterification, enzymatic cleavage, and the like, of the administered compound or salt or prodrug. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques know in the art. See, e.g., Bertolini et al, 1997, J Med Chem 40:2011-2016; Shan et al., J Pharm Sci 86:756-757; Bagshawe, 1995, DrugDev Res 34:220-230; Wermuth, supra.

As used herein, the term "active intermediate" refers to intermediate compound in the synthetic process, which exhibits the same or essentially the same biological activity as the final synthesized compound.

Compounds of the present disclosure can be formulated as or be in the form of pharmaceutically acceptable salts. Unless specified to the contrary, a compound provided herein includes pharmaceutically acceptable salts of such compound.

As used herein, the term "pharmaceutically acceptable" indicates that the substance or composition is compatible chemically and/or toxicologically, with the other ingredients comprising a formulation, and/or the subjects being treated therewith.

As used herein, the term "pharmaceutically acceptable salt", unless otherwise indicated, includes salts that retain the biological effectiveness of the free acids and bases of the specified compound and that are not biologically or otherwise undesirable. Contemplated pharmaceutically acceptable salt forms include, but are not limited to, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, $19^{th}$ ed., Mack Publishing Co., Easton, PA, Vol. 2, p. 1457, 1995; "Handbook of Pharmaceutical Salts: Properties, Selection, and Use" by Stahl and Wermuth, Wiley-VCH, Weinheim, Germany, 2002. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. Thus, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as L-glycine, L-lysine, and L-arginine, ammonia, primary, secondary, and tertiary amines, and cyclic amines, such as hydroxyethylpyrrolidine, piperidine, morpholine or piperazine, and inorganic salts derived from sodium, calcium, potassium, magnesium, manganese, iron, copper, zinc, aluminum and lithium.

It is also to be understood that the compounds of present disclosure can exist in unsolvated forms, solvated forms (e.g., hydrated forms), and solid forms (e.g., crystal or polymorphic forms), and the present disclosure is intended to encompass all such forms.

As used herein, the term "solvate" or "solvated form" refers to solvent addition forms that contain either stoichiometric or non stoichiometric amounts of solvent. Some compounds have a tendency to trap a fixed molar ratio of solvent molecules in the crystalline solid state, thus forming a solvate. If the solvent is water, the solvate formed is a hydrate; and if the solvent is alcohol, the solvate formed is an alcoholate. Hydrates are formed by the combination of one or more molecules of water with one molecule of the substance in which the water retains its molecular state as $H_2O$. Examples of solvents that form solvates include, but are not limited to, water, isopfopanol, ethanol, methanol, DMSO, ethyl acetate, acetic acid, and ethanolamine.

As used herein, the terms "crystal form", "crystalline form", "polymorphic forms" and "polymorphs" can be used interchangeably, and mean crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The present disclosure is also intended to include all isotopes of atoms in the compounds. Isotopes of an atom include atoms having the same atomic number but different mass numbers. For example, unless otherwise specified, hydrogen, carbon, nitrogen, oxygen, phosphorous, sulphur, fluorine, chlorine, bromide or iodine in the compounds of present disclosure are meant to also include their isotopes, such as but not limited to $^{1}H$, $^{2}H$, $^{3}H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{19}F$, $^{35}Cl$, $^{37}Cl$, $^{79}Br$, $^{81}Br$ $^{127}I$ and $^{131}I$. In some embodiments, hydrogen includes protium, deuterium and tritium. In some embodiments, carbon includes $^{12}C$ and $^{13}C$.

Synthesis of Compounds

Synthesis of the compounds provided herein, including pharmaceutically acceptable salts thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized in China for the purposes of research and potentially submission to regulatory agencies.

The reactions for preparing compounds of the present disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g. temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by one skilled in the art.

Preparation of compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g. $^{1}H$ or $^{13}C$), infrared spectroscopy, spectrophotometry (e.g. UV-visible), mass spectrometry, or by chromatographic methods such as high performance liquid chromatography (HPLC), liquid chromatography-mass spectroscopy (LCMS), or thin layer chromatography (TLC). Compounds can be purified by one skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety), and normal phase silica chromatography.

For illustrative purposes, the following shows general synthetic route for preparing the compounds of the present disclosure as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

The compounds of Formula (I) can be synthesized as shown in Schemes A to D.

General Scheme A: Synthesis of the compounds of Formula (I)
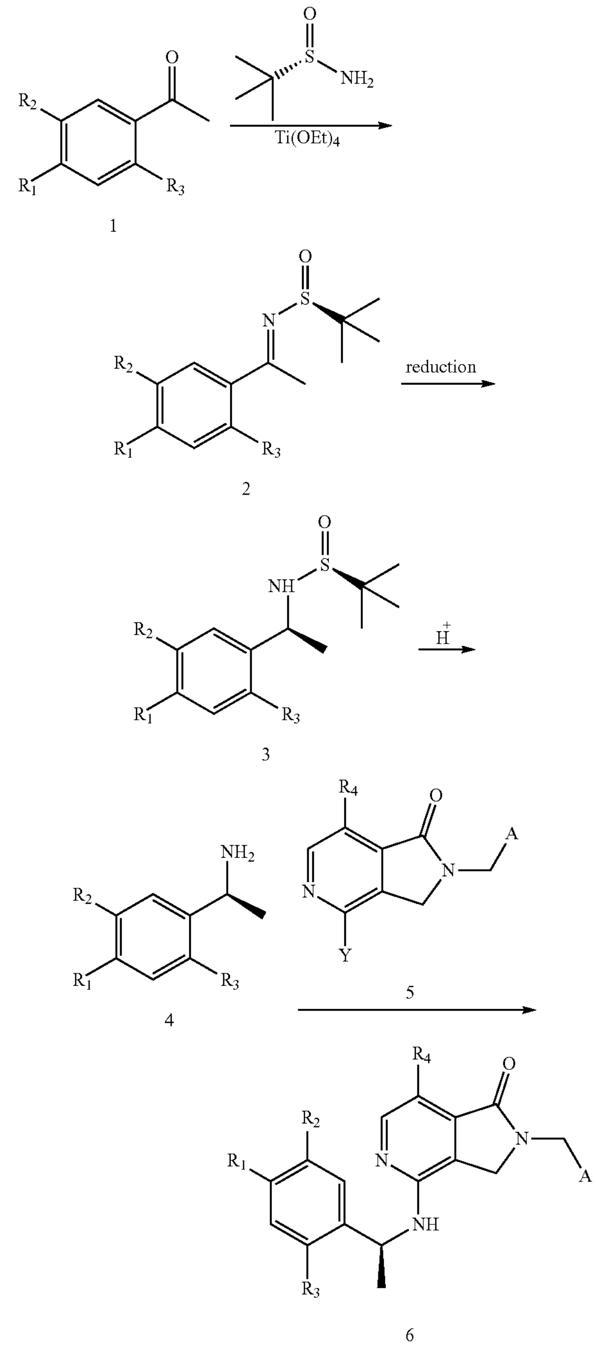
1
2
3
4
5
6
$R_1$ = H, Aryl, Alkyl, Aryloxyl, Alkoxyl
$R_2$, $R_3$, $R_4$ = H, F, $CH_3$
X = F, Cl
A = $CH_3$ or $OCH_3$ or $CH_2F$ or $CHF_2$
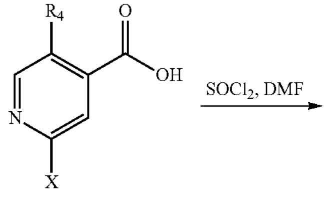
7
-continued
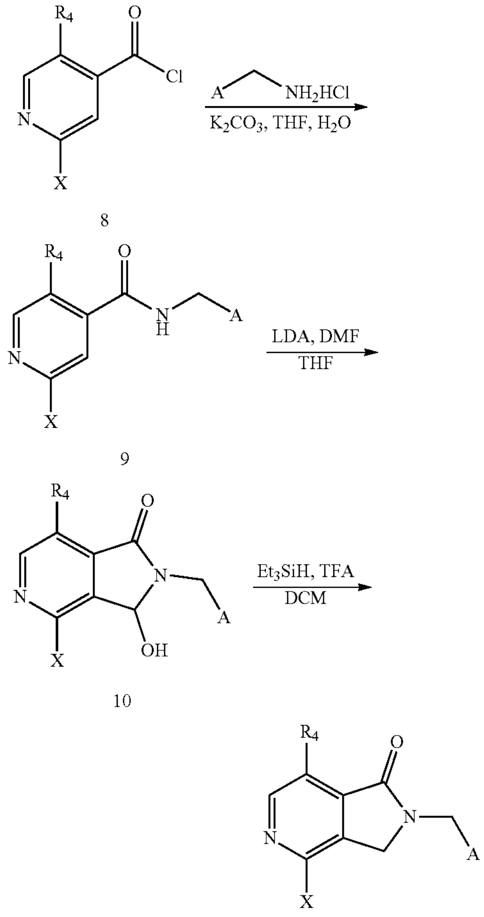
8
9
10
5
General Scheme B: Synthesis of the compounds of Formula (I)
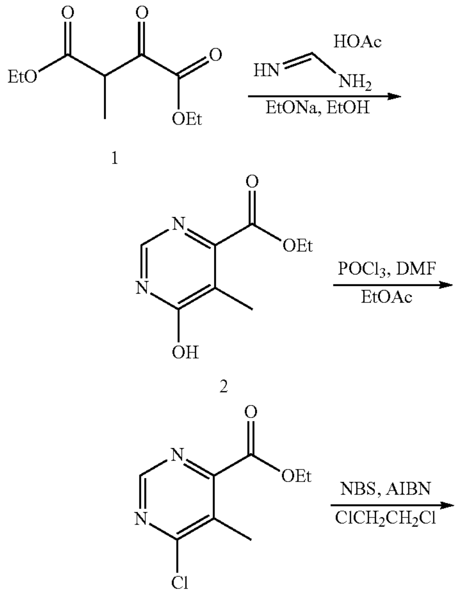
1
2
3

-continued
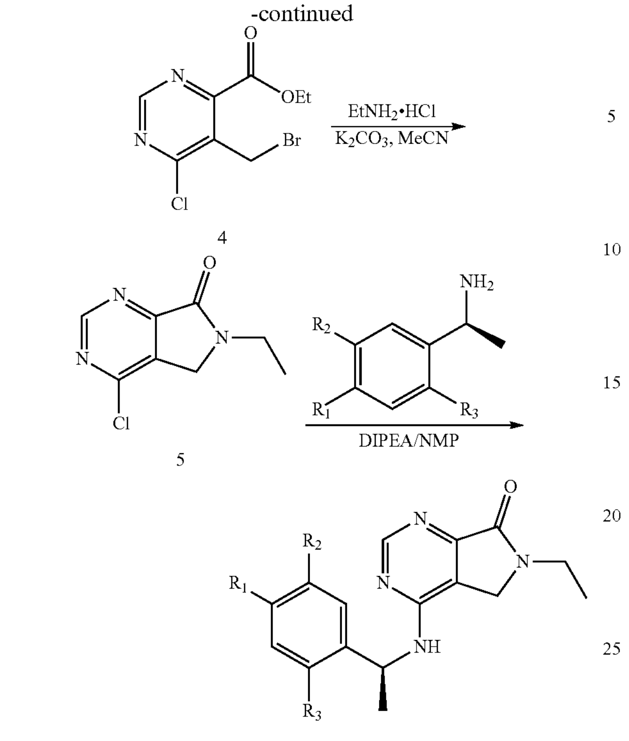
4
5
6
$R_1$ = H, Aryl, Alkyl, Aryloxyl, Alkoxyl
$R_2$, $R_3$ = H, F
General Scheme C: Synthesis of the compounds of Formula (I)
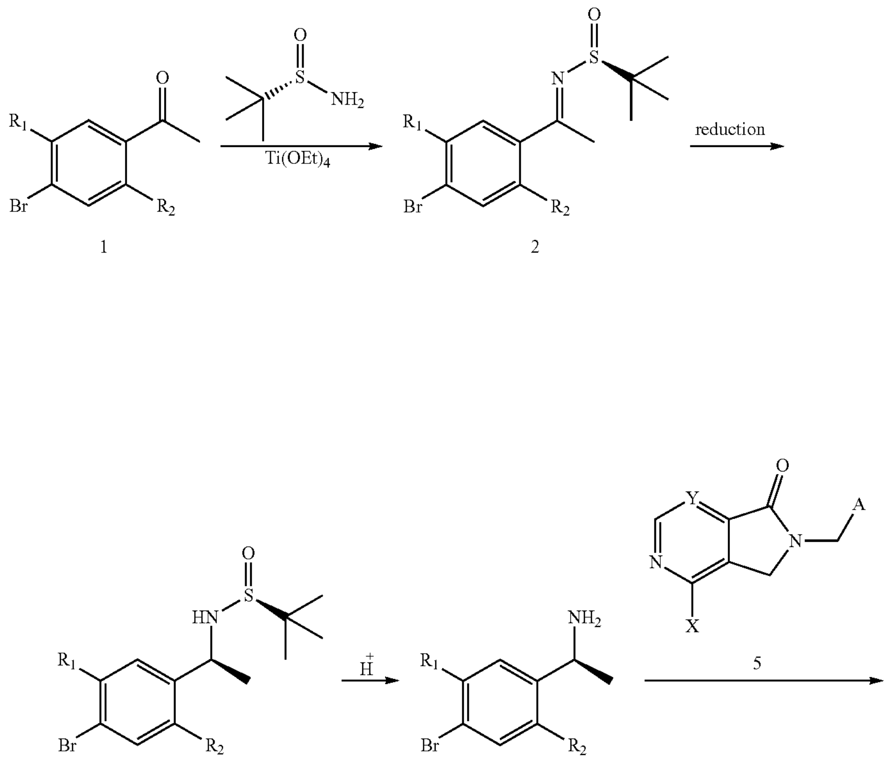
1
2
3
4

-continued

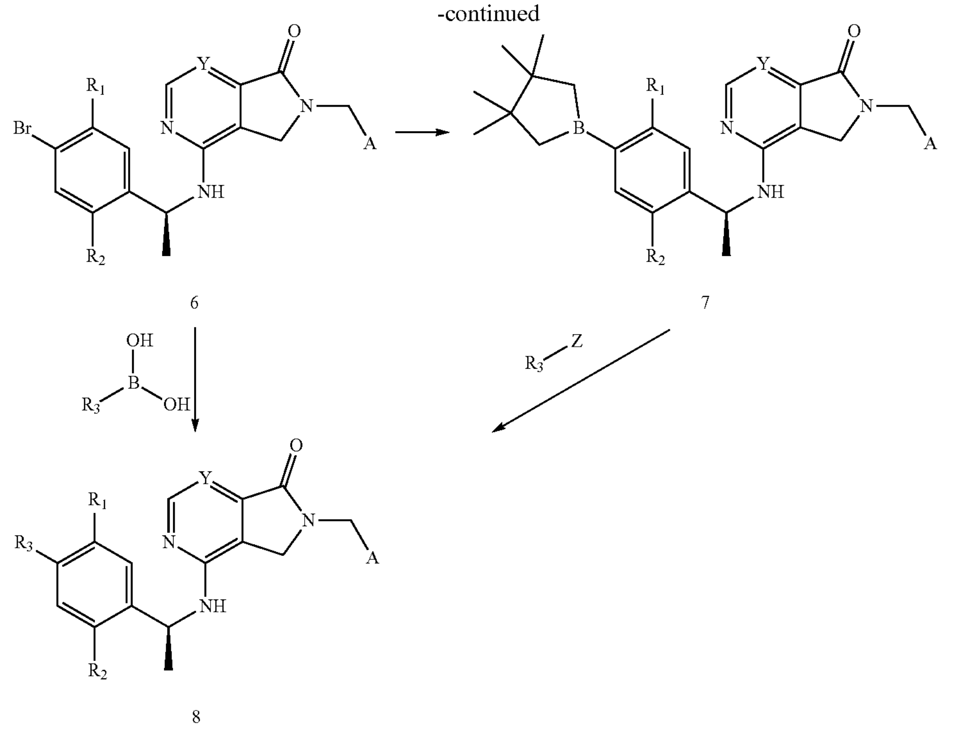

6

7

8

$R_1$, $R_2$ = H, F
$R_3$ = Aryl, Alkyl, cylcloalkyl
X = F, Cl
Y = CH, N, CF
Z = Cl, Br
A = $CH_3$ or $OCH_3$ or $CH_2F$ or $CHF_2$ General Scheme D: Synthesis of the compounds of Formula (i)

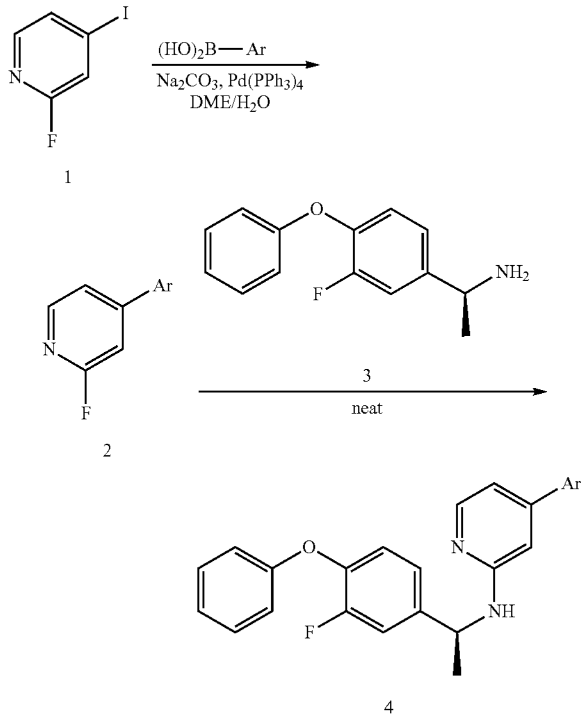

1

2

3

4

Use of Compounds

In an aspect, the compounds of Formula (I), Formula (Ia), Formula (Ib), Formula (Ic), Formula (Id), Formula (Ie), or pharmaceutically acceptable salts thereof can inhibit conversion of α-KG to D-2-HG.

In some embodiments, the compounds of present disclosure can inhibit the conversion of isocitrate to α-KG. In some embodiments, the compounds of present disclosure can inhibit both the conversion of α-KG to D-2-HG and the conversion of isocitrate to α-KG. In some embodiments, the compounds of the present disclosure can selectively inhibit conversion of α-KG to D-2-HG but not conversion of isocitrate to α-KG.

In another aspect, the compounds of Formula (I), Formula (Ia), Formula (Ib), Formula (Ic), Formula (Id), Formula (Ie), or pharmaceutically acceptable salts thereof can inhibit mutant IDH. In some embodiments, the compounds of Formula (I), Formula (Ia), Formula (Ib), Formula (Ic), Formula (Id), Formula (Ie), or pharmaceutically acceptable salts thereof can inhibit wild-type IDH. In some embodiments, the compounds of Formula (I), Formula (Ia), Formula (Ib), Formula (Ic), Formula (Id), Formula (Ie), or pharmaceutically acceptable salts thereof can inhibit both mutant IDH and wild-type IDH. In some embodiments, the compounds of Formula (I), Formula (Ia), Formula (Ib), Formula (Ic), Formula (Id), Formula (Ie), or pharmaceutically acceptable salts thereof can selectively inhibit mutant IDH but not wild-type IDH.

In some embodiments, compounds of the present disclosure inhibit wild-type IDH and/or mutant IDH with an $IC_{50}$ value of 0.01-1000 μM, 0.01-500 μM, 0.01-100 μM, 0.01-80 μM, 0.01-50 μM, 0.01-40 μM, 0.01-30 μM, or 0.01-20 μM, 0.01-10 μM, 0.01-5 μM, or 0.01-1 μM, 0.01-0.5 μM, 0.01-0.1 μM, or 0.01-0.05 μM.

As used herein, the term "selectively inhibit mutant IDH" means that a provided compound inhibits mutant IDH in at least one assay described herein over wild-type IDH. In some embodiments, the compounds of the present disclosure are at least 2 to 500-fold more selective for mutant IDH over wild-type IDH. In some embodiments, the compounds of the present disclosure are at least 2-fold, 5-fold, 10-fold, 20-fold, 30-fold, 40-fold, 50-fold, 60-fold, 70-fold, 80-fold, 90-fold, 100-fold, 200-fold, 300-fold, 400-fold, or at least 500-fold more selective for mutant IDH over wild-type IDH.

Pharmaceutical Composition

The present disclosure provides pharmaceutical compositions comprising at least one compound disclosed herein. In some embodiments, the pharmaceutical composition comprises more than one compounds disclosed herein. In some embodiments, the pharmaceutical composition comprises one or more compounds disclosed herein, and a pharmaceutical acceptable carrier.

The pharmaceutically acceptable carriers are conventional medicinal carriers in the art which can be prepared in a manner well known in the pharmaceutical art. In some embodiments, the compounds disclosed herein may be admixed with pharmaceutically acceptable carrier for the preparation of pharmaceutical composition.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments, compounds, materials, compositions, and/or dosage forms that are pharmaceutically acceptable refer to those approved by a regulatory agency (such as U.S. Food and Drug Administration, China Food and Drug Administration or European Medicines Agency) or listed in generally recognized pharmacopoeia (such as U.S. Pharmacopoeia, China Pharmacopoeia or European Pharmacopoeia) for use in animals, and more particularly in humans.

The term "pharmaceutically acceptable carrier" as used herein refers to a pharmaceutically acceptable material, composition or vehicle, such as a liquid or solid filler, diluent, excipient, solvent or encapsulating material, involved in carrying or transporting a compound provided herein from one location, body fluid, tissue, organ (interior or exterior), or portion of the body, to another location, body fluid, tissue, organ, or portion of the body. Pharmaceutically acceptable carriers can be vehicles, diluents, excipients, or other materials that can be used to contact the tissues of an animal without excessive toxicity or adverse effects. Exemplary pharmaceutically acceptable carriers include, sugars, starch, celluloses, malt, tragacanth, gelatin, Ringer's solution, alginic acid, isotonic saline, buffering agents, and the like. Pharmaceutically acceptable carrier that can be employed in present disclosure includes those generally known in the art, such as those disclosed in "Remington Pharmaceutical Sciences" Mack Pub. Co., New Jersey (1991), which is incorporated herein by reference.

Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18)Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The form of pharmaceutical compositions depends on a number of criteria, including, but not limited to, route of administration, extent of disease, or dose to be administered.

The pharmaceutical compositions can be formulated for oral, nasal, rectal, percutaneous, intravenous, or intramuscular administration. In accordance to the desired route of administration, the pharmaceutical compositions can be formulated in the form of tablets, capsule, pill, dragee, powder, granule, sachets, cachets, lozenges, suspensions, emulsions, solutions, syrups, aerosols (as a solid or in a liquid medium), spray, ointment, paste, cream, lotion, gel, patche, inhalant, or suppository.

The pharmaceutical compositions can be formulated so as to provide quick, sustained or delayed release of the active ingredient after administration to the patient by employing procedures known in the art. In some embodiments, the pharmaceutical composition is formulated in a sustained released form. As used herein, the term "sustained released form" refers to release of the active agent from the pharmaceutical composition so that it becomes available for bio-absorption in the subject, primarily in the gastrointestinal tract of the subject, over a prolonged period of time (extended release), or at a certain location (controlled release). In some embodiments, the prolonged period of time can be about 1 hour to 24 hours, 2 hours to 12 hours, 3 hours to 8 hours, 4 hours to 6 hours, 1 to 2 days or more. In certain embodiments, the prolonged period of time is at least about 4 hours, at least about 8 hours, at least about 12 hours, or at least about 24 hours. The pharmaceutical composition can be formulated in the form of tablet. For example, release rate of the active agent can not only be controlled by dissolution of the active agent in gastrointestinal fluid and subsequent diffusion out of the tablet or pills independent of pH, but can also be influenced by physical processes of disintegration and erosion of the tablet. In some embodiments, polymeric materials as disclosed in "Medical Applications of Controlled Release," Langer and Wise (eds.), CRC Pres., Boca Raton, Florida (1974); "Controlled Drug Bioavailability," Drug Product Design and Performance, Smolen and Ball (eds.), Wiley, New York (1984); Ranger and Peppas, 1983, J Macromol. Sci. Rev. Macromol Chem. 23:61; see also Levy et al., 1985, Science 228:190; During et al., 1989, Ann. Neurol. 25:351; Howard et al., 1989, J. Neurosurg. 71:105 can be used for sustained release. The above references are incorporated herein by reference in its entirety.

In certain embodiments, the pharmaceutical compositions comprise about 0.01 mg to about 1000 mg of the compounds provided herein (e.g. about 0.01 mg to about 10 mg, about 0.1 mg to about 10 mg, about 1 mg to about 10 mg, about 5 mg to about 10 mg, about 5 mg to about 20 mg, about 5 mg to about 30 mg, about 5 mg to about 40 mg, about 5 mg to about 50 mg, about 10 mg to about 100 mg, about 20 mg to about 100 mg, about 30 mg to about 100 mg, about 40 mg to about 100 mg, about 50 mg to about 100 mg, about 50 mg to about 200 mg, about 50 mg to about 300 mg, about 50 mg to about 400 mg, about 50 mg to about 500 mg, about 100 mg to about 200 mg, about 100 mg to about 300 mg, about 100 mg to about 400 mg, about 100 mg to about 500 mg, about 200 mg to about 500 mg, about 300 mg to about 500 mg, about 400 mg to about 500 mg, about 500 mg to about 1000 mg, about 600 mg to about 1000 mg, about 700 mg to about 1000 mg, about 800 mg to about 1000 mg, or about 900 mg to about 1000 mg). Suitable dosages per subject per day can be from about 5 mg to about 500 mg, preferably about 5 mg to about 50 mg, about 50 mg to about 100 mg, or about 50 mg to about 500 mg.

In certain embodiments, the pharmaceutical compositions can be formulated in a unit dosage form, each dosage containing from about 0.01 mg to about 10 mg, about 0.1 mg to about 10 mg, about 1 mg to about 10 mg, about 5 mg to about 10 mg, about 5 mg to about 20 mg, about 5 mg to about 30 mg, about 5 mg to about 40 mg, about 5 mg to about 50 mg, about 10 mg to about 100 mg, about 20 mg to about 100 mg, about 30 mg to about 100 mg, about 40 mg to about 100 mg, about 50 mg to about 100 mg, about 50 mg to about 200 mg, about 50 mg to about 300 mg, about 50 mg to about 400 mg, about 50 mg to about 500 mg, about 100 mg to about 200 mg, about 100 mg to about 300 mg, about 100 mg to about 400 mg, about 100 mg to about 500 mg, about 200 mg to about 500 mg, about 300 mg to about 500 mg, about 400 mg to about 500 mg, about 500 mg to about 1000 mg, about 600 mg to about 1000 mg, about 700 mg to about 1000 mg, about 800 mg to about 1000 mg, or about 900 mg to about 1000 mg of the compounds disclosed herein. The term "unit dosage forms" refers to physically discrete units suitable as unitary dosages for human subjects and other mammals, each unit containing a predetermined quantity of active material calculated to produce the desired therapeutic effect, in association with a suitable pharmaceutical carrier.

In some embodiments, the pharmaceutical compositions comprising one or more compounds disclosed herein as a first active ingredient, and further comprises a second active ingredient. The second active ingredient can be any anticancer agent known in the art. Representative examples of the anticancer agent for treating cancers or tumors may include, but are not limited to, cell signal transduction inhibitors (e.g., imatinib, gefitinib, bortezomib, erlotinib, sorafenib, sunitinib, dasatinib, vorinostat, lapatinib, temsirolimus, nilotinib, everolimus, pazopanib, trastuzumab, bevacizumab, cetuximab, ranibizumab, pegaptanib, panitumumab and the like), mitosis inhibitors (e.g., paclitaxel, vincristine, vinblastine and the like), alkylating agents (e.g., cisplatin, cyclophosphamide, chromabucil, carmustine and the like), anti-metabolites (e.g., methotrexate, 5-FU and the like), intercalating anticancer agents, (e.g., actinomycin, anthracycline, bleomycin, mitomycin-C and the like), topoisomerase inhibitors (e.g., irinotecan, topotecan, teniposide and the like), immunotherapic agents (e.g., interleukin, interferon and the like) and antihormonal agents (e.g., tamoxifen, raloxifene and the like). In some embodiments, the second active agent is one or more of Ibrutinib, Venetoclax, Imatinib Mesylate, Nilotinib Hydrochloride, Bosutinib, Dasatinib, Etoposide, Fludarabine Phosphate, Ponatinib, Vincristine Sulfate, Methotrexate, Cyclophosphamide, Lomustine, Teniposide, Temozolomide, Fotemustine, Carmustine, Bevacizumab, Picibanil, Fluorouracil, Melphalan, Emcitabine Hydrochloride.

Method for Treatment

The present disclosure provides a method of treating a disease associated with IDH, comprising administering to a subject an effective amount of one or more compounds, or pharmaceutically acceptable salts or the pharmaceutical composition disclosed herein.

As used herein, the term "subject" refers to an organism, tissue, or cell. A subject can include a human subject for medical purposes, such as diagnosis and/or treatment of an existing condition or disease or the prophylactic treatment for preventing the onset of a condition or disease, or an animal subject for medical, veterinary purposes, or developmental purposes. A subject also can include sample material from tissue culture, cell culture, organ replication, stem cell production and the like. Suitable animal subjects include mammals and avians. The term "mammal" as used herein includes, but is not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. The term "avian" as used herein includes, but is not limited to, chickens, ducks, geese, quail, turkeys, and pheasants. In some embodiments, the subject is a mammal or a mammalian cell. In some embodiments, the subject is a human or a human cell. Human subjects include, but are not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. A subject also can refer to cells or collections of cells in laboratory or bioprocessing culture in tests for viability, differentiation, marker production, expression, and the like.

As used herein, the term "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

In some embodiments, the one or more compounds or pharmaceutically acceptable salts thereof or the pharmaceutical composition disclosed herein is administered via a parenteral route or a non-parenteral route. In some embodiments, the one or more compounds or pharmaceutically acceptable salts thereof or the pharmaceutical composition is administered orally, enterally, buccally, nasally, intranasally, transmucosally, epidermally, transdermally, dermally, ophthalmically, pulmonary, sublingually, rectally, vaginally, topically, subcutaneously, intravenously, intramuscularly, intraarterially, intrathecally, intracapsularly, intraorbitally, intracardiacally, intradermally, intraperitoneally, transtracheally, subcuticularly, intra-articularly, subcapsularly, subarachnoidly, intraspinally, or intrasternally.

The compounds disclosed herein can be administrated in pure form, in a combination with other active ingredients or in the form of pharmaceutically composition of the present disclosure. In some embodiments, the compounds disclosed herein can be administered to a subject in need concurrently or sequentially in a combination with one or more anticancer agent(s) known in the art. In some embodiments, the administration is conducted once a day, twice a day, three times a day, or once every two days, once every three days, once every four days, once every five days, once every six days, once a week.

In certain embodiments, the present disclosure provides use of the compounds, pharmaceutically acceptable salts thereof, or pharmaceutical composition of the present disclosure in the manufacture of medicaments for treating diseases associated with the conversion of α-KG to D-2-HG. In certain embodiments, the present disclosure provides use of the compounds, pharmaceutically acceptable salts thereof, or pharmaceutical composition of the present disclosure in the manufacture of medicaments for treating diseases associated with the mutant IDH.

In certain embodiments, the diseases associated with the conversion of α-KG to D-2-HG are diseases associated with mutant IDH, including cancers.

In particular, the cancers include but are not limited to, leukemia, glioblastoma, melanoma, chondrosarcoma, cholangiocarcinoma, osteosarcoma, lymphoma, lung cancer, adenoma, myeloma, hepatocellular carcinoma, adrenocortical carcinoma, pancreatic cancer, breast cancer, prostate cancer, liver cancer, gastric cancer, colon cancer, colorectal cancer, ovarian cancer, cervical cancer, brain cancer, esophageal cancer, bone cancer, testicular cancer, skin cancer, kidney cancers, mesothelioma, neuroblastoma, thyroid cancer, head and neck cancers, esophageal cancers, eye cancers, prostate cancer, nasopharyngeal cancer, or oral cancer. In some embodiments, the cancers are leukemia, glioblastoma, or cholangiocarcinoma.

The compounds, pharmaceutically acceptable salts thereof, and pharmaceutical compositions thereof in the present disclosure can be used in the prevention or treatment of the onset or development of any of the diseases or conditions associated with the conversion of α-KG to D-2-HG in mammals especially in human. In some embodiments, the compounds, pharmaceutically acceptable salts thereof, and pharmaceutical compositions thereof in the present disclosure can be used in the prevention or treatment of the onset or development of any of the diseases or conditions associated with mutant IDH in mammals especially in human.

In such situation, the present disclosure also provides a method of screening patient suitable for treating with the compounds, pharmaceutically acceptable salts thereof, or pharmaceutical composition of the present disclosure alone or combined with other ingredients (e.g. an second active ingredient, e.g. anticancer agent). The method includes sequencing the tumor samples from patients and detecting the accumulation of D-2-HG in the patient or detecting the mutations status of IDH in the patient.

EXAMPLES

The followings further explain the general methods of the present disclosure. The compounds of the present disclosure may be prepared by the methods known in the art. The following illustrate the detailed preparation methods of the preferred compounds of the present disclosure. However, they are by no means limiting the preparation methods of the compounds of the present disclosure.

Synthetic Examples

The structures of the compounds in the following examples were characterized by nuclear magnetic resonance (NMR) or/and mass spectrometry (ESI). NMR shift (6) was given in the unit of $10^{-6}$ (ppm). $^1$H-NMR spectra was recorded in dimethyl sulfoxide-$d_6$ (DMSO-$d_6$) or $CDCl_3$ on a Varian Mercury VX 400 spectrometer with tetramethylsilane (TMS) as an internal standard.

ESI-HRMS measurement was carried out using Agilent 1260-6230 TOF LC-MS mass spectrometer.

High Performance Liquid Chromatography (HPLC) measurement was carried out on Agilent 1200 LC using the Phenomen C18 column (4.6 mm*150 mm, 0.4 m).

Thin layer chromatography was carried out using Yantai Huanghai HSGF254 silica gel plates. The silica gel plates used for thin layer chromatography (TLC) were 0.15 mm~0.2 mm. The silica gel plates used for separating and purifying products by TLC were 0.4 mm~0.5 mm.

Purified chromatographic column uses the silica gel as the carrier (200-300 mesh, producted by Yantai Huanghai co.).

The known starting materials of the present disclosure can be synthesized by using or according to the known methods in the art, or can be purchased from Alfa Aesar, Langcaster, TCI, Aldrich, Bepharm, and Scochem.

Unless otherwise specified, the reactions in the examples were all carried out under argon or nitrogen atmosphere. Argon or nitrogen atmosphere refers to that the reaction flask is connected to an argon or nitrogen balloon with a volume of about 1 L. Hydrogenation was usually carried out under vacuum, filled with hydrogen, and repeated for three times. Unless otherwise specified, the reaction temperature in the examples was ambient temperature, which was 20° C.-30° C.

The reaction progress in the examples was monitored by TLC. The eluent systems used for the reactions include dichloromethane-methanol system and petroleum ether-ethyl acetate system. The volume ratios of the solvents were adjusted according to the different polarities of compounds.

The elution system of column chromatography used for purifying compounds and eluent system of TLC include dichloromethane-methanol system and petroleum ether-ethyl acetate system. The volume ratios of the solvents were adjusted according to the different polarities of compounds. A small amount of alkaline or acidic agents such as triethylamine and acetic acid can be added for adjustment.

Abbreviations used in the following examples and elsewhere herein are:

| | |
|---|---|
| AcOH | acetic acid |
| AIBN | 2,2-azobis(2-methylpropionitrile) |
| ACN, MeCN | acetonitrile |
| DAST | diethylaminosulfur trifluoride |
| DCM | dichloromethane |
| DIPEA | N,N-diisopropylethylamine |
| DMAP | 4-(dimethylamino)pyridine |
| DMF | N,N-dimethylformamide |
| EtOAc | ethyl acetate |
| FA | formic acid |
| $H_2SO_4$ | sulfuricacid |
| HATU | o-(7-azabenzotriazol-1-yl)-N,N,N,N-tetramethyluroniumhexafluorophosphate |
| $K_2CO_3$ | potassium carbonate |
| KOAc | potassium acetate |
| LDA | lithium diisopropylamide |
| LiHMDS | lithium bis(trimethylsilyl)amide |
| MeOH | methanol |
| MOMCl | chloromethyl methyl ether |
| $N_2$ | nitrogen |
| $Na_2CO_3$ | sodium carbonate |
| $Na_2SO_4$ | sodium sulfate |
| NaHMDS | sodium bis(trimethylsilyl)amide |
| $NaBH_4$ | sodium borohydride |
| NBS | N-bromosuccinimide |
| NMP | 1-methyl-2-pyrrolidinone |
| $Pin_2B_2$ | bis(pinacolato)diboron |

| | |
|---|---|
| PMBCl | 4-methoxybenzyl chloride |
| Prep-HPLC | preparative HPLC |
| PPTS | pyridinium p-toluenesulfonate |
| Sphos | 2-dicyclohexylphosphino-2,6-dimethoxybiphenyl |
| TBAF | tetrabutylammonium fluoride |
| TEA | triethylamine |
| TFA | trifluoroaceticacid |
| THF | tetrahydrofuran |

Example 1

2-ethyl-4-[[(1S)-1-[3-fluoro-4-(1-methylindazol-5-yl)oxy-phenyl]ethyl]amino]-3H-pyrrolo[3,4-c]pyridin-1-one (1)

This compound was prepared according to General Scheme A. Specifically, the scheme was listed as follows.

Scheme 1

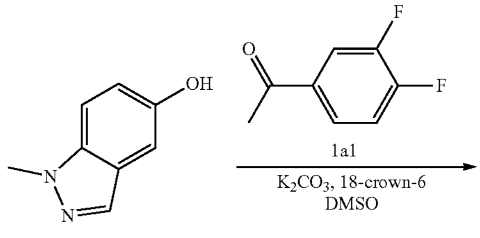

1a

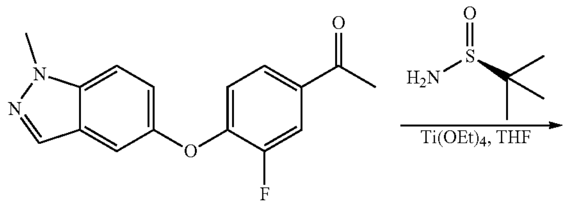

1b

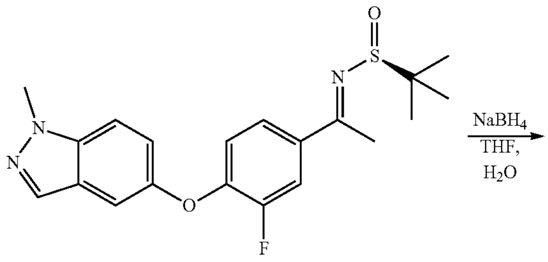

1c

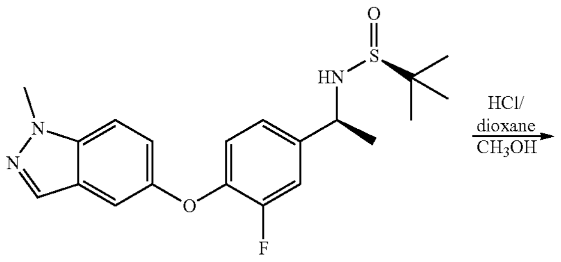

1d

-continued

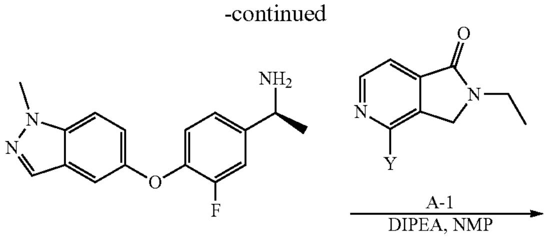

1e

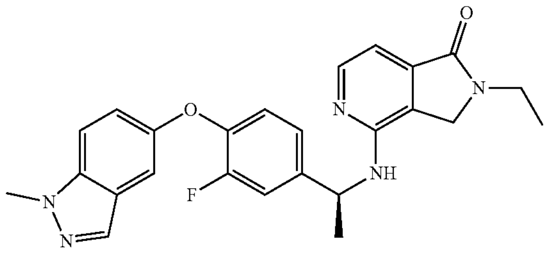

1

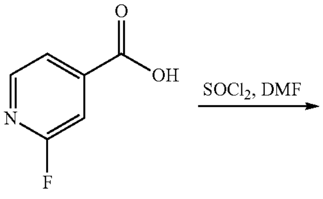

A-1a

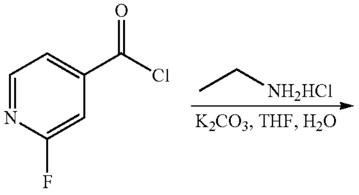

A-1b

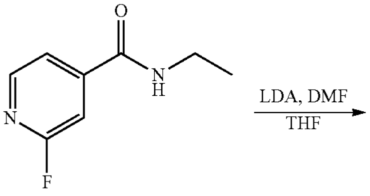

A-1c

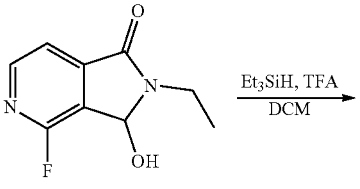

A-1d

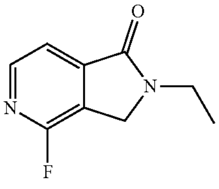

A-1

Step 1. 1-[3-fluoro-4-(1-methylindazol-5-yl)oxy-phenyl]ethanone (1b)

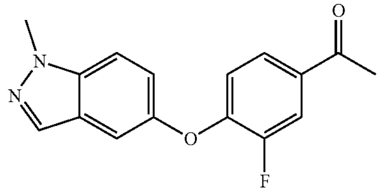 [SMILES: CC(=O)c1ccc(Oc2ccc3c(cnn3C)c2)c(F)c1]

To a mixture of 1-methylindazol-5-ol (1a, 1 g, 6.75 mmol), 1-(3,4-difluorophenyl)ethanone (1.16 g, 7.42 mmol), and 18-crown-6 (178 mg, 0.67 mmol) in DMSO (20 mL) was added $K_2CO_3$ (1.87 g, 13.5 mmol). Then the mixture was stirred at 120° C. under $N_2$ for 1 h. The mixture was poured into water (150 mL) and extracted with EtOAc (2×50 mL). The combined organic layers were washed with brine (50 mL), dried over $Na_2SO_4$, filtered, concentrated to give a residue. The residue was suspended in Petroleum ether (60 mL) and stirred for 30 min. An off-white solid was formed. The solid was filtered, collected and dried in vacuum to afford 1-[3-fluoro-4-(1-methylindazol-5-yl)oxy-phenyl] ethanone (1b, 1.7 g, 88.6% yield) as off-white solid.

$^1$H NMR (400 MHz, $CDCl_3$) δ: 7.95 (s, 1H), 7.81 (dd, J=2.0, 11.6 Hz, 1H), 7.65 (d, J=8.8 Hz, 1H), 7.44 (d, J=8.8 Hz, 1H), 7.39 (d, J=2.0 Hz, 1H), 7.21 (dd, J=2.4, 8.8 Hz, 1H), 6.88 (t, J=8.4 Hz, 1H), 4.12 (s, 3H), 2.58 (s, 3H). LC-MS: (ESI) m/z: 284.9 [M+H].

Step 2. N-[1-[3-fluoro-4-(1-methylindazol-5-yl)oxy-phenyl]ethylidene]-2-methyl-propane-2-sulfinamide (1c)

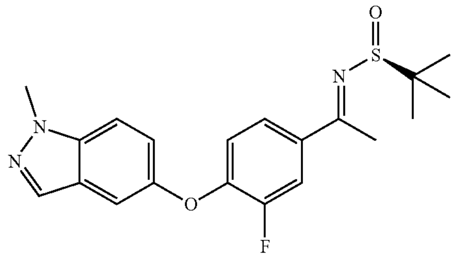 [SMILES: C/C(=N\[S@@](=O)C(C)(C)C)c1ccc(Oc2ccc3c(cnn3C)c2)c(F)c1]

To a mixture of 1-[3-fluoro-4-(1-methylindazol-5-yl)oxy-phenyl]ethanone (1b, 1.7 g, 5.98 mmol) and (S)-2-methyl-propane-2-sulfinamide (1.09 g, 8.97 mmol) in dry THF (30 mL) was added $Ti(OEt)_4$ (2.73 g, 11.96 mmol). Then the mixture was stirred at 70° C. under $N_2$ for 16 h. The mixture was poured into a mixture of water (100 mL) and EtOAc (100 mL) under stirring. After the mixture was stirred for 15 min, the mixture was filtered. The organic layer of the filtrate was separated and the aqueous layer was extracted with EtOAc (100 mL). The combined organic layers were washed with brine (100 mL), dried over $Na_2SO_4$ and filtered. The filtrate was concentrated and dried in vacuum to afford N-[1-[3-fluoro-4-(1-methylindazol-5-yl)oxy-phenyl]ethylidene]-2-methyl-propane-2-sulfinamide (1c, 2.3 g, 81.9% yield) as brown oil which will be used for the next step directly.

LC-MS: (ESI) m/z: 387.8 [M+H].

Step 3. (S)—N—((S)-1-(3-fluoro-4-((1-methyl-1H-indazol-5-yl)oxy)phenyl)ethyl)-2-methylpropane-2-sulfinamide (1d)

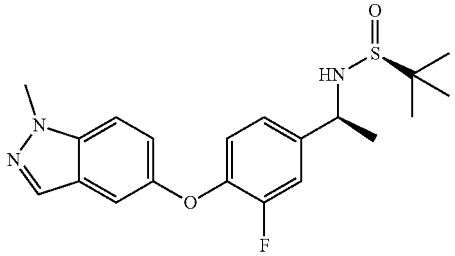 [SMILES: C[C@H](N[S@@](=O)C(C)(C)C)c1ccc(Oc2ccc3c(cnn3C)c2)c(F)c1]

To a solution of N-[1-[3-fluoro-4-(1-methylindazol-5-yl) oxy-phenyl]ethylidene]-2-methyl-propane-2-sulfinamide (1c, 2.3 g, 5.94 mmol) in THE (40 mL) and $H_2O$ (0.8 mL) was added $NaBH_4$ (674 mg, 17.81 mmol) at −50° C. in portions. After the mixture was stirred at −50° C. for 2 h, the mixture was warmed to 25° C. and stirred for 1 h. The mixture was poured into water (100 mL) and extracted with EtOAc (2×80 mL). The combined organic layers were washed with brine (100 mL), dried over $Na_2SO_4$, filtered and concentrated to give a residue. The residue was purified by flash chromatography on silica gel (Petroleum ether/EtOAc=1:1 (v/v)) to afford (S)—N—((S)-1-(3-fluoro-4-((1-methyl-1H-indazol-5-yl)oxy)phenyl)ethyl)-2-methylpropane-2-sulfinamide (1d, 2.0 g, 82% yield) as pale yellow oil.

$^1$H NMR (400 MHz, $CDCl_3$) δ: 7.90 (s, 1H), 7.39 (d, J=8.8 Hz, 1H), 7.25 (d, J=2.0 Hz, 1H), 7.22 (d, J=2.0 Hz, 1H), 7.20-7.18 (m, 1H), 7.05 (d, J=8.8 Hz, 1H), 6.96-6.90 (m, 1H), 4.53 (q, J=6.4 Hz, 1H), 4.09 (s, 3H), 3.42 (br s, 1H), 1.52 (d, J=6.4 Hz, 3H), 1.25 (s, 9H).

LC-MS: (ESI) m/z: 389.9 [M+H].

Step 4. (1S)-1-[3-fluoro-4-(1-methylindazol-5-yl) oxy-phenyl]ethanamine (1e)

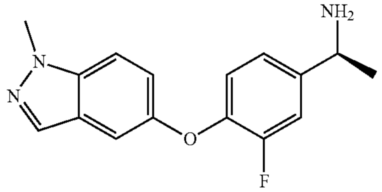 [SMILES: C[C@H](N)c1ccc(Oc2ccc3c(cnn3C)c2)c(F)c1]

To a mixture of (S)—N—((S)-1-(3-fluoro-4-((1-methyl-1H-indazol-5-yl)oxy)phenyl)ethyl)-2-methylpropane-2-sulfinamide (1d, 2.0 g, 5.13 mmol) in MeOH (20 mL) was added HCl/dioxane (4 M, 5 mL) dropwised. Then the mixture was stirred at 25° C. for 2 h. The mixture was poured into water (100 mL) and basified to pH=9 with solid $Na_2CO_3$. Then the mixture was extracted with EtOAc (2×50 mL). The combined organic layers were washed with brine (50 mL) and dried over $Na_2SO_4$. Then it was filtered, concentrated and dried in vacuum to afford (1S)-1-[3-fluoro-4-(1-methylindazol-5-yl)oxy-phenyl]ethanamine (1e, 1.5 g, crude) as brown oil which will be used for the next step directly.

LC-MS: (ESI) m/z: 286.8 [M+H].

Step 5. 2-fluoropyridine-4-carbonyl chloride (A-1b)

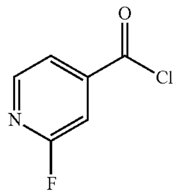

To a solution of 2-fluoropyridine-4-carboxylic acid (A-1a, 10 g, 70.87 mmol) in $SOCl_2$ (39 mL, 537.6 mmol) was added DMF (0.6 mL, 7.8 mmol) dropwise. The mixture was stirred at 80° C. for 1 h. The reaction mixture was concentrated and co-evaporated with DCM (2×100 mL) to afford 2-fluoropyridine-4-carbonyl chloride (A-1b, 13 g, 98.8% yield, 86% purity) as yellow oil, which was used for next step without purification.

Step 6. N-ethyl-2-fluoro-pyridine-4-carboxamide (A-1c)

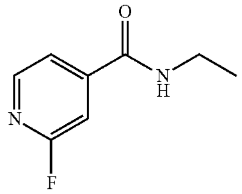

To a solution of ethanamine (6.9 g, 84.09 mmol, HCl salt) and $K_2CO_3$ (33.9 g, 245.3 mmol) in THF (150 mL) and $H_2O$ (75 mL) was added 2-fluoropyridine-4-carbonyl chloride (A-1b, 13 g, 70.07 mmol, 86% purity) at 0~4° C. The mixture was stirred at 0~4° C. for 2 h. The mixture was diluted with water (75 mL) and standing for 2 min. The organic layer was separated. The aqueous layer was extracted with EtOAc (3×50 mL). The combined organic layers were washed with brine (75 mL), dried over $Na_2SO_4$, filtered and concentrated to give brown oil. The residue was purified by flash silica gel chromatography (ISCO; 80 g SepaFlash Silica Flash Column, Eluent of 0~40% Ethyl acetate/Petroleum ether gradient, 80 mL/min) to afford N-ethyl-2-fluoro-pyridine-4-carboxamide (A-1c, 6.6 g, 56.2% yield) as a light-yellow solid.

$^1$H NMR (400 MHz, $CDCl_3$) δ: 8.31 (d, J=5.2 Hz, 1H), 7.51-7.48 (m, 1H), 7.30-7.27 (m, 1H), 6.50 (br s, 1H), 3.55-3.45 (m, 2H), 1.26 (t, J=7.2 Hz, 3H).

Step 7. 2-ethyl-4-fluoro-3-hydroxy-3H-pyrrolo[3,4-c]pyridin-1-one (A-1d)

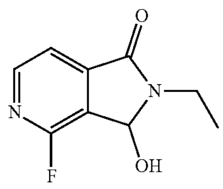

To a solution of N-ethyl-2-fluoro-pyridine-4-carboxamide (A-1c, 6.6 g, 39.42 mmol) in THF (200 mL) was added LDA (2 M in THF, 45 mL) dropwise at −65° C. under $N_2$. The mixture was stirred at −65° C. for 30 min. Then DMF (16 mL, 208 mmol) was added. The mixture stirred at −65° C. for another 1 h. The mixture was quenched with saturated $NH_4Cl$ solution (100 mL) and diluted with water (70 mL). The mixture was extracted with EtOAc (3×50 mL). The combined organic layers were washed with brine (75 mL), dried over $Na_2SO_4$, filtered and concentrated to give 2-ethyl-4-fluoro-3-hydroxy-3H-pyrrolo[3,4-c]pyridin-1-one (A-1d, 9.3 g, 98.9% yield, 82% purity) as a yellow solid, which was used for next step without purification.

$^1$H NMR (400 MHz, $CDCl_3$) δ: 8.37-8.35 (m, 1H), 7.52 (dd, J=2.4, 4.8 Hz, 1H), 6.05 (s, 1H), 4.34 (br s, 1H), 3.82-3.74 (m, 1H), 3.54-3.46 (m, 1H), 1.29 (t, J=7.2 Hz, 3H).

Step 8. 2-ethyl-4-fluoro-3H-pyrrolo[3,4-c]pyridin-1-one (A-1)

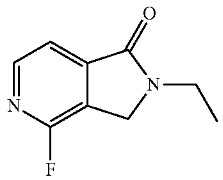

To a solution of 2-ethyl-4-fluoro-3-hydroxy-3H-pyrrolo[3,4-c]pyridin-1-one (A-1d, 9.3 g, 39 mmol, 82% purity) in TFA (30 mL) and DCM (80 mL) was added $Et_3SiH$ (16 mL, 100.17 mmol) at 0° C. Then the solution was stirred at 25° C. for 16 h. The mixture was added to a stirred saturated $NaHCO_3$ solution (800 mL) slowly and then extracted with DCM (3×200 mL). The combined organic layers were washed with brine (200 mL), dried over $Na_2SO_4$, filtered and concentrated to give yellow oil. The residue was purified by flash silica gel chromatography (ISCO; 80 g SepaFlash Silica Flash Column, Eluent of 0~40% Ethylacetate/Petroleum ethergradient, 60 mL/min) to afford 2-ethyl-4-fluoro-3H-pyrrolo[3,4-c]pyridin-1-one (A-1, 6.3 g, 90.8% yield) as a white solid.

$^1$H NMR (400 MHz, $CDCl_3$) δ: 8.38-8.34 (m, 1H), 7.64 (dd, J=2.8, 4.8 Hz, 1H), 4.49 (s, 2H), 3.72 (q, J=7.2 Hz, 2H), 1.31 (t, J=7.2 Hz, 3H).

Step 9. 2-ethyl-4-[[(1S)-1-[3-fluoro-4-(1-methylindazol-5-yl)oxy-phenyl]ethyl]amino]-3H-pyrrolo[3,4-c]pyridin-1-one (1)

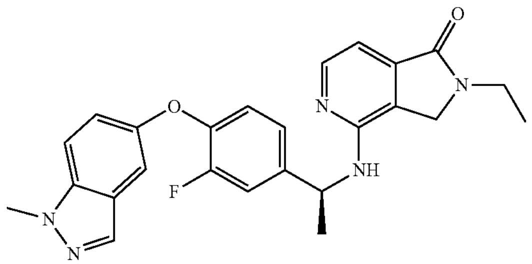 [SMILES: CCN1Cc2c(ccnc2N[C@@H](C)c2ccc(Oc3ccc4c(cnn4C)c3)c(F)c2)C1=O]

A mixture of crude (1S)-1-[3-fluoro-4-(1-methylindazol-5-yl)oxy-phenyl]ethanamine (1e, 300 mg, 1.05 mmol), 2-ethyl-4-fluoro-3H-pyrrolo[3,4-c]pyridin-1-one (A-1, 758 mg, 4.21 mmol) and DIPEA (544 mg, 4.21 mmol) in NMP (4 mL) was stirred at 180° C. under $N_2$ for 8 h. The reaction mixture was poured into water (30 mL) and extracted with EtOAc (2×30 mL). The combined organic layers were washed with brine (30 mL), dried over $Na_2SO_4$, filtered and concentrated to give a residue. The residue was purified by flash chromatography on silica gel (EtOAc) to afford crude 2-ethyl-4-[[(1S)-1-[3-fluoro-4-(1-methylindazol-5-yl)oxy-phenyl]ethyl]amino]-3H-pyrrolo[3,4-c]pyridin-1-one as colorless gum which was further purified by prep. HPLC (Column:DuraShell 150*25 mm*5 um; Mobile phase: water (0.05% HCl v/v)-ACN; Phase B %: 22%-52%; Flow rate: 25 mL/min) to afford 2-ethyl-4-[[(1S)-1-[3-fluoro-4-(1-methyl-indazol-5-yl)oxy-phenyl]ethyl]amino]-3H-pyrrolo[3,4-c]pyridin-1-one (1, 122.0 mg, 23.7% yield, HCl salt) as blue solid.

$^1$H NMR (400 MHz, $CD_3OD$) δ: 7.98-7.91 (m, 2H), 7.58 (d, J=8.8 Hz, 1H), 7.42 (dd, J=2.0, 11.6 Hz, 1H), 7.26 (d, J=8.8 Hz, 1H), 7.24-7.19 (m, 3H), 7.03 (t, J=8.4 Hz, 1H), 5.15 (q, J=6.4 Hz, 1H), 4.75-4.57 (m, 2H), 4.07 (s, 3H), 3.72 (q, J=7.2 Hz, 2H), 1.74 (d, J=6.4 Hz, 3H), 1.32 (t, J=7.2 Hz, 3H). LC-MS: (ESI) m/z: 446.1 [M+H].

Synthesis of Compounds 2 to 64

In general, Compounds 2 to 64 in Table 1 were prepared according to procedures described in General Scheme A. The synthetic method was similar with Example 1. Data for Compounds 2 to 64 is shown herein below in Table 1.

TABLE 1

| Cpd No. | Compound Structure | MS/$^1$H NMR |
|---|---|---|
| 2 | 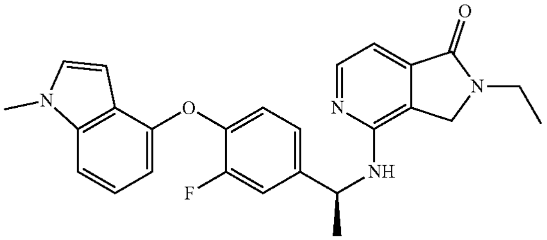 [SMILES: CCN1Cc2c(ccnc2N[C@@H](C)c2ccc(Oc3cccc4c3ccn4C)c(F)c2)C1=O] | LC-MS: (ESI) m/z 445.1 [M + H]. $^1$H NMR (400 MHz, $CD_3OD$) δ: 7.94 (d, J = 6.4 Hz, 1H), 7.39 (d, J = 11.6 Hz, 1H), 7.24-7.08 (m, 5H), 6.93 (t, J = 8.4 Hz, 1H), 6.54 (d, J = 7.6 Hz, 1H), 6.28-6.25 (m, 1H), 5.09 (q, J = 6.4 Hz, 1H), 4.70-4.57 (q, J = 7.2 Hz, 2H), 3.83 (s, 3H), 3.72 (q, J = 7.2 Hz, 2H), 1.74 (d, J = 6.4 Hz, 3H), 1.33 (t, J = 7.2 Hz, 3H). |
| 3 | 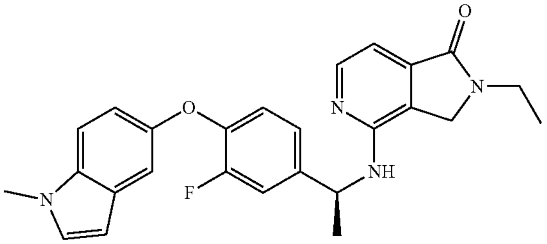 [SMILES: CCN1Cc2c(ccnc2N[C@@H](C)c2ccc(Oc3ccc4c(ccn4C)c3)c(F)c2)C1=O] | LC-MS: (ESI) m/z 445.2 [M + H]. $^1$H NMR (400 MHz, $CD_3OD$) δ: 8.06 (d, J = 5.2 Hz, 1H), 7.35-7.21 (m, 2H), 7.16-7.05 (m, 3H), 6.91-6.77 (m, 3H), 6.32 (d, J = 3.2 Hz, 1H), 5.30 (q, J = 6.8 Hz, 1H), 4.39 (s, 2H), 3.77 (s, 3H), 3.65 (q, J = 7.2 Hz, 2H), 1.56 (d, J = 7.2 Hz, 3H), 1.28 (t, J = 7.2 Hz, 3H). |
| 4 | 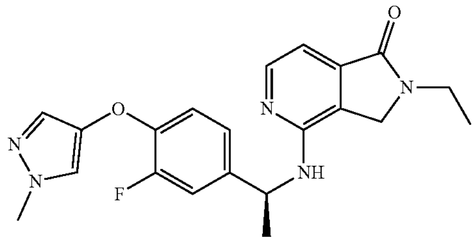 [SMILES: CCN1Cc2c(ccnc2N[C@@H](C)c2ccc(Oc3cnn(C)c3)c(F)c2)C1=O] | LC-MS: (ESI) m/z: 396.2 [M + H]. $^1$H NMR (400 MHz, $CDCl_3$) δ: 7.93 (d, J = 6.8 Hz, 1H), 7.58 (s, 1H), 7.39-7.31 (m, 2H), 7.21 (d, J = 6.4 Hz, 2H), 7.13-7.06 (m, 1H), 5.09 (q, J = 6.8 Hz, 1H), 4.65 (d, J = 10.8 Hz, 2H), 3.86 (s, 3H), 3.72 (q, J = 7.2 Hz, 2H), 1.72 (d, J = 6.8 Hz, 3H), 1.33 (t, J = 7.2 Hz, 3H). |
| 5 | 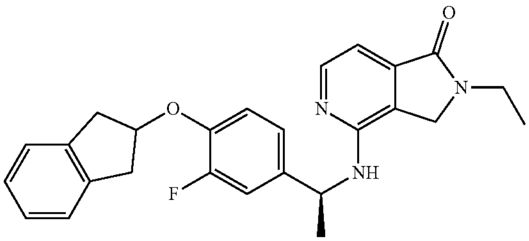 [SMILES: CCN1Cc2c(ccnc2N[C@@H](C)c2ccc(OC3Cc4ccccc4C3)c(F)c2)C1=O] | LC-MS: (ESI) m/z: 432.1 [M + H]. $^1$H NMR (400 MHz, $CDCl_3$) δ: 9.62 (br s, 1H), 7.95 (s, 1H), 7.50-7.40 (br s, 1H), 7.25-7.15 (m, 3H), 7.17-7.10 (m, 3H), 6.94 (s, 1H), 5.34 (br s, 1H), 5.08 (s, 1H), 4.85-4.70 (m, 1H), 4.65-4.40 (m, 1H), 3.65 (s, 2H), 3.34-3.27 (m, 2H), 3.13 (d, J = 16.8 Hz, 2H), 1.75-1.70 (m, 3H), 1.30-1.20 (m, 3H). |

TABLE 1-continued

| Cpd No. | Compound Structure | MS/$^1$H NMR |
|---|---|---|
| 6 | 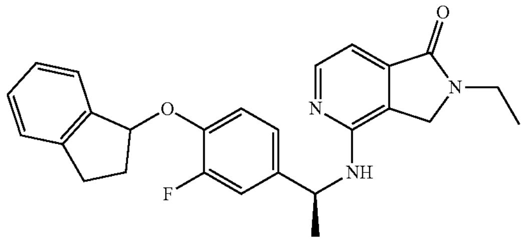 [SMILES: CCN1Cc2c(ccnc2N[C@@H](C)c2ccc(OC3CCc4ccccc43)c(F)c2)C1=O] | LC-MS: (ESI) m/z: 432.2 [M + H]. $^1$H NMR (400 MHz, $CDCl_3$) δ: 8.26-8.20 (m, 1H), 7.41 (d, J = 7.2 Hz, 1H), 7.32-7.29 (m, 2H), 7.23 (dd, J = 2.4, 7.6 Hz, 1H), 7.14 (s, 1H), 7.12 (d, J = 2.0 Hz, 2H), 7.09-7.04 (m, 3H), 6.75 (t, J = 8.8 Hz, 1H), 5.73 (dd, J = 4.0, 6.4 Hz, 1H), 5.44-5.18 (m, 2H), 4.34 (d, J = 7.6 Hz, 1H), 4.25-4.18 (m, 3H), 3.72-3.63 (m, 3H), 3.23-3.11 (m, 1H), 2.97-2.83 (m, 1H), 2.59-2.46 (m, 1H), 2.31-2.21 (m, 1H), 1.32-1.28 (m, 3H), 1.27-1.24 (m, 3H). |
| 7 | 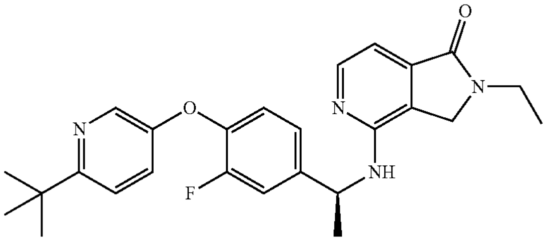 [SMILES: CCN1Cc2c(ccnc2N[C@@H](C)c2ccc(Oc3ccc(C(C)(C)C)nc3)c(F)c2)C1=O] | LC-MS: (ESI) m/z: 449.1 [M + H]. $^1$H NMR (400 MHz, $CDCl_3$) δ: 8.29 (d, J = 3.2 Hz, 1H), 8.23 (d, J = 5.2 Hz, 1H), 7.29-7.27 (m, 1H), 7.24 (dd, J = 2.0, 11.2 Hz, 1H), 7.21-7.14 (m, 2H), 7.07 (d, J = 5.2 Hz, 1H), 7.05-7.00 (m, 1H), 5.41 (q, J = 6.8 Hz, 1H), 4.37 (d, J = 7.2 Hz, 1H), 4.25 (s, 2H), 3.69 (q, J = 7.2 Hz, 2H), 1.61 (d, J = 6.8 Hz, 3H), 1.35 (s, 9H), 1.29 (t, J = 7.2 Hz, 3H). |
| 8 | 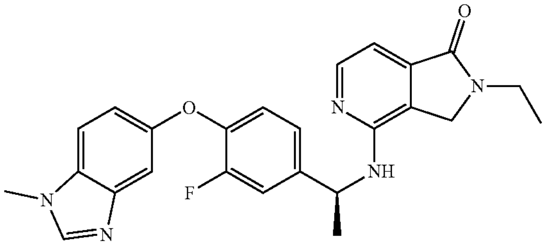 [SMILES: CCN1Cc2c(ccnc2N[C@@H](C)c2ccc(Oc3ccc4c(c3)ncn4C)c(F)c2)C1=O] | LC-MS: (ESI) m/z: 446.1 [M + H]. $^1$H NMR (400 MHz, $CDCl_3$) δ: 8.25 (d, J = 5.2 Hz, 1H), 7.86 (s, 1H), 7.37-7.32 (m, 2H), 7.24 (dd, J = 2.0 & 11.6 Hz, 1H), 7.12 (dd, J = 2.4 & 8.4 Hz, 2H), 7.08 (d, J = 5.2 Hz, 1H), 7.01-6.94 (m, 1H), 5.48-5.34 (m, 1H), 4.34 (s, 1H), 4.25 (d, J = 4.0 Hz, 2H), 3.86 (s, 3H), 3.69 (q, J = 7.2 Hz, 2H), 1.62 (d, J = 6.8 Hz, 3H), 1.29 (t, J = 7.2 Hz, 3H). |
| 9 | 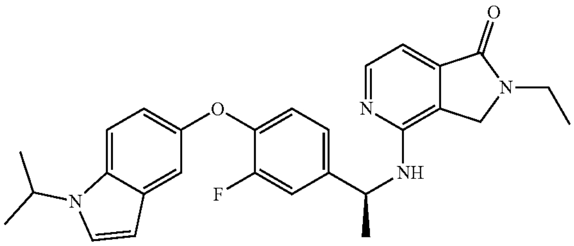 [SMILES: CCN1Cc2c(ccnc2N[C@@H](C)c2ccc(Oc3ccc4c(ccn4C(C)C)c3)c(F)c2)C1=O] | LC-MS: (ESI) m/z: 473.3 [M + H]. $^1$H NMR (400 MHz, $CDCl_3$) δ: 8.24 (d, J = 5.2 Hz, 1H), 7.33 (d, J = 8.8 Hz, 1H), 7.25 (d, J = 3.2 Hz, 1H), 7.24-7.19 (m, 2H), 7.09-7.01 (m, 2H), 6.96 (dd, J = 2.4, 8.8 Hz, 1H), 6.88 (t, J = 8.4 Hz, 1H), 6.44 (d, J = 2.8 Hz, 1H), 5.41-5.34 (m, 1H), 4.68-4.61 (m, 1H), 4.34 (d, J = 7.6 Hz, 1H), 4.18-4.27 (m, 2H), 3.67 (q, J = 7.2 Hz, 2H), 1.60 (m, 3H), 1.54 (d, J = 6.4 Hz, 6H), 1.28 (t, J = 7.2 Hz, 3H). |
| 10 | 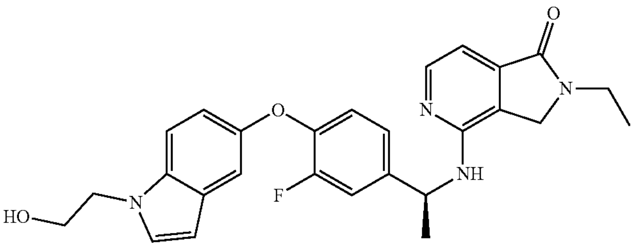 [SMILES: CCN1Cc2c(ccnc2N[C@@H](C)c2ccc(Oc3ccc4c(ccn4CCO)c3)c(F)c2)C1=O] | LC-MS: (ESI) m/z 475.3 [M + H]. $^1$H NMR (400 MHz, $CDCl_3$) δ: 8.24 (d, J = 4.8 Hz, 1H), 7.33 (d, J = 8.8 Hz, 1H), 7.25-7.19 (m, 3H), 7.09-7.04 (m, 2H), 6.98 (dd, J = 2.4, 8.8 Hz, 1H), 6.89 (t, J = 8.8 Hz, 1H), 6.46 (d, J = 3.2 Hz, 1H), 5.39 (quin, J = 6.8 Hz, 1H), 4.36-4.27 (m, 3H), 4.25-4.18 (m, 2H), 3.99 (t, J = 5.2 Hz, 2H), 3.68 (q, J = 7.2 Hz, 2H), 1.61 (d, J = 6.8 Hz, 3H), 1.28 (t, J = 7.2 Hz, 3H). |
| 11 | 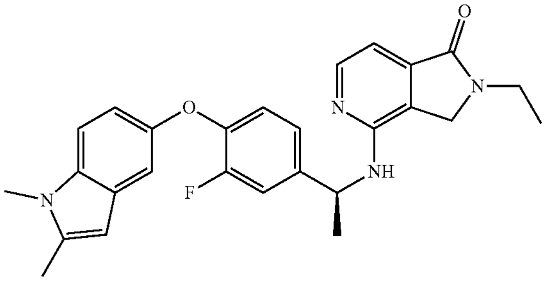 [SMILES: CCN1Cc2c(ccnc2N[C@@H](C)c2ccc(Oc3ccc4c(c3)cc(C)n4C)c(F)c2)C1=O] | LC-MS: (ESI) m/z: 459.2 [M + H]. $^1$H NMR (400 MHz, $CDCl_3$) δ: 8.24 (d, J = 5.2 Hz, 1H), 7.23-7.19 (m, 2H), 7.15 (d, J = 2.4 Hz, 1H), 7.06 (d, J = 5.2 Hz, 1H), 7.05-7.01 (m, 1H), 6.90 (dd, J = 2.4, 8.8 Hz, 1H), 6.83 (t, J = 8.4 Hz, 1H), 6.19 (s, 1H), 5.37 (q, J = 6.8 Hz, 1H), 4.35 (d, J = 7.2 Hz, 1H), 4.23 (d, J = 2.0 Hz, 2H), 3.71-3.66 (m, 5H), 2.42 (s, 3H), 1.59 (d, J = 6.8 Hz, 3H), 1.28 (t, J = 7.2 Hz, 3H). |

TABLE 1-continued

| Cpd No. | Compound Structure | MS/$^1$H NMR |
|---|---|---|
| 12 | 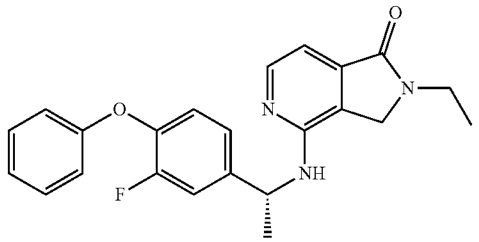 [SMILES: CCN1Cc2c(ccnc2N[C@H](C)c2ccc(Oc3ccccc3)c(F)c2)C1=O] | $^1$H NMR (500 MHz, $CDCl_3$) δ: 8.23 (d, J = 5.2 Hz, 1H), 7.35-7.28 (m, 2H), 7.23 (dd, J = 11.5, 2.2 Hz, 1H), 7.16-7.11 (m, 1H), 7.11-7.03 (m, 3H), 7.03-6.94 (m, 4H), 5.40 (d, J = 6.9 Hz, 1H), 4.42 (d, J = 7.3 Hz, 1H), 4.24 (d, J = 3.1 Hz, 2H), 3.74 (s, 2H), 3.67 (q, J = 7.3 Hz, 2H), 2.02 (s, 1H), 1.60 (d, J = 6.9 Hz, 3H), 1.48 (d, J = 6.9 Hz, 1H), 1.27 (t, J = 7.3 Hz, 3H). |
| 13 | 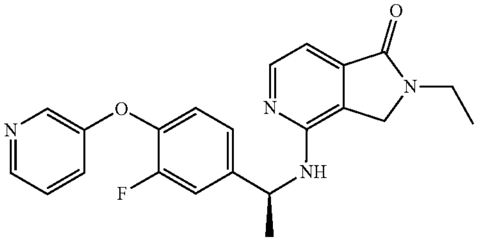 [SMILES: CCN1Cc2c(ccnc2N[C@@H](C)c2ccc(Oc3cccnc3)c(F)c2)C1=O] | $^1$H NMR (500 MHz, $CDCl_3$) δ: 8.35-8.20 (m, 2H), 8.15 (t, J = 6.0 Hz, 1H), 7.22-7.14 (m, 4H), 7.11 (dd, J = 8.2, 2.1 Hz, 1H), 6.98 (dd, J = 9.4, 6.8 Hz, 2H), 5.34 (q, J = 6.9 Hz, 1H), 4.59-4.48 (m, 1H), 4.44 (d, J = 7.2 Hz, 1H), 4.31 (s, 1H), 4.19 (d, J = 2.4 Hz, 2H), 3.96-3.87 (m, 1H), 3.61 (p, J = 7.1 Hz, 3H), 1.54 (d, J = 6.9 Hz, 3H), 1.21 (td, J = 7.3, 4.6 Hz, 6H). |
| 14 | 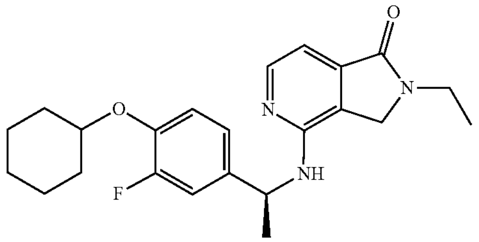 [SMILES: CCN1Cc2c(ccnc2N[C@@H](C)c2ccc(OC3CCCCC3)c(F)c2)C1=O] | $^1$H NMR (500 MHz, $CDCl_3$) δ: 8.23 (d, J = 5.2 Hz, 1H), 7.18-6.99 (m, 3H), 6.90 (t, J = 8.4 Hz, 1H), 5.33 (q, J = 6.9 Hz, 1H), 4.77 (t, J = 4.4 Hz, 1H), 4.35 (d, J = 6.7 Hz, 1H), 4.29-4.04 (m, 2H), 3.66 (q, J = 7.3 Hz, 2H), 1.88 (ddd, J = 10.4, 5.3, 2.9 Hz, 4H), 1.85-1.80 (m, 2H), 1.62 (dd, J = 6.6, 3.5 Hz, 2H), 1.57 (d, J = 6.8 Hz, 3H), 1.26 (d, J = 7.3 Hz, 3H), 0.89 (ddd, J = 19.6, 16.5, 9.7 Hz, 2H). |
| 15 | 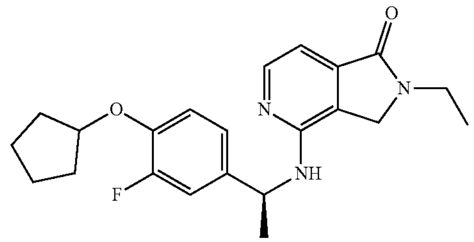 [SMILES: CCN1Cc2c(ccnc2N[C@@H](C)c2ccc(OC3CCCC3)c(F)c2)C1=O] | $^1$H NMR (500 MHz, $CDCl_3$) δ: 8.22 (d, J = 5.2 Hz, 1H), 7.11 (dd, J = 12.2, 2.2 Hz, 1H), 7.09-7.01 (m, 2H), 6.94 (t, J = 8.4 Hz, 1H), 5.34 (p, J = 6.9 Hz, 1H), 4.40 (d, J = 7.4 Hz, 1H), 4.24-4.07 (m, 3H), 3.66 (q, J = 7.3 Hz, 2H), 2.03-1.92 (m, 2H), 1.80 (dq, J = 9.3, 4.7, 4.0 Hz, 2H), 1.56 (dd, J = 13.3, 8.4 Hz, 5H), 1.34-1.30 (m, 2H), 1.25 (d, J = 7.3 Hz, 3H). |
| 16 | 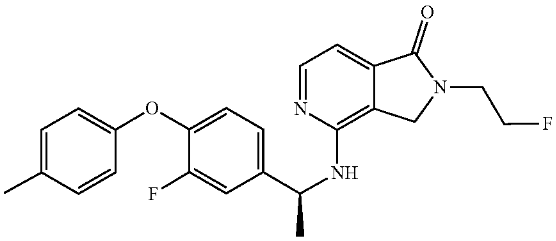 [SMILES: Cc1ccc(Oc2ccc([C@H](C)Nc3nccc4c3CN(CCF)C4=O)cc2F)cc1] | LC-MS: (ESI) m/z: 424.1 [M + H].<br>$^1$H NMR (400 MHz, $CD_3OD$) δ: 7.97 (d, J = 6.4 Hz, 1H), 7.35 (dd, J = 2.0, 12.0 Hz, 1H), 7.22 (d, J = 9.2 Hz, 1H), 7.18-7.12 (m, 3H), 7.02 (t, J = 8.4 Hz, 1H), 6.83 (d, J = 8.4 Hz, 2H), 5.14 (q, J = 6.8 Hz, 1H), 4.78 (t, J = 4.8 Hz, 1H), 4.70 (d, J = 6.4 Hz, 2H), 4.68-4.64 (m, 1H), 4.05-3.92 (m, 2H), 2.30 (s, 3H), 1.70 (d, J = 6.8 Hz, 3H). |
| 17 | 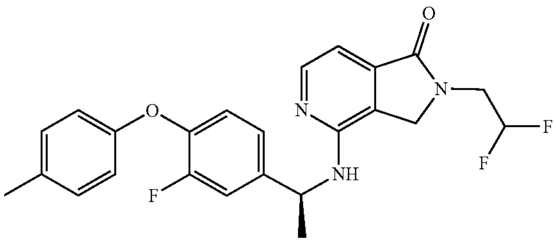 [SMILES: Cc1ccc(Oc2ccc([C@H](C)Nc3nccc4c3CN(CC(F)F)C4=O)cc2F)cc1] | LC-MS: (ESI) m/z: 442.1 [M + H].<br>$^1$H NMR (400 MHz, $CD_3OD$) δ: 7.96 (d, J = 6.4 Hz, 1H), 7.36 (d, J = 11.6 Hz, 1H), 7.26-7.20 (m, 2H), 7.15 (d, J = 8.0 Hz, 2H), 7.04 (t, J = 8.0 Hz, 1H), 6.84 (d, J = 8.4 Hz, 2H), 6.34-5.99 (m, 1H), 5.10 (d, J = 6.8 Hz, 1H), 4.80-4.68 (m, 2H), 4.17-4.01 (m, 2H), 2.31 (s, 3H), 1.73 (d, J = 6.8 Hz, 3H). |

TABLE 1-continued

| Cpd No. | Compound Structure | MS/$^{1}$H NMR |
| --- | --- | --- |
| 18 | 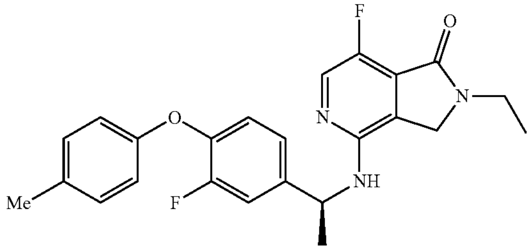 [SMILES: CCN1Cc2c(N[C@@H](C)c3ccc(Oc4ccc(C)cc4)c(F)c3)ncc(F)c2C1=O] | $^{1}$H NMR (500 MHz, $CDCl_3$) δ: 7.94 (d, J = 1.3 Hz, 1H), 7.11 (dd, J = 11.6, 2.1 Hz, 1H), 7.06-6.99 (m, 3H), 6.87 (t, J = 8.3 Hz, 1H), 6.82-6.77 (m, 2H), 5.20 (p, J = 6.8 Hz, 1H), 4.23 (d, J = 7.0 Hz, 1H), 4.16 (s, 2H), 3.57 (q, J = 7.3 Hz, 2H), 2.25 (s, 3H), 1.50 (d, J = 6.9 Hz, 3H), 1.20 (t, J = 7.3 Hz, 3H). |
| 19 | 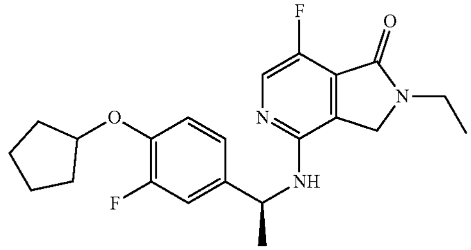 [SMILES: CCN1Cc2c(N[C@@H](C)c3ccc(OC4CCCC4)c(F)c3)ncc(F)c2C1=O] | $^{1}$H NMR (400 MHz, $CDCl_3$) δ: 7.95 (s, 1H), 7.05-6.88 (m, 2H), 6.82 (t, J = 8.4 Hz, 1H), 5.15 (p, J = 6.8 Hz, 1H), 4.69 (q, J = 4.3 Hz, 1H), 4.14 (d, J = 12.4 Hz, 3H), 3.57 (q, J = 7.3 Hz, 2H), 1.81 (qd, J = 6.2, 4.1 Hz, 4H), 1.59-1.51 (m, 2H), 1.48 (d, J = 6.8 Hz, 3H), 1.20-1.17 (m, 3H). |
| 20 | 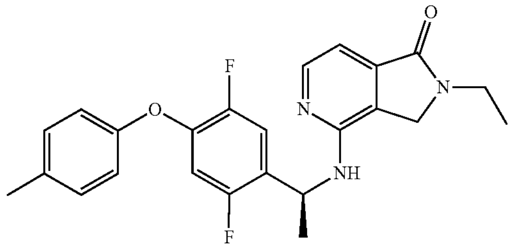 [SMILES: CCN1Cc2c(ccnc2N[C@@H](C)c2cc(F)c(Oc3ccc(C)cc3)cc2F)C1=O] | LC-MS: (ESI) m/z: 424.2 [M + H]. $^{1}$H NMR (400 MHz, $CD_3OD$) δ: 8.08 (d, J = 5.2 Hz, 1H), 7.25 (dd, J = 7.2, 11.4 Hz, 1H), 7.17 (dd, J = 0.8, 8.8 Hz, 2H), 6.92 (d, J = 5.2 Hz, 1H), 6.89-6.83 (m, 2H), 6.73 (dd, J = 6.8, 10.8 Hz, 1H), 5.51 (q, J = 6.8 Hz, 1H), 4.46 (d, J = 3.2 Hz, 2H), 3.70 (q, J = 7.2 Hz, 2H), 2.32 (s, 3H), 1.57 (d, J = 7.2 Hz, 3H), 1.32 (t, J = 7.2 Hz, 3H). |
| 21 | 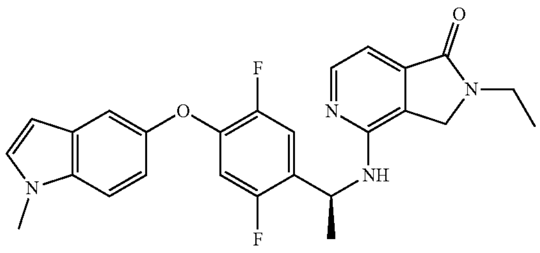 [SMILES: CCN1Cc2c(ccnc2N[C@@H](C)c2cc(F)c(Oc3ccc4c(ccn4C)c3)cc2F)C1=O] | LC-MS: (ESI) m/z: 463.2 [M + H]. $^{1}$H NMR (400 MHz, $CD_3OD$) δ: 8.08 (d, J = 5.2 Hz, 1H), 7.39 (d, J = 8.8 Hz, 1H), 7.27-7.14 (m, 3H), 6.96-6.84 (m, 2H), 6.54 (dd, J = 6.8, 11.2 Hz, 1H), 6.40 (d, J = 2.4 Hz, 1H), 5.49 (q, J = 6.8 Hz, 1H), 4.46 (d, J = 4.0 Hz, 2H), 3.82 (s, 3H), 3.69 (q, J = 7.2 Hz, 2H), 1.56 (d, J = 7.2 Hz, 3H), 1.31 (t, J = 7.2 Hz, 3H). |
| 22 | 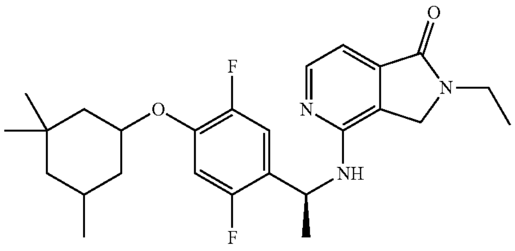 [SMILES: CCN1Cc2c(ccnc2N[C@@H](C)c2cc(F)c(OC3CC(C)CC(C)(C)C3)cc2F)C1=O] | LC-MS: (ESI) m/z: 458.3 [M + H]. $^{1}$H NMR (400 MHz, $CDCl_3$) δ: 8.20 (d, J = 4.4 Hz, 1H), 7.08-7.03 (m, 2H), 6.70-6.62 (m, 1H), 5.48-5.45 (m, 1H), 4.67 (d, J = 5.2 Hz, 1H), 4.58-4.54 (m, 0.4H), 4.29-4.25 (m, 2.6H), 3.67 (q, J = 7.2 Hz, 2H), 2.10-1.95 (m, 3H), 1.84-1.82 (m, 1H), 1.57 (d, J = 6.4 Hz, 3H), 1.50-1.20 (m, 5H), 1.06-0.80 (m, 11H). |
| 23 | 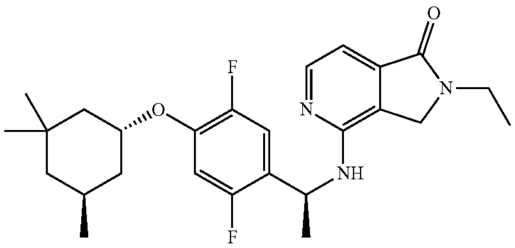 [SMILES: CCN1Cc2c(ccnc2N[C@@H](C)c2cc(F)c(O[C@@H]3C[C@@H](C)CC(C)(C)C3)cc2F)C1=O] | LC-MS: (ESI) m/z: 458.3 [M + H]. $^{1}$H NMR (400 MHz, $CD_3OD$) δ: 8.07 (d, J = 5.2 Hz, 1H), 7.13-7.08 (m, 1H), 6.90 (d, J = 5.2 Hz, 1H), 6.84 (dd, J = 6.8, 12.0 Hz, 1H), 5.48 (q, J = 6.8 Hz, 1H), 4.67 (t, J = 2.8 Hz, 1H), 4.44 (d, J = 2.4 Hz, 2H), 3.69 (q, J = 7.2 Hz, 2H), 2.06-1.90 (m, 2H), 1.87-1.78 (m, 1H), 1.55 (d, J = 6.8 Hz, 3H), 1.50-1.42 (m, 1H), 1.37-1.27 (m, 4H), 1.16-1.08 (m, 1H), 1.06 (d, J = 9.2 Hz, 3H), 0.95-0.85 (m, 7H). |

TABLE 1-continued

| Cpd No. | Compound Structure | MS/$^1$H NMR |
| --- | --- | --- |
| 24 | 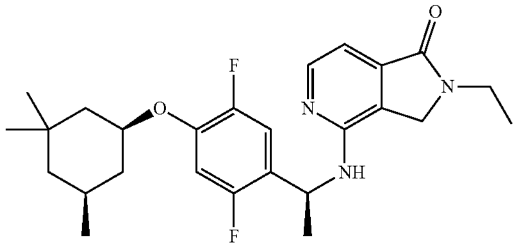 [SMILES: CCN1Cc2c(ccnc2N[C@@H](C)c2cc(F)c(O[C@H]3C[C@@H](C)CC(C)(C)C3)cc2F)C1=O] | LC-MS: (ESI) m/z: 458.3 [M + H]. $^1$H NMR (400 MHz, $CD_3OD$) δ: 8.06 (d, J = 5.2 Hz, 1H), 7.10 (dd, J = 7.2, 11.6 Hz, 1H), 6.89 (d, J = 5.2 Hz, 1H), 6.84 (dd, J = 6.8, 11.6 Hz, 1H), 5.47 (q, J = 6.8 Hz, 1H), 4.51-4.31 (m, 3H), 3.68 (q, J = 7.2 Hz, 2H), 2.08 (d, J = 10.8 Hz, 1H), 1.85-1.67 (m, 2H), 1.54 (d, J = 6.8 Hz, 3H), 1.42-1.34 (m, 1H), 1.30 (t, J = 7.2 Hz, 3H), 1.19-1.13 (m, 1H), 1.00-0.80 (m, 11H). |
| 25 | 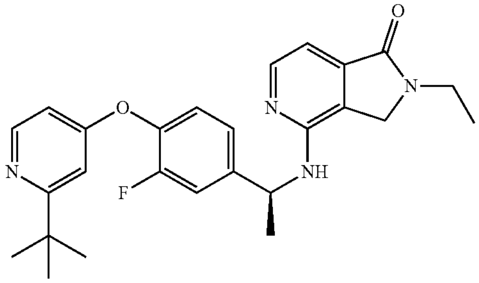 [SMILES: CCN1Cc2c(ccnc2N[C@@H](C)c2ccc(Oc3ccnc(C(C)(C)C)c3)c(F)c2)C1=O] | LC-MS: (ESI) m/z: 449.1 [M + H]. $^1$H NMR (400 MHz, DMSO-$d_6$) δ: 9.29 (br s, 1H), 8.64 (d, J = 6.4 Hz, 1H), 8.00 (d, J = 6.4 Hz, 1H), 7.84 (d, J = 11.6 Hz, 1H), 7.65-7.59 (m, 2H), 7.53 (t, J = 8.4 Hz, 1H), 7.12-7.04 (m, 2H), 5.70-5.61 (m, 1H), 4.62 (q, J = 7.2 Hz, 1H), 3.64-3.54 (m, 2H), 1.65 (d, J = 6.8 Hz, 3H), 1.44 (s, 9H), 1.21 (t, J = 7.2 Hz, 3H). |
| 26 | 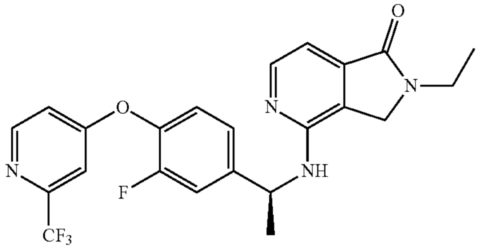 [SMILES: CCN1Cc2c(ccnc2N[C@@H](C)c2ccc(Oc3ccnc(C(F)(F)F)c3)c(F)c2)C1=O] | LC-MS: (ESI) m/z: 461.0 [M + H]. $^1$H NMR (400 MHz, $CD_3OD$) δ: 8.58 (d, J = 5.6 Hz, 1H), 7.97 (d, J = 6.4 Hz, 1H), 7.55 (d, J = 11.6 Hz, 1H), 7.47-7.38 (m, 2H), 7.32 (s, 1H), 7.24 (d, J = 6.4 Hz, 1H), 7.13 (d, J = 5.6 Hz, 1H), 5.21 (d, J = 6.8 Hz, 1H), 4.98-4.89 (m, 1H), 4.75-4.60 (q, J = 6.8 Hz, 2H), 3.73 (q, J = 7.2 Hz, 2H), 1.78 (d, J = 6.8 Hz, 3H), 1.33 (t, J = 7.2 Hz, 3H). |
| 27 | 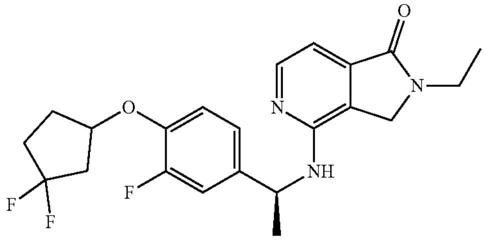 | LC-MS: (ESI) m/z 461.1 [M + H]. $^1$H NMR (400 MHz, $CD_3OD$) δ: 7.92 (d, J = 6.4 Hz, 1H), 7.30-7.18 (m, 3H), 7.09 (t, J = 8.0 Hz, 1H), 5.06 (q, J = 6.8 Hz, 1H), 4.99-4.90 (m, 1H), 4.71-4.57 (m, 2H), 3.72 (q, J = 7.2 Hz, 2H), 2.63-2.49 (m, 1H), 2.38-2.12 (m, 4H), 2.12-2.02 (m, 1H), 1.71 (d, J = 6.4 Hz, 3H), 1.33 (t, J = 7.2 Hz, 3H). |
| 28 | 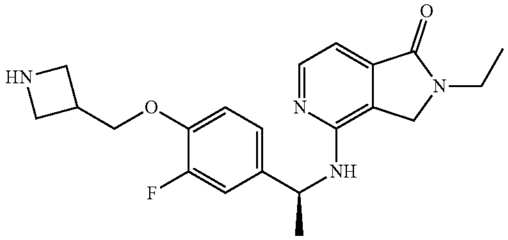 [SMILES: CCN1Cc2c(ccnc2N[C@@H](C)c2ccc(OCC3CNC3)c(F)c2)C1=O] | LC-MS: (ESI) m/z: 385.1 [M + H]. $^1$H NMR (400 MHz, DMSO-d6) δ: 9.21 (s, 2H), 7.98 (s, 1H), 7.55-7.20 (m, 2H), 7.18-6.82 (m, 2H), 5.42 (s, 1H), 4.53 (d, J = 14.8 Hz, 2H), 4.22 (br s, 2H), 4.03 (br s, 2H), 3.78 (br s, 3H), 3.18 (br s, 2H), 1.54 (br s, 3H), 1.20 (br s, 3H). |
| 29 | 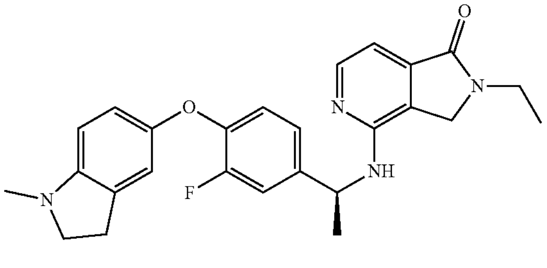 [SMILES: CCN1Cc2c(ccnc2N[C@@H](C)c2ccc(Oc3ccc4c(c3)CCN4C)c(F)c2)C1=O] | LC-MS: (ESI) m/z 447.3 [M + H] $^1$H NMR (400 MHz, $D_2O$) δ: 7.81 (d, J = 6.4 Hz, 1H), 7.43 (d, J = 8.4 Hz, 1H), 7.33 (d, J = 10.0 Hz, 1H), 7.26-7.17 (m, 1H), 7.18-7.08 (m, 2H), 7.08-6.96 (m, 2H), 5.18-5.04 (m, 1H), 4.69-4.58 (m, 2H), 4.03-3.83 (m, 2H), 3.64 (q, J = 6.8 Hz, 2H), 3.34-3.06 (m, 5H), 1.66 (d, J = 6.8 Hz, 3H), 1.23 (t, J = 7.2 Hz, 3H). |

TABLE 1-continued

| Cpd No. | Compound Structure | MS/$^1$H NMR |
|---|---|---|
| 30 | 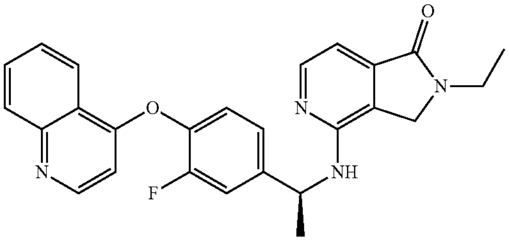 [SMILES: CCN1Cc2c(ccnc2N[C@@H](C)c2ccc(Oc3ccnc4ccccc34)c(F)c2)C1=O] | LC-MS: (ESI) m/z: 443.2 [M + H]. $^1$H NMR (400 MHz, $CDCl_3$) δ: 9.01 (d, J = 6.4 Hz, 1H), 8.69 (d, J = 8.0 Hz, 1H), 8.27-8.17 (m, 2H), 8.07-7.99 (m, 2H), 7.70-7.53 (m, 3H), 7.18 (dd, J = 6.4, 20.0 Hz, 2H), 5.32 (q, J = 6.8 Hz, 1H), 4.77-4.59 (m, 2H), 3.74 (q, J = 7.2 Hz, 2H), 1.80 (d, J = 6.4 Hz, 3H), 1.34 (t, J = 7.2 Hz, 3H). |
| 31 | 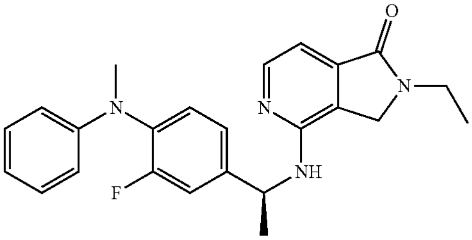 [SMILES: CCN1Cc2c(ccnc2N[C@@H](C)c2ccc(N(C)c3ccccc3)c(F)c2)C1=O] | $^1$H NMR (500 MHz, $CDCl_3$) δ: 8.24 (d, J = 5.2 Hz, 1H), 7.24-7.15 (m, 5H), 7.07 (d, J = 5.2 Hz, 1H), 6.79 (tt, J = 7.2, 1.1 Hz, 1H), 6.73 (d, J = 8.0 Hz, 2H), 5.42 (p, J = 7.2 Hz, 1H), 4.42 (s, 1H), 4.29-4.17 (m, 2H), 3.68 (q, J = 7.2 Hz, 2H), 3.26 (s, 3H), 1.61 (s, 3H), 1.28 (t, J = 7.2 Hz, 3H). |
| 32 | 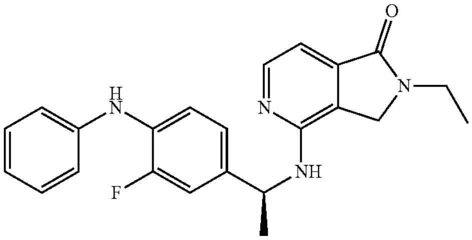 [SMILES: CCN1Cc2c(ccnc2N[C@@H](C)c2ccc(Nc3ccccc3)c(F)c2)C1=O] | $^1$H NMR (500 MHz, $CDCl_3$) δ: 8.24 (d, J = 5.2 Hz, 1H), 7.28 (dd, J = 8.4, 7.6 Hz, 3H), 7.14 (dd, J = 12.2, 2.0 Hz, 1H), 7.09 (d, J = 1.2 Hz, 1H), 7.09-7.06 (m, 1H), 7.05 (d, J = 5.2 Hz, 1H), 6.98 (tt, J = 7.2, 1.1 Hz, 1H), 5.85-5.71 (m, 1H), 5.34 (p, J = 6.8 Hz, 1H), 4.37 (d, J = 7.2 Hz, 1H), 4.22 (d, J = 3.2 Hz, 2H), 3.66 (q, J = 7.2 Hz, 2H), 1.59 (d, J = 6.8 Hz, 3H), 1.27 (d, J = 7.2 Hz, 3H). |
| 33 | 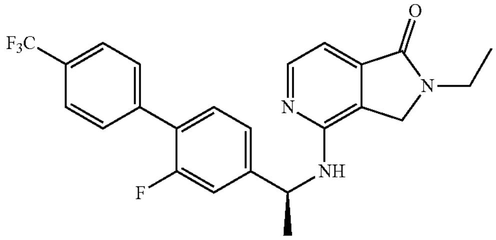 [SMILES: CCN1Cc2c(ccnc2N[C@@H](C)c2ccc(-c3ccc(C(F)(F)F)cc3)c(F)c2)C1=O] | LC-MS: (ESI) m/z: 444.1 [M + H]. $^1$H NMR (400 MHz, $CD_3OD$) δ: 7.95 (d, J = 6.4 Hz, 1H), 7.78-7.71 (m, 4H), 7.63-7.55 (m, 1H), 7.45-7.37 (m, 2H), 7.22 (d, J = 6.8 Hz, 1H), 5.20 (q, J = 6.8 Hz, 1H), 4.77-4.58 (m, 2H), 3.74 (q, J = 7.2 Hz, 2H), 1.78 (d, J = 6.8 Hz, 3H), 1.34 (t, J = 7.2 Hz, 3H). |
| 34 | 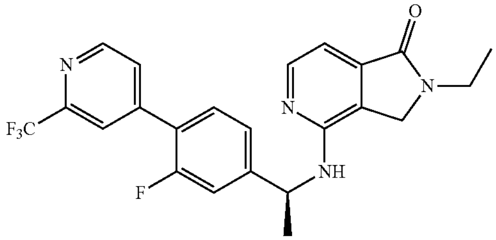 [SMILES: CCN1Cc2c(ccnc2N[C@@H](C)c2ccc(-c3ccnc(C(F)(F)F)c3)c(F)c2)C1=O] | LC-MS: (ESI) m/z: 445.2 [M + H]. $^1$H NMR (400 MHz, $CD_3OD$) δ: 8.79 (d, J = 5.2 Hz, 1H), 7.99 (s, 1H), 7.95 (d, J = 6.8 Hz, 1H), 7.86 (d, J = 5.2 Hz, 1H), 7.76-7.70 (m, 1H), 7.52-7.46 (m, 2H), 7.23 (d, J = 6.8 Hz, 1H), 5.28-5.21 (m, 1H), 4.79-4.62 (m, 2H), 3.74 (q, J = 7.2 Hz, 2H), 1.80 (d, J = 6.8 Hz, 3H), 1.35 (t, J = 7.2 Hz, 3H). |
| 35 | 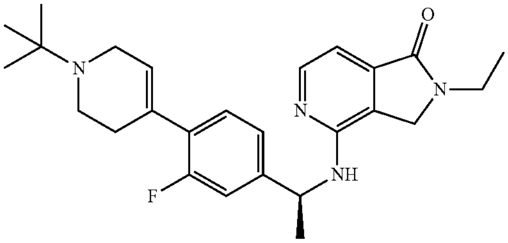 [SMILES: CCN1Cc2c(ccnc2N[C@@H](C)c2ccc(C3=CCN(C(C)(C)C)CC3)c(F)c2)C1=O] | LC-MS: (ESI) m/z: 437.2 [M + H]. $^1$H NMR (400 MHz, $CDCl_3$) δ: 8.23 (d, J = 5.2 Hz, 1H), 7.25 (s, 1H), 7.12 (d, J = 8.0 Hz, 1H), 7.09-7.04 (m, 2H), 5.99 (br s, 1H), 5.39 (t, J = 7.2 Hz, 1H), 4.35 (br s, 1H), 4.23 (d, J = 3.2 Hz, 2H), 3.68 (q, J = 7.2 Hz, 2H), 3.36 (br s, 2H), 2.78 (br s, 2H), 2.56 (br s, 2H), 1.62-1.58 (m, 12H), 1.30-1.27 (m, 3H). |

TABLE 1-continued

| Cpd No. | Compound Structure | MS/$^1$H NMR |
|---|---|---|
| 36 | 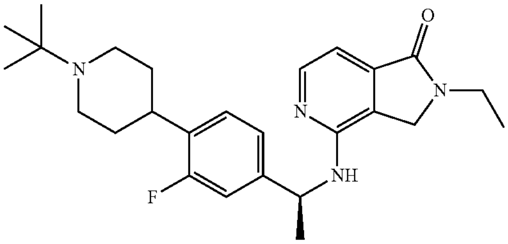 [SMILES: CCN1Cc2c(ccnc2N[C@@H](C)c2ccc(C3CCN(C(C)(C)C)CC3)c(F)c2)C1=O] | LC-MS: (ESI) m/z: 439.2 [M + H]. $^1$H NMR (400 MHz, $CD_3OD$) δ: 8.48 (br s, 1H), 8.02 (d, J = 5.2 Hz, 1H), 7.22 (d, J = 4.0 Hz, 2H), 7.13 (d, J = 12.4 Hz, 1H), 6.87 (d, J = 5.2 Hz, 1H), 5.28 (q, J = 7.2 Hz, 1H), 4.43 (s, 2H), 3.78-3.62 (m, 4H), 3.22-3.08 (m, 3H), 2.19-1.96 (m, 4H), 1.55 (d, J = 6.8 Hz, 3H), 1.44 (s, 9H), 1.30 (t, J = 7.2 Hz, 3H). |
| 37 | 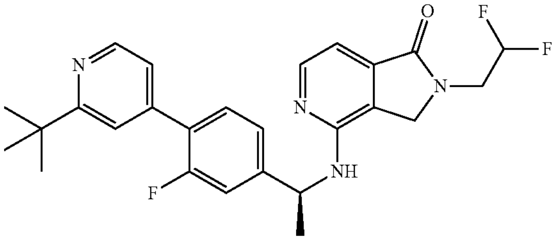 [SMILES: C[C@H](Nc1nccc2c1CN(CC(F)F)C2=O)c1ccc(-c2ccnc(C(C)(C)C)c2)c(F)c1] | LC-MS: (ESI) m/z: 469.1 [M + H]. $^1$H NMR (400 MHz, $CDCl_3$) δ: 8.62 (d, J = 5.2 Hz, 1H), 8.25 (d, J = 5.2 Hz, 1H), 7.48 (s, 1H), 7.43 (t, J = 8.0 Hz, 1H), 7.26-7.20 (m, 2H), 7.09 (d, J = 5.2 Hz, 1H), 6.14-5.85 (tt, J = 4.0, 55.2 Hz, 1H), 5.48-5.41 (m, 1H), 4.48 (d, J = 7.2 Hz, 1H), 4.42 (s, 2H), 4.03-3.94 (td, J = 4.0, 14.8 Hz, 2H), 1.65 (d, J = 7.2 Hz, 3H), 1.40 (s, 9H). |
| 38 | 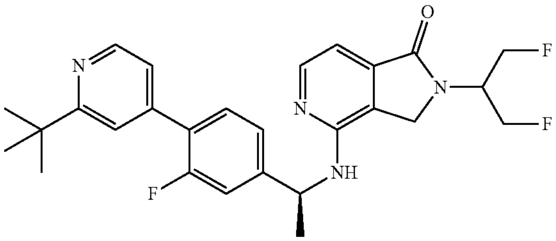 [SMILES: C[C@H](Nc1nccc2c1CN(C(CF)CF)C2=O)c1ccc(-c2ccnc(C(C)(C)C)c2)c(F)c1] | LC-MS: (ESI) m/z: 483.0 [M + H]. $^1$H NMR (400 MHz, $CDCl_3$) δ: 8.61 (d, J = 6.2 Hz, 1H), 8.25 (d, J = 5.2 Hz, 1H), 7.48 (s, 1H), 7.43 (t, J = 8.0 Hz, 1H), 7.31-7.28 (dd, J = 1.6, 8.0 Hz, 1H), 7.26-7.21 (m, 2H), 7.09 (d, J = 5.2 Hz, 1H), 5.49-5.42 (m, 1H), 4.89-4.70 (m, 5H), 4.50 (d, J = 7.2 Hz, 1H), 4.45 (s, 2H), 1.64 (d, J = 6.8 Hz, 3H), 1.40 (s, 9H). |
| 39 | 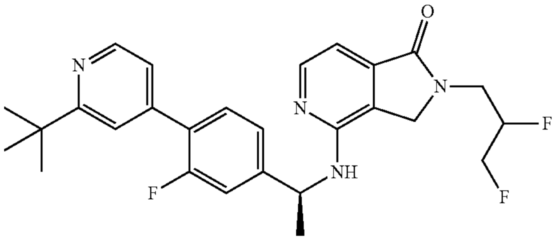 [SMILES: C[C@H](Nc1nccc2c1CN(CC(F)CF)C2=O)c1ccc(-c2ccnc(C(C)(C)C)c2)c(F)c1] | LC-MS: (ESI) m/z: 483.2 [M + H]. $^1$H NMR (400 MHz, $CDCl_3$) δ: 8.61 (d, J = 5.2 Hz, 1H), 8.24 (d, J = 5.2 Hz, 1H), 7.48 (s, 1H), 7.43 (d, J = 7.6 Hz, 1H), 7.31-7.28 (m, 1H), 7.27-7.18 (m, 2H), 7.07 (d, J = 5.2 Hz, 1H), 5.44 (q, J = 6.8 Hz, 1H), 5.11-4.86 (m, 1H), 4.84-4.45 (m, 4H), 4.44-4.34 (m, 1H), 4.16-4.00 (m, 1H), 3.93-3.76 (m, 1H), 1.64 (d, J = 7.2 Hz, 3H), 1.40 (s, 9H). |
| 40 | 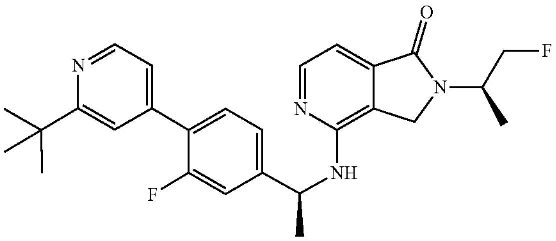 [SMILES: C[C@H](Nc1nccc2c1CN([C@H](C)CF)C2=O)c1ccc(-c2ccnc(C(C)(C)C)c2)c(F)c1] | LC-MS: (ESI) m/z: 465.2 [M + H]. $^1$H NMR (400 MHz, $CDCl_3$) δ: 8.61 (d, J = 5.6 Hz, 1H), 8.23 (d, J = 5.2 Hz, 1H), 7.48 (s, 1H), 7.46-7.40 (m, 1H), 7.30 (dd, J = 1.6, 8.0 Hz, 1H), 7.26-7.20 (m, 2H), 7.08 (d, J = 5.2 Hz, 1H), 5.46 (q, J = 6.8 Hz, 1H), 4.79-4.62 (m, 2H), 4.60-4.51 (m, 1H), 4.50 (d, J = 7.2 Hz, 1H), 4.42-4.29 (m, 2H), 1.64 (d, J = 6.8 Hz, 3H), 1.43 (d, J = 7.2 Hz, 3H), 1.40 (s, 9H). |
| 41 | 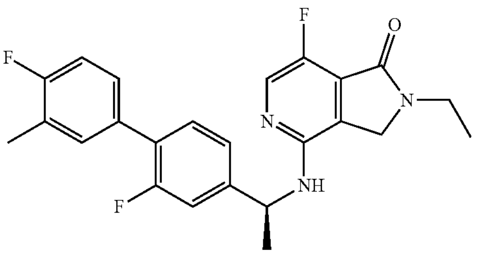 [SMILES: CCN1Cc2c(N[C@@H](C)c3ccc(-c4ccc(F)c(C)c4)c(F)c3)ncc(F)c2C1=O] | $^1$H NMR (500 MHz, $CDCl_3$) δ: 8.02 (d, J = 1.2 Hz, 1H), 7.37-7.31 (m, 2H), 7.29 (t, J = 6.8 Hz, 1H), 7.21 (dd, J = 8.0, 1.6 Hz, 1H), 7.15 (dd, J = 11.6, 1.6 Hz, 1H), 7.06 (t, J = 8.8 Hz, 1H), 5.31 (p, J = 6.8 Hz, 1H), 4.31 (d, J = 6.8 Hz, 1H), 4.25 (d, J = 1.2 Hz, 2H), 3.66 (q, J = 7.2 Hz, 2H), 2.32 (d, J = 2.0 Hz, 3H), 1.60 (s, 3H), 1.28 (t, J = 7.2 Hz, 3H). |

TABLE 1-continued

| Cpd No. | Compound Structure | MS/$^1$H NMR |
|---|---|---|
| 42 | 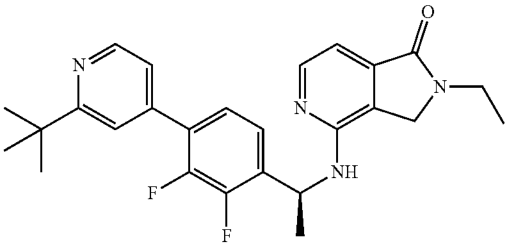 [SMILES: CCN1Cc2c(ccnc2N[C@@H](C)c2ccc(-c3ccnc(C(C)(C)C)c3)c(F)c2F)C1=O] | LC-MS: (ESI) m/z 451.2 [M + H]. 1H NMR (400 MHz, CD3OD) o: 8.80 (d, J = 6.0 Hz, 1H), 8.27 (s, 1H), 8.21-8.16 (m, 1H), 7.98 (d, J = 6.4 Hz, 1H), 7.68-7.62 (m, 1H), 7.58-7.52 (m, 1H), 7.27 (d, J = 6.4 Hz, 1H), 5.50 (q, J = 6.4 Hz, 1H), 4.81-4.63 (m, 2H), 3.75 (q, J = 7.2 Hz, 2H), 1.84 (d, J = 6.8 Hz, 3H), 1.58 (s, 9H), 1.35 (t, J = 7.2 Hz, 3H). |
| 43 | 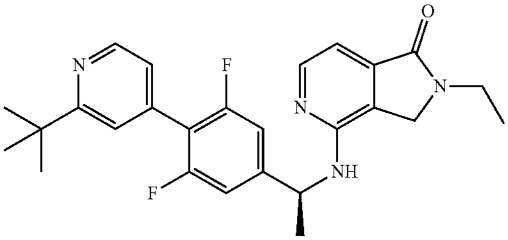 [SMILES: CCN1Cc2c(ccnc2N[C@@H](C)c2cc(F)c(-c3ccnc(C(C)(C)C)c3)c(F)c2)C1=O] | LC-MS: (ESI) m/z: 451.1 [M + H]. $^1$H NMR (400 MHz, $CD_3OD$) δ: 8.55 (d, J = 5.2 Hz, 1H), 8.09 (d, J = 5.2 Hz, 1H), 7.51 (s, 1H), 7.30-7.28 (dd, J = 1.2, 5.2 Hz, 1H), 7.21-7.18 (m, 2H), 6.93 (d, J = 5.2 Hz, 1H), 5.37-5.31 (q, J = 7.2 Hz, 1H), 4.54-4.43 (m, 2H), 3.74-3.68 (q, J = 7.2 Hz, 2H), 1.63 (d, J = 7.2 Hz, 3H), 1.39 (s, 9H), 1.33 (t, J = 7.2 Hz, 3H). |
| 44 | 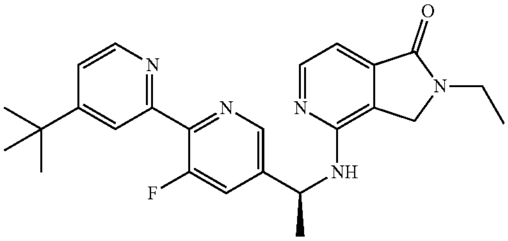 [SMILES: CCN1Cc2c(ccnc2N[C@@H](C)c2cnc(-c3cc(C(C)(C)C)ccn3)c(F)c2)C1=O] | LC-MS: (ESI) m/z: 434.2 [M + H]. $^1$H NMR (400 MHz, $CD_3OD$) δ: 8.59 (s, 1H), 8.56 (d, J = 4.8 Hz, 1H), 8.07 (d, J = 5.2 Hz, 1H), 7.92 (s, 1H), 7.78 (dd, J = 1.6, 12.0 Hz, 1H), 7.54 (dd, J = 1.6, 5.6 Hz, 1H), 6.92 (d, J = 5.2 Hz, 1H), 5.45 (q, J = 6.8 Hz, 1H), 4.47 (d, J = 3.2 Hz, 2H), 3.70 (q, J = 7.2 Hz, 2H), 1.68 (d, J = 7.2 Hz, 3H), 1.39 (s, 9H), 1.32 (t, J = 7.3 Hz, 4H). $^{19}$FNMR (400 MHz, $CD_3OD$) δ: −125.499. |
| 45 | 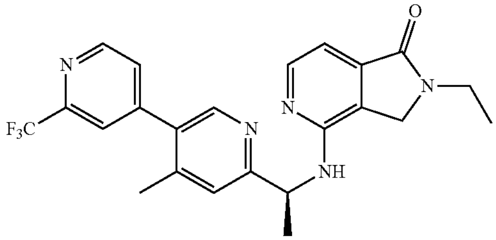 [SMILES: CCN1Cc2c(ccnc2N[C@@H](C)c2cc(C)c(-c3ccnc(C(F)(F)F)c3)cn2)C1=O] | $^1$H NMR (400 MHz, $CDCl_3$) δ: 8.84-8.83 (d, J = 5.2 Hz, 1H), 8.38 (s, 1H), 8.25-8.24 (d, J = 5.2 Hz, 1H), 7.67 (s, 1H), 7.48-7.46 (m, 1 H), 7.30-7.26 (d, J = 5.2 Hz, 1H), 7.05-7.04 (d, J = 5.2 Hz, 1H),5.59-5.57 (m, 1H), 5.51-5.30 (m, 1H),4.36-4.27 (m, 2H), 3.75-3.66 (m, 2H), 2.32 (s, 3H), 1.63-1.61 (d, J = 6.8 Hz, 3H), 1.31-1.24 (m, 3H). |
| 46 | 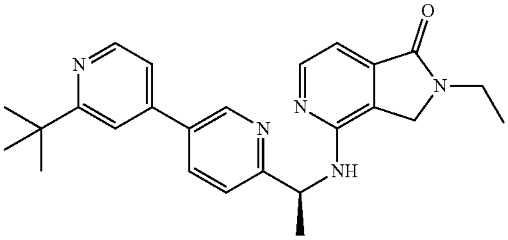 [SMILES: CCN1Cc2c(ccnc2N[C@@H](C)c2ccc(-c3ccnc(C(C)(C)C)c3)cn2)C1=O] | $^1$H NMR (400 MHz, $CDCl_3$) δ: 8.81(d, J = 2.0 Hz, 1H), 8.66 (d, J = 4.4 Hz, 1H), 8.24 (d, J = 5.2 Hz, 1H), 7.91 (dd, J = 8.0 Hz, 1H), 7.51 (s, 1H), 7.47(d, J = 8.0 Hz, 1H), 7.29(dd, J = 4.8 Hz, 1H), 7.05(d, J = 5.2 Hz, 1H), 5.17 (d, J = 7.2 Hz, 1H), 5.56-5.47 (m, 1H), 4.32 (d, J = 2.0 Hz, 2H), 3.71-3.66 (m, 2H), 1.64 (d, J = 6.8 Hz, 3H), 1.43 (s, 9H), 1.31 (t, J = 7.2 Hz, 3H). |
| 47 | 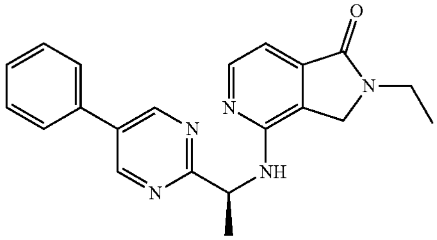 [SMILES: CCN1Cc2c(ccnc2N[C@@H](C)c2ncc(-c3ccccc3)cn2)C1=O] | $^1$H NMR (500 MHz, $CDCl_3$) δ: 8.92 (s, 2H), 8.24 (d, J = 5.2 Hz, 1H), 7.59-7.55 (m, 2H), 7.55-7.50 (m, 2H), 7.49-7.44 (m, 1H), 7.04 (d, J = 5.2 Hz, 1H), 5.62 (tt, J = 13.6, 7.2 Hz, 2H), 4.37 (s, 2H), 3.75 (s, 1H), 3.70 (q, J = 7.2 Hz, 2H), 1.70 (d, J = 6.4 Hz, 3H), 1.31 (t, J = 7.2 Hz, 3H). |

TABLE 1-continued

| Cpd No. | Compound Structure | MS/$^1$H NMR |
|---|---|---|
| 48 | 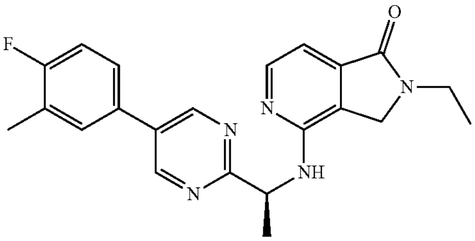 [SMILES: CCN1Cc2c(ccnc2N[C@@H](C)c2ncc(-c3ccc(F)c(C)c3)cn2)C1=O] | $^1$H NMR (500 MHz, $CDCl_3$) δ: 8.79 (s, 2H), 8.16 (d, J = 5.2 Hz, 1H), 7.36-7.22 (m, 2H), 7.07 (t, J = 8.8 Hz, 1H), 6.97 (d, J = 5.2 Hz, 1H), 5.52 (q, J = 5.6, 5.2 Hz, 2H), 4.29 (s, 2H), 3.63 (q, J = 7.2 Hz, 2H), 2.29 (d, J = 2.0 Hz, 3H), 1.61 (s, 3H), 1.24 (t, J = 7.2 Hz, 3H). |
| 49 | 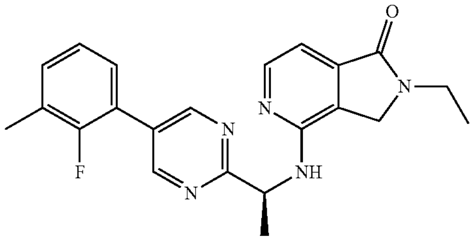 [SMILES: CCN1Cc2c(ccnc2N[C@@H](C)c2ncc(-c3cccc(C)c3F)cn2)C1=O] | $^1$H NMR (500 MHz, $CDCl_3$) δ: 8.89-8.78 (m, 2H), 8.17 (d, J = 5.2 Hz, 1H), 7.65 (t, J = 7.2 Hz, 1H), 7.58 (t, J = 7.2 Hz, 1H), 7.35 (t, J = 7.6 Hz, 1H), 6.98 (d, J = 5.2 Hz, 1H), 5.62-5.41 (m, 2H), 4.30 (s, 2H), 3.64 (q, J = 7.2 Hz, 2H). |
| 50 | 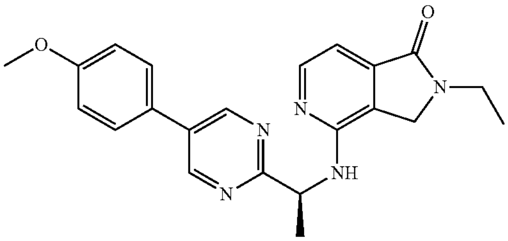 [SMILES: CCN1Cc2c(ccnc2N[C@@H](C)c2ncc(-c3ccc(OC)cc3)cn2)C1=O] | $^1$H NMR (500 MHz, $CDCl_3$) δ: 8.87 (s, 2H), 8.24 (d, J = 5.2 Hz, 1H), 7.56-7.43 (m, 2H), 7.04 (dd, J = 6.8, 2.0 Hz, 3H), 5.60 (dt, J = 13.6, 7.2 Hz, 2H), 4.36 (s, 2H), 3.87 (s, 3H), 3.70 (q, J = 7.2 Hz, 2H), 1.68 (s, 3H), 1.31 (t, J = 7.2 Hz, 3H). |
| 51 | 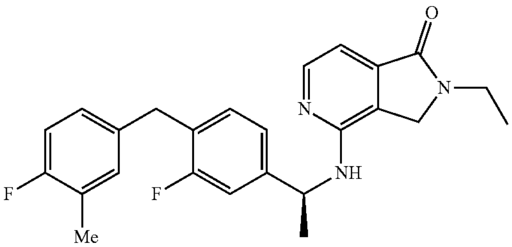 [SMILES: CCN1Cc2c(ccnc2N[C@@H](C)c2ccc(Cc3ccc(F)c(C)c3)c(F)c2)C1=O] | $^1$H NMR (400 MHz, $CDCl_3$) δ: 8.21 (d, J = 5.2 Hz, 1H), 7.09-6.94 (m, 6H), 6.87 (m, 1H), 5.40-5.33 (m, 1H), 4.39 (s, 1H), 4.21 (s, 2H), 3.87 (s, 2H), 3.68-3.63 (m, 2H), 2.22 (s, 3H), 1.58 (d, J = 6.8 Hz, 3H), 1.27 (t, J = 7.6 Hz, 3H). |
| 52 | 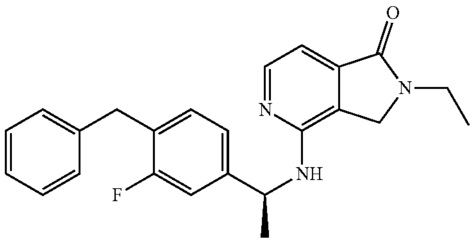 [SMILES: CCN1Cc2c(ccnc2N[C@@H](C)c2ccc(Cc3ccccc3)c(F)c2)C1=O] | $^1$H NMR (500 MHz, $CDCl_3$) δ: 8.14 (d, J = 5.2 Hz, 1H), 7.20 (dd, J = 6.4, 1.6 Hz, 2H), 7.16-7.10 (m, 3H), 7.06-6.96 (m, 4H), 5.30 (p, J = 6.8 Hz, 1H), 4.27 (d, J = 7.6 Hz, 1H), 4.13 (d, J = 3.6 Hz, 2H), 3.89 (s, 2H), 3.58 (q, J = 7.3 Hz, 2H), 1.50 (d, J = 6.8 Hz, 3H), 1.19 (t, J = 7.2 Hz, 3H). |
| 53 | 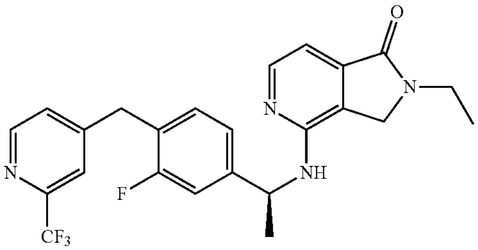 [SMILES: CCN1Cc2c(ccnc2N[C@@H](C)c2ccc(Cc3ccnc(C(F)(F)F)c3)c(F)c2)C1=O] | $^1$H NMR (400 MHz, $CDCl_3$) δ: 8.61 (d, J = 4.8 Hz, 1H), 8.21 (d, J = 5.2 Hz, 1H), 7.51 (s, 1H), 7.31 (d, J = 4.8 Hz, 1H), 7.15-7.11 (m, 3H), 7.06 (d, J = 5.2 Hz, 1H), 5.40-5.38 (m, 1H), 5.42 (d, J = 7.2 Hz), 4.23 (s, 2H), 4.03 (s, 2H), 3.69-3.64 (m, 2H), 1.60 (d, J = 6.8 Hz, 2H), 1.28 (t, J = 7.2 Hz, 3H). |

TABLE 1-continued

| Cpd No. | Compound Structure | MS/$^1$H NMR |
|---|---|---|
| 54 | 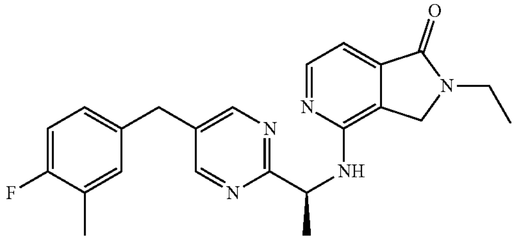 [SMILES: CCN1Cc2c(ccnc2N[C@@H](C)c2ncc(Cc3ccc(F)c(C)c3)cn2)C1=O] | $^1$H NMR (400 MHz, $CDCl_3$) δ: 8.45 (s, 2H), 8.15 (d, J = 4.8 Hz, 1H), 6.96 (d, J = 5.2 Hz, 1H), 6.91-6.86 (m, 3H), 5.38 (d, J = 7.2 Hz, 1H), 5.48-5.43 (m, 1H ), 4.24 (s, 2H), 3.81 (s, 2H), 3.64-3.58 (m, 2H), 2.17 (s, 3H), 1.57 (d, J = 6.8 Hz, 3H), 1.23 (t, J = 7.2 Hz, 3H). |
| 55 | 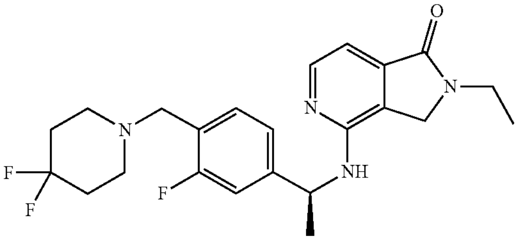 [SMILES: CCN1Cc2c(ccnc2N[C@@H](C)c2ccc(CN3CCC(F)(F)CC3)c(F)c2)C1=O] | $^1$H NMR (500 MHz, $CDCl_3$) δ: 8.21 (d, J = 5.2 Hz, 1H), 7.31 (t, J = 7.7 Hz, 1H), 7.28 (s, 1H), 7.16 (dd, J = 7.9, 1.7 Hz, 1H), 7.10-7.02 (m, 2H), 5.40 (p, J = 7.0 Hz, 1H), 4.41 (d, J = 7.4 Hz, 1H), 4.28-4.14 (m, 2H), 3.67 (q, J = 7.2 Hz, 2H), 3.59 (s, 2H), 2.58 (t, J = 5.7 Hz, 4H), 2.00 (dq, J = 13.0, 6.7, 6.0 Hz, 4H), 1.27 (t, J = 7.2 Hz, 3H). |
| 56 | 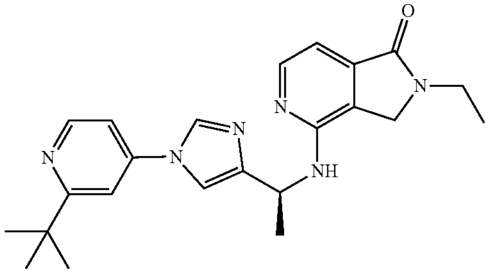 [SMILES: CCN1Cc2c(ccnc2N[C@@H](C)c2cn(-c3ccnc(C(C)(C)C)c3)cn2)C1=O] | LC-MS: (ESI) m/z: 405.3 [M + H]. $^1$H NMR (400 MHz, $CD_3OD$) δ: 8.56 (d, J = 5.6 Hz, 1H), 8.42 (br s, 1H), 8.13 (d, J = 5.2 Hz, 1H), 7.71 (br s, 1H), 7.65 (d, J = 2.0 Hz, 1H), 7.47-7.45 (dd, J = 2.0, 5.6 Hz, 1H), 6.92 (d, J = 5.2 Hz, 1H), 5.48-5.42 (q, J = 6.8 Hz, 1H), 4.49-4.38 (m, 2H), 3.72-3.66 (q, J = 7.2 Hz, 2H), 1.66 (d, J = 7.2 Hz, 3H), 1.42 (s, 9H), 1.31 (t, J = 7.2 Hz, 3H). |
| 57 | 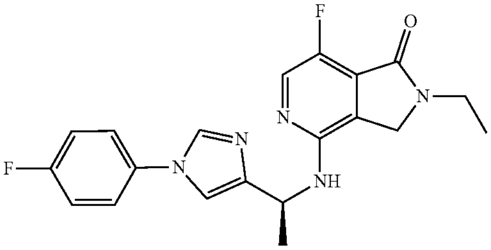 [SMILES: CCN1Cc2c(N[C@@H](C)c3cn(-c4ccc(F)cc4)cn3)ncc(F)c2C1=O] | $^1$H NMR (400 MHz, $CDCl_3$) δ: 8.04 (s, 1H), 7.73 (s, 1H), 7.35-7.32 (m, 2H), 7.19-7.14 (m, 3H), 5.41-5.37 (m, 1H), 4.95 (d, J = 8.0 Hz, 1H), 4.24 (s, 2H), 3.66-3.61 (m, 2H), 1.63 (d, J = 6.8 Hz, 3H), 1.27 (t, J = 6.6 Hz, 3H). |
| 58 | 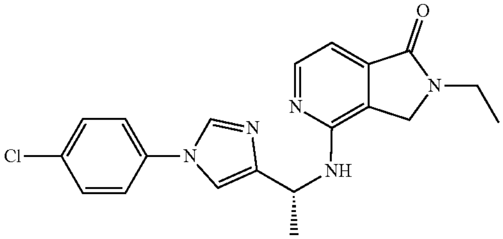 [SMILES: CCN1Cc2c(ccnc2N[C@H](C)c2cn(-c3ccc(Cl)cc3)cn2)C1=O] | $^1$H NMR (500 MHz, $CDCl_3$) δ: 8.25 (d, J = 5.2 Hz, 1H), 7.77 (s, 1H), 7.44 (d, J = 8.2 Hz, 2H), 7.30 (d, J = 8.2 Hz, 2H), 7.18 (s, 1H), 7.02 (d, J = 5.2 Hz, 1H), 5.49 (p, J = 7.0 Hz, 1H), 5.06 (d, J = 8.1 Hz, 1H), 4.24 (s, 2H), 3.65 (q, J = 7.3 Hz, 2H), 1.65 (s, 3H), 1.25 (t, J = 7.3 Hz, 3H). |
| 59 | 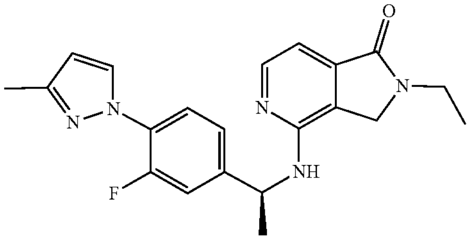 [SMILES: CCN1Cc2c(ccnc2N[C@@H](C)c2ccc(-n3ccc(C)n3)c(F)c2)C1=O] | $^1$H NMR (400 MHz, $CDCl_3$) δ: 8.14 (d, J = 4.0 Hz, 1H), 7.78-7.71 (m, 2H), 7.19-7.15 (m, 2H), 6.99 (d, J = 8.0 Hz, 1 H), 6.18 (d, J = 2.4 Hz, 1H), 5.35-5.32 (m, 1H), 4.35 (d, J = 4.8 Hz, 1H), 4.18 (d, J = 4.4 Hz, 2H), 3.63-3.58 (m, 2H), 2.29 (s, 3H), 1.54 (d, J = 6.8 Hz, 3H), 1.22-1.19 (m, 3H). |

TABLE 1-continued

| Cpd No. | Compound Structure | MS/$^1$H NMR |
|---|---|---|
| 60 | 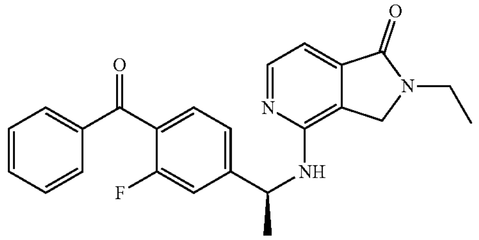 [SMILES: CCN1Cc2c(ccnc2N[C@@H](C)c2ccc(C(=O)c3ccccc3)c(F)c2)C1=O] | $^1$H NMR (500 MHz, $CDCl_3$) δ: 8.21 (d, J = 5.2 Hz, 1H), 7.82 (dt, J = 8.4, 1.2 Hz, 2H), 7.63-7.57 (m, 1H), 7.52 (t, J = 7.6 Hz, 1H), 7.49-7.43 (m, 2H), 7.30 (dd, J = 8.0, 1.6 Hz, 1H), 7.19 (dd, J = 10.8, 1.6 Hz, 1H), 7.08 (d, J = 5.2 Hz, 1H), 5.46 (p, J = 6.8 Hz, 1H), 4.55 (s, 1H), 4.37-4.19 (m, 2H), 3.68 (qd, J = 7.2, 1.6 Hz, 2H), 1.64 (s, 3H), 1.28 (t, J = 7.2 Hz, 3H). |
| 61 | 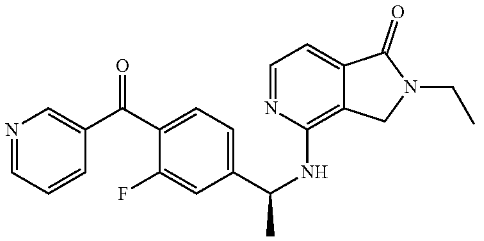 [SMILES: CCN1Cc2c(ccnc2N[C@@H](C)c2ccc(C(=O)c3cccnc3)c(F)c2)C1=O] | $^1$H NMR (500 MHz, $CDCl_3$) δ: 8.90 (s, 1H), 8.73 (dd, J = 4.8, 1.7 Hz, 1H), 8.13 (d, J = 5.2 Hz, 1H), 8.09-8.01 (m, 1H), 7.53 (t, J = 7.6 Hz, 1H), 7.36 (ddd, J = 8.0, 4.8, 0.9 Hz, 1H), 7.27 (dd, J = 7.9, 1.6 Hz, 1H), 7.14 (dd, J = 10.8, 1.6 Hz, 1H), 7.02 (d, J = 5.2 Hz, 1H), 5.39 (p, J = 6.8 Hz, 1H), 4.36 (d, J = 6.8 Hz, 1H), 4.29-4.11 (m, 2H), 3.62 (qd, J = 7.2, 2.0 Hz, 2H), 1.57 (d, J = 6.8 Hz, 3H), 1.24-1.21 (m, 3H). |
| 62 | 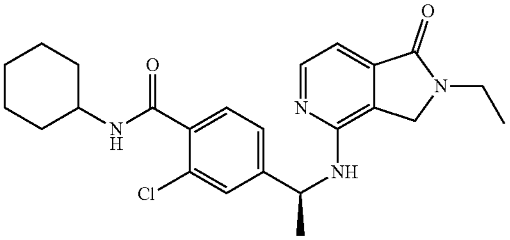 [SMILES: CCN1Cc2c(ccnc2N[C@@H](C)c2ccc(C(=O)NC3CCCCC3)c(Cl)c2)C1=O] | $^1$H NMR (500 MHz, $CDCl_3$) δ: 8.16 (d, J = 5.2 Hz, 1H), 7.54 (d, J = 8.0 Hz, 1H), 7.29 (dd, J = 8.0, 1.6 Hz, 2H), 7.03 (d, J = 5.2 Hz, 1H), 6.06 (d, J = 8.4 Hz, 1H), 5.34 (p, J = 6.8 Hz, 1H), 4.74 (d, J = 6.8 Hz, 1H), 4.28 (d, J = 2.4 Hz, 2H), 3.98 (m, 1H), 3.66 (q, J = 7.2 Hz, 2H), 2.09-2.00 (m, 2H), 1.74 (m, 4H), 1.53 (d, J = 6.8 Hz, 3H), 1.46-1.37 (m, 2H), 1.27 (t, J = 7.2 Hz, 4H). |
| 63 | 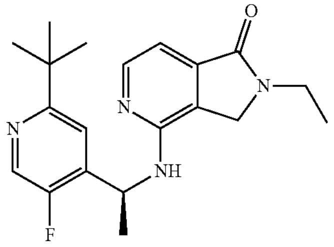 [SMILES: CCN1Cc2c(ccnc2N[C@@H](C)c2cc(C(C)(C)C)ncc2F)C1=O] | LC-MS: (ESI) m/z 357.2 [M + H].<br>$^1$H NMR (400 MHz, $CD_3OD$) δ: 8.25 (d, J = 2.4 Hz, 1H), 8.04 (d, J = 5.2 Hz, 1H), 7.45 (d, J = 6.0 Hz, 1H), 6.90 (d, J = 5.2 Hz, 1H), 5.53 (q, J = 7.2 Hz, 1H), 4.47 (s, 2H), 3.70 (q, J = 7.2 Hz, 2H), 1.60 (d, J = 7.2 Hz, 3H), 1.31 (t, J = 7.2 Hz, 3H), 1.26 (s, 9H). |
| 64 | 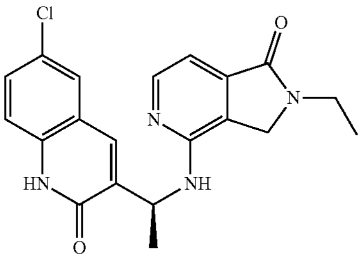 [SMILES: CCN1Cc2c(ccnc2N[C@@H](C)c2cc3cc(Cl)ccc3[nH]c2=O)C1=O] | LC-MS: (ESI) m/z 383.0 [M + H].<br>$^1$H NMR (400 MHz, $CDCl_3$) δ: 8.04 (d, J = 5.2 Hz, 1H), 7.81 (s, 1H), 7.61 (d, J = 2.4 Hz, 1H), 7.44 (dd, J = 2.4, 8.8 Hz, 1H), 7.31 (d, J = 8.8 Hz, 1H), 6.88 (d, J = 5.2 Hz, 1H), 5.41 (q, J = 6.8 Hz, 1H), 4.59-4.40 (m, 2H), 3.78-3.63 (m, 2H), 1.59 (d, J = 7.2 Hz, 3H), 1.32 (t, J = 7.2 Hz, 3H). |

Example 2 2-ethyl-4-[[(1S)-1-[3-fluoro-4-[[2-(trifluoromethyl)-4-pyridyl]oxy]phenyl]ethyl]amino]-3H-pyrrolo[3,4-c]pyridin-1-one (65)

Scheme 2

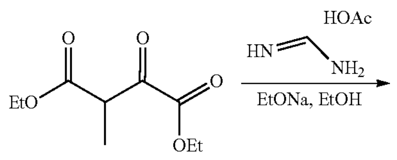

1

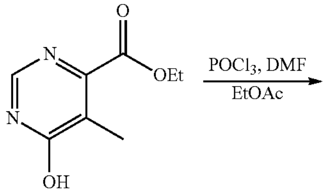

2

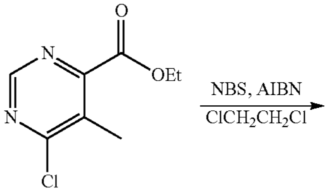

3

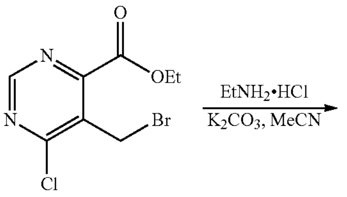

4

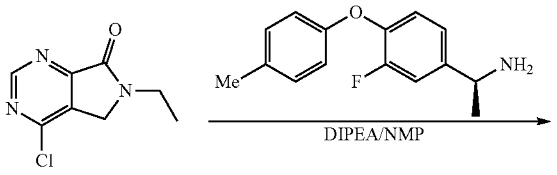

5

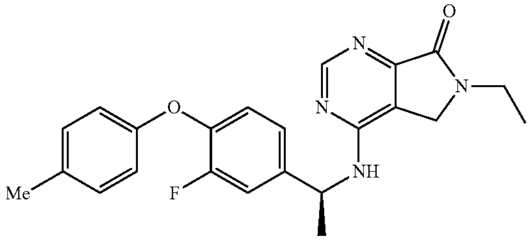

65

Step 1. ethyl 6-hydroxy-5-methyl-pyrimidine-4-carboxylate (2)

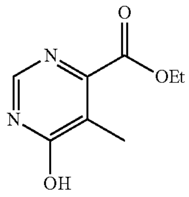

To a mixture of diethyl 2-methyl-3-oxo-butanedioate (1, 30 g, 148.4 mmol) in EtOH (350 mL) was added EtONa (16.15 g, 237.4 mmol) and formimidamide acetate (21.6 g, 207.7 mmol) at 20° C. Then the mixture was stirred at 90° C. for 16 h under $N_2$. The mixture was added 2 N HCl to adjust pH=7, then the mixture was added water (200 mL) and extracted with EtOAc (3×200 mL). The organic layer was collected and washed with brine (200 mL), dried over $Na_2SO_4$, filtered and concentrated in vacuum to give a residue as brown oil. The residue was purified by column chromatography on silica gel eluted with (Petroleum ether: EtOAc=1:3) to afford ethyl 6-hydroxy-5-methyl-pyrimidine-4-carboxylate (2, 6.0 g, 19.5% yield) as yellow solid.

$^1$H NMR (400 MHz, CD3OD) δ: 8.09 (s, 1H), 4.40 (q, J=7.2 Hz, 2H), 2.20 (s, 3H), 1.39 (t, J=7.2 Hz, 3H). LC-MS: (ESI) m/z: 182.9 [M+H].

Step 2. ethyl 6-chloro-5-methyl-pyrimidine-4-carboxylate (3)

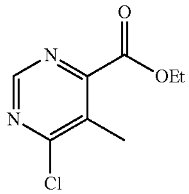

To a solution of ethyl 6-hydroxy-5-methyl-pyrimidine-4-carboxylate (2, 1.0 g, 5.49 mmol) in EtOAc (50 mL) was added oxalyl dichloride (1.44 mL, 16.47 mmol) slowly followed by DMF (84 μL, 1.1 mmol). Then the mixture was stirred at 80° C. for 2 h under $N_2$. The mixture was cooled and added ice water (50 mL) and extracted with EtOAc (3×60 mL). The organic layer was collected and washed with brine (60 mL), dried over $Na_2SO_4$, filtered and concentrated in vacuum to give a residue as brown oil. The residue was purified by column chromatography on silica gel eluted with (Petroleum ether:EtOAc=4:1 (v/v)) to afford ethyl 6-chloro-5-methyl-pyrimidine-4-carboxylate (3, 0.73 g, 61.2% yield) as yellow oil.

$^1$H NMR (400 MHz, CD3OD) δ: 8.85 (s, 1H), 4.45 (q, J=7.2 Hz, 2H), 2.50 (s, 3H), 1.41 (t, J=6.8 Hz, 3H). LC-MS: (ESI) m/z: 200.8 [M+H].

Step 3 ethyl 5-(bromomethyl)-6-chloro-pyrimidine-4-carboxylate (4)

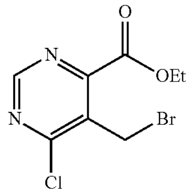 [SMILES: CCOC(=O)c1ncnc(Cl)c1CBr]

To a mixture of ethyl 6-chloro-5-methyl-pyrimidine-4-carboxylate (3, 0.73 g, 3.64 mmol), AIBN(60 mg, 0.36 mmol), NBS (1.62 g, 9.10 mmol) was dissolved 1,2-dichloroethane (30 mL) and the mixture was stirred at 100° C. for 12 h under $N_2$. The mixture was added water (50 mL) and extracted with EtOAc (3×50 mL). The organic layer was collected and washed with brine (50 mL), dried over $Na_2SO_4$, filtered and concentrated in vacuum to afford ethyl 5-(bromomethyl)-6-chloro-pyrimidine-4-carboxylate (4, 1.23 g, crude) as brown oil.

$^1$H NMR (400 MHz, CD3OD) δ: 8.99 (s, 1H), 4.54-4.48 (m, 2H), 2.69 (s, 2H), 1.46-1.42 (m, 3H). LC-MS: (ESI) m/z: 278.9 [M+H].

Step 4 4-chloro-6-ethyl-5H-pyrrolo[3,4-d]pyrimidin-7-one (5)

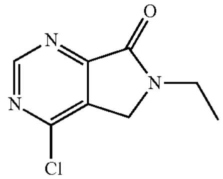

To a solution of ethyl 5-(bromomethyl)-6-chloro-pyrimidine-4-carboxylate (4, 1.18 g, 4.22 mmol), ethanamine hydrochloride (1.03 g, 12.66 mmol) in MeCN(40 mL) was added $K_2CO_3$ (1.17 g, 8.44 mmol) and the mixture was stirred at 25° C. for 6 h under $N_2$. The mixture was added water (50 mL) and extracted with EtOAc (3×50 mL). The organic layer was collected and washed with brine (50 mL), dried over $Na_2SO_4$, filtered and concentrated in vacuum to give a residue as brown oil. The residue was purified via flash chromatography on silica gel (Petroleum ether/EtOAc=1:1) to afford 4-chloro-6-ethyl-5H-pyrrolo[3,4-d]pyrimidin-7-one (5, 0.31 g, 29.7% yield) as brown solid.

$^1$H NMR (400 MHz, CD3OD) δ: 9.15 (s, 1H), 4.66 (s, 2H), 3.75 (q, J=7.6 Hz, 2H), 1.32 (t, J=7.2 Hz, 3H). LC-MS: (ESI) m/z: 197.9 [M+H].

Step 5 6-ethyl-4-[[(LS)-1-[3-fluoro-4-(4-methylphenoxy)phenyl]ethyl]amino]-5H-pyrrolo[3,4-d]pyrimidin-7-one (65)

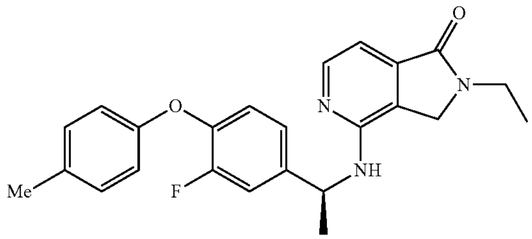 [SMILES: CCN1Cc2c(ccnc2N[C@@H](C)c2ccc(Oc3ccc(C)cc3)c(F)c2)C1=O]

To a mixture of 4-chloro-6-ethyl-5H-pyrrolo[3,4-d]pyrimidin-7-one (5, 0.08 g, 0.4 mmol) and (1S)-1-[3-fluoro-4-(4-methylphenoxy)phenyl]ethanamine (129 mg, 0.53 mmol) in dioxane (4 mL) was added DIPEA (262 mg, 2.02 mmol) and the resulting mixture was stirred at 80° C. for 4 h. The mixture was cooled to room temperature and diluted with water (20 mL), extracted with EtOAc (3×20 mL). The organic layer was washed with brine (20 mL), dried over $Na_2SO_4$, filtered and concentrated to give a residue. The residue was purified by prep-HPLC (column: DuraShell 150*25 mm*5 m; mobile phase: [water (0.05% HCl)-ACN]; B %: 41%-61%, 10 min) to afford 6-ethyl-4-[[(1S)-1-[3-fluoro-4-(4-methylphenoxy)phenyl]ethyl]amino]-5H-pyrrolo[3,4-d]pyrimidin-7-one (65, 30.3 mg, 18.2% yield) as off-white solid.

$^1$H NMR (400 MHz, $CD_3OD$) δ: 8.78 (s, 1H), 7.35 (dd, J=2.0, 11.2 Hz, 1H), 7.23 (d, J=8.4 Hz, 1H), 7.14 (d, J=8.0 Hz, 2H), 7.01 (t, J=8.0 Hz, 1H), 6.81 (d, J=8.4 Hz, 2H), 5.68 (q, J=7.2 Hz, 1H), 4.56 (s, 2H), 3.70 (q, J=7.2 Hz, 2H), 2.30 (s, 3H), 1.69 (d, J=6.8 Hz, 3H), 1.31 (t, J=7.6 Hz, 3H). LC-MS: (ESI) m/z: 407.2 [M+H].

Synthesis of Compounds 66 and 67

In general, Compounds 66 and 67 in Table 2 were prepared according to procedures described in General Scheme B. The synthetic method was similar with Example 2. The data for Compounds 66 and 67 is shown herein below in Table 2.

TABLE 2

| Cpd No. | Compound Structure | MS/$^1$H NMR |
|---|---|---|
| 66 | 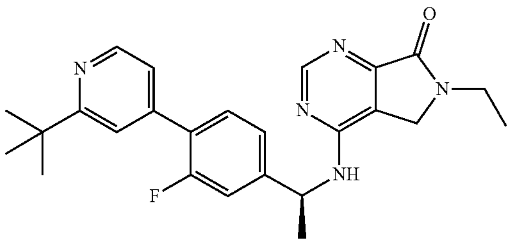 [SMILES: CCN1Cc2c(N[C@@H](C)c3ccc(-c4ccnc(C(C)(C)C)c4)c(F)c3)ncnc2C1=O] | LC-MS: (ESI) m/z: 434.2 [M + H]. $^1$H NMR (400 MHz, $CD_3OD$) δ: 8.51 (t, J = 2.4 Hz, 2H), 7.60 (s, 1H), 7.53 (t, J = 8.0 Hz, 1H), 7.41-7.35 (m, 2H), 7.31 (d, J = 12.0 Hz, 1H), 5.51 (q, J = 6.8 Hz, 1H), 4.45 (s, 2H), 3.70 (q, J = 7.2 Hz, 2H), 1.64 (d, J = 6.8 Hz, 3H), 1.40 (s, 9H), 1.31 (t, J = 7.2 Hz, 3H). |
| 67 | 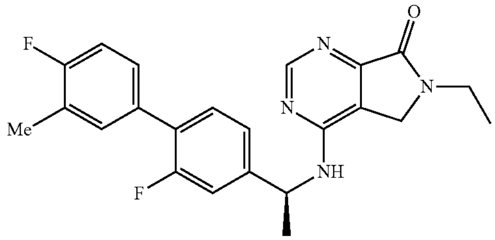 [SMILES: CCN1Cc2c(N[C@@H](C)c3ccc(-c4ccc(F)c(C)c4)c(F)c3)ncnc2C1=O] | LC-MS: (ESI) m/z: 408.9 [M + H]. $^1$H NMR (400 MHz, DMSO-$d_6$) δ: 8.52 (s, 1H), 8.16 (d, J = 7.6 Hz, 1H), 7.49-7.42 (m, 2H), 7.40-7.29 (m, 3H), 7.27-7.17 (m, 1H), 5.50-5.38 (m, 1H), 4.49-4.30 (m, 2H), 3.63-3.51 (m, 2H), 2.29 (d, J = 1.6 Hz, 3H), 1.54 (d, J = 7.2 Hz, 3H), 1.21 (t, J = 7.2 Hz, 3H). |

Example 3

2-ethyl-4-[[(1S)-1-[3-fluoro-4-[4-(trifluoromethyl)phenyl]phenyl]ethyl]amino]-3H-pyrrolo[3,4-c]pyridin-1-one (68)

This compound was prepared according to General Scheme C. Specifically, the scheme is listed as follows.

Scheme 3

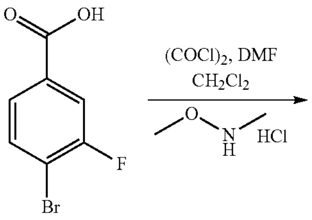

C-1a

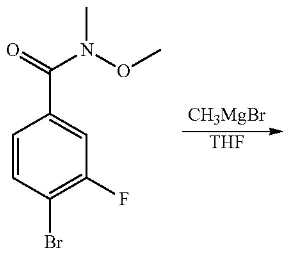

C-1b

-continued

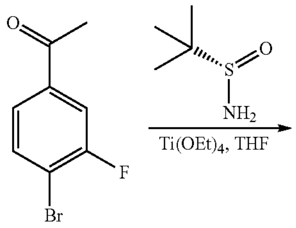

C-1c

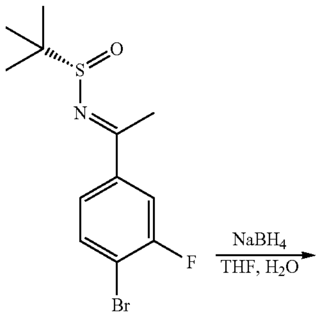

C-1d

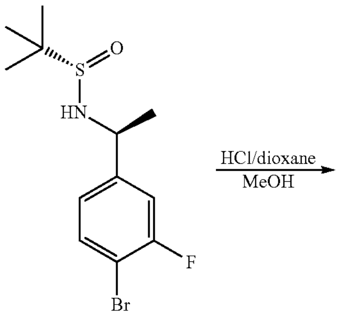

C-1e

-continued

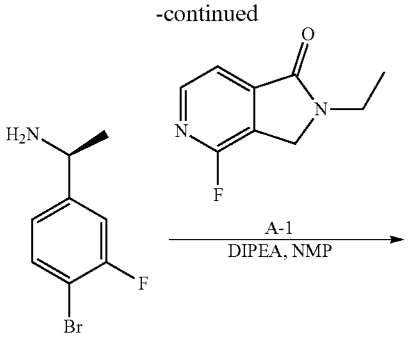

C-1f

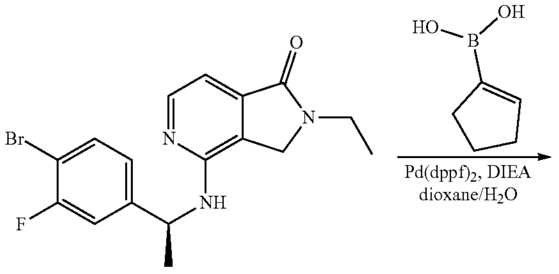

C-1

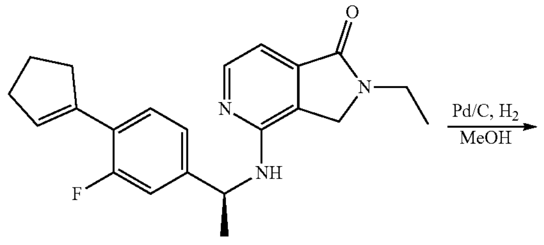

35a

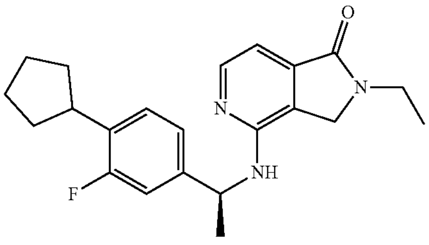

35

Step 1. 4-bromo-3-fluoro-N-methoxy-N-methyl-benzamide (C-1b)

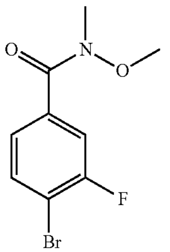

To a mixture of 4-bromo-3-fluoro-benzoic acid (C-1a, 150 g, 0.68 mol) in DCM (1 L) and DMF (3 mL, 0.039 mol) was added $(COCl)_2$ (66 mL, 0.75 mol) dropwise slowly at 0° C. The reaction was stirred at 25-30° C. for 12 h. The mixture was cooled to 0-5° C. and then N-methoxymethanamine hydrochloride (100 g, 1.03 mol) was added, followed by slow addition of TEA (400 mL, 2.87 mol). The reaction was stirred at 25-30° C. for another 2 h. The mixture was filtered off and the filter cake was washed with DCM (2×200 mL). The mixture was diluted with water (800 mL) and extracted with DCM (3×300 mL). The combined organic layers were washed with 1.0 M HCl solution (2×500 mL), brine (500 mL), dried over $Na_2SO_4$, filtered and concentrated. The resulting oil was cooled in dry ice/EtOH bath until the solid was formed. The mixture was diluted with Petroleum ether (100 mL) and then filtered. The filter cake was collected and dried to afford 4-bromo-3-fluoro-N-methoxy-N-methyl-benzamide (C-1b, 170 g, 94.7% yield) as an off-white solid.

$^1$H NMR (400 MHz, $CDCl_3$) δ: 7.60 (dd, J=6.8, 8.4 Hz, 1H), 7.50 (dd, J=2.0, 8.8 Hz, 1H), 7.41 (dd, J=1.6, 8.4 Hz, 1H), 3.55 (s, 3H), 3.36 (s, 3H). LC-MS: (ESI) m/z: 261.9/263.9 [M+H].

Step 2. 1-(4-bromo-3-fluoro-phenyl)ethanone (C-1c)

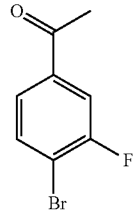

To a solution of 4-bromo-3-fluoro-N-methoxy-N-methyl-benzamide (C-1b, 170 g, 0.65 mol) in THE (1.5 L) was added MeMgBr (3 M in ether, 325 mL) at 0-5° C. under nitrogen. The reaction was stirred at 0-5° C. for 3 h. The mixture was quenched with saturated $NH_4Cl$ solution (1 L) at 0-10° C. and the mixture was extracted with EtOAc (3×600 mL). The combined organic layers were washed with brine (500 mL), dried over $Na_2SO_4$, filtered and concentrated. The resulting oil was cooled in dry ice-EtOH bath until the solid was formed. The mixture was diluted with Petroleum ether (100 mL) and then filtered. The solid was collected and dried to afford 1-(4-bromo-3-fluoro-phenyl)ethanone (C-1c, 121 g, 85.9% yield) as an off-white solid.

$^1$H NMR (400 MHz, $CDCl_3$) δ: 7.72-7.64 (m, 2H), 7.61 (dd, J=2.0, 8.4 Hz, 1H), 2.59 (s, 3H).

Step 3. (S)—N-[1-(4-bromo-3-fluoro-phenyl)ethylidene]-2-methyl-propane-2-sulfinamide (C-1d)

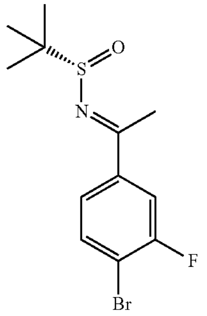 [SMILES: C/C(=N\[S@@](=O)C(C)(C)C)c1ccc(Br)c(F)c1]

A mixture of 1-(4-bromo-3-fluoro-phenyl)ethanone (C-1c, 121 g, 0.56 mol.), 2-methylpropane-2-sulfinamide (81 g, 0.67 mol) and $Ti(OEt)_4$ (255 g, 1.12 mol) in THE (1 L) was stirred at 80° C. for 8 h. The mixture was poured into water (1 L) and then diluted with EtOAc (600 mL). The mixture was filtered off and the filter cake was washed with EtOAc (2×600 mL). The organic layer was separated and the aqueous layer was extracted with EtOAc (2×600 mL). The combined organic layers were washed with brine (800 mL), dried over $Na_2SO_4$, filtered and concentrated to afford (S)—N-[1-(4-bromo-3-fluoro-phenyl)ethylidene]-2-methyl-propane-2-sulfinamide (C-1d, 170 g, 95.2% yield) as yellow oil.

$^1$H NMR (400 MHz, $CDCl_3$) δ: 7.68-7.59 (m, 2H), 7.53 (dd, J=1.6, 8.4 Hz, 1H), 2.75 (s, 3H), 1.33 (s, 9H).

Step 4. N-[(1S)-1-(4-bromo-3-fluoro-phenyl)ethyl]-2-methyl-propane-2-sulfinamide (C-1e)

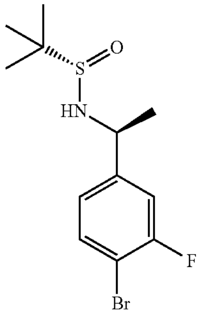 [SMILES: C[C@H](N[S@@](=O)C(C)(C)C)c1ccc(Br)c(F)c1]

To a mixture of (S)—N-[1-(4-bromo-3-fluoro-phenyl)ethylidene]-2-methyl-propane-2-sulfinamide (C-1d, 160 g, 0.5 mol) in THE (1 L) and water (20 mL) was added $NaBH_4$ (56.7 g, 1.50 mol) portionwise at −60∼−40° C. The reaction was stirred at −60∼−40° C. for 3 h. The mixture was poured into saturated $NH_4Cl$ solution (2 L) and the mixture was extracted with EtOAc (3×800 mL). The combined organic layers were washed with brine (800 mL), dried over $Na_2SO_4$, filtered and concentrated. The resulting oil was dissolved in Petroleum ether (300 mL) and placed at 15-20° C. for 12 h. The white precipitate was collected, washed with Petroleum ether (2×50 mL) and dried to afford the desired product (66 g) as a white solid. The filtrate was concentrated in vacuo and the residue was purified by column chromatography ($SiO_2$, Petroleum ether/Ethyl acetate=5/1 to 3:1) to afford pure product (103 g) as a white solid. N-[(1S)-1-(4-bromo-3-fluoro-phenyl)ethyl]-2-methyl-propane-2-sulfinamide (C-1e, 103 g, 64% yield) was obtained in total as a white solid.

$^1$H NMR (400 MHz, $CDCl_3$) δ: 7.52 (dd, J=7.2, 8.0 Hz, 1H), 7.14 (dd, J=2.0, 9.2 Hz, 1H), 7.04 (dd, J=2.0, 8.4 Hz, 1H), 4.55-4.48 (m, 1H), 3.41 (d, J=2.4 Hz, 1H), 1.50 (d, J=6.4 Hz, 3H), 1.24 (s, 9H). LC-MS: (ESI) m/z: 323.7 [M+H].

Step 5. (1S)-1-(4-bromo-3-fluoro-phenyl)ethanamine (C-1f)

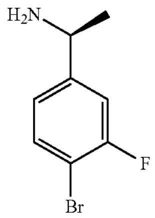

To a solution of N-[(1S)-1-(4-bromo-3-fluoro-phenyl)ethyl]-2-methyl-propane-2-sulfinamide (C-1e, 50 g, 155.17 mmol) in MeOH (250 mL) was added HCl/dioxane (4 M, 80 mL) at 20-25° C. and the reaction was stirred for 2 h. The solvent was concentrated in vacuo and the residue was diluted with water (300 mL). The mixture was extracted with EtOAc (3×150 mL). The organic layer was abandoned. The aqueous layer was adjusted to pH=7-8 with saturated $NaHCO_3$ solution. The mixture was extracted with EtOAc (3×150 mL). The combined organic layers were washed with brine (200 mL), dried over $Na_2SO_4$, filtered and concentrated to afford (1S)-1-(4-bromo-3-fluoro-phenyl)ethanamine (C-1f, 30.1 g, 89% yield) as colorless gum.

$^1$H NMR (400 MHz, $CDCl_3$) δ: 7.48 (dd, J=7.2, 8.0 Hz, 1H), 7.16 (dd, J=2.0, 10.0 Hz, 1H), 7.02 (dd, J=2.0, 8.0 Hz, 1H), 4.11 (q, J=6.4 Hz, 1H), 1.36 (d, J=6.8 Hz, 3H). LC-MS: (ESI) m/z: 200.7/202.7 [M+H].

Step 6. 4-[[(1S)-1-(4-bromo-3-fluoro-phenyl)ethyl]amino]-2-ethyl-3H-pyrrolo[3,4-c]pyridin-1-one (C-1)

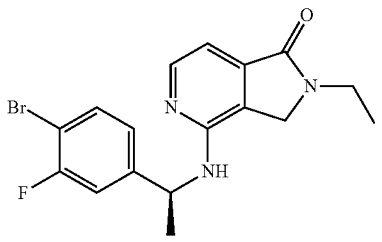 [SMILES: CCN1Cc2c(ccnc2N[C@@H](C)c2ccc(Br)c(F)c2)C1=O]

A mixture of (1S)-1-(4-bromo-3-fluoro-phenyl)ethanamine (C-1f, 20 g, 91.72 mmol), 2-ethyl-4-fluoro-3H-pyrrolo[3,4-c]pyridin-1-one (A-1, 50 g, 277.5 mmol) and DIPEA (48 mL, 275.58 mmol) in NMP (100 mL) was stirred at 170° C. for 6 h. The mixture was poured into water (800 mL) and then extracted with EtOAc (5×300 mL). The combined organic layers were washed with brine (500 mL), dried over $Na_2SO_4$, filtered and concentrated. The residue was purified by column chromatography ($SiO_2$, Petroleum ether/Ethyl acetate=3/1 to 1:1) to afford 4-[[(1S)-1-(4-bromo-3-fluoro-phenyl)ethyl]amino]-2-ethyl-3H-pyrrolo[3,4-c]pyridin-1-one (C-1, 25 g, 72.1% yield) as an off-white solid.

$^1$H NMR (400 MHz, $CDCl_3$) δ: 8.20 (d, J=5.2 Hz, 1H), 7.48 (dd, J=7.2, 8.4 Hz, 1H), 7.17 (dd, J=2.0, 9.6 Hz, 1H), 7.08 (dd, J=2.0, 8.0 Hz, 1H), 7.06 (d, J=4.8 Hz, 1H), 5.36 (quin, J=6.8 Hz, 1H), 4.41 (d, J=6.8 Hz, 1H), 4.30-4.20 (m, 2H), 3.68 (q, J=7.2 Hz, 2H), 1.58 (d, J=6.8 Hz, 3H), 1.28 (t, J=7.2 Hz, 3H). LC-MS: (ESI) m/z: 377.8/379.8 [M+H].

Step 7. 4-[[(1S)-1-[4-(cyclopenten-1-yl)-3-fluoro-phenyl]ethyl]amino]-2-ethyl-3H-pyrrolo[3,4-c]pyridin-1-one (35a)

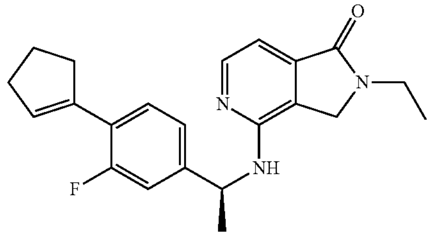 [SMILES: CCN1Cc2c(ccnc2N[C@@H](C)c2ccc(C3=CCCC3)c(F)c2)C1=O]

A mixture of 4-[[(1S)-1-(4-bromo-3-fluoro-phenyl)ethyl]amino]-2-ethyl-3H-pyrrolo [3,4-c]pyridin-1-one (C-1, 100 mg, 0.26 mmol), 2-(cyclopenten-1-yl)-4,4,5,5-tetramethyl-1,3,2-dioxaborolane (51 mg, 0.26 mmol), Pd(dppf)$Cl_2 \cdot CH_2Cl_2$ (22 mg, 0.026 mmol) and DIPEA (92 μL, 0.53 mmol) in 1,4-dioxane (1 mL) and $H_2O$ (1 mL) was stirred at 85° C. for 2 h under $N_2$. The reaction mixture was added to $H_2O$ (100 mL), extracted with EtOAc (3×30 mL). The combined organic phase was dried over anhydrous $Na_2SO_4$, concentrated to give the crude product under the reduced pressure. The crude product was purified by silica gel chromatography (Petroleum ether/EtOAc=3/1 (v/v)) to give 4-[[(1S)-1-[4-(cyclopenten-1-yl)-3-fluoro-phenyl]ethyl]amino]-2-ethyl-3H-pyrrolo[3,4-c] pyridin-1-one (35a, 50 mg, 51.6% yield) as yellow oil.

LC-MS: (ESI) m/z: 366.1 [M+H].

Step 8. 4-[[(1S)-1-(4-cyclopentyl-3-fluoro-phenyl)ethyl]amino]-2-ethyl-3H-pyrrolo[3,4-c]pyridin-1-one (35)

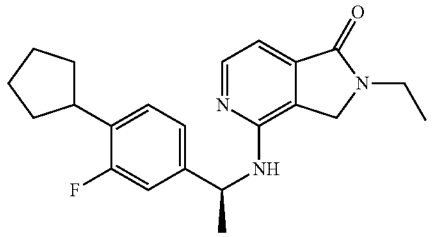 [SMILES: CCN1Cc2c(ccnc2N[C@@H](C)c2ccc(C3CCCC3)c(F)c2)C1=O]

A mixture of 4-[[(1S)-1-[4-(cyclopenten-1-yl)-3-fluoro-phenyl]ethyl]amino]-2-ethyl-3H-pyrrolo[3,4-c]pyridin-1-one (35a, 50 mg, 0.14 mmol) and Pd/C (5 mg, 10% by weight) in MeOH (10 mL) was stirred at 25° C. for 20 min under $H_2$ atmosphere (15 psi). The reaction mixture was filtered to give the filtrate. Then the solvent was removed to give the crude product under the reduced pressure. The crude product was purified by prep-HPLC (column: Boston Prime C18 150*30 mm*5 m; mobile phase: [water (0.05% ammonia hydroxide v/v)-ACN]; B %: 65%-85%, 9 min) to give 4-[[(1S)-1-(4-cyclopentyl-3-fluoro-phenyl)ethyl]amino]-2-ethyl-3H-pyrrolo[3,4-c]pyridin-1-one (35, 26.1 mg, 51.9% yield) as a white solid.

$^1$H NMR (400 MHz, $CDCl_3$) δ: 8.24 (d, J=5.2 Hz, 1H), 7.24-7.19 (m, 1H), 7.11 (d, J=8.0 Hz, 1H), 7.08-7.02 (m, 2H), 5.38 (q, J=6.8 Hz, 1H), 4.37 (d, J=7.2 Hz, 1H), 4.28-4.16 (m, 2H), 3.67 (q, J=7.2 Hz, 2H), 3.21 (q, J=8.2 Hz, 1H), 2.10-1.99 (m, 2H), 1.86-1.76 (m, J=5.2 Hz, 2H), 1.71-1.64 (m, 4H), 1.59 (d, J=6.8 Hz, 3H), 1.27 (t, J=7.2 Hz, 3H). LC-MS: (ESI) m/z: 368.2 [M+H].

Example 4

2-[4-[4-[(1S)-1-[(2-ethyl-1-oxo-3H-pyrrolo[3,4-c]pyridin-4-yl)amino]ethyl]-2-fluoro-phenyl]-2-pyridyl]-2-methyl-propanenitrile (69)

This compound was prepared according to General Scheme C. Specifically, the scheme is listed as follows.

Scheme 4

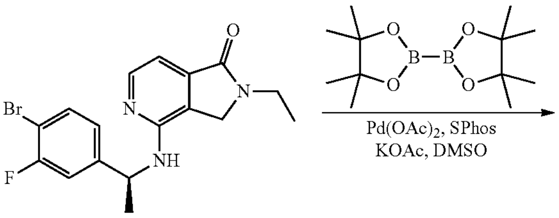

C-1

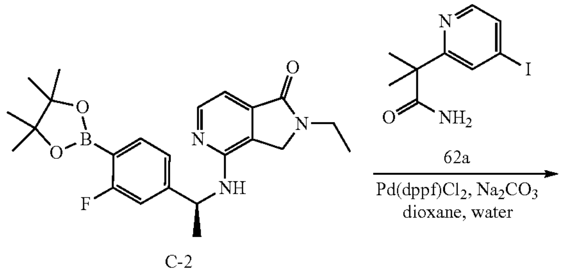

C-2

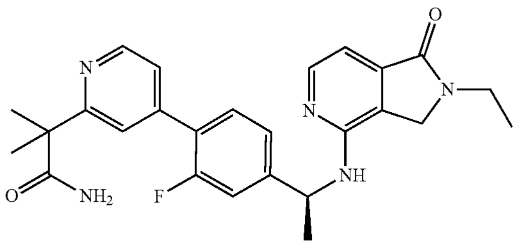

69

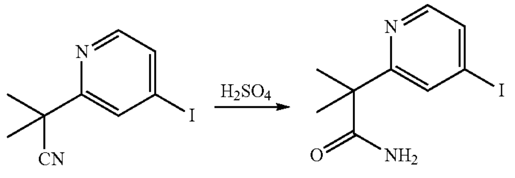

61b 62a

Step 1. 4-[[(1S)-1-(4-bromo-3-fluoro-phenyl)ethyl]amino]-2-ethyl-3H-pyrrolo[3,4-c]pyridin-1-one (C-2)

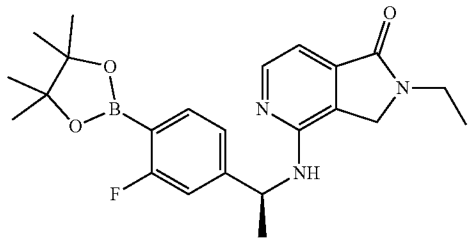 [SMILES: CCN1Cc2c(ccnc2N[C@@H](C)c2ccc(B3OC(C)(C)C(C)(C)O3)c(F)c2)C1=O]

To a mixture of 4-[[(1S)-1-(4-bromo-3-fluoro-phenyl)ethyl]amino]-2-ethyl-3H-pyrrolo[3,4-c] pyridin-1-one (C-1, 0.05 g, 0.13 mmol) and 4,4,5,5-tetramethyl-2-(4,4,5,5-tetramethyl-1,3,2-dioxaborolan-2-yl)-1,3,2-dioxaborolane (134 mg, 0.53 mol) in DMSO (2 mL) was added KOAc (26 mg, 0.26 mmol) at 20° C. The mixture was purged by $N_2$ for 3 times and was added $Pd(dppf)Cl_2 \cdot CH_2Cl_2$ (10.8 mg, 0.013 mmol). Then the mixture was purged by $N_2$ for 3 times again and stirred at 100° C. for 2 h under $N_2$. The reaction mixture (combined with another batch of 50 mg C-1 in dioxane, another batch of 50 mg C-1 in DMF) was added water (20 mL) and extracted with EtOAc (3×20 mL). The organic layer was collected and washed with brine (20 mL), dried over $Na_2SO_4$, filtered and concentrated in vacuum to give a residue as brown oil. The residue was purified by column chromatography on silica gel eluted with (Petroleum ether: EtOAc=1:1) to afford 2-ethyl-4-[[(1S)-1-[3-fluoro-4-(4,4,5,5-tetramethyl-1,3,2-dioxaborolan-2-yl)phenyl]ethyl]amino]-3H-pyrrolo[3,4-c]pyridin-1-one (C-2, 0.1 g, 59.3% yield) as brown gum.

$^1$H NMR (400 MHz, $CDCl_3$) δ: 8.18 (d, J=5.2 Hz, 1H), 7.71 (dd, J=6.8, 7.6 Hz, 1H), 7.18 (d, J=7.6 Hz, 1H), 7.09-7.04 (m, 2H), 5.35 (t, J=6.8 Hz, 1H), 4.96-4.36 (m, 1H), 4.31-4.17 (m, 2H), 3.67 (dq, J=3.2, 7.2 Hz, 2H), 1.35 (s, 12H), 1.30-1.26 (m, 6H). LC-MS: (ESI) m/z: 426.2 [M+H].

Step 2. 2-(4-iodo-2-pyridyl)-2-methyl-propanamide (62a)

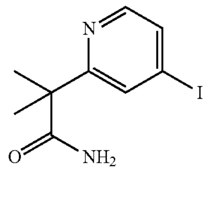

A mixture of 2-(4-iodo-2-pyridyl)-2-methyl-propanenitrile (61b, 150 mg, 0.55 mmol.) in concentrated $H_2SO_4$ (2 mL) was stirred at 20~25° C. for 12 h. The mixture was poured into water (20 mL) and adjusted to pH=8 with saturated $NaHCO_3$ solution. The mixture was extracted with EtOAc (3×30 mL). The combined organic layers were washed with brine (50 mL), dried over $Na_2SO_4$, filtered and concentrated to afford 2-(4-iodo-2-pyridyl)-2-methyl-propanamide (62a, 145 mg, 90.7% yield) as a white solid.

$^1$H NMR (400 MHz, $CDCl_3$) δ: 8.25 (d, J=5.6 Hz, 1H), 7.80 (dd, J=0.4, 1.6 Hz, 1H), 7.59 (dd, J=1.6, 5.2 Hz, 1H), 6.62 (br s, 1H), 5.32 (br s, 1H), 1.64 (s, 6H). LC-MS: (ESI) m/z: 290.7 [M+Na].

Step 3. 2-[4-[4-[(1S)-1-[(2-ethyl-1-oxo-3H-pyrrolo[3,4-c]pyridin-4-yl)amino]ethyl]-2-fluoro-phenyl]-2-pyridyl]-2-methyl-propanamide (69)

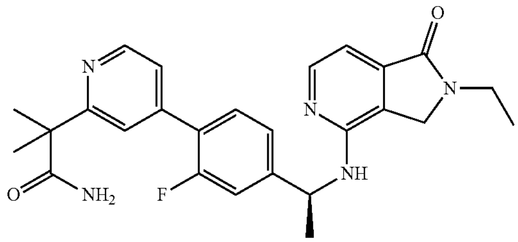 [SMILES: CCN1Cc2c(ccnc2N[C@@H](C)c2ccc(-c3ccnc(C(C)(C)C(N)=O)c3)c(F)c2)C1=O]

To a mixture of 2-(4-iodo-2-pyridyl)-2-methyl-propanamide (62a, 60 mg, 0.21 mmol), 2-ethyl-4-[[(1S)-1-[3-fluoro-4-(4,4,5,5-tetramethyl-1,3,2-dioxaborolan-2-yl)phenyl]ethyl]amino]-3H-pyrrolo[3,4-c]pyridin-1-one (C-2, 100 mg, 0.24 mmol) and $Na_2CO_3$ (44 mg, 0.42 mmol) in dioxane (2 mL) and water (0.5 mL) was added $Pd(dppf)Cl_2 \cdot CH_2Cl_2$ (9 mg, 0.011 mmol) under nitrogen. The reaction was stirred at 90~100° C. for 2 h. The mixture was diluted with EtOAc (20 mL) and filtered through Celite. The filtrate was evaporated and the residue was purified by prep-HPLC (column: DuraShell 150*25 mm*5 m; mobile phase: [water (0.05% ammonia hydroxide v/v)-ACN]; B %: 14%-54%, 10 min) to afford 2-[4-[4-[(1S)-1-[(2-ethyl-1-oxo-3H-pyrrolo[3,4-c]pyridin-4-yl)amino]ethyl]-2-fluoro-phenyl]-2-pyridyl]-2-methyl-propanamide (69, 47.2 mg, 49.5% yield) as a white solid.

$^1$H NMR (400 MHz, $CDCl_3$) δ: 8.64 (d, J=5.2 Hz, 1H), 8.22 (d, J=4.8 Hz, 1H), 7.56 (s, 1H), 7.42 (t, J=8.0 Hz, 1H), 7.38-7.34 (m, 1H), 7.30 (dd, J=1.6, 8.0 Hz, 1H), 7.23 (dd, J=1.6, 12.0 Hz, 1H), 7.08 (d, J=5.2 Hz, 1H), 6.82 (br s, 1H), 5.45 (quin, J=7.2 Hz, 1H), 5.29 (br s, 1H), 4.44 (d, J=7.2 Hz, 1H), 4.32-4.23 (m, 2H), 3.69 (q, J=7.2 Hz, 2H), 1.70 (s, 6H), 1.67-1.63 (m, 3H), 1.30 (t, J=7.2 Hz, 3H). LC-MS: (ESI) m/z 462.1 [M+H].

Synthesis of Compounds 70 to 165

In general, Compound 70 to 165 in table 3 was prepared according to General Scheme C. The synthetic method was similar with Example 3 or Example 4. Data for Compounds 70 to 139 and 141 to 165 are shown below in Table 3.

TABLE 3

| Cpd No. | Compound Structure | MS/$^1$H NMR |
|---|---|---|
| 70 | 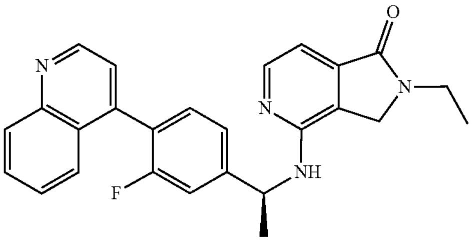 [SMILES: CCN1Cc2c(ccnc2N[C@@H](C)c2ccc(-c3ccnc4ccccc34)c(F)c2)C1=O] | LC-MS: (ESI) m/z: 427.2 [M + H]. $^1$H NMR (400 MHz, DMSO-$d_6$) δ: 8.96 (d, J = 4.2 Hz, 1H), 8.13-8.06 (m, 2H), 7.79 (td, J = 4.2, 8.4 Hz, 1H), 7.59 (d, J = 4.4 Hz, 2H), 7.51-7.43 (m, 4H), 7.27 (d, J = 8.0 Hz, 1H), 6.79 (d, J = 5.2 Hz, 1H), 5.46 (q, J = 7.2 Hz, 1H), 4.52-4.37 (m, 2H), 3.57 (q, J = 7.2 Hz, 2H), 1.58 (d, J = 6.8 Hz, 3H), 1.20 (t, J = 7.2 Hz, 3H). |
| 71 | 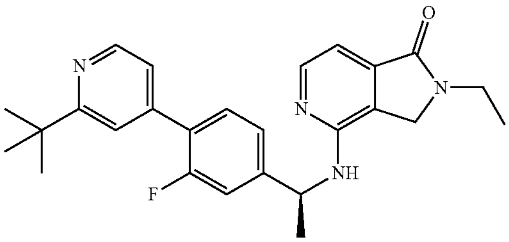 [SMILES: CCN1Cc2c(ccnc2N[C@@H](C)c2ccc(-c3ccnc(C(C)(C)C)c3)c(F)c2)C1=O] | LC-MS: (ESI) m/z 433.2 [M + H]. $^1$H NMR (400 MHz, $CD_3OD$) δ: 8.77 (d, J = 6.4 Hz, 1H), 8.24 (s, 1H), 8.16 (d, J = 6.4 Hz, 1H), 7.97 (d, J = 6.4 Hz, 1H), 7.89 (d, J = 8.0 Hz, 1H), 7.67-7.54 (m, 2H), 7.23 (d, J = 6.4 Hz, 1H), 5.34 (q, J = 6.8 Hz, 1H), 4.83-4.64 (m, 2H), 3.75 (q, J = 7.2 Hz, 2H), 1.81 (d, J = 7.2 Hz, 3H), 1.58 (s, 9H), 1.35 (t, J = 7.2 Hz, 3H). |
| 72 | 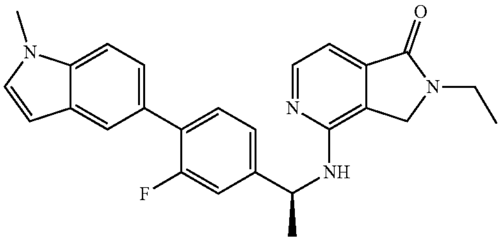 [SMILES: CCN1Cc2c(ccnc2N[C@@H](C)c2ccc(-c3ccc4c(ccn4C)c3)c(F)c2)C1=O] | LC-MS: (ESI) m/z 429.2 [M + H]. $^1$H NMR (400 MHz, $CDCl_3$) δ: 8.26 (d, J = 5.2 Hz, 1H), 7.78 (s, 1H), 7.47 (t, J = 8.4 Hz, 1H), 7.43-7.36 (m, 2H), 7.27-7.18 (m, 2H), 7.12-7.05 (m, 2H), 6.53 (d, J = 3.2 Hz, 1H), 5.50-5.42 (m, 1H), 4.44 (d, J = 7.6 Hz, 1H), 4.32-4.20 (m, 2H), 3.83 (s, 3H), 3.68 (q, J = 7.2 Hz, 2H), 1.65 (d, J = 6.8 Hz, 3H), 1.28 (t, J = 7.2 Hz, 3H). |
| 73 | 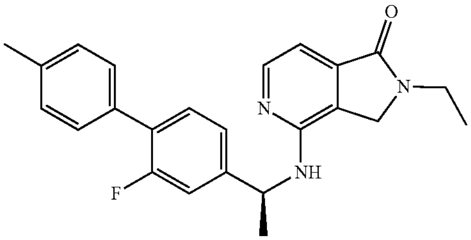 [SMILES: CCN1Cc2c(ccnc2N[C@@H](C)c2ccc(-c3ccc(C)cc3)c(F)c2)C1=O] | LC-MS: (ESI) m/z: 390.2 [M + H]. $^1$H NMR (400 MHz, $CDCl_3$) δ: 8.25 (d, J = 5.2 Hz, 1H), 7.46-7.37 (m, 3H), 7.27-7.23 (m, 3H), 7.19 (dd, J = 1.6, 11.6 Hz, 1H), 7.07 (d, J = 5.2 Hz, 1H), 5.45 (q, J = 6.8 Hz, 1H), 4.44 (d, J = 7.2 Hz, 1H), 4.26 (d, J = 2.7 Hz, 2H), 3.68 (q, J = 7.2 Hz, 2H), 2.40 (s, 3H), 1.64 (d, J = 6.8 Hz, 3H), 1.28 (t, J = 7.2 Hz, 3H). |
| 74 | 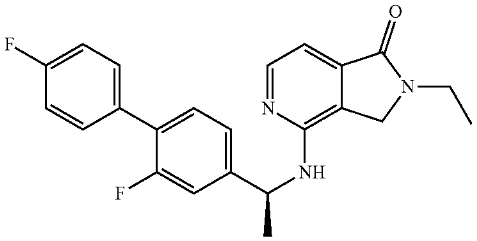 [SMILES: CCN1Cc2c(ccnc2N[C@@H](C)c2ccc(-c3ccc(F)cc3)c(F)c2)C1=O] | LC-MS: (ESI) m/z: 394.2 [M + H]. $^1$H NMR (400 MHz, $CD_3OD$) δ: 7.95 (d, J = 6.4 Hz, 1H), 7.57-7.48 (m, 3H), 7.41-7.34 (m, 2H), 7.24-7.16 (m, 3H), 5.20 (q, J = 6.4 Hz, 1H), 4.79-4.54 (m, 2H), 3.74 (q, J = 7.2 Hz, 2H), 1.78 (d, J = 6.8 Hz, 3H), 1.34 (t, J = 7.6 Hz, 3H). |
| 75 | 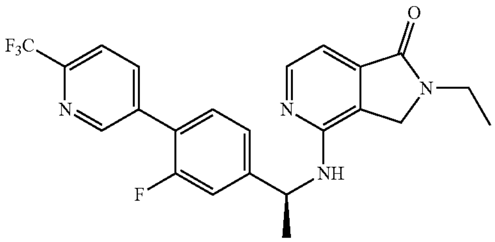 | LC-MS: (ESI) m/z: 445.1 [M + H]. $^1$H NMR (400 MHz, $CDCl_3$) δ: 8.88 (s, 1H), 8.22 (d, J = 2.4 Hz, 1H), 8.04 (d, J = 8.0 Hz, 1H), 7.77-7.75 (m, 1H), 7.43-7.35 (m, 1H), 7.33-7.28 (m, 1H), 7.26-7.25 (m, 1H), 7.08 (d, J = 5.2 Hz, 1H), 5.50-5.42 (m, 1H), 4.43 (d, J = 6.8 Hz, 1H), 4.29 (s, 2H), 3.70 (q, J = 7.2 Hz, 2H), 1.65 (d, J = 6.8 Hz, 3H), 1.30 (t, J = 7.2 Hz, 3H). |

TABLE 3-continued

| Cpd No. | Compound Structure | MS/$^1$H NMR |
|---|---|---|
| 76 | 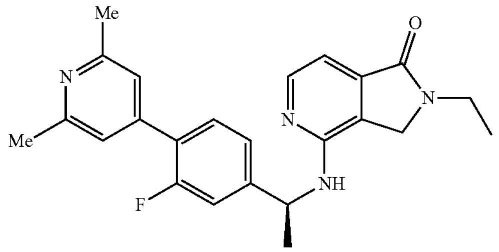 [SMILES: CCN1Cc2c(ccnc2N[C@@H](C)c2ccc(-c3cc(C)nc(C)c3)c(F)c2)C1=O] | LC-MS: (ESI) m/z 405.2 [M + H]. $^1$H NMR (400 MHz, $CDCl_3$) δ: 8.22 (d, J = 5.2 Hz, 1H), 7.41 (t, J = 8.0 Hz, 1H), 7.30-7.27 (m, 1H), 7.21 (d, J = 12.0 Hz, 1H), 7.12 (s, 2H), 7.07 (d, J = 5.2 Hz, 1H), 5.44 (quin, J = 6.8 Hz, 1H), 4.45 (d, J = 6.8 Hz, 1H), 4.32-4.21 (m, 2H), 3.69 (q, J = 7.2 Hz, 2H), 2.57 (s, 6H), 1.63 (d, J = 7.2 Hz, 3H), 1.29 (t, J = 7.2 Hz, 3H). |
| 77 | 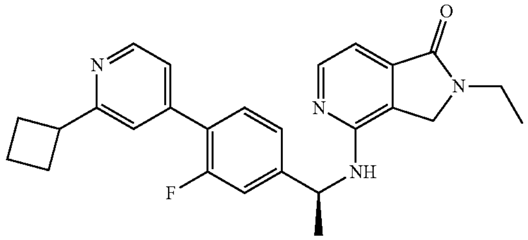 [SMILES: CCN1Cc2c(ccnc2N[C@@H](C)c2ccc(-c3ccnc(C4CCC4)c3)c(F)c2)C1=O] | LC-MS: (ESI) m/z: 431.1 [M + H]. $^1$H NMR (400 MHz, $CD_3OD$) δ: 8.49 (d, J = 5.2 Hz, 1H), 8.06 (d, J = 5.2 Hz, 1H), 7.52 (t, J = 8.0 Hz, 1H), 7.46 (s, 1H), 7.40-7.36 (m, 1H), 7.32-7.28 (dd, J = 1.2, 12.4 Hz, 1H), 6.91 (d, J = 5.2 Hz, 1H), 5.39-5.34 (q, J = 6.8 Hz, 2H), 4.48 (d, J = 2.4 Hz, 2H), 3.79-3.67 (m, 3H), 2.41-2.29 (m, 4H), 2.17-2.08 (m, 1H), 1.96-1.90 (m, 1H), 1.63 (d, J = 7.2 Hz, 3H), 1.32 (t, J = 7.2 Hz, 3H). |
| 78 | 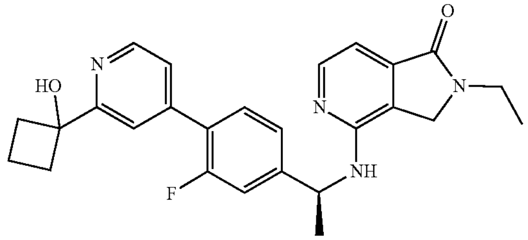 [SMILES: CCN1Cc2c(ccnc2N[C@@H](C)c2ccc(-c3ccnc(C4(O)CCC4)c3)c(F)c2)C1=O] | LC-MS: (ESI) m/z: 447.1 [M + H]. $^1$H NMR (400 MHz, $CD_3OD$) δ: 8.58 (d, J = 5.2 Hz, 1H), 8.07 (d, J = 5.2 Hz, 1H), 7.80 (s, 1H), 7.54 (t, J = 8.0 Hz, 1H), 7.47-7.45 (m, 1H), 7.39-7.37 (dd, J = 1.6, 8.0 Hz, 1H), 7.32-7.29 (dd, J = 1.6, 12.4 Hz, 1H), 6.91 (d, J = 5.2 Hz, 1H), 5.40-5.35 (q, J = 6.8 Hz, 1H), 4.48 (d, J = 2.4 Hz, 2H), 3.73-3.68 (q, J = 7.2 Hz, 2H), 2.73-2.68 (m, 2H), 2.36-2.32 (m, 2H), 2.12-2.07 (m, 1H), 1.94-1.87 (m, 1H), 1.63 (d, J = 7.2 Hz, 3H), 1.33 (t, J = 7.2 Hz, 3H). |
| 79 | 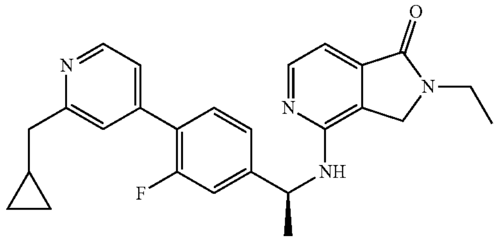 [SMILES: CCN1Cc2c(ccnc2N[C@@H](C)c2ccc(-c3ccnc(CC4CC4)c3)c(F)c2)C1=O] | LC-MS: (ESI) m/z 431.1 [M + H]. $^1$H NMR (400 MHz, $CD_3OD$) δ: 8.77 (d, J = 6.4 Hz, 1H), 8.28 (s, 1H), 8.15 (d, J = 6.4 Hz, 1H), 7.96 (d, J = 6.4 Hz, 1H), 7.87 (t, J = 8.0 Hz, 1H), 7.58 (d, J = 7.6 Hz, 2H), 7.24 (d, J = 6.8 Hz, 1H), 5.30 (q, J = 6.4 Hz, 1H), 4.81-4.60 (m, 2H), 3.74 (q, J = 7.2 Hz, 2H), 3.04 (d, J = 7.2 Hz, 2H), 1.80 (d, J = 6.8 Hz, 3H), 1.35 (t, J = 7.2 Hz, 3H), 1.28-1.16 (m, 1H), 0.76-0.66 (m, 2H), 0.48-0.38 (m, 2H). |
| 80 | 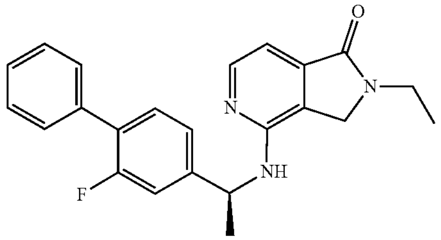 [SMILES: CCN1Cc2c(ccnc2N[C@@H](C)c2ccc(-c3ccccc3)c(F)c2)C1=O] | $^1$H NMR (500 MHz, $CDCl_3$) δ: 8.23 (d, J = 5.2 Hz, 1H), 7.52 (dt, J = 8.1, 1.6 Hz, 2H), 7.46-7.30 (m, 4H), 7.25 (d, J = 6.2 Hz, 1H), 7.19 (dd, J = 11.7, 1.8 Hz, 1H), 7.06 (d, J = 5.2 Hz, 1H), 5.44 (p, J = 6.9 Hz, 1H), 4.52 (d, J = 7.3 Hz, 1H), 4.31-4.19 (m, 2H), 3.67 (q, J = 7.3 Hz, 2H), 1.63 (d, J = 6.9 Hz, 3H), 1.28 (d, J = 7.2 Hz, 3H). |
| 81 | 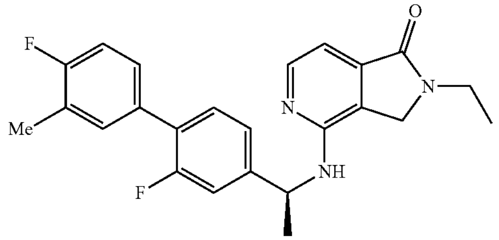 [SMILES: CCN1Cc2c(ccnc2N[C@@H](C)c2ccc(-c3ccc(F)c(C)c3)c(F)c2)C1=O] | $^1$H NMR (500 MHz, $CDCl_3$) δ: 8.23 (d, J = 5.2 Hz, 1H), 7.33 (ddd, J = 14.5, 10.8, 7.3 Hz, 3H), 7.23 (dd, J = 7.9, 1.8 Hz, 1H), 7.18 (dd, J = 11.6, 1.8 Hz, 1H), 7.05 (dd, J = 10.4, 7.1 Hz, 2H), 5.43 (p, J = 6.9 Hz, 1H), 4.41 (d, J = 7.3 Hz, 1H), 4.34-4.18 (m, 2H), 3.68 (q, J = 7.3 Hz, 2H), 2.32 (d, J = 2.0 Hz, 3H), 1.28 (t, J = 7.3 Hz, 3H). |

TABLE 3-continued

| Cpd No. | Compound Structure | MS/$^1$H NMR |
|---|---|---|
| 82 | 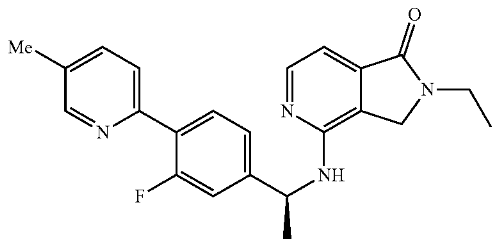 [SMILES: CCN1Cc2c(ccnc2N[C@@H](C)c2ccc(-c3ccc(C)cn3)c(F)c2)C1=O] | $^1$H NMR (400 MHz, $CDCl_3$) δ: 8.46 (s, 1H), 8.15 (d, J = 5.2 Hz, 1H), 7.84 (t, J = 8.0 Hz, 1H), 7.60-7.46 (m, 2H), 7.22-7.09 (m, 2 H), 6.99 (d, J = 4.8 Hz, 1H), 5.39-5.32 (m, 1H), 4.39 (d, J = 6.8 Hz, 1H), 4.18 (d, J = 4.4 Hz, 2H), 3.63-3.57 (m, 2H), 2.30 (s, 3H), 1.56 (d, J = 6.8 Hz, 3H), 1.18 (s, 3H). |
| 83 | 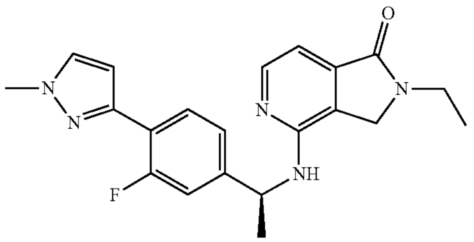 [SMILES: CCN1Cc2c(ccnc2N[C@@H](C)c2ccc(-c3ccn(C)n3)c(F)c2)C1=O] | $^1$H NMR (400 MHz, $CDCl_3$) δ: 8.15 (d, J = 5.2 Hz, 1H), 7.85 (t, J = 8.0 Hz, 1H), 7.32 (d, J = 2.0 Hz, 1H), 7.15-7.06 (m, 2H), 6.99 (d, J = 5.2Hz, 1 H), 6.59-6.57 (m, 1H), 5.35-5.32 (m, 1H), 4.36-4.35 (m, 1H), 4.17 (d, J = 5.2 Hz, 2H), 3.89 (s, 3H), 3.61-3.59 (m, 2H), 1.55 (d, J = 6.8 Hz, 3H), 1.18 (s, 3H). |
| 84 | 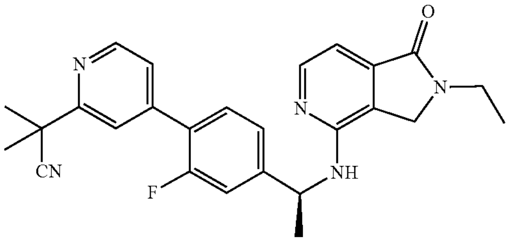 [SMILES: CCN1Cc2c(ccnc2N[C@@H](C)c2ccc(-c3ccnc(C(C)(C)C#N)c3)c(F)c2)C1=O] | LC-MS: (ESI) m/z 444.2 [M + H]. $^1$H NMR (400 MHz, $CDCl_3$) δ: 8.64 (dd, J = 0.8, 5.2 Hz, 1H), 8.22 (d, J = 4.8 Hz, 1H), 7.73 (s, 1H), 7.44 (t, J = 8.0 Hz, 1H), 7.41 (dt, J = 1.6, 5.2 Hz, 1H), 7.32 (dd, J = 1.6, 8.0 Hz, 1H), 7.24 (dd, J = 1.6, 12.0 Hz, 1H), 7.08 (d, J = 5.2 Hz, 1H), 5.44 (quin, J = 6.8 Hz, 1H), 4.58 (br s, 1H), 4.38-4.22 (m, 2H), 3.69 (q, J = 7.2 Hz, 2H), 1.80 (s, 6H), 1.64 (d, J = 7.2 Hz, 3H), 1.29 (t, J = 7.2 Hz, 3H). |
| 85 | 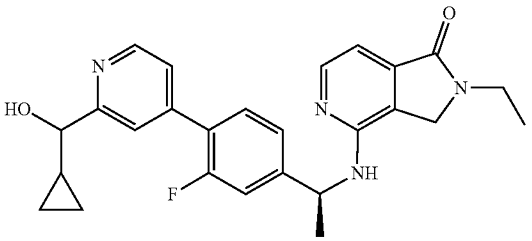 [SMILES: CCN1Cc2c(ccnc2N[C@@H](C)c2ccc(-c3ccnc(C(O)C4CC4)c3)c(F)c2)C1=O] | LCMS: (ESI) m/z 447.1 [M + H] $^1$H NMR (400 MHz, $CD_3OD$) δ: 8.50 (d, J = 5.6 Hz, 1H), 8.06 (d, J = 5.2 Hz, 1H), 7.73 (s, 1H), 7.54 (t, J = 8.0 Hz, 1H), 7.51-7.46 (m, 1H), 7.38 (dd, J = 1.6, 8.0 Hz, 1H), 7.30 (dd, J = 1.2, 12.4 Hz, 1H), 6.90 (d, J = 5.2 Hz, 1H), 5.37 (q, J = 6.8 Hz, 1H), 4.53-4.39 (m, 2H), 4.16 (d, J = 8.0 Hz, 1H), 3.69 (q, J = 7.2 Hz, 2H), 1.62 (d, J = 7.2 Hz, 3H), 1.32 (t, J = 7.2 Hz, 3H), 1.24-1.14 (m, 1H), 0.63-0.43 (m, 4H). |
| 86 | 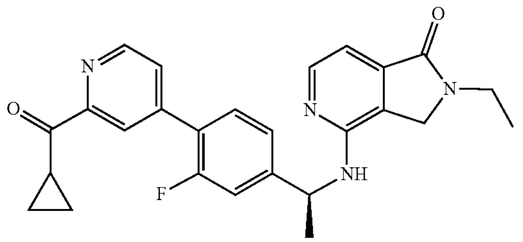 [SMILES: CCN1Cc2c(ccnc2N[C@@H](C)c2ccc(-c3ccnc(C(=O)C4CC4)c3)c(F)c2)C1=O] | LC-MS: (ESI) m/z 445.1 [M + H]. $^1$H NMR (400 MHz, $CD_3OD$) δ: 8.76 (d, J = 5.2 Hz, 1H), 8.16 (s, 1H), 8.06 (d, J = 5.2 Hz, 1H), 7.79 (d, J = 4.8 Hz, 1H), 7.57 (t, J = 8.0 Hz, 1H), 7.39 (d, J = 2.0, 8.4 Hz, 1H), 7.32 (dd, J = 1.6, 12.0 Hz, 1H), 6.90 (d, J = 5.6 Hz, 1H), 5.37 (q, J = 7.2 Hz, 1H), 4.51-4.43 (m, 2H), 3.69 (q, J = 7.2 Hz, 2H), 3.56-3.45 (m, 1H), 1.62 (d, J = 7.2 Hz, 3H), 1.32 (t, J = 7.2 Hz, 3H), 1.21-1.11 (m, 4H). |
| 87 | 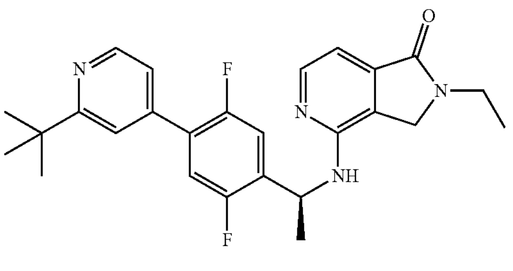 [SMILES: CCN1Cc2c(ccnc2N[C@@H](C)c2cc(F)c(-c3ccnc(C(C)(C)C)c3)cc2F)C1=O] | LC-MS: (ESI) m/z 451.3 [M + H]. $^1$H NMR (400 MHz, $CDCl_3$) δ: 8.63 (d, J = 4.8 Hz, 1H), 8.22 (d, J = 4.8 Hz, 1H), 7.45 (s, 1H), 7.25-7.14 (m, 3H), 7.08 (d, J = 5.2 Hz, 1H), 5.57 (quin, J = 7.2 Hz, 1H), 4.55 (d, J = 6.4 Hz, 1H), 4.29 (s, 2H), 3.70 (q, J = 7.2 Hz, 2H), 1.66 (d, J = 7.2 Hz, 3H), 1.40 (s, 9H), 1.30 (t, J = 7.2 Hz, 3H). |

TABLE 3-continued

| Cpd No. | Compound Structure | MS/$^1$H NMR |
|---|---|---|
| 88 | 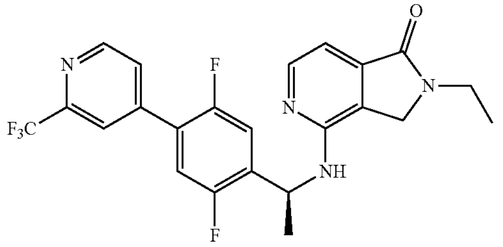 [SMILES: CCN1Cc2c(ccnc2N[C@@H](C)c2cc(F)c(-c3ccnc(C(F)(F)F)c3)cc2F)C1=O] | LC-MS: (ESI) m/z: 463.1 [M + H] $^1$H NMR (400 MHz, $CD_3OD$) δ: 8.81 (d, J = 5.2 Hz, 1H), 8.00 (s, 1H), 7.97 (d, J = 6.4 Hz, 1H), 7.86 (d, J = 5.2 Hz, 1H), 7.62 (dd, J = 6.4, 10.4 Hz, 1H), 7.48 (dd, J = 6.4, 10.8 Hz, 1H), 7.24 (d, J = 6.4 Hz, 1H), 5.41 (q, J = 6.8 Hz, 1H), 4.68 (q, J = 19.6 Hz, 2H), 3.74 (q, J = 7.2 Hz, 2H), 1.79 (d, J = 6.8 Hz, 3H), 1.34 (t, J = 7.2 Hz, 3H). |
| 89 | 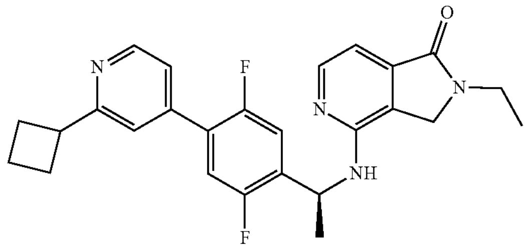 [SMILES: CCN1Cc2c(ccnc2N[C@@H](C)c2cc(F)c(-c3ccnc(C4CCC4)c3)cc2F)C1=O] | LC-MS: (ESI) m/z: 449.1 [M + H]. $^1$H NMR (400 MHz, $CD_3OD$) δ: 8.51 (d, J = 5.2 Hz, 1H), 8.07 (d, J = 5.2 Hz, 1H), 7.46 (s, 1H), 7.42-7.40 (m, 1H), 7.38-7.34 (m, 1H), 7.30-7.26 (m, 1H), 6.92 (d, J = 5.2 Hz, 1H), 5.59-5.54 (q, J = 6.8 Hz, 1H), 4.55-4.45 (m, 2H), 3.77-3.68 (m, 3H), 2.41-2.32 (m, 4H), 2.17-2.03 (m, 1H), 1.96-1.89 (m, 1H), 1.63 (d, J = 6.8 Hz, 3H), 1.33 (t, J = 7.2 Hz, 3H). |
| 90 | 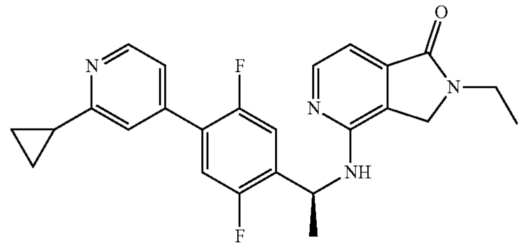 [SMILES: CCN1Cc2c(ccnc2N[C@@H](C)c2cc(F)c(-c3ccnc(C4CC4)c3)cc2F)C1=O] | LC-MS: (ESI) m/z: 435.1 [M + H]. $^1$H NMR (400 MHz, $CD_3OD$) δ: 8.39 (d, J = 5.2 Hz, 1H), 8.07 (d, J = 5.2 Hz, 1H), 7.38-7.24 (m, 4H), 6.92 (d, J = 5.2 Hz, 1H), 5.54-5.59 (q, J = 6.8 Hz, 1H), 4.55-4.44 (m, 2H), 3.73-3.68 (q, J = 7.2 Hz, 2H), 2.17-2.11 (m, 1H), 1.63 (d, J = 6.8 Hz, 3H), 1.33 (t, J = 7.2 Hz, 3H), 1.09-0.98 (m, 4H). |
| 91 | 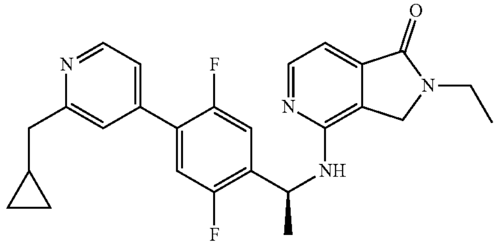 [SMILES: CCN1Cc2c(ccnc2N[C@@H](C)c2cc(F)c(-c3ccnc(CC4CC4)c3)cc2F)C1=O] | LC-MS: (ESI) m/z: 449.1 [M + H]. $^1$H NMR (400 MHz, $CD_3OD$) δ: 8.50 (d, J = 4.8 Hz, 1H), 8.08 (d, J = 5.2 Hz, 1H), 7.59 (s, 1H), 7.46-7.44 (m, 1H), 7.39-7.35 (dd, J = 6.0, 10.4 Hz, 1H), 7.31-7.26 (dd, J = 6.0, 11.2 Hz, 1H), 6.93 (d, J = 9.2 Hz, 1H), 5.60-5.54 (q, J = 7.2 Hz, 1H), 4.56-4.45 (m, 2H), 3.74-3.69 (q, J = 7.2 Hz, 2H), 2.76 (d, J = 7.2 Hz, 2H), 1.63 (d, J = 7.2 Hz, 3H), 1.34 (t, J = 7.2 Hz, 3H), 1.18-1.08 (m, 1H), 0.59-0.54 (m, 2H), 0.31-0.27 (m, 2H). |
| 92 | 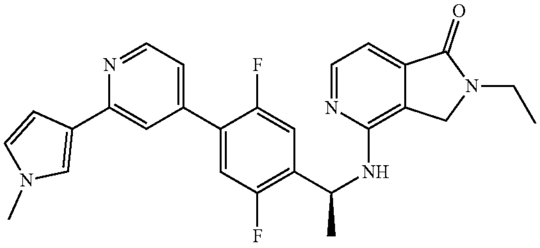 [SMILES: CCN1Cc2c(ccnc2N[C@@H](C)c2cc(F)c(-c3ccnc(-c4ccn(C)c4)c3)cc2F)C1=O] | LC-MS: (ESI) m/z 474.1 [M + H]. $^1$H NMR (400 MHz, $CDCl_3$) δ: 8.56 (d, J = 5.2 Hz, 1H), 8.22 (d, J = 5.2 Hz, 1H), 7.57 (s, 1H), 7.35 (br s, 1H), 7.25-7.13 (m, 3H), 7.08 (d, J = 5.2 Hz, 1H), 6.70-6.60 (m, 2H), 5.57 (quin, J = 7.2 Hz, 1H), 4.57 (d, J = 7.2 Hz, 1H), 4.36-4.22 (m, 2H), 3.76-3.64 (m, 5H), 1.66 (d, J = 7.2 Hz, 3H), 1.30 (t, J = 7.2 Hz, 3H). |
| 93 | 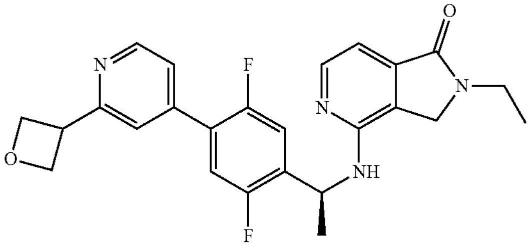 [SMILES: CCN1Cc2c(ccnc2N[C@@H](C)c2cc(F)c(-c3ccnc(C4COC4)c3)cc2F)C1=O] | LC-MS: (ESI) m/z: 451.1 [M + H]. LC-MS: (ESI) m/z: 451.3 [M + H]. $^1$H NMR (400 MHz, $CDCl_3$) δ: 8.70 (d, J = 5.2 Hz, 1H), 8.21 (d, J = 5.2 Hz, 1H), 7.40 (s, 1H), 7.33 (d, J = 5.2 Hz, 1H), 7.19 (dt, J = 6.0, 11.2 Hz, 2H), 7.08 (d, J = 5.2 Hz, 1H), 5.56 (quin, J = 7.2 Hz, 1H), 5.10 (dd, J = 6.0, 8.4 Hz, 2H), 4.98 (t, J = 6.0 Hz, 2H), 4.57 (d, J = 7.2 Hz, 1H), 4.48-4.36 (m, 1H), 4.30 (s, 2H), 3.70 (q, J = 7.2 Hz, 2H), 1.65 (br s, 3H), 1.30 (t, J = 7.2 Hz, 3H). |

TABLE 3-continued

| Cpd No. | Compound Structure | MS/$^1$H NMR |
|---|---|---|
| 94 | 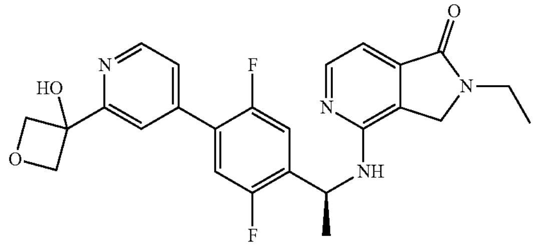 [SMILES: CCN1Cc2c(ccnc2N[C@@H](C)c2cc(F)c(-c3ccnc(C4(O)COC4)c3)cc2F)C1=O] | LC-MS: (ESI) m/z: 467.1 [M + H] $^1$H NMR (400 MHz, $CDCl_3$) δ: 8.57 (d, J = 5.2 Hz, 1H), 8.21 (d, J = 5.2 Hz, 1H), 8.11 (s, 1H), 7.47 (d, J = 5.2 Hz, 1H), 7.26-7.21 (m, 2H), 7.08 (d, J = 5.2 Hz, 1H), 5.95 (s, 1H), 5.58 (t, J = 7.2 Hz, 1H), 5.13 (d, J = 7.2 Hz, 2H), 4.76 (d, J = 7.2 Hz, 2H), 4.55 (br d, J = 7.2 Hz, 1H), 4.31 (s, 2H), 3.71 (q, J = 7.2 Hz, 2H), 1.67 (d, J = 7.2 Hz, 3H), 1.31 (t, J = 7.2 Hz, 3H). |
| 95 | 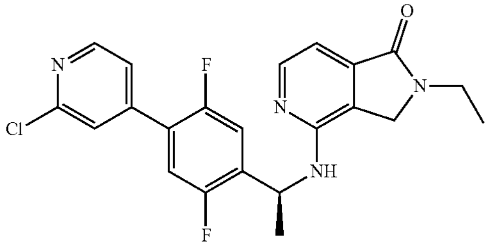 [SMILES: CCN1Cc2c(ccnc2N[C@@H](C)c2cc(F)c(-c3ccnc(Cl)c3)cc2F)C1=O] | LC-MS: (ESI) m/z: 429.1 [M + H]. $^1$H NMR (400 MHz, $CDCl_3$) δ: 8.45 (d, J = 4.8 Hz, 1H), 8.20 (d, J = 5.2 Hz, 1H), 7.49 (s, 1H), 7.40-7.36 (m, 1H), 7.25-7.14 (m, 2H), 7.08 (d, J = 5.2 Hz, 1H), 5.56 (q, J = 6.8 Hz, 1H), 4.53 (d, J = 6.8 Hz, 1H), 4.36-4.25 (m, 2H), 3.70 (q, J = 7.2 Hz, 2H), 1.65 (d, J = 6.8 Hz, 3H), 1.31 (t, J = 7.2 Hz, 3H). |
| 96 | 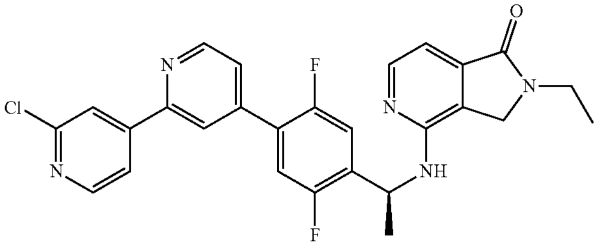 [SMILES: CCN1Cc2c(ccnc2N[C@@H](C)c2cc(F)c(-c3ccnc(-c4ccnc(Cl)c4)c3)cc2F)C1=O] | LC-MS: (ESI) m/z: 506.0 [M + H]. $^1$H NMR (400 MHz, $CDCl_3$) δ: 8.81 (dd, J = 0.8, 5.2 Hz, 1H), 8.51 (dd, J = 0.4, 5.2 Hz, 1H), 8.21 (d, J = 4.8 Hz, 1H), 8.01-7.99 (m, 1H), 7.91 (s, 1H), 7.85 (dd, J = 1.6, 5.2 Hz, 1H), 7.53-7.49 (m, 1H), 7.26-7.21 (m, 2H), 7.08 (d, J = 5.2 Hz, 1H), 5.58 (q, J = 7.2 Hz, 1H), 4.58 (d, J = 7.2 Hz, 1H), 4.37-4.26 (m, 2H), 3.70 (q, J = 7.2 Hz, 2H), 1.67 (d, J = 7.2 Hz, 3H), 1.31 (t, J = 7.2 Hz, 3H). |
| 97 | 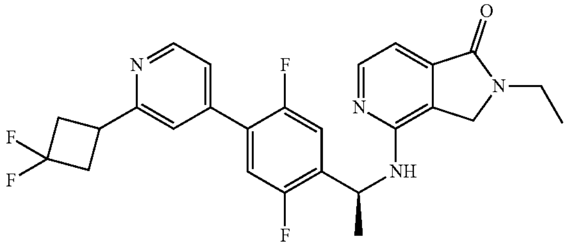 [SMILES: CCN1Cc2c(ccnc2N[C@@H](C)c2cc(F)c(-c3ccnc(C4CC(F)(F)C4)c3)cc2F)C1=O] | LC-MS: (ESI) m/z 485.1 [M + H]. $^1$H NMR (400 MHz, $CDCl_3$) δ: 8.66 (d, J = 4.8 Hz, 1H), 8.21 (d, J = 5.2 Hz, 1H), 7.33-7.28 (m, 2H), 7.23-7.14 (m, 2H), 7.08 (d, J = 5.6 Hz, 1H), 5.57 (quin, J = 7.2 Hz, 1H), 4.53 (br d, J = 6.8 Hz, 1H), 4.30 (s, 2H), 3.70 (q, J = 7.2 Hz, 2H), 3.57-3.41 (m, 1H), 3.10-2.90 (m, 4H), 1.65 (d, J = 6.8 Hz, 3H), 1.31 (t, J = 7.2 Hz, 3H). |
| 98 | 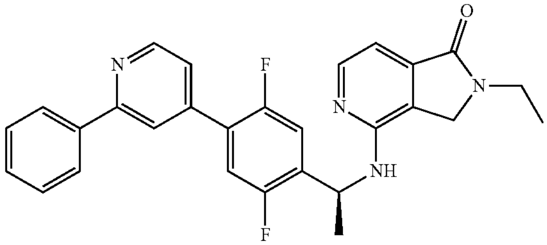 [SMILES: CCN1Cc2c(ccnc2N[C@@H](C)c2cc(F)c(-c3ccnc(-c4ccccc4)c3)cc2F)C1=O] | LC-MS: (ESI) m/z: 471.1 [M + H]. $^1$H NMR (400 MHz, $CDCl_3$) δ: 8.76 (d, J = 5.2 Hz, 1H), 8.22 (d, J = 5.2 Hz, 1H), 8.04-7.99 (m, 2H), 7.86 (s, 1H), 7.53-7.42 (m, 3H), 7.39-7.36 (m, 1H), 7.27-7.20 (m, 2H), 7.08 (d, J = 5.2 Hz, 1H), 5.58 (q, J = 7.2 Hz, 1H), 4.58 (d, J = 7.2 Hz, 1H), 4.36-4.24 (m, 2H), 3.70 (q, J = 7.2 Hz, 2H), 1.67 (d, J = 6.8 Hz, 3H), 1.31 (t, J = 7.2 Hz, 3H). |
| 99 | 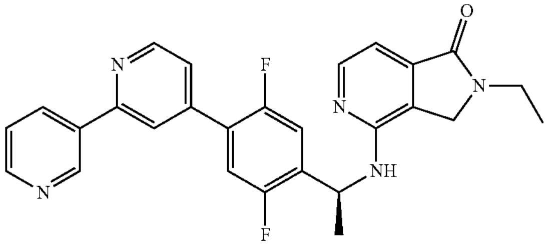 [SMILES: CCN1Cc2c(ccnc2N[C@@H](C)c2cc(F)c(-c3ccnc(-c4cccnc4)c3)cc2F)C1=O] | LC-MS: (ESI) m/z: 472.2 [M + H]. $^1$H NMR (400 MHz, DMSO-$d_6$) δ: 9.34 (d, J = 2.0 Hz, 1H), 8.78 (d, J = 4.2 Hz, 1H), 8.65 (dd, J = 2.0, 4.4 Hz, 1H), 8.51 (dt, J = 1.6, 8.0 Hz, 1H), 8.23 (s, 1H), 8.05 (d, J = 5.2 Hz, 1H), 7.72 (dd, J = 6.8, 10.0 Hz, 1H), 7.64-7.60 (m, 1H), 7.54 (dd, J = 4.8, 7.9 Hz, 1H), 7.45 (dd, J = 6.0, 11.6 Hz, 1H), 7.27 (d, J = 7.6 Hz, 1H), 6.79 (d, J = 4.8 Hz, 1H), 5.62-5.52 (m, 1H), 4.61-4.33 (m, 2H), 3.57 (q, J = 7.2 Hz, 2H), 1.53 (d, J = 7.0 Hz, 3H), 1.22 (t, J = 7.2 Hz, 3H). |

TABLE 3-continued

| Cpd No. | Compound Structure | MS/$^1$H NMR |
|---|---|---|
| 100 | 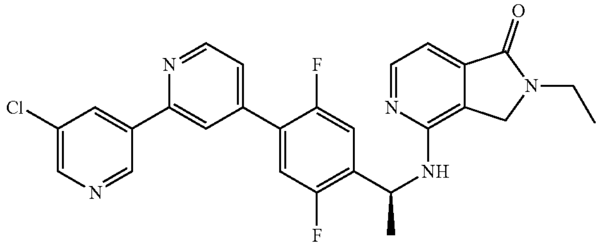 [SMILES: CCN1Cc2c(ccnc2N[C@@H](C)c2cc(F)c(-c3ccnc(-c4cncc(Cl)c4)c3)cc2F)C1=O] | LC-MS: (ESI) m/z: 506.2 [M + H] $^1$H NMR (400 MHz, $CD_3OD$) δ: 9.14 (d, J= 1.6 Hz, 1H), 8.75 (d, J = 5.2 Hz, 1H), 8.63 (d, J = 2.0 Hz, 1H), 8.54 (t, J = 2.0 Hz, 1H), 8.13 (s, 1H), 8.06 (d, J = 5.6 Hz, 1H), 7.63 (d, J = 5.2 Hz, 1H), 7.50 (dd, J = 6.0, 10.0 Hz, 1H), 7.30 (dd, J = 6.0, 11.2 Hz, 1H), 6.91 (d, J = 5.2 Hz, 1H), 5.57 (q, J = 6.8 Hz, 1H), 4.56-4.43 (m, 2H), 3.70 (q, J = 7.2 Hz, 2H), 1.63 (d, J = 6.8 Hz, 3H), 1.32 (t, J = 7.2 Hz, 3H). $^{19}$F NMR (400 MHz, $CD_3OD$) δ: −120.260, −120.309, −121.446, δ121.495. |
| 101 | 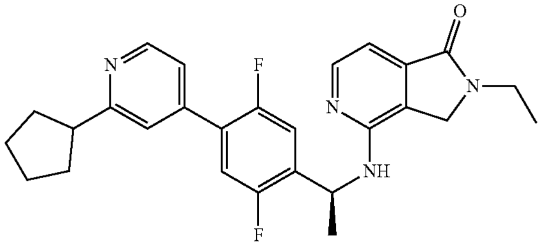 [SMILES: CCN1Cc2c(ccnc2N[C@@H](C)c2cc(F)c(-c3ccnc(C4CCCC4)c3)cc2F)C1=O] | LC-MS: (ESI) m/z: 463.1 [M + H]. $^1$H NMR (400 MHz, $CDCl_3$) δ: 8.59 (d, J = 5.2 Hz, 1H), 8.21 (d, J = 5.2 Hz, 1H), 7.30 (s, 1H), 7.24-7.14 (m, 3H), 7.07 (d, J = 5.2 Hz, 1H), 5.57 (q, J = 7.6 Hz, 1H), 4.59 (d, J = 7.2 Hz, 1H), 4.35-4.23 (m, 2H), 3.69 (q, J = 7.6 Hz, 2H), 3.22 (q, J = 8.4 Hz, 1H), 2.17-2.05 (m, 2H), 1.90-1.72 (m, 6H), 1.65 (d, J = 7.2 Hz, 3H), 1.30 (t, J = 7.2 Hz, 3H). |
| 102 | 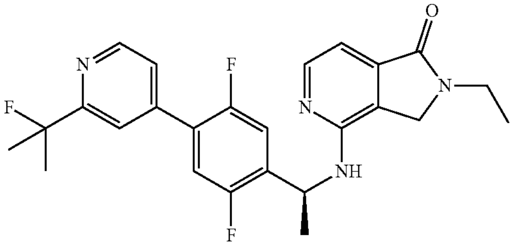 [SMILES: CCN1Cc2c(ccnc2N[C@@H](C)c2cc(F)c(-c3ccnc(C(C)(C)F)c3)cc2F)C1=O] | LC-MS: (ESI) m/z: 455.1 [M + H]. $^1$H NMR (400 MHz, $CD_3OD$) δ: 8.53 (d, J = 5.2 Hz, 1H), 8.03 (d, J = 5.2 Hz, 1H), 7.69 (s, 1H), 7.44-7.42 (m, 1H), 7.33-7.24 (m, 2H), 6.87 (d, J = 5.2 Hz, 1H), 5.57-5.52 (q, J = 6.8 Hz, 1H), 4.52-4.41 (m, 2H), 3.70-3.64 (q, J = 7.2 Hz, 2H), 1.68 (d, J = 22 Hz, 6H), 1.60 (d, J = 7.2 Hz, 3H), 1.30 (t, J = 7.2 Hz, 3H). |
| 103 | 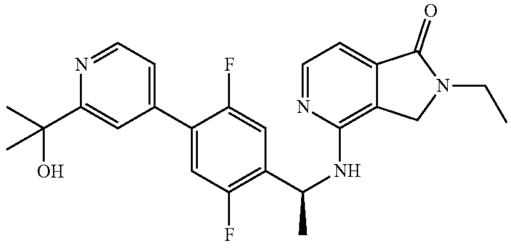 | LC-MS: (ESI) m/z: 453.1 [M + H]. $^1$H NMR (400 MHz, $CDCl_3$) δ: 8.58 (d, J = 5.2 Hz, 1H), 8.21 (d, J = 5.2 Hz, 1H), 7.50 (s, 1H), 7.37-7.31 (m, 1H), 7.25-7.14 (m, 2H), 7.07 (d, J = 5.2 Hz, 1H), 5.57 (q, J = 7.2 Hz, 1H), 4.89 (brs, 1H), 4.58 (d, J = 7.2 Hz, 1H), 4.30 (s, 2H), 3.70 (q, J = 7.2 Hz, 2H), 1.66 (brs, 3H), 1.58 (s, 6H), 1.30 (t, J = 7.2 Hz, 3H). |
| 104 | 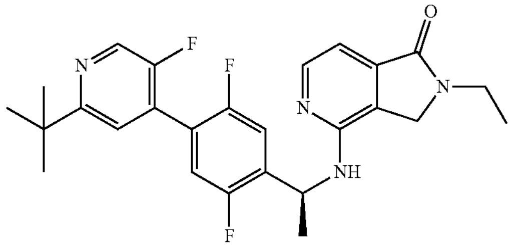 [SMILES: CCN1Cc2c(ccnc2N[C@@H](C)c2cc(F)c(-c3cc(C(C)(C)C)ncc3F)cc2F)C1=O] | LC-MS: (ESI) m/z: 469.1 [M + H]. $^1$H NMR (400 MHz, $CD_3OD$) δ: 8.44 (d, J = 1.2 Hz, 1H), 8.08 (d, J = 5.2 Hz, 1H), 7.47 (d, J = 5.6 Hz, 1H), 7.31-7.25 (m, 2H), 6.93 (d, J = 5.2 Hz, 1H), 5.60-5.55 (q, J = 6.8 Hz, 1H), 4.56-4.45 (m, 2H), 3.74-3.68 (q, J = 7.2 Hz, 2H), 1.64 (d, J = 7.2 Hz, 3H), 1.38 (s, 9H), 1.34 (t, J = 7.2 Hz, 3H). |
| 105 | 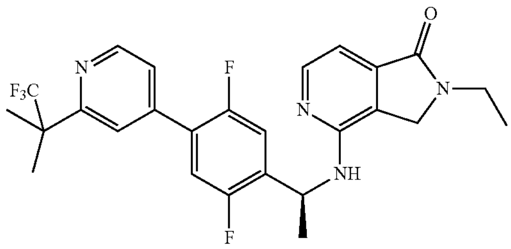 [SMILES: CCN1Cc2c(ccnc2N[C@@H](C)c2cc(F)c(-c3ccnc(C(C)(C)C(F)(F)F)c3)cc2F)C1=O] | LC-MS: (ESI) m/z: 505.2 [M + H]. $^1$H NMR (400 MHz, $CDCl_3$) δ: 8.68 (d, J = 5.2 Hz, 1H), 8.21 (d, J = 5.2 Hz, 1H), 7.62 (s, 1H), 7.38-7.35 (m, 1H), 7.24-7.13 (m, 2H), 7.08 (d, J = 5.2 Hz, 1H), 5.57 (q, J = 7.2 Hz, 1H), 4.58 (d, J = 7.2 Hz, 1H), 4.36-4.24 (m, 2H), 3.70 (q, J = 7.2 Hz, 2H), 1.68-1.66 (m, 3H), 1.65-1.63 (m, 6H), 1.30 (t, J = 7.2 Hz, 3H). |

TABLE 3-continued

| Cpd No. | Compound Structure | MS/$^1$H NMR |
| --- | --- | --- |
| 106 | 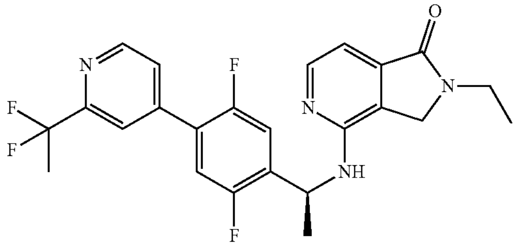 [SMILES: CCN1Cc2c(ccnc2N[C@@H](C)c2cc(F)c(-c3ccnc(C(C)(F)F)c3)cc2F)C1=O] | LC-MS: (ESI) m/z: 459.1 [M + H]. $^1$H NMR (400 MHz, $CD_3OD$) δ: 8.69 (d, J = 5.2 Hz, 1H), 8.07 (d, J = 5.2 Hz, 1H), 7.88 (s, 1H), 7.70 (d, J = 5.2 Hz, 1H), 7.44 (dd, J = 6.0, 10.4 Hz, 1H), 7.32 (dd, J = 6.0, 11.4 Hz, 1H), 6.93 (d, J = 5.2 Hz, 1H), 5.58 (q, J = 6.8 Hz, 1H), 4.59-4.42 (m, 2H), 3.72 (q, J = 7.2 Hz, 2H), 2.03 (t, J = 18.8 Hz, 3H), 1.64 (d, J = 7.2 Hz, 3H), 1.34 (t, J = 7.2 Hz, 3H). $^{19}$FNMR (400 MHz, $CD_3OD$) δ: − 92.621, −124.442, −124.491, −125.245, −125.293. |
| 107 | 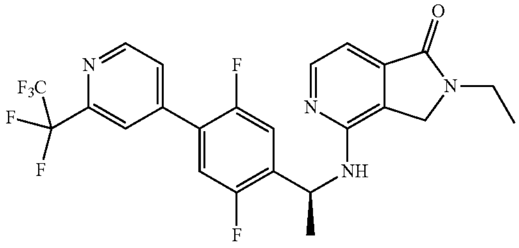 [SMILES: CCN1Cc2c(ccnc2N[C@@H](C)c2cc(F)c(-c3ccnc(C(F)(F)C(F)(F)F)c3)cc2F)C1=O] | LC-MS: (ESI) m/z: 513.0 [M + H]. $^1$H NMR (400 MHz, $CD_3OD$) δ: 8.82 (d, J = 4.8 Hz, 1H), 8.07 (d, J = 4.8 Hz, 1H), 8.02 (s, 1H), 7.87 (d, J = 4.8 Hz, 1H), 7.49-7.45 (dd, J = 6.4, 10.4 Hz, 1H), 7.36-7.31 (dd, J = 6.4, 11.2 Hz, 1H), 6.93 (d, J = 5.2 Hz, 1H), 5.60-5.55 (q, J = 7.2 Hz, 1H), 4.56-4.46 (m, 2H), 3.74-3.69 (q, J = 7.2 Hz, 2H), 1.64 (d, J = 6.8 Hz, 3H), 1.34 (t, J = 7.2 Hz, 3H). |
| 108 | 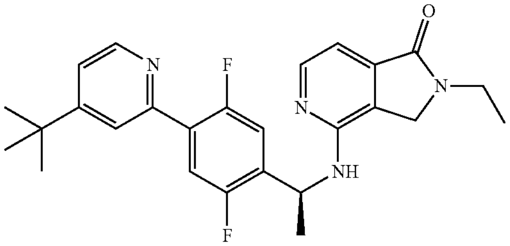 [SMILES: CCN1Cc2c(ccnc2N[C@@H](C)c2cc(F)c(-c3cc(C(C)(C)C)ccn3)cc2F)C1=O] | LC-MS: (ESI) m/z: 451.3 [M + H]. $^1$H NMR (400 MHz, $CD_3OD$) δ: 8.53 (dd, J = 0.8, 5.2 Hz, 1H), 8.06 (d, J = 5.2 Hz, 1H), 7.80-7.74 (m, 1H), 7.53 (dd, J = 6.0, 10.8 Hz, 1H), 7.45 (dd, J = 2.0, 5.6 Hz, 1H), 7.26 (dd, J = 6.0, 11.2 Hz, 1H), 6.91 (d, J = 5.2 Hz, 1H), 5.57 (q, J = 6.8 Hz, 1H), 4.57-4.37 (m, 2H), 3.71 (q, J = 7.2 Hz, 2H), 1.62 (d, J = 6.8 Hz, 3H), 1.36 (s, 9H), 1.33 (t, J = 7.2 Hz, 3H). $^{19}$FNMR (400 MHz, $CD_3OD$) δ: −124.619, −126.102. |
| 109 | 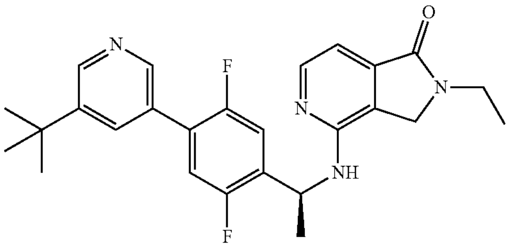 [SMILES: CCN1Cc2c(ccnc2N[C@@H](C)c2cc(F)c(-c3cncc(C(C)(C)C)c3)cc2F)C1=O] | LC-MS: (ESI) m/z: 451.2 [M + H]. $^1$H NMR (400 MHz, $CD_3OD$) δ: 8.61 (d, J = 2.4 Hz, 1H), 8.51(t, J = 1.6 Hz, 1H), 8.06 (d, J = 5.2 Hz, 1H), 8.00 (d, J = 1.2 Hz, 1H), 7.33-7.26 (m, 2H), 6.91 (d, J = 5.2 Hz, 1H), 5.59-5.54 (q, J = 6.8 Hz, 1H), 4.55-4.44 (m, 2H), 1.63 (d, J = 7.2 Hz, 3H), 1.40 (s, 9H), 1.33 (t, J = 7.2 Hz, 3H). |
| 110 | 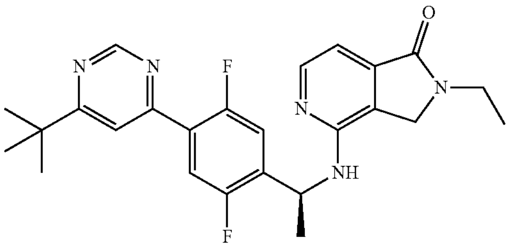 | LC-MS: (ESI) m/z 452.1 [M + H]. $^1$H NMR (400 MHz, $CDCl_3$) δ: 9.21 (d, J = 1.2 Hz, 1H), 8.20 (d, J = 5.2 Hz, 1H), 7.87 (dd, J = 6.0, 11.6 Hz, 1H), 7.81 (s, 1H), 7.20 (dd, J = 6.0, 11.2 Hz, 1H), 7.07 (d, J = 5.2 Hz, 1H), 5.59-5.51 (m, 1H), 4.57 (br d, J = 7.6 Hz, 1H), 4.34-4.24 (m, 2H), 3.70 (q, J = 7.6 Hz, 2H), 1.66 (d, J = 7.2 Hz, 3H), 1.39 (s, 9H), 1.30 (t, J = 7.2 Hz, 3H). |
| 111 | 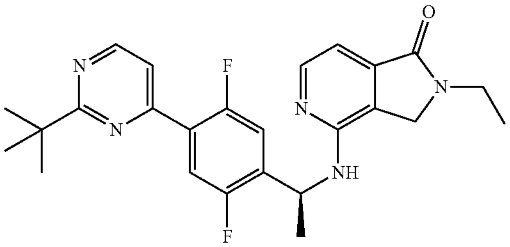 [SMILES: CCN1Cc2c(ccnc2N[C@@H](C)c2cc(F)c(-c3ccnc(C(C)(C)C)n3)cc2F)C1=O] | LC-MS: (ESI) m/z 452.3 [M + H]. $^1$H NMR (400 MHz, $CDCl_3$) δ: 8.73 (d, J = 5.2 Hz, 1H), 8.20 (d, J = 5.2 Hz, 1H), 8.03 (dd, J = 6.0, 11.6 Hz, 1H), 7.62 (dd, J = 1.6, 5.2 Hz, 1H), 7.18 (dd, J = 6.0, 11.6 Hz, 1H), 7.06 (d, J = 5.2 Hz, 1H), 5.60-5.50 (m, 1H), 4.60 (d, J = 7.2 Hz, 1H), 4.36-4.22 (m, 2H), 3.69 (q, J = 7.2 Hz, 2H), 1.65 (d, J = 7.2 Hz, 3H), 1.46 (s, 9H), 1.30 (t, J = 7.2 Hz, 3H). |

TABLE 3-continued

| Cpd No. | Compound Structure | MS/$^1$H NMR |
|---|---|---|
| 112 | 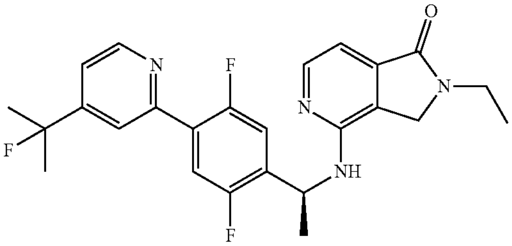 [SMILES: CCN1Cc2c(ccnc2N[C@@H](C)c2cc(F)c(-c3cc(C(C)(C)F)ccn3)cc2F)C1=O] | LC-MS: (ESI) m/z: 455.1 [M + H]. $^1$H NMR (400 MHz, $CD_3OD$) δ: 8.63 (d, J = 5.2 Hz, 1H), 8.06 (d, J = 5.2 Hz, 1H), 7.78 (s, 1H), 7.59 (dd, J = 6.4, 10.8 Hz, 1H), 7.42 (dd, J = 1.6, 5.2 Hz, 1H), 7.26 (dd, J = 6.0, 11.6 Hz, 1H), 6.91 (d, J = 5.2 Hz, 1H), 5.56 (q, J = 7.2 Hz, 1H), 4.57-4.40 (m, 2H), 3.70 (q, J = 7.2 Hz, 2H), 1.72 (s, 3H), 1.66 (s, 3H), 1.62 (d, J = 6.8 Hz, 3H), 1.32 (t, J = 7.2 Hz, 3H). $^{19}$FNMR (400 MHz, $CD_3OD$) δ: −92.135, −124.333, −124.382, −126.011, −126.059, −143.298. |
| 113 | 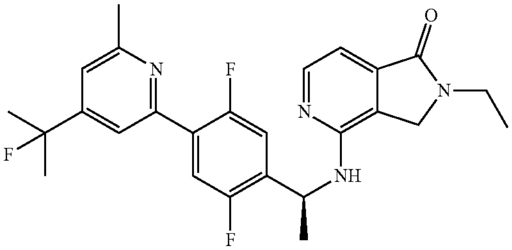 [SMILES: CCN1Cc2c(ccnc2N[C@@H](C)c2cc(F)c(-c3cc(C(C)(C)F)cc(C)n3)cc2F)C1=O] | LC-MS: (ESI) m/z: 469.2 [M + H]. $^1$H NMR (400 MHz, $CDCl_3$) δ: 8.20 (d, J = 5.2 Hz, 1H), 7.70 (dd, J = 6.2, 11.2 Hz, 1H), 7.51 (s, 1H), 7.20-7.12 (m, 2H), 7.06 (d, J = 5.2 Hz, 1H), 5.53 (quin, J = 7.2 Hz, 1H), 4.68 (br s, 1H), 4.36-4.21 (m, 2H), 3.78-3.64 (m, 2H), 2.63 (s, 3H), 1.73-1.64 (m, 9H), 1.30 (t, J = 7.2 Hz, 3H). |
| 114 | 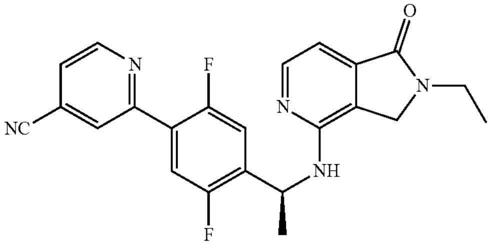 [SMILES: CCN1Cc2c(ccnc2N[C@@H](C)c2cc(F)c(-c3cc(C#N)ccn3)cc2F)C1=O] | LC-MS: (ESI) m/z: 420.1 [M + H]. $^1$H NMR (400 MHz, $CD_3OD$) δ: 8.88 (dd, J = 0.8, 4.8 Hz, 1H), 8.11-8.10 (m, 1H), 8.05 (d, J = 5.2 Hz, 1H), 7.76 (dd, J = 6.4, 10.8 Hz, 1H), 7.68 (dd, J = 1.2, 5.2 Hz, 1H), 7.28 (dd, J = 6.0, 11.6 Hz, 1H), 6.91 (d, J = 5.2 Hz, 1H), 5.56 (q, J = 6.8 Hz, 1H), 4.58-4.36 (m, 2H), 3.70 (q, J = 7.2 Hz, 2H), 1.62 (d, J = 6.8 Hz, 3H), 1.33 (t, J = 7.2 Hz, 3H). FNMR (400 MHz, $CD_3OD$) δ: −123.537, −123.585, −125.646, −125.695. |
| 115 | 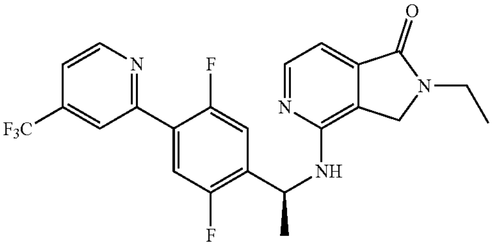 | LC-MS: (ESI) m/z 463.0 [M + H]. $^1$H NMR (400 MHz, $CDCl_3$) δ: 8.88 (d, J = 4.8 Hz, 1H), 8.20 (d, J = 5.6 Hz, 1H), 8.03 (s, 1H), 7.82 (dd, J = 6.4, 11.2 Hz, 1H), 7.49 (d, J = 4.8 Hz, 1H), 7.22 (dd, J = 6.0, 11.2 Hz, 1H), 7.08 (d, J = 5.2 Hz, 1H), 5.56 (quin, J = 6.8 Hz, 1H), 4.76 (br s, 1H), 4.38-4.21 (m, 2H), 3.76-3.60 (m, 2H), 1.66 (d, J = 6.4 Hz, 3H), 1.30 (t, J = 7.2 Hz, 3H). |
| 116 | 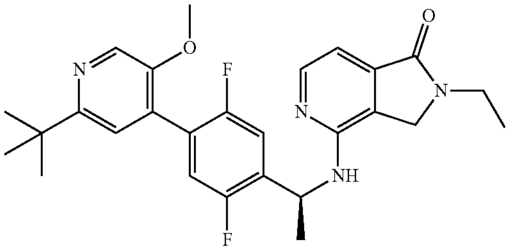 [SMILES: CCN1Cc2c(ccnc2N[C@@H](C)c2cc(F)c(-c3cc(C(C)(C)C)ncc3OC)cc2F)C1=O] | LC-MS: (ESI) m/z: 481.1 [M + H]. $^1$H NMR (400 MHz, $CD_3OD$) δ: 8.27 (s, 1H), 8.09 (d, J = 5.2 Hz, 1H), 7.32 (s, 1H), 7.23-7.13 (m, 2H), 6.93 (d, J = 5.2 Hz, 1H), 5.60-5.55 (q, J = 6.8 Hz, 1H), 4.55-4.40 (m, 2H), 3.89 (s, 3H), 3.74-3.68 (q, J = 7.2 Hz, 2H), 1.63 (d, J = 6.8 Hz, 3H), 1.36-1.31 (m, 12H). |
| 117 | 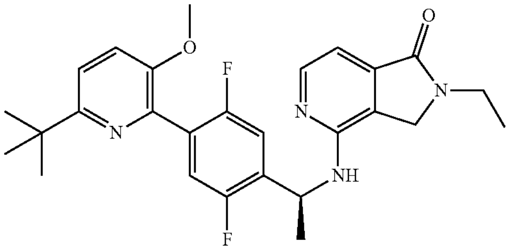 | LC-MS: (ESI) m/z: 481.1 [M + H]. $^1$H NMR (400 MHz, $CDCl_3$) δ = 8.24 (d, J = 5.2 Hz, 1H), 7.34-7.30 (m, 1H), 7.27-7.19 (m, 2H), 7.13 (dd, J = 6.0 & 9.6 Hz, 1H), 7.07 (d, J = 5.2 Hz, 1H), 5.60 (t, J = 7.2 Hz, 1H), 4.61 (brs, 1H), 4.33-4.20 (m, 2H), 3.82 (s, 3H), 3.69 (q, J = 7.2 Hz, 2H), 1.65 (d, J = 7.2 Hz, 3H), 1.36 (s, 9H), 1.29 (t, J = 7.2 Hz, 3H). |

TABLE 3-continued

| Cpd No. | Compound Structure | MS/$^1$H NMR |
| --- | --- | --- |
| 118 | 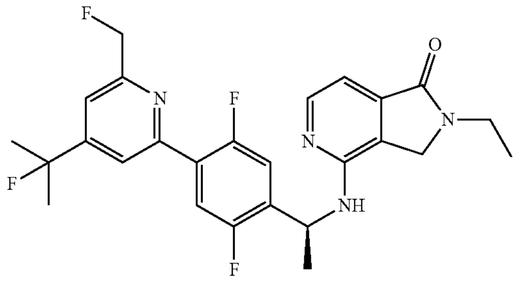 [SMILES: CCN1Cc2c(ccnc2N[C@@H](C)c2cc(F)c(-c3cc(C(C)(C)F)cc(CF)n3)cc2F)C1=O] | LC-MS: (ESI) m/z 487.3 [M + H]. $^1$H NMR (400 MHz, $CD_3OD$) δ: 8.06 (d, J = 5.2 Hz, 1H), 7.76 (s, 1H), 7.68 (dd, J = 6.0, 10.8 Hz, 1H), 7.51 (s, 1H), 7.25 (dd, J = 6.0, 11.6 Hz, 1H), 6.91 (dd, J = 1.2, 5.2 Hz, 1H), 5.65-5.42 (m, 3H), 4.57-4.41 (m, 2H), 3.70 (q, J = 7.2 Hz, 2H), 1.72 (s, 3H), 1.70 (d, J = 22.0 Hz, 6H), 1.32 (t, J = 7.2 Hz, 3H). |
| 119 | 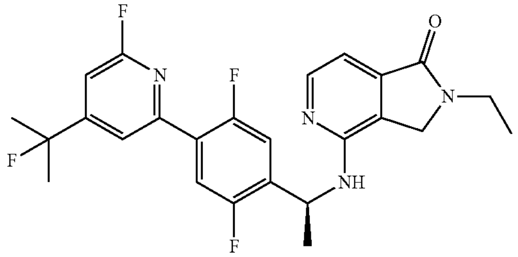 [SMILES: CCN1Cc2c(ccnc2N[C@@H](C)c2cc(F)c(-c3cc(C(C)(C)F)cc(F)n3)cc2F)C1=O] | LC-MS: (ESI) m/z 473.3 [M + H]. $^1$H NMR (400 MHz, $CD_3OD$) δ: 7.97 (d, J = 6.8 Hz, 1H), 7.84 (dd, J = 6.4, 11.2 Hz, 1H), 7.79 (s, 1H), 7.43 (dd, J = 6.4, 11.2 Hz, 1H), 7.25 (d, J = 6.4 Hz, 1H), 7.12 (s, 1H), 5.40 (q, J = 6.4 Hz, 1H), 4.78-4.58 (m, 2H), 3.74 (q, J = 7.2 Hz, 2H), 1.80 (d, J = 6.8 Hz, 3H), 1.71 (d, J = 22.0 Hz, 6H), 1.34 (t, J = 7.2 Hz, 3H). |
| 120 | 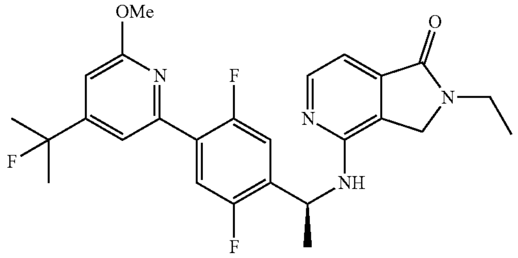 [SMILES: CCN1Cc2c(ccnc2N[C@@H](C)c2cc(F)c(-c3cc(C(C)(C)F)cc(OC)n3)cc2F)C1=O] | LC-MS: (ESI) m/z 485.3 [M + H]. $^1$H NMR (400 MHz, $CD_3OD$) δ: 8.06 (d, J = 5.6 Hz, 1H), 7.81 (dd, J = 6.4, 11.6 Hz, 1H), 7.42 (s, 1H), 7.22 (dd, J = 6.4, 12.0 Hz, 1H), 6.91 (d, J = 5.2 Hz, 1H), 6.75 (d, J = 0.8 Hz, 1H), 5.55 (q, J = 6.8 Hz, 1H), 4.56-4.42 (m, 2H), 3.99 (s, 3H), 3.70 (q, J = 7.2 Hz, 2H), 1.70-1.58 (m, 9H), 1.32 (t, J = 7.2 Hz, 3H). |
| 121 | 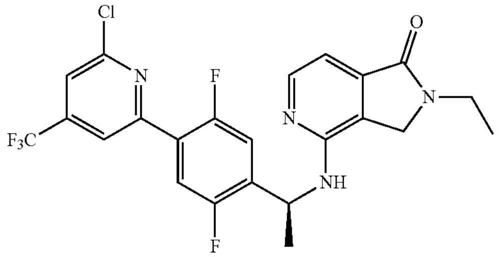 | LC-MS: (ESI) m/z 497.2 [M + H]. $^1$H NMR (400 MHz, $CD_3OD$) δ: 8.05 (d, J = 5.2 Hz, 1H), 8.04 (s, 1H), 7.81 (dd, J = 6.0, 11.2 Hz, 1H), 7.78 (s, 1H), 7.30 (dd, J = 6.0, 12.0 Hz, 1H), 6.91 (d, J = 5.6 Hz, 1H), 5.66-5.45 (m, 1H), 4.59-4.35 (m, 2H), 3.70 (q, J = 7.2 Hz, 2H), 1.62 (d, J = 7.2 Hz, 3H), 1.33 (t, J = 7.2 Hz, 3H). |
| 122 | 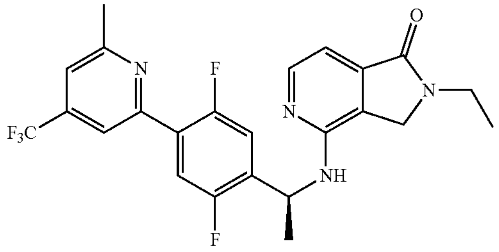 [SMILES: CCN1Cc2c(ccnc2N[C@@H](C)c2cc(F)c(-c3cc(C(F)(F)F)cc(C)n3)cc2F)C1=O] | LC-MS: (ESI) m/z: 477.1 [M + H]. $^1$H NMR (400 MHz, $CD_3OD$) δ: 8.05 (d, J = 5.2 Hz, 1H), 7.83 (s, 1H), 7.78 (dd, J = 6.0, 10.4 Hz, 1H), 7.54 (s, 1H), 7.27 (dd, J = 6.0, 11.6 Hz, 1H), 6.91 (d, J = 5.2 Hz, 1H), 5.56 (q, J = 6.8 Hz, 1H), 4.56-4.43 (m, 2H), 3.70 (q, J = 7.2 Hz, 2H), 2.69 (s, 3H), 1.62 (d, J = 7.2 Hz, 3H), 1.32 (t, J = 7.2 Hz, 3H). |

TABLE 3-continued

| Cpd No. | Compound Structure | MS/$^1$H NMR |
|---|---|---|
| 123 | 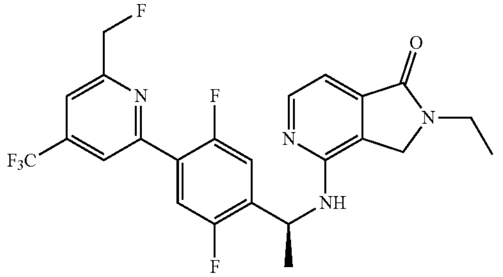 [SMILES: CCN1Cc2c(ccnc2N[C@@H](C)c2cc(F)c(-c3cc(C(F)(F)F)cc(CF)n3)cc2F)C1=O] | LC-MS: (ESI) m/z: 495.0 [M + H]. $^1$H NMR (400 MHz, $CD_3OD$) δ: 8.08-8.00 (m, 2H), 7.83 (dd, J = 6.4, 11.2 Hz, 1H), 7.74 (s, 1H), 7.29 (dd, J = 6.4, 11.2 Hz, 1H), 6.91 (d, J = 5.2 Hz, 1H), 5.69 (s, 1H), 5.59-5.52 (m, 2H), 4.56-4.44 (m, 2H), 3.70 (q, J = 7.2 Hz, 2H), 1.62 (d, J = 6.8 Hz, 3H), 1.33 (t, J = 7.2 Hz, 3H). |
| 124 | 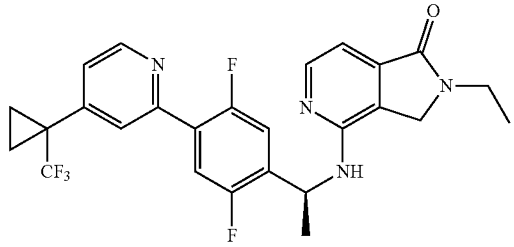 [SMILES: CCN1Cc2c(ccnc2N[C@@H](C)c2cc(F)c(-c3cc(C4(C(F)(F)F)CC4)ccn3)cc2F)C1=O] | LC-MS: (ESI) m/z: 503.2 [M + H]. $^1$H NMR (400 MHz, $CDCl_3$) δ: 8.68 (d, J = 5.2 Hz, 1H), 8.21 (d, J = 4.8 Hz, 1H), 7.83 (s, 1H), 7.73 (dd, J = 6.0, 11.2 Hz, 1H), 7.34 (d, J = 4.4 Hz, 1H), 7.18 (dd, J = 6.0, 11.2 Hz, 1H), 7.07 (d, J = 4.8 Hz, 1H), 5.55 (q, J = 6.8 Hz, 1H), 4.59 (d, J = 7.6 Hz, 1H), 4.34-4.22 (m, 2H), 3.76-3.64 (m, 2H), 1.65 (d, J = 7.2 Hz, 3H), 1.49-1.42 (m, 2H), 1.34-1.28 (m, 3H), 1.16-1.08 (m, 2H). |
| 125 | 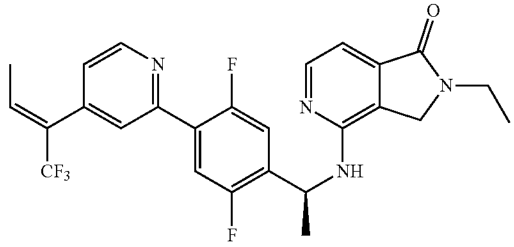 [SMILES: C/C=C(\c1ccnc(-c2cc(F)c([C@H](C)Nc3nccc4c3CN(CC)C4=O)cc2F)c1)C(F)(F)F] | LC-MS: (ESI) m/z: 503.2 [M + H]. $^1$H NMR (400 MHz, $CD_3OD$) δ: 8.74 (d, J = 4.8 Hz, 1H), 8.06 (d, J = 5.2 Hz, 1H), 7.72-7.64 (m, 2H), 7.31 (d, J = 4.8 Hz, 1H), 7.27 (dd, J = 6.0,11.6 Hz, 1H), 6.91 (d, J = 5.2 Hz, 1H), 6.79-6.71 (m, 1H), 5.57 (q, J = 6.8 Hz, 1H), 4.56-4.42 (m, 2H), 3.70 (q, J = 7.2 Hz, 2H), 1.77-1.71 (m, 3H), 1.62 (d, J = 6.8 Hz, 3H), 1.32 (t, J = 7.2 Hz, 3H). |
| 126 | 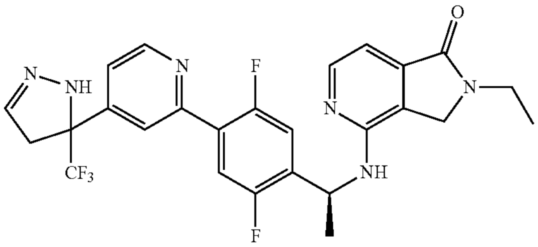 [SMILES: CCN1Cc2c(ccnc2N[C@@H](C)c2cc(F)c(-c3cc(C4(C(F)(F)F)CC=NN4)ccn3)cc2F)C1=O] | LC-MS: (ESI) m/z: 531.1 [M + H]. $^1$H NMR (400 MHz, $CD_3OD$) δ: 8.69 (d, J = 5.2 Hz, 1H), 8.06 (d, J = 4.4 Hz, 1H), 7.92 (s, 1H), 7.66-7.59 (m, 1H), 7.53 (d, J = 5.2 Hz, 1H), 7.31-7.23 (m, 1H), 6.91 (d, J = 5.2 Hz, 1H), 6.78 (s, 1H), 5.56 (q, J = 6.8 Hz, 1H), 4.57-4.43 (m, 2H), 3.70 (q, J = 7.2 Hz, 2H), 3.64-3.55 (m, 1H), 3.22 (d, J= 18.4 Hz, 1H), 1.62 (d, J = 7.2 Hz, 3H), 1.32 (t, J = 7.2 Hz, 3H). |
| 127 | 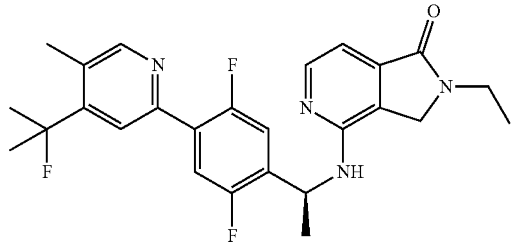 [SMILES: CCN1Cc2c(ccnc2N[C@@H](C)c2cc(F)c(-c3cc(C(C)(C)F)c(C)cn3)cc2F)C1=O] | LC-MS: (ESI) m/z 469.3 [M + H]. $^1$H NMR (400 MHz, $CD_3OD$) δ: 8.42 (s, 1H), 8.05 (d, J = 5.2 Hz, 1H), 7.71 (s, 1H), 7.56 (dd, J = 6.4, 10.8 Hz, 1H), 7.24 (dd, J = 6.0, 11.6 Hz, 1H), 6.90 (d, J = 5.2 Hz, 1H), 5.55 (q, J = 6.8 Hz, 1H), 4.55-4.40 (m, 2H), 3.69 (q, J = 7.2 Hz, 2H), 2.50 (d, J = 3.2 Hz, 3H), 1.74 (d, J = 22.4 Hz, 6H), 1.61 (d, J = 6.8 Hz, 3H), 1.32 (t, J = 7.2 Hz, 3H). |
| 128 | 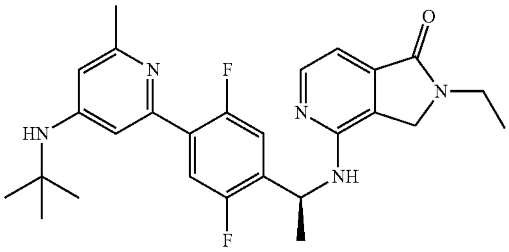 [SMILES: CCN1Cc2c(ccnc2N[C@@H](C)c2cc(F)c(-c3cc(NC(C)(C)C)cc(C)n3)cc2F)C1=O] | LC-MS: (ESI) m/z: 480.2 [M + H]. $^1$H NMR (400 MHz, $CD_3OD$) δ: 8.07 (d, J = 5.2 Hz, 1H), 7.39-7.35 (dd, J = 6.0, 10.8 Hz, 1H), 7.23-7.19 (dd, J = 6.0, 10.8 Hz, 1H), 6.91 (d, J = 5.2 Hz, 1H), 6.75 (t, J = 1.6 Hz, 1H), 6.52 (d, J = 2.0 Hz, 1H), 5.59-5.54 (q, J = 6.8 Hz, 1H), 4.54-4.44 (m, 2H), 3.71-3.68 (q, J = 7.2 Hz, 2H), 2.38 (s, 3H), 1.62 (d, J = 7.2 Hz, 3H), 1.40 (s, 9H), 1.33 (t, J = 7.2 Hz, 3H). |

TABLE 3-continued

| Cpd No. | Compound Structure | MS/$^1$H NMR |
| --- | --- | --- |
| 129 | 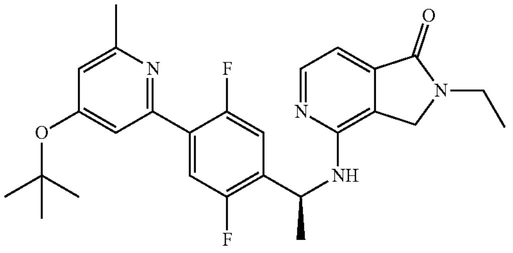 [SMILES: CCN1Cc2c(ccnc2N[C@@H](C)c2cc(F)c(-c3cc(OC(C)(C)C)cc(C)n3)cc2F)C1=O] | LC-MS: (ESI) m/z: 481.3 [M + H]. $^1$H NMR (400 MHz, $CD_3OD$) δ: 8.05 (d, J = 5.2 Hz, 1H), 7.50 (dd, J = 6.0, 10.8 Hz, 1H), 7.22 (dd, J = 6.0, 11.2 Hz, 1H), 7.10 (s, 1H), 6.90 (d, J = 5.2 Hz, 1H), 6.86 (d, J = 2.0 Hz, 1H), 5.55 (q, J = 6.8 Hz, 1H), 4.57-4.39 (m, 2H), 3.70 (q, J = 7.2 Hz, 2H), 2.50 (s, 3H), 1.61 (d, J = 7.2 Hz, 3H), 1.49 (s, 9H), 1.32 (t, J = 7.3 Hz, 3H). $^{19}$FNMR (400 MHz, $CD_3OD$) δ: −124.467, −126.272. |
| 130 | 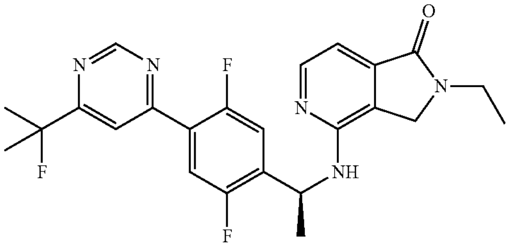 [SMILES: CCN1Cc2c(ccnc2N[C@@H](C)c2cc(F)c(-c3cc(C(C)(C)F)ncn3)cc2F)C1=O] | LC-MS: (ESI) m/z: 456.3 [M + H]. $^1$H NMR (400 MHz, $CD_3OD$) δ: 9.18 (s, 1H), 8.17-8.03 (m, 2H), 7.91 (dd, J = 6.0, 10.8 Hz, 1H), 7.31 (dd, J = 6.0, 12.0 Hz, 1H), 6.91 (d, J = 5.2 Hz, 1H), 5.56 (q, J = 6.8 Hz, 1H), 4.60 (s, 2H), 4.56-4.43 (m, 2H), 3.70 (q, J = 7.2 Hz, 2H), 1.73 (d, J = 1.6 Hz, 3H), 1.68 (d, J = 1.6 Hz, 3H), 1.62 (d, J = 7.2 Hz, 3H), 1.33 (t, J = 7.3 Hz, 3H). $^{19}$FNMR (400 MHz, $CD_3OD$) δ: −121.762, −125.433, −149.012. |
| 131 | 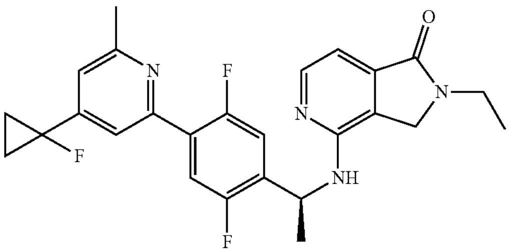 [SMILES: CCN1Cc2c(ccnc2N[C@@H](C)c2cc(F)c(-c3cc(C4(F)CC4)cc(C)n3)cc2F)C1=O] | LC-MS: (ESI) m/z 467.3 [M + H]. $^1$H NMR (400 MHz, $CD_3OD$) δ: 8.05 (d, J = 5.2 Hz, 1H), 7.57 (dd, J = 6.4, 10.8 Hz, 1H), 7.37 (s, 1H), 7.24 (dd, J = 6.4, 11.2 Hz, 1H), 7.08 (s, 1H), 6.90 (d, J = 5.2 Hz, 1H), 5.56 (q, J = 6.8 Hz, 1H), 4.58-4.41 (m, 2H), 3.70 (q, J = 7.2 Hz, 2H), 2.57 (s, 3H), 1.68-1.54 (m, 5H), 1.32 (t, J = 7.2 Hz, 3H), 1.29-1.20 (m, 2H). |
| 132 | 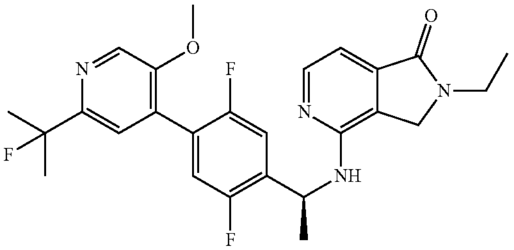 [SMILES: CCN1Cc2c(ccnc2N[C@@H](C)c2cc(F)c(-c3cc(C(C)(C)F)ncc3OC)cc2F)C1=O] | LC-MS: (ESI) m/z: 485.3 [M + H]. $^1$H NMR (400 MHz, $CD_3OD$) δ: 8.32 (s, 1H), 8.08 (d, J = 5.2 Hz, 1H), 7.44 (s, 1H), 7.26-7.11 (m, 2H), 6.92 (d, J = 5.2 Hz, 1H), 5.57 (q, J = 6.8 Hz, 1H), 4.57-4.41 (m, 2H), 3.90 (s, 3H), 3.70 (q, J = 7.2 Hz, 2H), 1.71 (s, 3H), 1.66 (s, 3H), 1.62 (d, J = 6.8 Hz, 3H), 1.32 (t, J = 7.2 Hz, 3H). $^{19}$FNMR (400 MHz, $CD_3OD$) δ: −121.415, −126.558, −126.606, 142.386. |
| 133 | 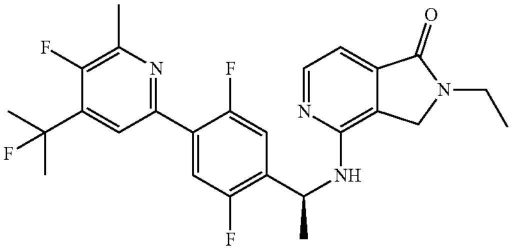 [SMILES: CCN1Cc2c(ccnc2N[C@@H](C)c2cc(F)c(-c3cc(C(C)(C)F)c(F)c(C)n3)cc2F)C1=O] | LC-MS: (ESI) m/z: 487.3 [M + H]. $^1$H NMR (400 MHz, $CD_3OD$) δ: 8.06 (d, J = 5.2 Hz, 1H), 7.73 (d, J = 5.2 Hz, 1H), 7.64 (dd, J = 6.4, 10.8 Hz, 1H), 7.23 (dd, J = 6.0, 11.6 Hz, 1H), 6.91 (d, J = 5.2 Hz, 1H), 5.56 (q, J = 6.8 Hz, 1H), 4.49 (d, J = 5.6 Hz, 2H), 3.70 (q, J = 7.2 Hz, 2H), 2.55 (d, J = 3.2 Hz, 3H), 1.77 (s, 3H), 1.72 (s, 3H), 1.61 (d, J = 7.2 Hz, 3H), 1.32 (t, J = 7.2 Hz, 3H). |
| 134 | 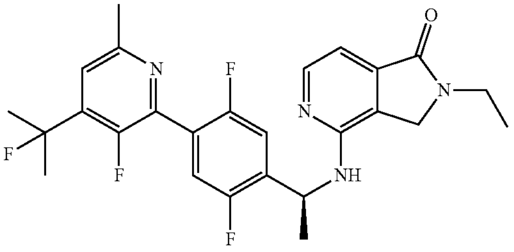 [SMILES: CCN1Cc2c(ccnc2N[C@@H](C)c2cc(F)c(-c3nc(C)cc(C(C)(C)F)c3F)cc2F)C1=O] | LC-MS: (ESI) m/z 487.2 [M + H]. $^1$H NMR (400 MHz, $CDCl_3$) δ: 8.21 (d, J = 4.8 Hz, 1H), 7.36 (d, J = 5.2 Hz, 1H), 7.32-7.27 (m, 1H), 7.16 (dd, J = 6.0, 9.6 Hz, 1H), 7.06 (d, J = 5.2 Hz, 1H), 5.57 (quin, J = 7.2 Hz, 1H), 4.59 (d, J = 7.6 Hz, 1H), 4.28 (s, 2H), 3.77-3.62 (m, 2H), 2.59 (s, 3H), 1.74 (d, J = 22.8 Hz, 6H), 1.64 (d, J = 6.8 Hz, 3H), 1.30 (t, J = 6.8 Hz, 3H). |

TABLE 3-continued

| Cpd No. | Compound Structure | MS/$^{1}$H NMR |
|---|---|---|
| 135 | 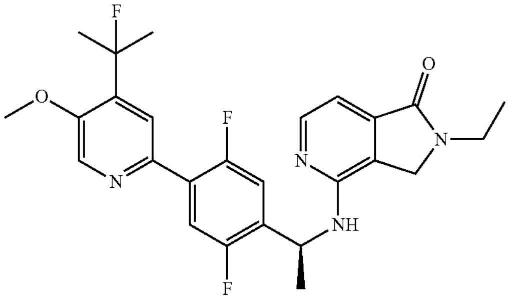 [SMILES: CCN1Cc2c(ccnc2N[C@@H](C)c2cc(F)c(-c3cc(C(C)(C)F)c(OC)cn3)cc2F)C1=O] | LC-MS: (ESI) m/z: 485.2 [M + H]. $^{1}$H NMR (400 MHz, $CD_3OD$) δ: 8.37 (s, 1H), 8.06 (d, J = 5.2 Hz, 1H), 7.83 (d, J = 1.6 Hz, 1H), 7.57 (dd, J = 6.4, 11.0 Hz, 1H), 7.23 (dd, J = 6.0, 11.5 Hz, 1H), 6.90 (d, J = 5.2 Hz, 1H), 5.56 (q, J = 6.8 Hz, 1H), 4.55-4.42 (m, 2H), 4.01 (s, 3H), 3.70 (q, J = 7.2 Hz, 2H), 1.72 (d, J = 23.6 Hz, 6H), 1.61 (d, J = 6.8 Hz, 3H), 1.32 (t, J = 7.2 Hz, 3H). |
| 136 | 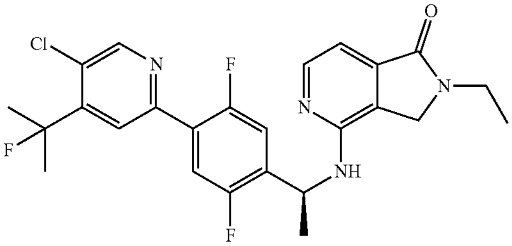 [SMILES: CCN1Cc2c(ccnc2N[C@@H](C)c2cc(F)c(-c3cc(C(C)(C)F)c(Cl)cn3)cc2F)C1=O] | LC-MS: (ESI) m/z 489.2 [M + H]. $^{1}$H NMR (400 MHz, $CD_3OD$) δ: 8.59 (s, 1H), 8.04 (d, J = 4.8 Hz, 1H), 8.00 (s, 1H), 7.68 (dd, J = 6.4, 10.8 Hz, 1H), 7.25 (dd, J = 6.0, 11.6 Hz, 1H), 6.89 (d, J = 5.2 Hz, 1H), 5.55 (q, J = 7.2 Hz, 1H), 4.48 (d, J = 7.2 Hz, 2H), 3.69 (q, J = 7.6 Hz, 2H), 1.82 (d, J = 23.2 Hz, 6H), 1.61 (d, J = 7.2 Hz, 3H), 1.31 (t, J = 7.2 Hz, 3H). |
| 137 | 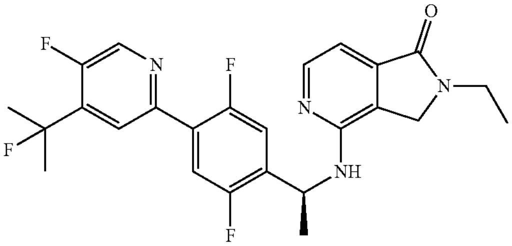 [SMILES: CCN1Cc2c(ccnc2N[C@@H](C)c2cc(F)c(-c3cc(C(C)(C)F)c(F)cn3)cc2F)C1=O] | LC-MS: (ESI) m/z: 473.1 [M + H]. $^{1}$H NMR (400 MHz, $CD_3OD$) δ: 8.52 (d, J = 2.8 Hz, 1H), 8.06 (d, J = 5.2 Hz, 1H), 7.92 (d, J = 6.4 Hz, 1H), 7.66 (dd, J = 6.4, 11.2 Hz, 1H), 7.25 (dd, J = 6.2, 11.8 Hz, 1H), 6.90 (d, J = 5.2 Hz, 1H), 5.56 (q, J = 6.8 Hz, 1H), 4.56-4.42 (m, 2H), 3.70 (q, J = 7.2 Hz, 2H), 1.79 (s, 3H), 1.73 (s, 3H), 1.61 (d, J = 7.2 Hz, 3H), 1.32 (t, J = 7.2 Hz, 3H). (ES9799-152-P1A) |
| 138 | 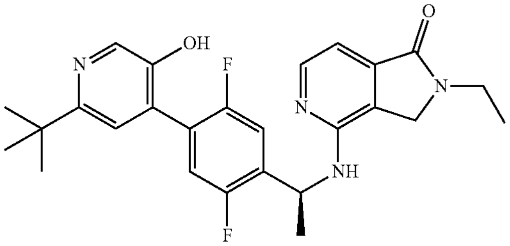 [SMILES: CCN1Cc2c(ccnc2N[C@@H](C)c2cc(F)c(-c3cc(C(C)(C)C)ncc3O)cc2F)C1=O] | LC-MS: (ESI) m/z: 467.1 [M + H]. $^{1}$H NMR (400 MHz, $CD_3OD$) δ: 8.11 (s, 1H), 8.08 (d, J = 5.2 Hz, 1H), 7.26 (s, 1H), 7.24-7.17 (m, 2H), 6.91 (d, J = 5.2 Hz, 1H), 5.57 (q, J = 6.8 Hz, 1H), 4.48 (d, J = 4.8 Hz, 2H), 3.70 (q, J = 7.2 Hz, 2H), 1.62 (d, J = 6.8 Hz, 3H), 1.33 (s, 9H), 1.319 (t, J = 7.2 Hz, 3H). $^{19}$FNMR (400 MHz, $CD_3OD$) δ: −125.499. |
| 139 | 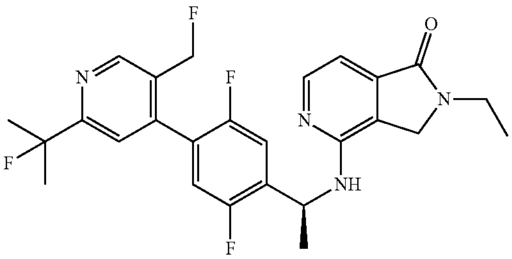 [SMILES: CCN1Cc2c(ccnc2N[C@@H](C)c2cc(F)c(-c3cc(C(C)(C)F)ncc3CF)cc2F)C1=O] | LC-MS: (ESI) m/z: 487.2 [M + H]. $^{1}$H NMR (400 MHz, $CD_3OD$) δ: 8.69 (s, 1H), 8.08 (d, J = 4.8 Hz, 1H), 7.52 (s, 1H), 7.30 (dd, J = 6.0, 10.0 Hz, 1H), 7.17 (dd, J = 6.0, 10.0 Hz, 1H), 6.92 (d, J = 5.2 Hz, 1H), 5.59 (q, J = 6.8 Hz, 1H), 5.44-5.21 (m, 2H), 4.57-4.42 (m, 2H), 3.70 (q, J = 7.2 Hz, 2H), 1.79-1.65 (m, 6H), 1.63 (d, J = 7.2 Hz, 3H), 1.32 (t, J = 7.2 Hz, 3H). |
| 141 | 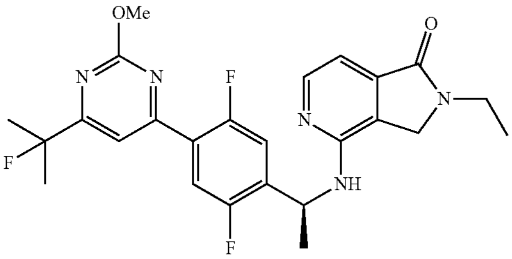 [SMILES: CCN1Cc2c(ccnc2N[C@@H](C)c2cc(F)c(-c3cc(C(C)(C)F)nc(OC)n3)cc2F)C1=O] | LC-MS: (ESI) m/z: 486.2 [M + H]. $^{1}$H NMR (400 MHz, $CD_3OD$) δ: 8.03 (d, J = 5.2 Hz, 1H), 7.89-7.84 (dd, J = 6.0, 10.8 Hz, 1H), 7.63 (s, 1H), 7.29-7.24 (dd, J = 6.0, 12.0 Hz, 1H), 6.87 (d, J = 5.2 Hz, 1H), 5.56-5.51 (q, J = 6.8 Hz, 1H), 4.52-4.41 (m, 2H), 4.05 (s, 3H), 3.70-3.65 (q, J = 7.2 Hz, 2H), 1.69 (d, J = 2.0 Hz, 3H), 1.63 (d, J = 2.0 Hz, 3H), 1.60 (d, J = 6.8 Hz, 3H), 1.30 (t, J = 7.2 Hz, 3H). |

TABLE 3-continued

| Cpd No. | Compound Structure | MS/$^{1}$H NMR |
| --- | --- | --- |
| 142 | 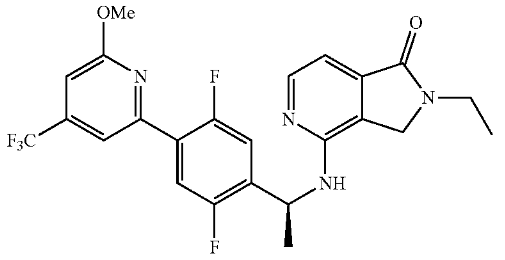 | LC-MS: (ESI) m/z 493.1 [M + H]. $^{1}$H NMR (400 MHz, $CDCl_3$) δ: 8.20 (d, J = 4.8 Hz, 1H), 7.86 (dd, J = 6.0, 11.2 Hz, 1H), 7.65 (s, 1H), 7.19 (dd, J = 6.0, 11.6 Hz, 1H), 7.07 (d, J = 5.2 Hz, 1H), 6.95 (s, 1H), 5.57 (t, J = 7.2 Hz, 1H), 4.63 (br s, 1H), 4.36-4.22 (m, 2H), 4.05 (s, 3H), 3.70 (q, J = 7.2 Hz, 2H), 1.66 (d, J = 7.2 Hz, 3H), 1.30 (t, J = 7.6 Hz, 3H). |
| 143 | 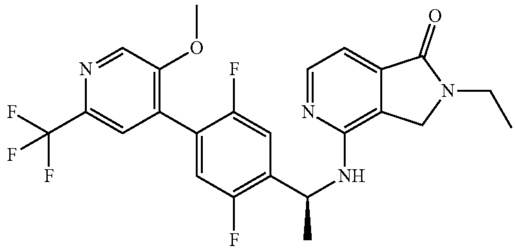 [SMILES: CCN1Cc2c(ccnc2N[C@@H](C)c2cc(F)c(-c3cc(C(F)(F)F)ncc3OC)cc2F)C1=O] | LC-MS: (ESI) m/z: 493.2 [M + H]. $^{1}$H NMR (400 MHz, $CD_3OD$) δ: 8.54 (s, 1H), 8.07 (d, J = 5.2 Hz, 1H), 7.69 (s, 1H), 7.30-7.17 (m, 2H), 6.92 (d, J = 5.2 Hz, 1H), 5.57 (q, J = 7.2 Hz, 1H), 4.49 (d, J = 4.4 Hz, 2H), 4.00 (s, 3H), 3.70 (q, J = 7.2 Hz, 2H), 1.62 (d, J = 7.2 Hz, 3H), 1.32 (t, J = 7.2 Hz, 3H). |
| 144 | 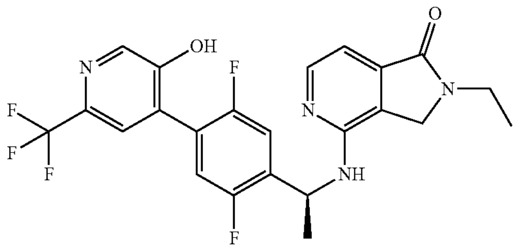 [SMILES: CCN1Cc2c(ccnc2N[C@@H](C)c2cc(F)c(-c3cc(C(F)(F)F)ncc3O)cc2F)C1=O] | LC-MS: (ESI) m/z: 479.2 [M + H]. $^{1}$H NMR (400 MHz, $CD_3OD$) δ: 8.28 (s, 1H), 8.07 (d, J = 5.2 Hz, 1H), 7.63 (s, 1H), 7.32-7.20 (m, 2H), 6.91 (d, J = 5.2 Hz, 1H), 5.57 (q, J = 6.8 Hz, 1H), 4.56-4.40 (m, 2H), 3.69 (q, J = 7.2 Hz, 2H), 1.62 (d, J = 7.2 Hz, 3H), 1.32 (t, J = 7.2 Hz, 3H). |
| 145 | 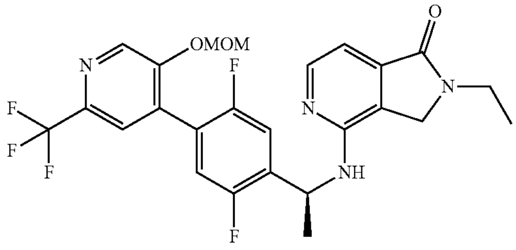 | LC-MS: (ESI) m/z: 523.0 [M + H]. $^{1}$H NMR (400 MHz, $CD_3OD$) δ: 8.65 (s, 1H), 8.07 (d, J = 5.2 Hz, 1H), 7.73 (s, 1H), 7.31-7.18 (m, 2H), 6.92 (d, J = 5.2 Hz, 1H), 5.58 (q, J = 6.8 Hz, 1H), 5.32 (s, 2H), 4.49 (d, J = 4.0 Hz, 2H), 3.70 (q, J = 7.2 Hz, 2H), 3.41 (s, 3H), 1.62 (d, J = 7.2 Hz, 3H), 1.32 (t, J = 7.2 Hz, 3H). |
| 146 | 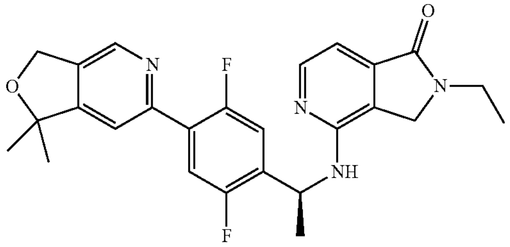 [SMILES: CCN1Cc2c(ccnc2N[C@@H](C)c2cc(F)c(-c3cc4c(cn3)COC4(C)C)cc2F)C1=O] | LC-MS: (ESI) m/z: 465.2 [M + H]. $^{1}$H NMR (400 MHz, $CD_3OD$) δ: 8.57 (s, 1H), 8.07 (d, J = 4.4 Hz, 1H), 7.63 (s, 1H), 7.61-7.57 (m, 1H), 7.29-7.25 (dd, J = 5.6, 11.2 Hz, 1H), 6.92 (d, J = 4.4 Hz, 1H), 5.64-5.52 (m, 1H), 5.15 (s, 2H), 4.55-4.45 (m, 2H), 3.79-3.64 (m, 2H), 1.64 (d, J = 6.8 Hz, 3H), 1.52 (s, 6H), 1.33 (t, J = 6.8 Hz, 3H). |
| 147 | 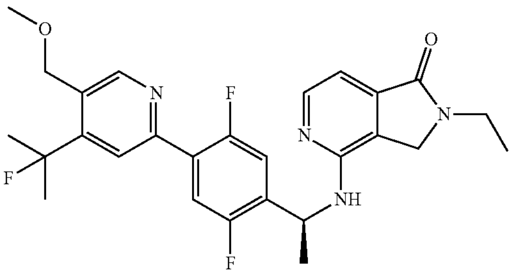 [SMILES: CCN1Cc2c(ccnc2N[C@@H](C)c2cc(F)c(-c3cc(C(C)(C)F)c(COC)cn3)cc2F)C1=O] | LC-MS: (ESI) m/z: 499.2 [M + H]. $^{1}$H NMR (400 MHz, $CD_3OD$) δ: 8.70 (s, 1H), 8.05 (d, J = 5.2 Hz, 1H), 7.73 (s, 1H), 7.60 (dd, J = 6.0, 10.8 Hz, 1H), 7.25 (dd, J = 6.0, 11.6 Hz, 1H), 6.90 (d, J = 5.6 Hz, 1H), 5.55 (q, J = 6.8 Hz, 1H), 4.72 (d, J = 1.6 Hz, 2H), 4.56-4.40 (m, 2H), 3.70 (q, J = 7.6 Hz, 2H), 3.47 (s, 3H), 1.76 (d, J = 22.4 Hz, 6H), 1.61 (d, J = 7.2 Hz, 3H), 1.32 (t, J = 7.2 Hz, 3H). |

TABLE 3-continued

| Cpd No. | Compound Structure | MS/$^1$H NMR |
|---|---|---|
| 148 | 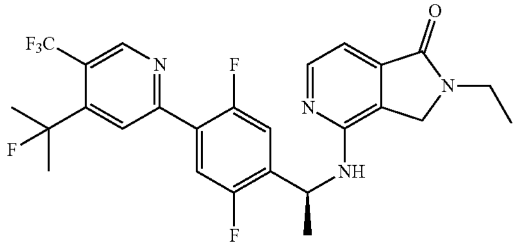 | LC-MS: (ESI) m/z: 523.3 [M + H]. $^1$H NMR (400 MHz, $CD_3OD$) δ: 9.01 (s, 1H), 8.05 (d, J = 5.2 Hz, 1H), 7.92 (s, 1H), 7.77 (dd, J = 6.4, 10.8 Hz, 1H), 7.29 (dd, J = 6.4, 12.0 Hz, 1H), 6.91 (d, J = 5.2 Hz, 1H), 5.55 (q, J = 7.2 Hz, 1H), 4.56-4.43 (m, 2H),, 3.70 (q, J = 7.2 Hz, 2H), 1.78 (dd, J= 2.4, 22.0 Hz, 6H), 1.62 (d, J = 6.8 Hz, 3H), 1.33 (t, J = 7.2 Hz, 3H). |
| 149 | 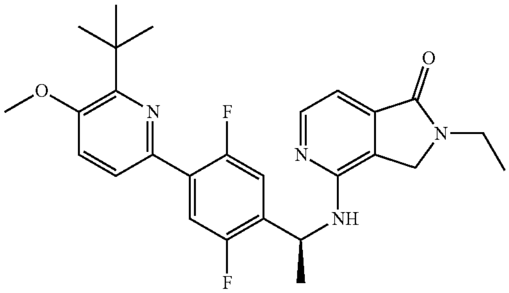 [SMILES: CCN1Cc2c(ccnc2N[C@@H](C)c2cc(F)c(-c3ccc(OC)c(C(C)(C)C)n3)cc2F)C1=O] | LC-MS: (ESI) m/z: 481.3 [M + H]. $^1$H NMR (400 MHz, $CD_3OD$) δ: 8.09 (d, J = 5.2 Hz, 1H), 7.89-7.85 (dd, J = 11.6, 6.4 Hz, 1H), 7.74-7.71 (dd, J = 8.4, 1.6 Hz, 1H), 7.36 (d, J = 8.4 Hz, 1H), 7.20-7.15 (dd, J = 12.0, 6.0 Hz, 1H), 6.92 (d, J = 5.2 Hz, 1H), 5.58-5.53 (q, J = 7.2 Hz, 1H), 4.55-4.44 (m, 2H), 3.91 (s, 3H), 3.74-3.69 (q, J = 7.2 Hz, 2H), 1.62 (d, J = 7.2 Hz, 3H), 1.46 (s, 9H), 1.34 (t, J = 7.2 Hz, 3H). |
| 150 | 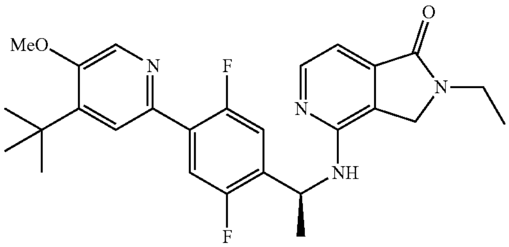 [SMILES: CCN1Cc2c(ccnc2N[C@@H](C)c2cc(F)c(-c3cc(C(C)(C)C)c(OC)cn3)cc2F)C1=O] | LC-MS: (ESI) m/z: 481.3 [M + H]. $^1$H NMR (400 MHz, $CD_3OD$) δ: 8.28 (s, 1H), 8.06 (d, J = 5.2 Hz, 1H), 7.64 (d, J = 1.6 Hz, 1H), 7.50 (dd, J = 6.4, 10.8 Hz, 1H), 7.22 (dd, J = 6.0, 11.6 Hz, 1H), 6.90 (d, J = 5.2 Hz, 1H), 5.55 (q, J = 6.8 Hz, 1H), 4.55-4.42 (m, 2H), 4.01 (s, 3H), 3.70 (q, J = 7.2 Hz, 2H), 1.61 (d, J = 7.2 Hz, 3H), 1.39 (s, 9H), 1.32 (t, J = 7.2 Hz, 3H). |
| 151 | 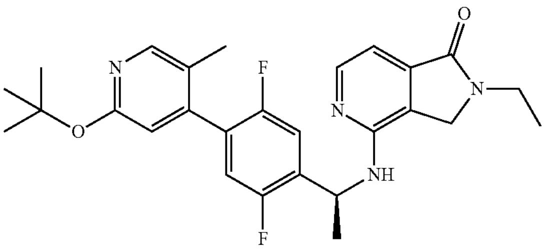 [SMILES: CCN1Cc2c(ccnc2N[C@@H](C)c2cc(F)c(-c3cc(OC(C)(C)C)ncc3C)cc2F)C1=O] | LC-MS: (ESI) m/z: 481.3 [M + H]. $^1$H NMR (400 MHz, $CD_3OD$) δ: 8.07 (d, J = 5.2 Hz, 1H), 8.00 (s, 1H), 7.24 (dd, J = 6.0, 10.0 Hz, 1H), 7.02 (dd, J = 6.0, 10.0 Hz, 1H), 6.91 (d, J = 5.2 Hz, 1H), 6.54 (s, 1H), 5.58 (q, J = 6.8 Hz, 1H), 4.54-4.40 (m, 2H), 3.69 (q, J = 7.2 Hz, 2H), 2.05 (s, 3H), 1.62 (d, J = 7.2 Hz, 3H), 1.53 (s, 9H), 1.32 (t, J = 7.2 Hz, 3H). |
| 152 | 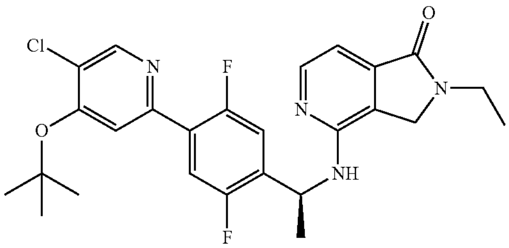 [SMILES: CCN1Cc2c(ccnc2N[C@@H](C)c2cc(F)c(-c3cc(OC(C)(C)C)c(Cl)cn3)cc2F)C1=O] | LC-MS: (ESI) m/z: 501.3 [M + H]. $^1$H NMR (400 MHz, $CD_3OD$) δ: 8.49 (s, 1H), 8.04 (d, J = 5.2 Hz, 1H), 7.63 (dd, J = 6.4, 10.8 Hz, 1H), 7.57 (d, J = 0.4 Hz, 1H), 7.25 (dd, J = 6.0, 11.8 Hz, 1H), 6.89 (d, J = 5.2 Hz, 1H), 5.54 (q, J = 6.8 Hz, 1H), 4.55-4.39 (m, 2H), 3.69 (q, J = 7.2 Hz, 2H), 1.61 (d, J = 6.8 Hz, 3H), 1.53 (s, 9H), 1.31 (t, J = 7.2 Hz, 3H). |
| 153 | 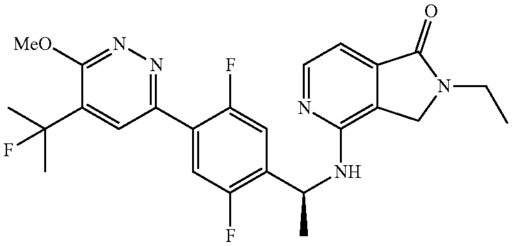 [SMILES: CCN1Cc2c(ccnc2N[C@@H](C)c2cc(F)c(-c3cc(C(C)(C)F)c(OC)nn3)cc2F)C1=O] | LC-MS: (ESI) m/z: 486.2 [M + H]. $^1$H NMR (400 MHz, $CD_3OD$) δ: 8.04 (d, J = 5.2 Hz, 1H), 7.93 (d, J = 1.6 Hz, 1H), 7.63 (dd, J = 6.4, 10.8 Hz, 1H), 7.29 (dd, J = 6.0, 11.2 Hz, 1H), 6.89 (d, J = 5.2 Hz, 1H), 5.56 (q, J = 6.8 Hz, 1H), 4.56-4.40 (m, 2H), 4.19 (s, 3H), 3.69 (q, J = 7.2 Hz, 2H), 1.86 (dd, J = 1.2, 23.2 Hz, 1H), 1.73 (dd, J = 1.6, 23.2 Hz, 5H), 1.62 (d, J = 6.8 Hz, 3H), 1.31 (t, J = 7.2 Hz, 3H). |

TABLE 3-continued

| Cpd No. | Compound Structure | MS/$^1$H NMR |
|---|---|---|
| 154 | 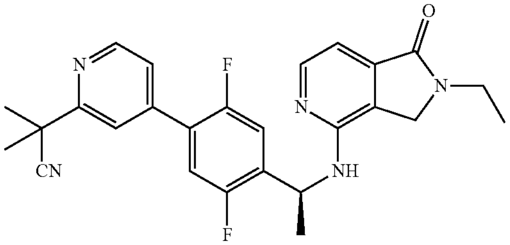 [SMILES: CCN1Cc2c(ccnc2N[C@@H](C)c2cc(F)c(-c3ccnc(C(C)(C)C#N)c3)cc2F)C1=O] | LC-MS: (ESI) m/z 462.1 [M + H]. $^1$H NMR (400 MHz, $CDCl_3$) δ: 8.66 (dd, J = 0.8, 5.2 Hz, 1H), 8.21 (d, J = 4.8 Hz, 1H), 7.70 (s, 1H), 7.39 (dt, J = 1.6, 5.2 Hz, 1H), 7.20 (td, J = 6.0, 11.2 Hz, 2H), 7.08 (d, J = 5.2 Hz, 1H), 5.57 (quin, J = 6.8 Hz, 1H), 4.57 (d, J = 7.2 Hz, 1H), 4.37-4.23 (m, 2H), 3.70 (q, J = 7.2 Hz, 2H), 1.80 (s, 6H), 1.66 (d, J = 6.8 Hz, 3H), 1.31 (t, J = 7.2 Hz, 3H). |
| 155 | 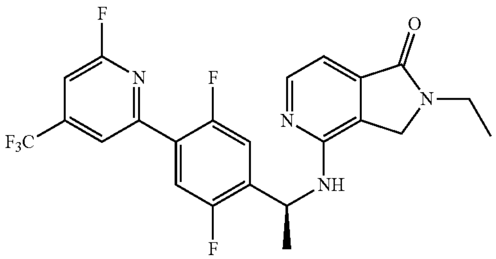 [SMILES: CCN1Cc2c(ccnc2N[C@@H](C)c2cc(F)c(-c3cc(C(F)(F)F)cc(F)n3)cc2F)C1=O] | LC-MS: (ESI) m/z 481.2 [M + H]. $^1$H NMR (400 MHz, $CD_3OD$) δ: 8.05 (d, J = 5.2 Hz, 1H), 8.01 (s, 1H), 7.81 (dd, J-6.0, 10.8 Hz, 1H), 7.44 (s, 1H), 7.30 (dd, J = 6.0, 12.0 Hz, 1H), 6.91 (d, J = 5.2 Hz, 1H), 5.55 (q, J = 6.8 Hz, 1H), 4.57-4.42 (m, 2H), 3.70 (q, J = 7.2 Hz, 2H), 1.62 (d, J = 6.8 Hz, 3H), 1.32 (t, J = 7.2 Hz, 3H). |
| 156 | 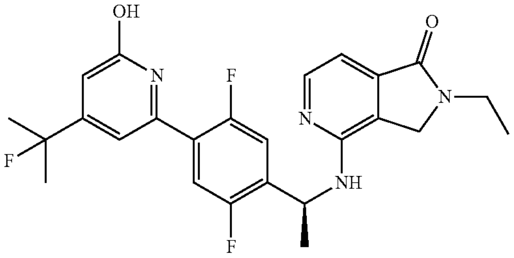 [SMILES: CCN1Cc2c(ccnc2N[C@@H](C)c2cc(F)c(-c3cc(C(C)(C)F)cc(O)n3)cc2F)C1=O] | LC-MS: (ESI) m/z: 471.1 [M + H]. $^1$H NMR (400 MHz, $CD_3OD$) δ: 8.02 (d, J = 5.2 Hz, 1H), 7.37 (dd, J = 5.6, 10.0 Hz, 1H), 7.28 (dd, J = 6.0, 10.8 Hz, 1H), 6.91 (d, J = 5.2 Hz, 1H), 6.59-6.51 (m, 2H), 5.53 (q, J = 6.8 Hz, 1H), 4.57-4.41 (m, 2H), 3.70 (q, J = 7.2 Hz, 2H), 1.68-1.56 (m, 9H), 1.32 (t, J = 7.2 Hz, 3H). |
| 157 | 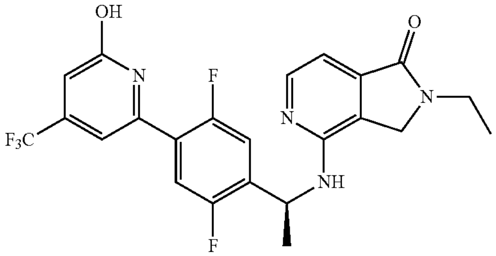 [SMILES: CCN1Cc2c(ccnc2N[C@@H](C)c2cc(F)c(-c3cc(C(F)(F)F)cc(O)n3)cc2F)C1=O] | LC-MS: (ESI) m/z 479.0 [M + H]. $^1$H NMR (400 MHz, $CDCl_3$) δ: 11.38 (br s, 1H), 8.18 (d, J = 4.8 Hz, 1H), 7.36 (dd, J = 6.0, 10.4 Hz, 1H), 7.26-7.20 (m, 1H), 7.08 (d, J = 5.2 Hz, 1H), 6.83 (s, 1H), 6.63 (s, 1H), 5.56 (t, J = 6.8 Hz, 1H), 4.56 (d, J = 6.8 Hz, 1H), 4.31 (d, J = 1.6 Hz, 2H), 3.70 (q, J = 7.2 Hz, 2H), 1.65 (d, J = 6.8 Hz, 3H), 1.31 (t, J = 7.2 Hz, 3H). |
| 158 | 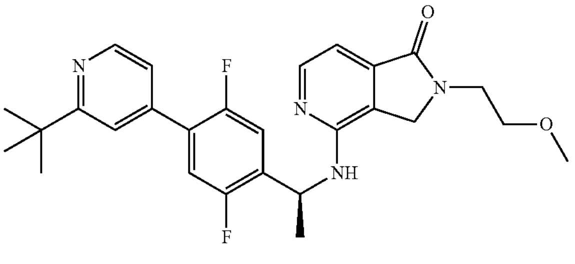 [SMILES: COCCN1Cc2c(ccnc2N[C@@H](C)c2cc(F)c(-c3ccnc(C(C)(C)C)c3)cc2F)C1=O] | LC-MS: (ESI) m/z: 481.0 [M + H]. $^1$H NMR (400 MHz, $CDCl_3$) δ: 8.63 (d, J = 5.2 Hz, 1H), 8.21 (d, J = 4.8 Hz, 1H), 7.45 (s, 1H), 7.25-7.22 (m, 1H), 7.21-7.14 (m, 2H), 7.08 (d, J = 4.8 Hz, 1H), 5.58-5.54 (m, 1H), 4.56 (d, J = 7.2 Hz, 1H), 4.44 (s, 2H), 3.83-3.80 (m, 2H), 3.65 (t, J = 4.8 Hz, 2H), 3.39 (s, 3H), 1.66 (s, 2H), 1.40 (s, 9H). |
| 159 | 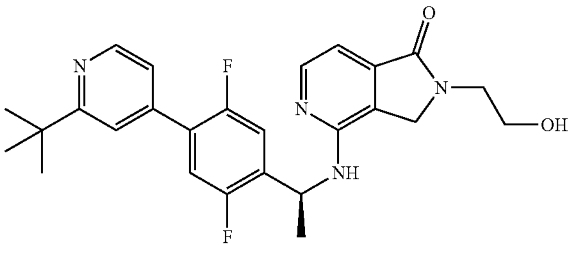 [SMILES: C[C@H](Nc1nccc2c1CN(CCO)C2=O)c1cc(F)c(-c2ccnc(C(C)(C)C)c2)cc1F] | LC-MS: (ESI) m/z: 467.2 [M + H]. $^1$H NMR (400 MHz, $CD_3OD$) δ: 8.52 (d, J = 4.8 Hz, 1H), 8.06 (d, J = 5.2 Hz, 1H), 7.59 (s, 1H), 7.40-7.37 (m, 1H), 7.34 (dd, J = 6.4, 10.8 Hz, 1H), 7.25 (dd, J = 6.4, 11.2 Hz, 1H), 6.92 (d, J = 5.2 Hz, 1H), 5.56 (q, J = 6.8 Hz, 1H), 4.72-4.51 (m, 2H), 3.88-3.81 (m, 2H), 3.80-3.70 (m, 2H), 1.61 (d, J = 7.2 Hz, 3H), 1.39 (s, 9H). $^{19}$F NMR (400 MHz, $CD_3OD$) δ: −124.655, −125.616. |

TABLE 3-continued

| Cpd No. | Compound Structure | MS/$^1$H NMR |
| --- | --- | --- |
| 160 | 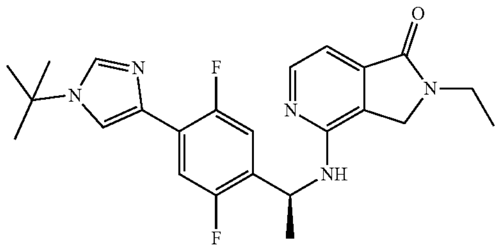 [SMILES: CCN1Cc2c(ccnc2N[C@@H](C)c2cc(F)c(-c3cn(C(C)(C)C)cn3)cc2F)C1=O] | LC-MS: (ESI) m/z: 440.1 [M + H]. $^1$H NMR (400 MHz, $CD_3OD$) δ: 8.08 (d, J = 5.2 Hz, 1H), 7.91 (br s, 1H), 7.67-7.63 (m, 2H), 7.20-7.15 (dd, J = 6.0, 11.2 Hz, 1H), 6.91 (d, J = 5.2 Hz, 1H), 5.57-5.51 (q, J = 6.8 Hz, 1H), 4.54-4.43 (m, 2H), 3.73-3.68 (q, J = 7.2 Hz, 2H), 1.63 (s, 9H), 1.61 (d, J = 7.2 Hz, 3H), 1.33 (t, J = 7.2 Hz, 3H). |
| 161 | 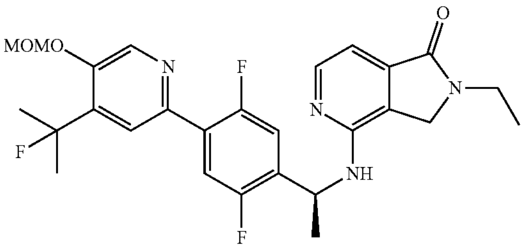 | LC-MS: (ESI) m/z: 515.3 [M + H]. $^1$H NMR (400 MHz, $CDCl_3$) δ: 8.53 (s, 1H), 8.21 (d, J = 5.2 Hz, 1H), 7.92 (d, J = 1.2 Hz, 1H), 7.66 (dd, J = 6.0, 11.2 Hz, 1H), 7.15 (dd, J = 6.0, 11.2 Hz, 1H), 7.06 (d, J = 5.2 Hz, 1H), 5.55 (quin, J = 7.2 Hz, 1H), 5.32 (s, 2H), 4.65 (br s, 1H), 4.35-4.20 (m, 2H), 3.72-3.65 (m, 2H), 3.53 (s, 3H), 1.81-1.74 (m, 6H), 1.64 (d, J = 6.8 Hz, 3H), 1.29 (t, J = 7.2 Hz, 3H). |
| 162 | 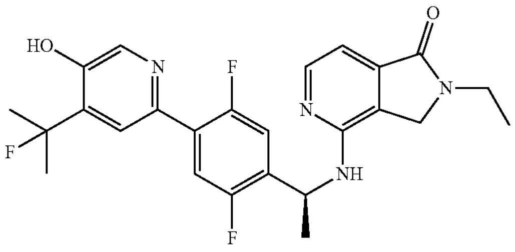 [SMILES: CCN1Cc2c(ccnc2N[C@@H](C)c2cc(F)c(-c3cc(C(C)(C)F)c(O)cn3)cc2F)C1=O] | LC-MS: (ESI) m/z: 471.2 [M + H]. $^1$H NMR (400 MHz, $CDCl_3$) δ: 8.31 (s, 1H), 8.20 (d, J = 5.2 Hz, 1H), 7.66 (dd, J = 6.4, 11.6 Hz, 1H), 7.56 (s, 1H), 7.14 (dd, J = 6.0, 11.2 Hz, 1H), 7.06 (d, J = 5.2 Hz, 1H), 5.52 (quin, J = 6.8 Hz, 1H), 4.71 (d, J = 7.6 Hz, 1H), 4.38-4.20 (m, 2H), 3.73-3.63 (m, 2H), 1.86-1.76 (m, 6H), 1.64 (d, J = 6.8 Hz, 3H), 1.30 (t, J = 7.2 Hz, 3H). |
| 163 | 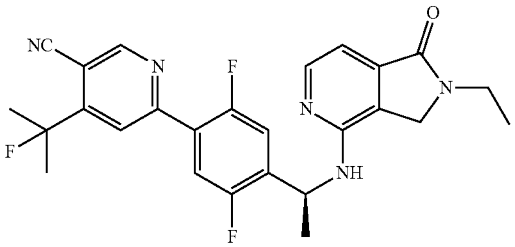 [SMILES: CCN1Cc2c(ccnc2N[C@@H](C)c2cc(F)c(-c3cc(C(C)(C)F)c(C#N)cn3)cc2F)C1=O] | LC-MS: (ESI) m/z: 480.2 [M + H]. $^1$H NMR (400 MHz, $CDCl_3$) δ: 8.93 (s, 1H), 8.19 (d, J = 5.6 Hz, 1H), 8.08 (s, 1H), 7.82 (dd, J = 6.0, 11.2 Hz, 1H), 7.21 (dd, J = 6.0, 11.2 Hz, 1H), 7.07 (d, J = 5.2 Hz, 1H), 5.56 (quin, J = 7.2 Hz, 1H), 4.57 (d, J = 7.2 Hz, 1H), 4.35-4.25 (m, 2H), 3.70 (q, J = 7.2 Hz, 2H), 1.87 (d, J = 22.8 Hz, 6H), 1.66 (d, J = 7.2 Hz, 3H), 1.30 (t, J = 7.3 Hz, 2H). |
| 164 | 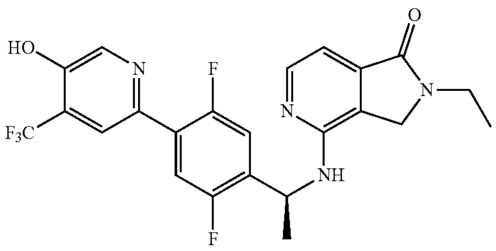 [SMILES: CCN1Cc2c(ccnc2N[C@@H](C)c2cc(F)c(-c3cc(C(F)(F)F)c(O)cn3)cc2F)C1=O] | LC-MS: (ESI) m/z: 479.1 [M + H]. $^1$H NMR (400 MHz, $CDCl_3$) δ: 8.17 (d, J = 5.2 Hz, 1H), 8.06 (s, 1H), 7.78 (s, 1H), 7.39 (dd, J = 6.4, 11.2 Hz, 1H), 7.10 (d, J = 5.2 Hz, 1H), 7.06 (dd, J = 6.0, 11.2 Hz, 1H), 5.43 (quin, J = 7.2 Hz, 1H), 4.69 (d, J = 7.6 Hz, 1H), 4.44 - 4.30 (m, 2H), 3.73 (q, J = 7.2 Hz, 2H), 1.65 (d, J = 6.8 Hz, 3H), 1.33 (t, J = 7.2 Hz, 3H). |
| 165 | 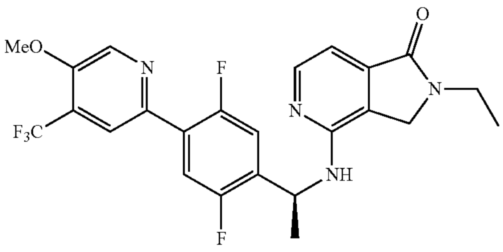 [SMILES: CCN1Cc2c(ccnc2N[C@@H](C)c2cc(F)c(-c3cc(C(F)(F)F)c(OC)cn3)cc2F)C1=O] | LC-MS: (ESI) m/z: 493.1 [M + H]. $^1$H NMR (400 MHz, $CDCl_3$) δ: 8.54 (s, 1H), 8.21 (d, J = 5.2 Hz, 1H), 7.97 (s, 1H), 7.72 (dd, J = 6.4, 11.2 Hz, 1H), 7.17 (dd, J = 6.0, 11.6 Hz, 1H), 7.06 (d, J = 5.2 Hz, 1H), 5.56 (quin, J = 7.2 Hz, 1H), 4.59 (d, J = 7.2 Hz, 1H), 4.33-4.23 (m, 2H), 4.08 (s, 3H), 3.69 (q, J = 7.2 Hz, 2H), 1.65 (d, J = 7.2 Hz, 3H), 1.30 (t, J = 7.2 Hz, 3H). |

Example 5

3-[2-[[(1S)-1-(3-fluoro-4-phenoxy-phenyl)ethyl]amino]-4-pyridyl]benzonitrile (166)

This compound was prepared according to General Scheme D. Specifically, the scheme is listed as follows.

Scheme 4

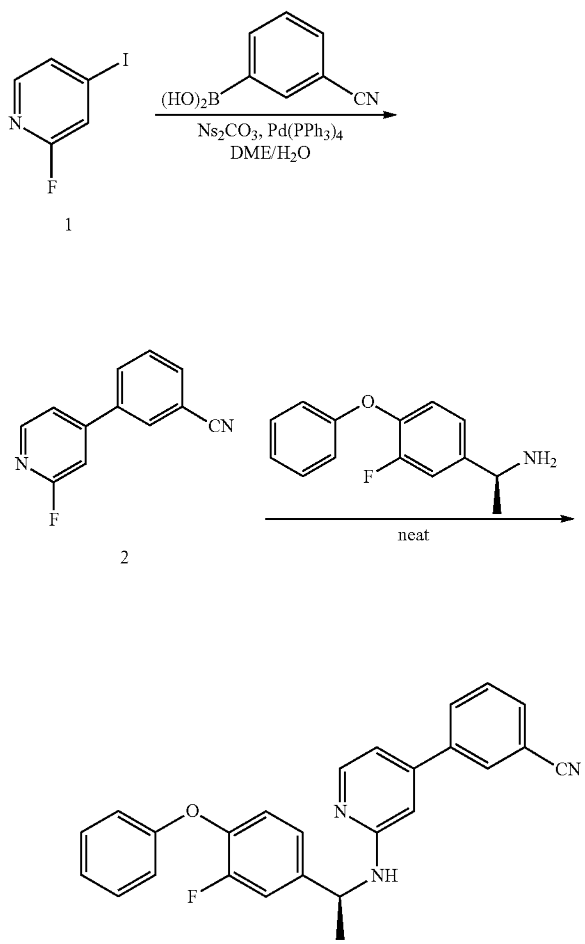

1

2

166

Step 1. 3-(2-fluoropyridin-4-yl)benzonitrile (166b)

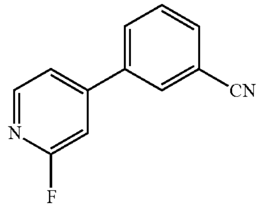 [SMILES: N#Cc1cccc(-c2ccnc(F)c2)c1]

To a solution of 2-fluoro-4-iodopyridine (166a, 1.2 g, 5.38 mmol) in 1,2-dimethoxyethane (20 mL) under nitrogen was added (3-cyanophenyl)boronic acid (166a1, 0.87 g, 5.92 mmol), $Pd(PPh_3)_4$ (186 mg, 0.16 mmol) and aqueous $Na_2CO_3$ solution (2 mol/L, 6 mL). The reaction mixture was heated at 80° C. for 12 h. The reaction mixture was diluted with ethyl acetate (100 mL) and water (30 mL). The separated aqueous layer was extracted with ethyl acetate (2×50 mL). The combined organic layers were washed with brine, dried over sodium sulfate, filtered and concentrated. The residue was diluted with ethyl acetate (10 mL) and stirred for 30 min. The solid was isolated by filtration and dried to give 3-(2-fluoropyridin-4-yl)benzonitrile (166b, 0.69 g, yield 64.0%).

$^1$H NMR (400 MHz, DMSO-$d_6$) δ: 8.41 (s, 1H), 8.37 (d, J=5.2 Hz, 1H), 8.23 (d, J=8.0 Hz, 1H), 8.00 (d, J=7.6 Hz, 1H), 7.82-7.73 (m, 2H), 7.68 (s, 1H). LC-MS: (ESI) m/z: 199.1 [M+H].

Step 2. 3-[2-[[(1S)-1-(3-fluoro-4-phenoxy-phenyl)ethyl]amino]-4-pyridyl]benzonitrile (166)

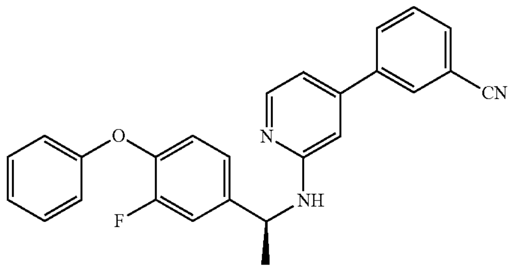 [SMILES: C[C@H](Nc1cc(-c2cccc(C#N)c2)ccn1)c1ccc(Oc2ccccc2)c(F)c1]

(S)-1-(3-fluoro-4-phenoxyphenyl)ethanamine hydrochloride (166b1, 200 mg, 0.72 mmol) was added into saturated $NaHCO_3$ solution (10 mL) and the mixture was stirred at room temperature for 30 min. Then the mixture was extracted with EtOAc for three times. The combined organic layers were washed with brine, dried over sodium sulfate, filtered and concentrated to give free base (S)-1-(3-fluoro-4-phenoxyphenyl)ethanamine, which was used in next step. The above free base (S)-1-(3-fluoro-4-phenoxyphenyl)ethanamine and 3-(2-fluoropyridin-4-yl)benzonitrile (166b, 24 mg, 0.12 mmol) was mixed and heated at 160° C. for 5 h. After cooling to room temperature, the crude product was purified by preparative TLC to give 3-[2-[[(1S)-1-(3-fluoro-4-phenoxy-phenyl)ethyl]amino]-4-pyridyl]benzonitrile (166, 22 mg, yield 44.4%).

$^1$H NMR (400 MHz, DMSO-$d_6$) δ: 8.18 (d, J=5.2 Hz, 1H), 7.76 (s, 1H), 7.69-7.54 (m, 3H), 7.33-7.24 (m, 3H), 7.14-6.95 (m, 5H), 6.77 (dd, J=5.6 Hz, 1H), 6.36 (s, 1H), 5.00-4.87 (m, 2H), 1.60 (d, J=7.6 Hz, 3H). LC-MS: (ESI) m/z: 410.1 [M+H].

Synthesis of Compounds 167 to 169

In general, the synthetic method of Compound 167 to 169 in table 4 was similar with Example 5. Data for Compounds 167 to 169 are shown herein below in Table 4.

TABLE 4

| Cpd No. | Compound Structure | MS/$^1$H NMR |
|---|---|---|
| 167 | 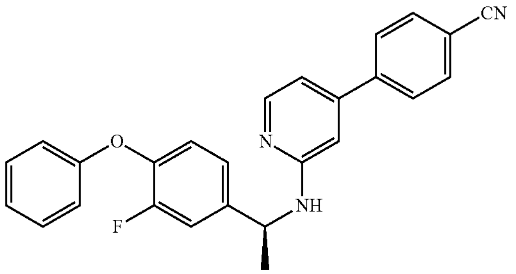 [SMILES: C[C@H](Nc1cc(-c2ccc(C#N)cc2)ccn1)c1ccc(Oc2ccccc2)c(F)c1] | $^1$H NMR (400 MHz, DMSO-$d_6$) δ: 8.18 (d, J = 5.2 Hz, 1H), 7.72 (d, J = 5.2 Hz, 2H), 7.57 (d, J = 5.6 Hz, 2H), 7.32-7.26 (m, 2H), 7.24-6.94 (m, 6H), 6.78 (d, J = 5.2 Hz, 1H), 5.02-4.85 (m, 2H), 1.60 (d, J = 7.6 Hz, 2H). |
| 168 | 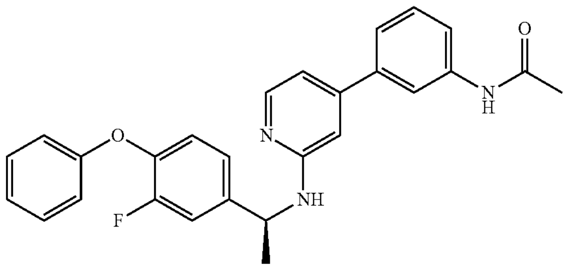 [SMILES: CC(=O)Nc1cccc(-c2ccnc(N[C@@H](C)c3ccc(Oc4ccccc4)c(F)c3)c2)c1] | $^1$H NMR (400 MHz, $CDCl_3$) δ: 8.10 (d, J = 5.2 Hz, 1H), 7.57 (d, J = 8.4 Hz, 2H), 7.45 (d, J = 8.8 Hz, 2H), 7.32-7.24 (m, 2H ), 7.25 (d, J = 8.2 Hz, 1H), 7.15 (d, J = 8.2 Hz, 1H), 7.09-6.99 (m, 2H), 6.96 (d, J = 8.0 Hz, 2H), 6.80 (d, J = 4.0 Hz, 1H), 6.43 (s, 1H), 5.12-5.14 (m, 1H), 4.88-4.85 (m, 1H), 2.20 (s, 3H), 1.59 (s, 3H). |
| 169 | 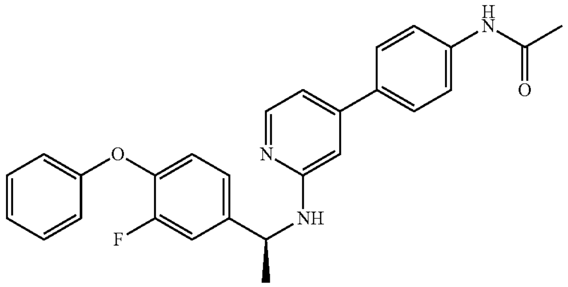 [SMILES: CC(=O)Nc1ccc(-c2ccnc(N[C@@H](C)c3ccc(Oc4ccccc4)c(F)c3)c2)cc1] | $^1$H NMR (400 MHz, $CDCl_3$) δ: 8.10 (d, J = 5.2 Hz, 1H), 7.57 (d, J = 8.4 Hz, 2H), 7.45 (d, J = 8.8 Hz, 2H), 7.32-7.24 (m, 2H), 7.25 (d, J = 8.2 Hz, 1H), 7.15 (d. J = 8.2 Hz, 1H), 7.09-6.99 (m, 2H), 6.96 (d, J = 8.0 Hz, 2H), 6.80 (dd, J = 4.0 Hz, 1H), 6.39 (s, 1H), 5.12 (m, 1H), 4.85 (m, 1H), 2.20 (s, 3H), 1.59 (d, J = 6.8 Hz, 3H). |

Example 6

4-[[(1S)-1-[2,5-difluoro-4-[2-(1-fluoro-1-methyl-ethyl)-4-pyridyl]phenyl]ethyl]amino]-2-ethyl-3H-pyrrolo[3,4-c]pyridin-1-one (102)

This compound was prepared according to Scheme 5 listed as follows.

Scheme 5

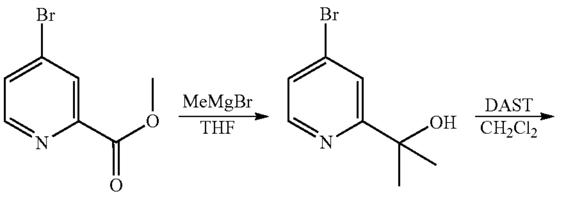

1 2

-continued

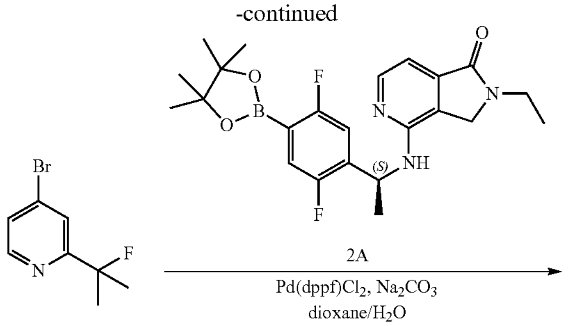

3

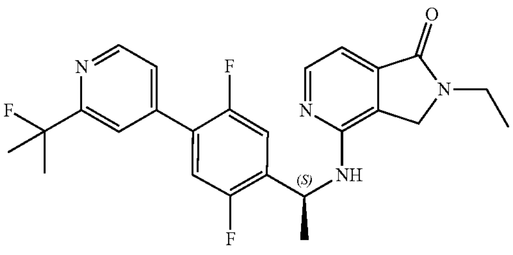

102

-continued

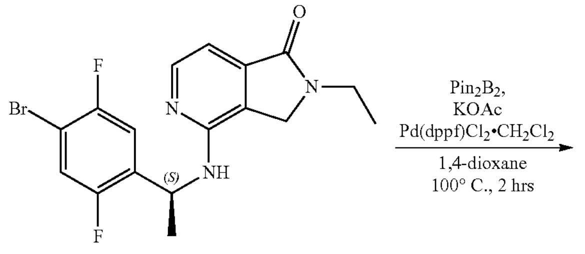

2B

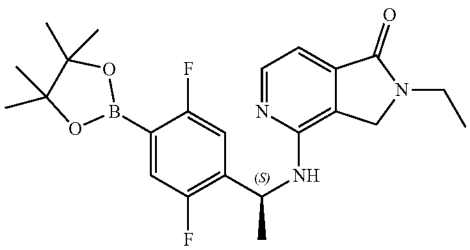

2A

Step 1. 2-(4-bromo-2-pyridyl)propan-2-ol (2)

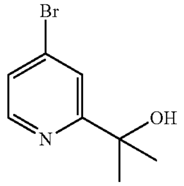

To a solution of methyl 4-bromopyridine-2-carboxylate (1, 5 g, 23.14 mmol, 1 eq.) in THF (100 mL) was added MeMgBr (3 M, 16.20 mL, 2.1 eq.) dropwise at 0-4° C. under $N_2$. Then the mixture was stirred at 20-25° C. for 0.5 hr. TLC (PE/EA=3/1, $R_f$=0.6) showed the reaction was completed. The mixture was cooled to 0-4° C. and quenched with saturated $NH_4Cl$ solution (30 mL) slowly. The mixture was diluted with water (50 mL), extracted with EtOAc (50 mL×2), washed with brine (100 mL), dried over $Na_2SO_4$, filtered, concentrated. The residue was purified by column chromatography ($SiO_2$, Petroleum ether/Ethyl acetate=95/5 to 85/15). 2-(4-bromo-2-pyridyl)propan-2-ol (2, 2.5 g, 49.99% yield) was obtained as light yellow liquid.

$^1$H NMR (400 MHz, $CDCl_3$) δ: 8.36 (d, J=5.2 Hz, 1H), 7.60-7.59 (dd, J=0.4, 2.0 Hz, 1H), 7.40-7.38 (dd, J=2.0, 5.2 Hz, 1H), 4.57 (s, 1H), 1.56 (s, 9H).

Step 2. 4-bromo-2-(1-fluoro-1-methyl-ethyl)pyridine (3)

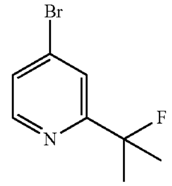

To a solution of 2-(4-bromo-2-pyridyl)propan-2-ol (2, 1 g, 4.63 mmol, 1 eq.) in DCM (30 mL) was added DAST (1.12 g, 6.94 mmol, N/A, 1.5 eq.) dropwise at 0-4° C. Then the mixture was stirred at 0-4° C. for 1.5 hr. TLC (PE/EA=3/1, $R_f$=0.8) showed the reaction was completed. The mixture was poured into saturated $NaHCO_3$ solution (100 mL), extracted with DCM (30 mL×2), washed with brine (50 mL), dried over $Na_2SO_4$, filtered, concentrated. The residue was purified by column chromatography ($SiO_2$, Petroleum ether/Ethyl acetate=98/2) (LCMS: ES9778-173-PiMA). 4-bromo-2-(1-fluoro-1-methyl-ethyl)pyridine (3, 700 mg, 69.36% yield) was obtained as yellow liquid.

$^1$H NMR (400 MHz, $CDCl_3$) δ: 8.36 (d, J=5.2 Hz, 1H), 7.75 (t, J=1.2 Hz, 1H), 7.38-7.36 (dd, J=2.0, 5.2 Hz, 1H), 1.70 (d, J=22.0 Hz, 6H). LC-MS: (ESI) m/z: 218.1 $[M+H]^+$, $t_R$=0.809 min.

Step 3. 4-[[(1S)-1-[2,5-difluoro-4-(4,4,5,5-tetramethyl-1,3,2-dioxaborolan-2-yl)phenyl]ethyl]amino]-2-ethyl-3H-pyrrolo[3,4-c]pyridin-1-one (2A)

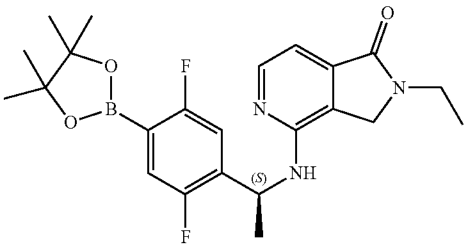

A mixture of 4-[[(1S)-1-(4-bromo-2,5-difluoro-phenyl)ethyl]amino]-2-ethyl-3H-pyrrolo[3,4-c]pyridin-1-one (2B, 2 g, 5.05 mmol, 1 eq.), 4,4,5,5-tetramethyl-2-(4,4,5,5-tetramethyl-1,3,2-dioxaborolan-2-yl)-1,3,2-dioxaborolane (3.20 g, 12.62 mmol, 2.5 eq.), $Pd(dppf)Cl_2 \cdot CH_2Cl_2$ (412.20 mg, 504.76 umol, 0.1 eq.) and KOAc (990.76 mg, 10.10 mmol, 2 eq.) in 1,4-dioxane (50 mL) was stirred at 100° C. for 2 hours under $N_2$. LCMS (ES9799-190-P1A) showed 4-[[(1S)-1-(4-bromo-2,5-difluoro-phenyl)ethyl]amino]-2-ethyl-3H-pyrrolo[3,4-c]pyridin-1-one was consumed completely and one main peak with desired MS detected. TLC (PE/EtOAc=1/1) showed no new spot detected. The solvent was removed to give a crude product under the reduced pressure. The crude product was purified by silica gel column (PE/EtOAc=1/1) to give 4-[[(1S)-1-[2,5-difluoro-4-(4,4,5,5-tetramethyl-1,3,2-dioxaborolan-2-yl)phenyl]ethyl]amino]-2-ethyl-3H-pyrrolo[3,4-c]pyridin-1-one (2A, 2.2 g, crude) as yellow oil, which was confirmed by LCMS. LC-MS: (ESI) m/z: 444.2 $[M+H]^+$, $t_R$=0.817 min.

Step 4. 4-[[(1S)-1-[2,5-difluoro-4-[2-(1-fluoro-1-methyl-ethyl)-4-pyridyl]phenyl]ethyl]amino]-2-ethyl-3H-pyrrolo[3,4-c]pyridin-1-one (102)

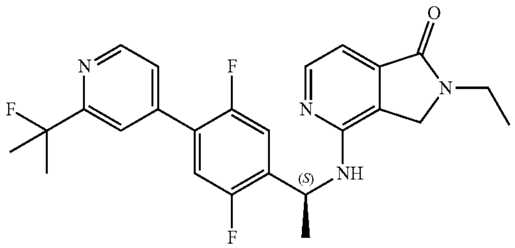

A mixture of 4-[[(1S)-1-[2,5-difluoro-4-(4,4,5,5-tetramethyl-1,3,2-dioxaborolan-2-yl)phenyl]ethyl]amino]-2-ethyl-3H-pyrrolo[3,4-c]pyridin-1-one (2A, 200 mg, 451.17 umol, 1 eq.), 4-bromo-2-(1-fluoro-1-methyl-ethyl)pyridine (3, 130 mg, 596.15 umol, 1.32 eq.), $Pd(dppf)Cl_2 \cdot CH_2Cl_2$ (37 mg, 45.31 umol, 0.1 eq.), $Na_2CO_3$ (100 mg, 943.49 umol, 2.09 eq.) in dioxane (6 mL) and $H_2O$ (2 mL) as degassed and purged with $N_2$ for 3 times, and then the mixture was stirred at 90° C. for 1 hr under $N_2$ atmosphere. LCMS (ES9778-175-P1LA) showed the reaction was completed. The mixture was cooled and filtered via Celite. The Celite was washed with EtOAc (50 mL×2). The filtrate was concentrated. The residue was purified by prep-HPLC (column: DuraShell 150×25 mm×5 m; mobile phase: [water (0.05% ammonia hydroxide v/v)-ACN]; B %: 46-66%, 10 min). 4-[[(1S)-1-[2,5-difluoro-4-[2-(1-fluoro-1-methyl-ethyl)-4-pyridyl]phenyl]ethyl]amino]-2-ethyl-3H-pyrrolo[3,4-c]pyridin-1-one (102, 65.9 mg, 32.14% yield, 100% purity) was obtained as light yellow solid.

LC-MS: (ESI) m/z: 455.1 $[M+H]^+$, $t_R$=3.687 min. $^1H$ NMR (400 MHz, MeOD) δ: 8.53 (d, J=5.2 Hz, 1H), 8.03 (d, J=5.2 Hz, 1H), 7.69 (s, 1H), 7.44-7.42 (m, 1H), 7.33-7.24 (m, 2H), 6.87 (d, J=5.2 Hz, 1H), 5.57-5.52 (q, J=6.8 Hz, 1H), 4.52-4.41 (m, 2H), 3.70-3.64 (q, J=7.2 Hz, 2H), 1.68 (d, J=22 Hz, 6H), 1.60 (d, J=7.2 Hz, 3H), 1.30 (t, J=7.2 Hz, 3H).

Biological Assay

Test 1: Purification of Wild-Type and Mutant IDH Proteins

Purification of IDH1 and IDH2 Proteins

The present disclosure provides the method for expression and purification of mutant and wild-type recombinant IDH1 and IDH2 proteins in *E. coli.* pSJ3 plasmids containing cDNA sequences coding for full length wild-type or mutant IDH1 proteins (IDH1-R132H or IDH1-R132C), partial IDH2 proteins with the first N-terminal 40 amino acid residues deleted, wild type or mutant (IDH2-R140Q or IDH2-R172K) are transformed into BL21 strains and IDH proteins are expressed at 16° C. overnight with the presence of 0.5 mM IPTG. By using the six tandem histidine tag fused to the expressed proteins, IDH proteins are purified via Ni Sepharose 4B (purchased from GE Lifescience) as described in the user manual. Eluted proteins are concentrated into TBS buffer by using Amicon 3,000 Da MWCO filter unit and the final protein products are stored at −80° C. in TBS solution containing 10% glycerol. The quantification of protein concentration is done by Bradford kit from Shanghai Sangon.

Test 2: Biochemical Assay for IDH Inhibition and Selectivity of the Compounds

The present disclosure provides a biochemical assay method for detecting the IDH inhibition and selectivity of the compounds by detecting IDH enzyme activity directly.

FIG. 1 shows reactions catalyzed by wild-type and mutant IDH1/2. Wild-type IDH enzymes convert $NADP^+$ to NADPH when catalyzing the α-KG producing reaction. Mutant IDH enzymes convert NADPH to $NADP^+$ when catalyzing the D-2-HG producing reaction. So, the activity of wild-type and mutant IDH1/2 could be measured by monitoring NADPH level change as NADPH is fluorescent (Excitation 340 nm, Emission 460 nm). By monitoring the change of NADPH level in the reaction, the enzyme activity could be determined rapidly and efficiently and $IC_{50}$ of a compound could also be assayed.

The test compounds are prepared into 50 mM stock solutions in DMSO and stored at −20° C. Each test compound stock is further diluted to obtain a 100× stock solution at a concentration of 400 μM, 200 μM, 100 μM, 50 μM, 25 μM, 12.5 μM, 6.25 μM and 3.125 μM, respectively, for the final use on the day of test (the concentration range of 100× stock solutions might be adjusted to cover the estimated $IC_{50}$ of a specific test compound).

Inhibition of wild-type IDH1:

To establish isocitrate to α-KG reaction catalyzed by wild-type IDH1 protein, purified wild-type IDH1 protein is first diluted into 2.7 nM in 20 mM Tris-HCl pH7.5, 150 mM NaCl, 10 mM $MgCl_2$, 1 mM DTT, 0.05 mg/ml BSA and 107 μM isocitrate. 148 μL 2.7 nM wild-type IDH1 protein solution is mixed with 2 μL DMSO (vehicle control for test compounds) or an above-mentioned 100× stock solution of a test compound and incubated for 1 hour at room temperature. Extra reactions containing 148 μL no-enzyme solution (20 mM Tris-HCl pH7.5, 150 mM NaCl, 10 mM $MgCl_2$, 1 mM DTT, 0.05 mg/ml BSA and 107 μM isocitrate) and 2 μL DMSO are also set up as background controls. Then each reaction is initiated by adding 50 μL 200 μM NADP+ solution prepared in 20 mM Tris-HCl pH7.5, 150 mM NaCl, 10 mM $MgCl_2$, 1 mM DTT and 0.05 mg/ml BSA. BioTek Synergy H1 Microplate reader (BioTek Instruments Inc., Winooski, U.S.) is employed to monitor the NADPH fluorescence (Excitation 340 nm, Emission 460 nm) every 42 seconds for 15 minutes. NADPH change rate is determined according to the linear phase of the fluorescence-time curve and results from the background control reactions are used as background subtraction to calculate the net NADPH change rates of other reactions. The net NADPH change rates from the vehicle control reactions are used as 100% enzymatic activity and thus the relative enzymatic activity of reactions with test compounds added could be determined. Then a dose-response curve is drawn for each test compound and the corresponding $IC_{50}$ is calculated. The $IC_{50}$ value is used to evaluate the inhibition and selectivity of each test compound on the IDH enzymatic activity.

Inhibition of Mutant IDH1 (R132H or R132C):

To assay the enzymatic activity of mutant IDH1 proteins, 25 nM IDH1-R132C or 50 nM IDH1-R132H protein solutions are prepared in 20 mM Tris-HCl pH7.5, 150 mM NaCl, 10 mM $MgCl_2$, 1 mM DTT, 0.05 mg/ml BSA and 1.33 mM α-KG. 148 μL 25 nM IDH1-R132C or 50 nM IDH1-R132H protein solutions are mixed with 2 μL DMSO (vehicle control for test compounds) or an above-mentioned 100× stock solution of a test compound and incubated for 1 hour at room temperature. Extra reactions containing 148 μL no-enzyme solution (20 mM Tris-HCl pH7.5, 150 mM NaCl, 10 mM $MgCl_2$, 1 mM DTT, 0.05 mg/ml BSA and 1.33 mM α-KG) and 2 μL DMSO are also set up as background controls. Then each reaction is initiated by adding 50 μL 80

μM NADPH solution prepared in 20 mM Tris-HCl pH7.5, 150 mM NaCl, 10 mM $MgCl_2$, 1 mM DTT and 0.05 mg/ml BSA. BioTek Synergy H1 Microplate reader (BioTek Instruments Inc., Winooski, U.S.) is employed to monitor the NADPH fluorescence (Excitation 340 nm, Emission 460 nm) every 42 seconds for 15 minutes. NADPH change rate is determined according to the linear phase of the fluorescence-time curve and results from the background control reactions are used as background subtraction to calculate the net NADPH change rates of other reactions. The net NADPH change rates from the vehicle control reactions are used as 100% enzymatic activity and thus the relative enzymatic activity of reactions with test compounds added could be determined. Then a dose-response curve is drawn for each test compound and the corresponding $IC_{50}$ is calculated. The $IC_{50}$ value is used to evaluate the inhibition and selectivity of each test compound on the IDH enzymatic activity.

Test 3: Cell-Based Assay for IDH Inhibition and Selectivity of the Compounds

The present disclosure also provides a cell-based method for assaying IDH inhibition and selectivity of the compounds in human fibrosarcoma cell line HT1080 and cholangiocarcinoma cell line HCCC 9810, which harbor endogenous heterozygous IDH1 R132C and R132H mutation respectively and accumulate D-2-HG. Tumor -derived IDH mutant lost its normal activity of producing α-KG, and gained a new activity of producing D-2-HG. D-2-HG is a metabolite specifically elevated in tumor cells expressing mutant IDH1 or IDH2 proteins. When treating such mutant IDH-expressing tumor cells with an effective IDH inhibitor, the synthesis of D-2-HG is blocked, and D-2-HG concentration is decreased by the oxidation reaction catalyzed by the endogenous D-2-HG dehydrogenase. Hence, the IDH inhibition activity and selectivity of the compounds of present disclosure could be assayed by the decrease of D-2-HG in cell metabolite.

To perform a cell-based IDH inhibition assay, HT1080 and HCCC 9810 cells (or other cell lines harboring different IDH mutations) are cultured in DMEM supplemented with 10% FBS. The cells are treated with compounds of present disclosure at various different concentrations. 16 hours after the treatment, culture medium supernatants are removed and cell metabolites are extracted by 40% methanol and 40% acetonitrile in water (pre-chilled under −80° C.) at 4° C. for 1 hour. The extract supernatants are collected and cell debris are removed via high speed centrifugation. The resulting metabolite extracts are analyzed on an Agilent LC-MS system (model: 1290-6470) for 2-HG and glutamate concentration. A HILIC-Z column (2.1 mm×100 mm, 2.7 m) is employed on HPLC. Mobile phase A is 15 mM $CH_3COONH_4$ and 0.3% $NH_3{\cdot}H_2O$ in water. Mobile phase B is 15 mM $CH_3COONH_4$ and 0.3% $NH_3{\cdot}H_2O$ in 90% MeCN/10% $H_2O$ solvent. An 19% solvent A and 81% solvent B isocratic gradient method is used at a flow rate of 0.3 ml/min. D-2-HG is ionized under negative ion spray mode and detected through the multiple-reaction monitoring of a mass transition pair at m/z=147.0/128.9 and 147.0/85.1. Glutamate is ionized under ion spray mode and detected on negative polarity multiple-reaction monitoring of a mass transition pair at m/z=146/102 and 146/128 and its level is used to normalize 2-HG concentration. The activity of cellular mutant IDH proteins in the presence of each test compound at different concentrations can be represented by relative D-2-HG concentration to negative control samples (i.e., cells are treated with DMSO only), and the $IC_{50}$ value could be determined to evaluate the inhibition and selectivity of each test compound on the IDH enzymatic activity.

Test 4: Metabolic Stability Assay in Liver Microsomes

The liver microsomes of mouse, rat (from Xenotech), dog, monkey and human (from Corning Inc.) are used to test the in vitro metabolic stability of compounds. All liver microsomes are stored at −60° C. prior to use. Testosterone, diclofenac and propafenone are used as controls.

Each of the test compounds or control compounds is co-incubated with 0.5 $mg{\cdot}mL^{-1}$ mouse, rat, dog, monkey or human liver microsomes in PBS (100 mM, pH 7.4) with 3 mM $MgCl_2$ in a 37° C. water bath at a pre-set initial concentration of 1 μM. Reactions are initiated by adding NADPH to a final concentration of 1 mM. The final volume of each reaction mixture is 0.2 ml, and all reactions are performed in duplicate. At each set time point (0, 5, 15, 30 and 60 min), a small aliquot (e.g., 20 l) is transferred from the reaction system into ice-cold internal standard (1S) containing acetonitrile to quench the reaction and to precipitate the protein. After vortexing and centrifugation at 3700 rpm for 10 min, the supernatant is injected into LC-MS/MS for analysis.

In vitro microsomal clearance is estimated based on determination of elimination half-life ($T_{1/2}$) of each compound disappearance from its initial concentration. Peak area ratios of each compound (test or control) to 1S is calculated. Ln (% Control) versus incubation Time (min) curve is plotted, and the slope of a linear fitting line is calculated. Drug elimination rate constant k ($min^{-1}$), $T_{1/2}$ (min), and in vitro intrinsic clearance $CL_{int}$($mL{\cdot}min^{-1}{\cdot}mg^{-1}$ proteins) is calculated according to the following equations:

$$k=-\text{slope}$$

$$T_{1/2}=0.693/k$$

$$CL_{in}t=k/C_{protein}$$

where $C_{protein}$ ($mg{\cdot}mL^{-1}$) is the microsomal protein concentration in the incubation system.

Test 5: In Vivo Pharmacokinetics Assay

The pharmacokinetic properties of the compounds of the present disclosure can be assessed in ICR mice (male, 6-8 weeks, 20.0-25.3 g) via p.o. or i.v. administration.

The ICR mice are purchased from Vital River Laboratory Technology Co., Ltd. (Beijing, China), housed in solid bottom polypropylene cages with sterilized bedding, kept in a room with 40% to 70% humidity, 20 to 25° C., 10 to 20 air changes/hour, and on a 12-hour light/dark cycle except when interruptions are necessitated by study activities. The mice are fed with sterilized diet from Shanghai SLAC Laboratory Animal Co., Ltd. (Shanghai, China) and sterilized water. All animals are examined upon receipt and are acclimated for at least 3 days. Only the ones that appear to be healthy are selected for the study basing on overall health, body weight, or other relevant data as appropriate. Individual animal in each group is identified by ear notch.

The mice are fasted overnight prior to dosing, but have free access to drinking water all the time. Before dosing, each mouse is weighed and the actual dose volume for each mouse is calculated by using the formula below:

$$\text{Dose Volume (mL)}[\text{Nominal Dose } (mg{\cdot}kg^{-1})\text{Dose Concentration } (mg{\cdot}mL^{-1})]\times\text{Animal Body Weight (kg)}$$

The actual body weights and the actual dose volumes are recorded accordingly.

For each test group, nine mice are used, and mice in different groups are given a single p.o dose of the test compound at 10 mg·kg$^{-1}$, or a single i.v. dose of 2 mg·kg$^{-1}$ respectively. Blood samples are sampled and collected into EDTA-$K_2$ containing tubes at pre-determined time points, for example, pre-dose or 5 min, 15 min, 30 min, 1 h, 2 h, 4 h, 8 h, 12 h, and 24 h post-dose. Each mouse is collected for blood sample at three discontinuous time point, and three mice are used for sampling at each time point. The collected samples are centrifuged at 5500 rpm for 10 min to obtain plasma samples, which are later analyzed by LC-MS/MS. Data of drug concentration in plasma vs. time are processed by linear regression analysis. All pharmacokinetic parameters are calculated using non-compartment model of WinNonlin 8.0.

Test 6: Inhibition of Anchorage Independent Growth of IDH Mutant Cells

It is well established that anchorage-independent cell growth is a fundamental property of cancer cells. The ability of anchorage independent growth tightly correlates with tumorigenic and metastatic potentials of tumor cells in vivo.

Previous work has shown that deletion of the mutant IDH1 in HT1080 cells (harboring endogenous IDH1-R132C mutation) has little effect on cell proliferation under normal culture condition, but strongly inhibits the anchorage independent growth of the HT1080 cells ["D-2-hydroxyglutarate is essential for maintaining oncogenic property of mutant IDH-containing cancer cells but dispensable for cell growth", Ma, S., et al., Oncotarget, (2015)]. As IDH1 mutants promote tumorigenesis via 2-HG, anchorage independent growth (formation of cell colonies in soft agar) can be also used as a convenient and valuable in vitro assay for measuring the activity of compounds in tumor inhibition.

Tumor cell lines harboring endogenous IDH1-R132X mutations such as HT1080 (containing IDH1-R132C mutation) or HCCC9810 (containing IDH1-R132H mutation) cells are seeded in 0.35% agar (the top agar layer) in proper culture medium (e.g, DMEM with 10% FBS for HT1080 cells or HCCC9810 cells) with the test compound or DMSO on top of a layer of 0.65% agar (the bottom agar layer) in proper culture medium (e.g, DMEM with 10% FBS for HT1080 cells or HCCC9810 cells). Above the top agar layer, proper medium (e.g, DMEM with 10% FBS for HT1080 cells or HCCC9810 cells) with the test compound or DMSO is added to keep the moisture of the agar layer. The final concentration of the test compound in the top agar layer or the medium above is usually higher than the $IC_{50}$ value tested in HT1080 cells. Cells in the agar will be cultured for about 4 weeks and the medium with the test compound or DMSO above the top agar layer is changed every week. At the end of the experiment, the soft agar plates are stained with crystal violet and cell colonies are imaged under microscope for quantification. The difference of colony numbers between plates with the test compound and the DMSO reflects the inhibitory effect of the test compound on anchorage independent growth of IDH mutant cells.

Test 7: Inhibition of IDH Mutant in Tumors from HT1080 Xenograft-Bearding Mice

To test the inhibitory effect of the test compound on IDH mutant in tumors, HT1080 cells are first innoculated subcutaneously in BALB/c nude mice (five million HT1080 cells per mouse). When the HT1080 tumor volume reaches about 200 mm$^3$, mice are grouped by random and each group of mice receive the test compound orally. At different time points such as pre-dose or 2 hours, 4 hours, 8 hours, 12 hours and 24 hours post dose, a group of mice are sacrificed for blood and HT1080 tumor tissue. After homogenization and extraction, 2-HG level in tumor tissue is determined by LC-MS/MS and the inhibition ratio of the test compound on IDH1-R132C mutant activity producing 2-HG in HT 1080 tumor at different time points post dose is calculated.

WORKING EXAMPLES

Example 1: Compounds Inhibit the Activity of IDH R132H and IDH1 R132C

The IDH inhibition activity of the compounds were assessed according to Test 2 of the Biological Assay section. The test for mutant IDH1 R132H and IDH1 R132C inhibition of each compound was carried out in triplet. The $IC_{50}$ values of representative compounds to IDH1 R132H and IDH1 R132C are shown in Table 5. As used in Table 5, "A" refers to an inhibitory activity against IDH1 R132H or IDH1 R132C with an $IC_{50}$<0.1 μM; "B" refers to an inhibitory activity against IDH1 R132H or IDH1 R132C with an $IC_{50}$ from 0.1 μM to 0.5 μM; "C" refers to an inhibitory activity against IDH1 R132H or IDH1 R132C with an $IC_{50}$ from 0.5 μM to 1 μM; "D" refers to an inhibitory activity against IDH1 R132H or IDH1 R132C with an $IC_{50}$>1 μM.

TABLE 5

IDH1 inhibitory activities of representative compounds of Formula (I)

| Cpd No. | IDH1 R132H $IC_{50}$ (μM) | IDH1 R132C $IC_{50}$ (μM) |
|---|---|---|
| 1 | B | B |
| 2 | B | B |
| 3 | B | B |
| 4 | D | D |
| 5 | C | C |
| 6 | C | D |
| 7 | B | D |
| 8 | D | D |
| 9 | B | B |
| 10 | C | D |
| 11 | B | B |
| 12 | D | D |
| 13 | D | D |
| 14 | D | D |
| 15 | B | C |
| 16 | C | C |
| 17 | B | B |
| 18 | B | D |
| 19 | D | D |
| 20 | B | B |
| 21 | A | B |
| 22 | A | A |
| 23 | A | A |
| 24 | A | A |
| 25 | B | B |
| 26 | D | D |
| 27 | D | D |
| 28 | D | D |
| 29 | B | C |
| 30 | C | D |
| 31 | D | D |
| 32 | D | D |
| 33 | C | D |
| 34 | D | D |
| 35 | D | D |
| 36 | D | D |
| 37 | B | B |
| 38 | A | B |
| 39 | B | D |
| 40 | A | B |
| 41 | B | C |
| 42 | A | B |
| 43 | A | A |
| 44 | D | D |
| 45 | D | D |
| 46 | D | D |
| 47 | D | D |

TABLE 5-continued

| IDH1 inhibitory activities of representative compounds of Formula (I) | | |
|---|---|---|
| Cpd No. | IDH1 R132H $IC_{50}$ (μM) | IDH1 R132C $IC_{50}$ (μM) |
| 48 | D | D |
| 49 | D | D |
| 50 | D | D |
| 51 | B | B |
| 52 | B | B |
| 53 | D | D |
| 54 | D | D |
| 55 | D | D |
| 56 | D | D |
| 57 | D | D |
| 58 | D | D |
| 59 | D | D |
| 60 | D | D |
| 61 | D | D |
| 62 | D | D |
| 63 | D | D |
| 64 | B | D |
| 65 | D | D |
| 66 | B | D |
| 67 | D | D |
| 68 | C | D |
| 69 | D | D |
| 70 | D | D |
| 71 | A | A |
| 72 | B | C |
| 73 | B | D |
| 74 | D | D |
| 75 | D | D |
| 76 | D | D |
| 77 | B | B |
| 78 | D | D |
| 79 | B | B |
| 80 | D | D |
| 81 | B | C |
| 82 | D | D |
| 83 | D | D |
| 84 | B | D |
| 85 | D | D |
| 86 | D | D |
| 87 | A | A |
| 88 | C | D |
| 89 | A | B |
| 90 | B | D |
| 91 | B | C |
| 92 | D | D |
| 93 | D | D |
| 94 | D | D |
| 95 | D | D |
| 96 | B | C |
| 97 | B | C |
| 98 | C | D |
| 99 | D | D |
| 100 | B | C |
| 101 | A | B |
| 102 | A | B |
| 103 | D | D |
| 104 | A | A |
| 105 | A | A |
| 106 | B | B |
| 107 | A | A |
| 108 | A | A |
| 109 | A | A |
| 110 | A | A |
| 111 | A | B |
| 112 | A | A |
| 113 | A | A |
| 114 | D | D |
| 115 | A | B |
| 116 | A | A |
| 117 | A | A |
| 118 | A | A |
| 119 | A | A |
| 120 | A | A |
| 121 | A | B |
| 122 | A | A |

TABLE 5-continued

| IDH1 inhibitory activities of representative compounds of Formula (I) | | |
|---|---|---|
| Cpd No. | IDH1 R132H $IC_{50}$ (μM) | IDH1 R132C $IC_{50}$ (μM) |
| 123 | A | A |
| 124 | A | A |
| 125 | A | A |
| 126 | A | B |
| 127 | A | A |
| 128 | A | B |
| 129 | A | A |
| 130 | A | B |
| 131 | A | A |
| 132 | A | A |
| 133 | A | A |
| 134 | A | A |
| 135 | A | A |
| 136 | A | A |
| 137 | A | A |
| 138 | A | A |
| 139 | A | B |
| 141 | A | A |
| 142 | A | B |
| 143 | A | B |
| 144 | D | D |
| 145 | A | A |
| 146 | A | A |
| 147 | A | A |
| 148 | A | A |
| 149 | A | B |
| 150 | A | A |
| 151 | A | B |
| 152 | A | A |
| 153 | A | A |
| 154 | B | C |
| 155 | A | B |
| 156 | B | C |
| 157 | B | D |
| 158 | B | D |
| 159 | B | B |
| 160 | B | B |
| 161 | A | A |
| 162 | B | B |
| 163 | A | B |
| 164 | B | C |
| 165 | A | A |

From Table 5, it shows that the compounds of the present disclosure demonstrate good inhibition against mutant IDH1.

Example 2: Compounds Inhibit the Activity of IDH in Cell-Based Assay

The IDH inhibition activity of the compounds were assessed in human fibrosarcoma cell line HIT1080 according to Test 3 of the Biological Assay section. The test for IDH inhibition of each compound was carried out in triplet. The $IC_{50}$ values of representative compounds to IDH are shown in Table 6. As used in Table 6, "A" refers to an IDH inhibitory activity with an $IC_{50}$<0.1 μM; "B" refers to an IDH inhibitory activity with an $IC_{50}$ from 0.1 μM to 0.5 μM; "C" refers to an IDH inhibitory activity with an $IC_{50}$ from 0.5 μM to 1 μM; "D" refers to an IDH inhibitory activity with an $IC_{50}$>1 μM.

TABLE 6

IDH inhibitory activities of representative compounds of Formula (I) in cell-based assay

| Cpd No. | $IC_{50}$ in HT1080 cell |
|---|---|
| 1 | C |
| 2 | C |
| 3 | C |
| 4 | D |
| 5 | D |
| 6 | D |
| 7 | C |
| 8 | D |
| 9 | B |
| 10 | D |
| 11 | D |
| 12 | D |
| 13 | D |
| 14 | D |
| 15 | D |
| 16 | D |
| 17 | D |
| 18 | D |
| 19 | D |
| 20 | C |
| 21 | D |
| 22 | A |
| 23 | A |
| 24 | A |
| 25 | C |
| 26 | D |
| 27 | D |
| 28 | D |
| 29 | D |
| 30 | D |
| 31 | D |
| 32 | D |
| 33 | D |
| 34 | D |
| 35 | D |
| 36 | D |
| 37 | C |
| 38 | C |
| 39 | D |
| 40 | B |
| 41 | D |
| 42 | B |
| 43 | B |
| 44 | C |
| 45 | D |
| 46 | D |
| 47 | D |
| 48 | D |
| 49 | D |
| 50 | D |
| 51 | D |
| 52 | D |
| 53 | B |
| 53 | D |
| 54 | D |
| 55 | D |
| 56 | D |
| 57 | D |
| 58 | D |
| 59 | D |
| 60 | D |
| 61 | D |
| 62 | D |
| 63 | D |
| 64 | D |
| 65 | B |
| 66 | C |
| 67 | B |
| 68 | D |
| 69 | C |
| 70 | D |
| 71 | B |
| 72 | D |
| 73 | D |
| 74 | D |

TABLE 6-continued

IDH inhibitory activities of representative compounds of Formula (I) in cell-based assay

| Cpd No. | $IC_{50}$ in HT1080 cell |
|---|---|
| 75 | D |
| 76 | D |
| 77 | C |
| 78 | C |
| 79 | C |
| 80 | D |
| 81 | D |
| 82 | D |
| 83 | D |
| 84 | D |
| 85 | D |
| 86 | D |
| 87 | A |
| 88 | D |
| 89 | B |
| 90 | C |
| 91 | B |
| 92 | B |
| 93 | D |
| 94 | D |
| 95 | C |
| 96 | B |
| 97 | B |
| 98 | B |
| 99 | C |
| 100 | B |
| 101 | B |
| 102 | B |
| 103 | D |
| 104 | A |
| 105 | A |
| 106 | B |
| 107 | B |
| 108 | A |
| 109 | A |
| 110 | A |
| 111 | B |
| 112 | A |
| 113 | A |
| 114 | C |
| 115 | B |
| 116 | A |
| 117 | A |
| 118 | A |
| 119 | A |
| 120 | A |
| 121 | C |
| 122 | B |
| 123 | B |
| 124 | A |
| 125 | A |
| 126 | B |
| 127 | A |
| 128 | B |
| 129 | A |
| 130 | B |
| 131 | A |
| 132 | B |
| 133 | A |
| 134 | A |
| 135 | A |
| 136 | A |
| 137 | A |
| 138 | A |
| 139 | A |
| 141 | A |
| 142 | B |
| 143 | B |
| 144 | D |
| 145 | B |
| 146 | A |
| 147 | A |
| 148 | A |
| 149 | B |
| 150 | A |

TABLE 6-continued

| IDH inhibitory activities of representative compounds of Formula (I) in cell-based assay | |
|---|---|
| Cpd No. | $IC_{50}$ in HT1080 cell |
| 151 | A |
| 152 | A |
| 153 | A |
| 154 | B |
| 155 | B |
| 156 | B |
| 157 | D |
| 158 | D |
| 159 | B |
| 160 | B |
| 161 | A |
| 162 | B |
| 163 | A |
| 164 | C |
| 165 | A |

As shown in Table 6, the compounds of the present disclosure also demonstrate good inhibition against mutant IDH1 in cell-based assay.

The foregoing description is considered as illustrative only of the principles of the present disclosure. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise", "comprising", "include", "including", and "includes" when used in this specification and in the following claims are intended to specify the presence of stated features, integers, components, or steps, but they do not preclude the presence or addition of one or more other features, integers, components, steps, or groups thereof.

What is claimed is:

1. A compound of Formula (Ie):

Formula (Ie)

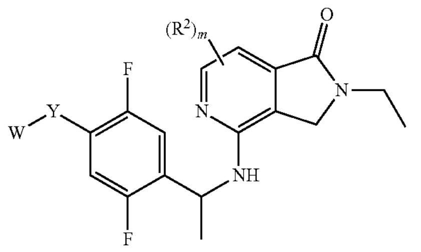

or a pharmaceutically acceptable salt thereof, wherein,

Y is selected from a group consisting of null, a bond, —$CR^5R^6$—, —$O(CH_2)_n$—, —$N(R^a)$—, —S—, —S(═O)—, —S(═O)$_2$—, —C(O)—, and —C(O)N($R^b$)—;

W is selected from a group consisting of null, saturated or partially unsaturated cycloalkyl, saturated or partially unsaturated heterocyclyl, aryl, and heteroaryl, wherein said saturated or partially unsaturated cycloalkyl, saturated or partially unsaturated heterocyclyl, aryl, and heteroaryl are optionally substituted by one or more $R^7$;

$R^2$ is selected from the group consisting of halogen, hydroxyl, cyano, and nitro;

$R^5$ and $R^6$ are each independently selected from the group consisting of hydrogen, halogen, hydroxyl, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein said alkyl, alkenyl, alkynyl, heteroalkyl, heteroalkenyl, heteroalkynyl, alkoxy, saturated and partially unsaturated cycloalkyl, saturated and partially unsaturated heterocyclyl, aryl, and heteroaryl are optionally substituted with one or more groups independently selected from the group consisting of halogen, cyano, alkyl, alkenyl, alkynyl, heteroalkyl, heteroalkenyl, heteroalkynyl, saturated and partially unsaturated cycloalkyl, saturated and partially unsaturated heterocyclyl, aryl, and heteroaryl;

$R^7$ is independently selected from the group consisting of halogen, hydroxyl, cyano, nitro, alkoxyl, alkyl, alkenyl, alkynyl, heteroalkyl, heteroalkenyl, heteroalkynyl, haloalkyl, saturated or partially unsaturated cycloalkyl, saturated or partially unsaturated heterocyclyl, aryl, heteroaryl, —$NR^cR^d$, and —$C(O)R^e$, wherein said alkoxyl, alkyl, alkenyl, alkynyl, heteroalkyl, heteroalkenyl, heteroalkynyl, haloalkyl, saturated or partially unsaturated cycloalkyl, saturated or partially unsaturated heterocyclyl, aryl, heteroaryl are optionally substituted with one or more groups independently selected from the group consisting of halogen, hydroxyl, cyano, alkyl, haloalkyl, alkoxyl, saturated or partially unsaturated cycloalkyl, —$C(O)N(R^c)(R^d)$;

$R^a$, $R^b$, $R^c$, and $R^d$ are each independently selected from the group consisting of hydrogen, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein said alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl are optionally substituted with one or more groups independently selected from the group consisting of halogen, hydroxyl, cyano, nitro, carboxy, carbamoyl, alkyl, alkenyl, alkynyl, and alkoxyl;

$R^e$ is selected from the group consisting of alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein said alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl are optionally substituted with one or more groups independently selected from the group consisting of halogen, hydroxyl, cyano, nitro, carboxy, carbamoyl, alkyl, alkenyl, alkynyl, and alkoxyl;

m is 0, 1 or 2; and n is 0, 1 or 2.

2. The compound of Formula (Ie) or a pharmaceutically acceptable salt thereof, as claimed in claim 1, wherein Y is selected from the group consisting of a bond, —$CR^5R^6$—, —$O(CH_2)_n$—, —$N(R^a)$—, —C(O)—, and —$C(O)N(R^b)$—.

3. The compound of Formula (Ie) or a pharmaceutically acceptable salt thereof, as claimed in claim 1, wherein W is null, 3 to 10 membered saturated or partially unsaturated cycloalkyl, 3 to 10 membered saturated or partially unsaturated heterocyclyl, 3 to 10 membered aryl, and 3 to 10 membered heteroaryl, wherein said saturated or partially unsaturated cycloalkyl, saturated or partially unsaturated heterocyclyl, aryl, and heteroaryl are optionally substituted by one or more $R^7$.

4. The compound of Formula (Ie) or a pharmaceutically acceptable salt thereof, as claimed in claim 1, wherein W is null, or is selected from the group consisting of:

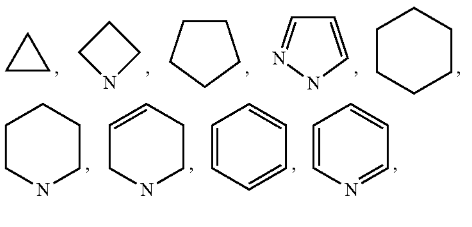

-continued

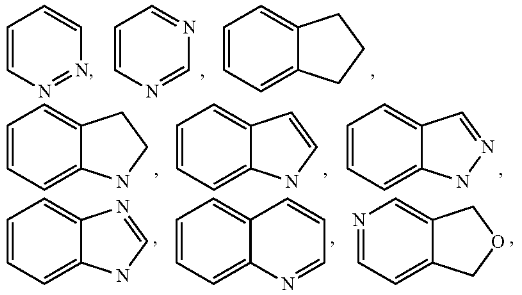

each of which is optionally substituted by one or more $R^7$.

5. The compound of Formula (Ie) or a pharmaceutically acceptable salt thereof, as claimed in claim 1, wherein $R^2$ is halogen.

6. The compound of Formula (Ie) or a pharmaceutically acceptable salt thereof, as claimed in claim 1, wherein $R^5$ and $R^6$ are each independently selected from the group consisting of hydrogen, halogen, hydroxyl, alkyl, alkenyl, alkynyl, heteroalkyl, heteroalkenyl, and heteroalkynyl, wherein said alkyl, alkenyl, alkynyl, heteroalkyl, heteroalkenyl, and heteroalkynyl are optionally substituted with one or more groups independently selected from the group consisting of halogen, cyano, alkyl, alkenyl, alkynyl, heteroalkyl, heteroalkenyl, heteroalkynyl, saturated and partially unsaturated cycloalkyl, saturated and partially unsaturated heterocyclyl, aryl, and heteroaryl.

7. The compound of Formula (Ie) or a pharmaceutically acceptable salt thereof, as claimed in claim 1, wherein $R^7$ is selected from the group consisting of halogen, hydroxyl, cyano, alkoxyl, alkyl, alkenyl, haloalkyl, saturated or partially unsaturated cycloalkyl, saturated or partially unsaturated heterocyclyl, aryl, heteroaryl, —$NR^cR^d$, and —$C(O)R^e$, wherein said alkoxyl, alkyl, alkenyl, haloalkyl, saturated or partially unsaturated cycloalkyl, saturated or partially unsaturated heterocyclyl, aryl, heteroaryl are optionally substituted with one or more groups independently selected from the group consisting of halogen, hydroxyl, cyano, alkyl, haloalkyl, alkoxyl, saturated or partially unsaturated cycloalkyl, —$C(O)N(R^c)(Rd)$.

8. The compound of Formula (Ie) or a pharmaceutically acceptable salt thereof, as claimed in claim 1, wherein $R^a$, $R^b$, $R^e$, and $R^d$ are each independently selected from the group consisting of hydrogen, alkyl, alkenyl, alkynyl, heteroalkyl, heteroalkenyl, and heteroalkynyl, wherein said alkyl, alkenyl, alkynyl, heteroalkyl, heteroalkenyl, and heteroalkynyl, are optionally substituted with one or more groups independently selected from the group consisting of halogen, hydroxyl, cyano, nitro, carboxy, carbamoyl, alkyl, alkenyl, alkynyl, and alkoxyl.

9. The compound of Formula (Ie) or a pharmaceutically acceptable salt thereof, as claimed in claim 1, wherein $R^e$ is selected from the group consisting of saturated or partially unsaturated cycloalkyl, saturated or partially unsaturated heterocyclyl, aryl, and heteroaryl, wherein said saturated or partially unsaturated cycloalkyl, saturated or partially unsaturated heterocyclyl, aryl, and heteroaryl are optionally substituted with one or more groups independently selected from the group consisting of halogen, hydroxyl, cyano, nitro, carboxy, carbamoyl, alkyl, alkenyl, alkynyl, and alkoxyl.

10. The compound of Formula (Ie) or a pharmaceutically acceptable salt thereof, as claimed in claim 1, wherein m is 0 or 1.

11. The compound of Formula (Ie) or a pharmaceutically acceptable salt thereof, as claimed in claim 1, wherein n is 0 or 1.

12. The compound of Formula (Ie) or a pharmaceutically acceptable salt thereof, as claimed in claim 1, wherein Y is a bond or —O—.

13. The compound of claim 1 or a pharmaceutically acceptable salt thereof, wherein the compound is selected from the group consisting of:

(S)-4-((1-(2,5-difluoro-4-(p-tolyloxy)phenyl)ethyl)amino)-2-ethyl-2,3-dihydro-1H-pyrrolo[3,4-c]pyridin-1-one;

(S)-4-((1-(2,5-difluoro-4-((1-methyl-1H-indol-5-yl)oxy)phenyl)ethyl)amino)-2-ethyl-2,3-dihydro-1H-pyrrolo[3,4-c]pyridin-1-one;

4-(((1S)-1-(2,5-difluoro-4-((3,3,5-trimethylcyclohexyl)oxy)phenyl)ethyl)amino)-2-ethyl-2,3-dihydro-1H-pyrrolo[3,4-c]pyridin-1-one;

4-(((S)-1-(2,5-difluoro-4-(((1R,5S)-3,3,5-trimethylcyclohexyl)oxy)phenyl)ethyl)amino)-2-ethyl-2,3-dihydro-1H-pyrrolo[3,4-c]pyridin-1-one;

4-(((S)-1-(2,5-difluoro-4-(((1S,5S)-3,3,5-trimethylcyclohexyl)oxy)phenyl)ethyl)amino)-2-ethyl-2,3-dihydro-1H-pyrrolo[3,4-c]pyridin-1-one;

(S)-4-((1-(4-(2-(tert-butyl)pyridin-4-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(2-(trifluoromethyl)pyridin-4-yl)phenyl)ethyl)amino)-2-ethyl-2,3-dihydro-1H-pyrrolo[3,4-c]pyridin-1-one;

(S)-4-((1-(4-(2-cyclobutylpyridin-4-yl)-2,5-difluorophenyl)ethyl)amino)-2-ethyl-2,3-dihydro-1H-pyrrolo[3,4-c]pyridin-1-one;

(S)-4-((1-(4-(2-cyclopropylpyridin-4-yl)-2,5-difluorophenyl)ethyl)amino)-2-ethyl-2,3-dihydro-1H-pyrrolo[3,4-c]pyridin-1-one;

(S)-4-((1-(4-(2-(cyclopropylmethyl)pyridin-4-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(2-(1-methyl-1H-pyrrol-3-yl)pyridin-4-yl)phenyl)ethyl)amino)-2-ethyl-2,3-dihydro-1H-pyrrolo[3,4-c]pyridin-1-one;

(S)-4-((1-(2,5-difluoro-4-(2-(oxetan-3-yl)pyridin-4-yl)phenyl)ethyl)amino)-2-ethyl-2,3-dihydro-1H-pyrrolo[3,4-c]pyridin-1-one;

(S)-4-((1-(2,5-difluoro-4-(2-(3-hydroxyoxetan-3-yl)pyridin-4-yl)phenyl)ethyl)amino)-2-ethyl-2,3-dihydro-1H-pyrrolo[3,4-c]pyridin-1-one;

(S)-4-((1-(4-(2-chloropyridin-4-yl)-2,5-difluorophenyl)ethyl)amino)-2-ethyl-2,3-dihydro-1H-pyrrolo[3,4-c]pyridin-1-one;

(S)-4-((1-(4-(2'-chloro-[2,4'-bipyridin]-4-yl)-2,5-difluorophenyl)ethyl)amino)-2-ethyl-2,3-dihydro-1H-pyrrolo[3,4-c]pyridin-1-one;

(S)-4-((1-(4-(2-(3,3-difluorocyclobutyl)pyridin-4-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(2-phenylpyridin-4-yl)phenyl)ethyl)amino)-2-ethyl-2,3-dihydro-1H-pyrrolo[3,4-c]pyridin-1-one;

(S)-4-((1-(4-([2,3'-bipyridin]-4-yl)-2,5-difluorophenyl)ethyl)amino)-2-ethyl-2,3-dihydro-1H-pyrrolo[3,4-c]pyridin-1-one;

(S)-4-((1-(4-(5'-chloro-[2,3'-bipyridin]-4-yl)-2,5-difluorophenyl)ethyl)amino)-2-ethyl-2,3-dihydro-1H-pyrrolo[3,4-c]pyridin-1-one;

(S)-4-((1-(4-(2-cyclopentylpyridin-4-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(2-(2-fluoropropan-2-yl)pyridin-4-yl)phenyl)ethyl)amino)-2-ethyl-2,3-dihydro-1H-pyrrolo[3,4-c]pyridin-1-one;

(S)-4-((1-(2,5-difluoro-4-(2-(2-hydroxypropan-2-yl)pyridin-4-yl)phenyl)ethyl)amino)-2-ethyl-2,3-dihydro-1H-pyrrolo[3,4-c]pyridin-1-one;

(S)-4-((1-(4-(2-(tert-butyl)-5-fluoropyridin-4-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(2-(1,1,1-trifluoro-2-methylpropan-2-yl)pyridin-4-yl)phenyl)ethyl)amino)-2-ethyl-2,3-dihydro-1H-pyrrolo[3,4-c]pyridin-1-one;

(S)-4-((1-(4-(2-(1,1-difluoroethyl)pyridin-4-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(2-(perfluoroethyl)pyridin-4-yl)phenyl)ethyl)amino)-2-ethyl-2,3-dihydro-1H-pyrrolo[3,4-c]pyridin-1-one;

(S)-4-((1-(4-(4-(tert-butyl)pyridin-2-yl)-2,5-difluorophenyl)ethyl)amino)-2-ethyl-2,3-dihydro-1H-pyrrolo[3,4-c]pyridin-1-one;

(S)-4-((1-(4-(5-(tert-butyl)pyridin-3-yl)-2,5-difluorophenyl)ethyl)amino)-2-ethyl-2,3-dihydro-1H-pyrrolo[3,4-c]pyridin-1-one;

(S)-4-((1-(4-(6-(tert-butyl)pyrimidin-4-yl)-2,5-difluorophenyl)ethyl)amino)-2-ethyl-2,3-dihydro-1H-pyrrolo[3,4-c]pyridin-1-one;

(S)-4-((1-(4-(2-(tert-butyl)pyrimidin-4-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(4-(2-fluoropropan-2-yl)pyridin-2-yl)phenyl)ethyl)amino)-2-ethyl-2,3-dihydro-1H-pyrrolo[3,4-c]pyridin-1-one;

(S)-4-((1-(2,5-difluoro-4-(4-(2-fluoropropan-2-yl)-6-methylpyridin-2-yl)phenyl)ethyl)amino)-2-ethyl-2,3-dihydro-1H-pyrrolo[3,4-c]pyridin-1-one;

(S)-2-(4-(1-((2-ethyl-1-oxo-2,3-dihydro-1H-pyrrolo[3,4-c]pyridin-4-yl)amino) ethyl)-2,5-difluorophenyl)isonicotinonitrile;

(S)-4-((1-(2,5-difluoro-4-(4-(trifluoromethyl)pyridin-2-yl)phenyl)ethyl)amino)-2-ethyl-2,3-dihydro-1H-pyrrolo[3,4-c]pyridin-1-one;

(S)-4-((1-(4-(2-(tert-butyl)-5-methoxypyridin-4-yl)-2,5-difluorophenyl)ethyl)amino)-2-ethyl-2,3-dihydro-1H-pyrrolo[3,4-c]pyridin-1-one;

(S)-4-((1-(4-(6-(tert-butyl)-3-methoxypyridin-2-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(6-(fluoromethyl)-4-(2-fluoropropan-2-yl)pyridin-2-yl)phenyl)ethyl)amino)-2-ethyl-2,3-dihydro-1H-pyrrolo[3,4-c]pyridin-1-one;

(S)-4-((1-(2,5-difluoro-4-(6-fluoro-4-(2-fluoropropan-2-yl)pyridin-2-yl)phenyl)ethyl)amino)-2-ethyl-2,3-dihydro-1H-pyrrolo[3,4-c]pyridin-1-one;

(S)-4-((1-(2,5-difluoro-4-(4-(2-fluoropropan-2-yl)-6-methoxypyridin-2-yl)phenyl)ethyl)amino)-2-ethyl-2,3-dihydro-1H-pyrrolo[3,4-c]pyridin-1-one;

(S)-4-((1-(4-(6-chloro-4-(trifluoromethyl)pyridin-2-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(6-methyl-4-(trifluoromethyl)pyridin-2-yl)phenyl)ethyl)amino)-2-ethyl-2,3-dihydro-1H-pyrrolo[3,4-c]pyridin-1-one;

(S)-4-((1-(2,5-difluoro-4-(6-(fluoromethyl)-4-(trifluoromethyl)pyridin-2-yl)phenyl)ethyl)amino)-2-ethyl-2,3-dihydro-1H-pyrrolo[3,4-c]pyridin-1-one;

(S)-4-((1-(2,5-difluoro-4-(4-(1-(trifluoromethyl)cyclopropyl)pyridin-2-yl)phenyl)ethyl)amino)-2-ethyl-2,3-dihydro-1H-pyrrolo[3,4-c]pyridin-1-one;

(S,E)-4-((1-(2,5-difluoro-4-(4-(1,1,1-trifluorobut-2-en-2-yl)pyridin-2-yl)phenyl)ethyl)amino)-2-ethyl-2,3-dihydro-1H-pyrrolo[3,4-c]pyridin-1-one;

4-(((1S)-1-(2,5-difluoro-4-(4-(5-(trifluoromethyl)-4,5-dihydro-1H-pyrazol-5-yl)pyridin-2-yl)phenyl)ethyl)amino)-2-ethyl-2,3-dihydro-1H-pyrrolo[3,4-c]pyridin-1-one;

(S)-4-((1-(2,5-difluoro-4-(4-(2-fluoropropan-2-yl)-5-methylpyridin-2-yl)phenyl)ethyl)amino)-2-ethyl-2,3-dihydro-1H-pyrrolo[3,4-c]pyridin-1-one;

(S)-4-((1-(4-(4-(tert-butylamino)-6-methylpyridin-2-yl)-2,5-difluorophenyl)ethyl)amino)-2-ethyl-2,3-dihydro-1H-pyrrolo[3,4-c]pyridin-1-one;

(S)-4-((1-(4-(4-(tert-butoxy)-6-methylpyridin-2-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(6-(2-fluoropropan-2-yl)pyrimidin-4-yl)phenyl)ethyl)amino)-2-ethyl-2,3-dihydro-1H-pyrrolo[3,4-c]pyridin-1-one;

(S)-4-((1-(2,5-difluoro-4-(4-(1-fluorocyclopropyl)-6-methylpyridin-2-yl)phenyl)ethyl)amino)-2-ethyl-2,3-dihydro-1H-pyrrolo[3,4-c]pyridin-1-one;

(S)-4-((1-(2,5-difluoro-4-(2-(2-fluoropropan-2-yl)-5-methoxypyridin-4-yl)phenyl)ethyl)amino)-2-ethyl-2,3-dihydro-1H-pyrrolo[3,4-c]pyridin-1-one;

(S)-4-((1-(2,5-difluoro-4-(5-fluoro-4-(2-fluoropropan-2-yl)-6-methylpyridin-2-yl)phenyl)ethyl)amino)-2-ethyl-2,3-dihydro-1H-pyrrolo[3,4-c]pyridin-1-one;

(S)-4-((1-(2,5-difluoro-4-(3-fluoro-4-(2-fluoropropan-2-yl)-6-methylpyridin-2-yl)phenyl)ethyl)amino)-2-ethyl-2,3-dihydro-1H-pyrrolo[3,4-c]pyridin-1-one;

(S)-4-((1-(2,5-difluoro-4-(4-(2-fluoropropan-2-yl)-5-methoxypyridin-2-yl)phenyl)ethyl)amino)-2-ethyl-2,3-dihydro-1H-pyrrolo[3,4-c]pyridin-1-one;

(S)-4-((1-(4-(5-chloro-4-(2-fluoropropan-2-yl)pyridin-2-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(5-fluoro-4-(2-fluoropropan-2-yl)pyridin-2-yl)phenyl)ethyl)amino)-2-ethyl-2,3-dihydro-1H-pyrrolo[3,4-c]pyridin-1-one;

(S)-4-((1-(4-(2-(tert-butyl)-5-hydroxypyridin-4-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(5-(fluoromethyl)-2-(2-fluoropropan-2-yl)pyridin-4-yl)phenyl)ethyl)amino)-2-ethyl-2,3-dihydro-1H-pyrrolo[3,4-c]pyridin-1-one;

(S)-4-((1-(2,5-difluoro-4-(6-(2-fluoropropan-2-yl)-2-methoxypyrimidin-4-yl)phenyl)ethyl)amino)-2-ethyl-2,3-dihydro-1H-pyrrolo[3,4-c]pyridin-1-one;

(S)-4-((1-(2,5-difluoro-4-(6-methoxy-4-(trifluoromethyl)pyridin-2-yl)phenyl)ethyl)amino)-2-ethyl-2,3-dihydro-1H-pyrrolo[3,4-c]pyridin-1-one;

(S)-4-((1-(2,5-difluoro-4-(5-methoxy-2-(trifluoromethyl)pyridin-4-yl)phenyl)ethyl)amino)-2-ethyl-2,3-dihydro-1H-pyrrolo[3,4-c]pyridin-1-one;

(S)-4-((1-(2,5-difluoro-4-(5-hydroxy-2-(trifluoromethyl)pyridin-4-yl)phenyl)ethyl)amino)-2-ethyl-2,3-dihydro-1H-pyrrolo[3,4-c]pyridin-1-one;

(S)-4-((1-(2,5-difluoro-4-(5-(methoxymethoxy)-2-(trifluoromethyl)pyridin-4-yl)phenyl)ethyl)amino)-2-ethyl-2,3-dihydro-1H-pyrrolo[3,4-c]pyridin-1-one;

(S)-4-((1-(4-(1,1-dimethyl-1,3-dihydrofuro [3,4-c]pyridin-6-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(4-(2-fluoropropan-2-yl)-5-(methoxymethyl)pyridin-2-yl)phenyl)ethyl)amino)-2-ethyl-2,3-dihydro-1H-pyrrolo[3,4-c]pyridin-1-one;

(S)-4-((1-(2,5-difluoro-4-(4-(2-fluoropropan-2-yl)-5-(trifluoromethyl)pyridin-2-yl)phenyl)ethyl)amino)-2-ethyl-2,3-dihydro-1H-pyrrolo[3,4-c]pyridin-1-one;

(S)-4-((1-(4-(6-(tert-butyl)-5-methoxypyridin-2-yl)-2,5-difluorophenyl)ethyl)amino)-2-ethyl-2,3-dihydro-1H-pyrrolo[3,4-c]pyridin-1-one;

(S)-4-((1-(4-(4-(tert-butyl)-5-methoxypyridin-2-yl)-2,5-difluorophenyl)ethyl)amino)-2-ethyl-2,3-dihydro-1H-pyrrolo[3,4-c]pyridin-1-one;

(S)-4-((1-(4-(2-(tert-butoxy)-5-methylpyridin-4-yl)-2,5-difluorophenyl)ethyl)amino)-2-ethyl-2,3-dihydro-1H-pyrrolo[3,4-c]pyridin-1-one;

(S)-4-((1-(4-(4-(tert-butoxy)-5-chloropyridin-2-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(5-(2-fluoropropan-2-yl)-6-methoxypyridazin-3-yl)phenyl)ethyl)amino)-2-ethyl-2,3-dihydro-1H-pyrrolo[3,4-c]pyridin-1-one;

(S)-2-(4-(4-(1-((2-ethyl-1-oxo-2,3-dihydro-1H-pyrrolo[3,4-c]pyridin-4-yl)amino) ethyl)-2,5-difluorophenyl)pyridin-2-yl)-2-methylpropanenitrile;

(S)-4-((1-(2,5-difluoro-4-(6-fluoro-4-(trifluoromethyl)pyridin-2-yl)phenyl)ethyl)amino)-2-ethyl-2,3-dihydro-1H-pyrrolo[3,4-c]pyridin-1-one;

(S)-4-((1-(2,5-difluoro-4-(4-(2-fluoropropan-2-yl)-6-hydroxypyridin-2-yl)phenyl)ethyl)amino)-2-ethyl-2,3-dihydro-1H-pyrrolo[3,4-c]pyridin-1-one;

(S)-4-((1-(2,5-difluoro-4-(6-hydroxy-4-(trifluoromethyl)pyridin-2-yl)phenyl)ethyl)amino)-2-ethyl-2,3-dihydro-1H-pyrrolo[3,4-c]pyridin-1-one;

(S)-4-((1-(4-(2-(tert-butyl)pyridin-4-yl)-2,5-difluorophenyl)ethyl)amino)-2-(2-methoxyethyl)-2,3-dihydro-1H-pyrrolo[3,4-c]pyridin-1-one;

(S)-4-((1-(4-(2-(tert-butyl)pyridin-4-yl)-2,5-difluorophenyl)ethyl)amino)-2-(2-hydroxyethyl)-2,3-dihydro-1H-pyrrolo[3,4-c]pyridin-1-one;

(S)-4-((1-(4-(1-(tert-butyl)-1H-imidazol-4-yl)-2,5-difluorophenyl)ethyl)amino)-2-ethyl-2,3-dihydro-1H-pyrrolo[3,4-c]pyridin-1-one;

(S)-4-((1-(2,5-difluoro-4-(4-(2-fluoropropan-2-yl)-5-(methoxymethoxy)pyridin-2-yl)phenyl)ethyl)amino)-2-ethyl-2,3-dihydro-1H-pyrrolo[3,4-c]pyridin-1-one;

(S)-4-((1-(2,5-difluoro-4-(4-(2-fluoropropan-2-yl)-5-hydroxypyridin-2-yl)phenyl)ethyl)amino)-2-ethyl-2,3-dihydro-1H-pyrrolo[3,4-c]pyridin-1-one;

(S)-6-(4-(1-((2-ethyl-1-oxo-2,3-dihydro-1H-pyrrolo[3,4-c]pyridin-4-yl)amino) ethyl)-2,5-difluorophenyl)-4-(2-fluoropropan-2-yl)nicotinonitrile;

(S)-4-((1-(2,5-difluoro-4-(5-hydroxy-4-(trifluoromethyl)pyridin-2-yl)phenyl)ethyl)amino)-2-ethyl-2,3-dihydro-1H-pyrrolo[3,4-c]pyridin-1-one; and (S)-4-((1-(2,5-difluoro-4-(5-methoxy-4-(trifluoromethyl)pyridin-2-yl)phenyl)ethyl)amino)-2-ethyl-2,3-dihydro-1H-pyrrolo[3,4-c]pyridin-1-one.

14. A pharmaceutical composition comprising a compound of Formula (Ie) or a pharmaceutically acceptable salt thereof, as claimed in claim 1, and at least one pharmaceutically acceptable excipient.

* * * * *